(12) United States Patent
Liberg et al.

(10) Patent No.: US 11,479,610 B2
(45) Date of Patent: Oct. 25, 2022

(54) ANTI-IL1RAP ANTIBODY

(71) Applicant: Cantargia AB, Lund (SE)

(72) Inventors: David Liberg, Lomma (SE); Camilla Rydberg Millrud, Limhamn (SE); Gabriel Svensson Birkedal, Höör (SE); Sara Rattik, Åkarp (SE); Kjell Sjöström, Lund (SE); Karin von Wachenfeldt, Lund (SE); Caitríona Grönberg, Torna-Hällestad (SE)

(73) Assignee: Cantargia AB, Lund (SE)

( * ) Notice: Subject to any disclaimer, the term of this patent is extended or adjusted under 35 U.S.C. 154(b) by 16 days.

(21) Appl. No.: 17/559,227

(22) Filed: Dec. 22, 2021

(65) Prior Publication Data
US 2022/0242950 A1 Aug. 4, 2022

(30) Foreign Application Priority Data

| Dec. 23, 2020 | (EP) | ..................................... 20216926 |
| Apr. 26, 2021 | (GB) | ..................................... 2105933 |
| Dec. 3, 2021 | (EP) | ..................................... 21212368 |

(51) Int. Cl.
| *A61K 39/395* | (2006.01) |
| *A61K 39/00* | (2006.01) |
| *G01N 33/53* | (2006.01) |
| *C12N 1/20* | (2006.01) |
| *C12N 15/00* | (2006.01) |
| *C07K 16/00* | (2006.01) |
| *C07K 16/46* | (2006.01) |
| *C07H 21/04* | (2006.01) |
| *C07K 16/28* | (2006.01) |
| *A61P 35/00* | (2006.01) |
| *C12N 15/63* | (2006.01) |

(52) U.S. Cl.
CPC ............ *C07K 16/283* (2013.01); *A61P 35/00* (2018.01); *C12N 15/63* (2013.01); *A61K 2039/505* (2013.01); *C07K 2317/565* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| 4,235,871 A | 11/1980 | Papahadjopoulos et al. |
| 4,816,567 A | 3/1989 | Cabilly et al. |
| 5,851,451 A | 12/1998 | Takechi et al. |
| 7,960,512 B2 | 6/2011 | Stavenhagen et al. |

FOREIGN PATENT DOCUMENTS

| EP | 0213303 B1 | 9/1991 |
| EP | 2213683 B1 | 6/2013 |
| WO | WO 00/61739 | 10/2000 |
| WO | WO 2011/021014 A2 | 2/2011 |
| WO | WO 2012/098407 A1 | 7/2012 |
| WO | WO 2015/132602 A1 | 9/2015 |
| WO | WO 2016/207304 A2 | 12/2016 |
| WO | WO 2019/028190 A1 | 2/2019 |
| WO | WO 2020/035577 A1 | 2/2020 |
| WO | WO 2020/037154 A1 | 2/2020 |

OTHER PUBLICATIONS

Rattik et al. Blocking IL1, IL33 and IL36 signaling by an anti-IL1RAP antibody is an efficient anti-inflammatory treatment that improves heart function in a model of autoimmune myocarditis. J Immunol May 1, 2021, 206 (1 Supplement) 18.02; (Year: 2021).*
Biacore Assay Handbook (2012).
Al-Lazikani et al: "Standard Conformations for the Canonical Structures of Immunoglobulins", J. Mol. Biol. (1997), 273, pp. 927-948.
Angov, Evelina: "Codon usage: Nature's roadmap to expression and folding of protein", Biotechnology Journal (2011), 6, pp. 650-659, doi: 10.1002/biot.201000332.
Armour et al: "Recombinant human IgG molecules lacking Fcγ receptor I binding and monocyte triggering activities", Eur. J. Immunol. (1999) 29: 2613-2624.
Arndt et al: "Methods in molecular biology: Protein engineering protocols", Humana Press (2007).
Askmyr et al: "Selective killing of candidate AML stem cells by antibody targeting of IL1RAP", Blood, May 2, 2013, vol. 121, No. 18, pp. 3709-3713.
Attucci et al: "EPI-hNE4, a Proteolysis-Resistant Inhibitor of Human Neutrophil Elastase and Potential Anti-Inflammatory Drug for Treating Cystic Fibrosis", Journal of Pharmacol Exp Ther (2006), vol. 318, No. 2, pp. 803-809.
Barreyro et al: Overexpression of IL-1 receptor accessory protein in stem and progenitor cells and outcome correlation in AML and MDS, Blood, Aug. 9, 2012, vol. 120, No. 6, pp. 1290-1298.

(Continued)

*Primary Examiner* — Maher M Haddad
(74) *Attorney, Agent, or Firm* — McNeill Baur PLLC

(57) ABSTRACT

The present invention relates to an antibody or antigen-binding fragment thereof with binding specificity for interleukin-1 receptor accessory protein (IL1RAP). Furthermore, it relates to a polynucleotide encoding said antibody, a vector comprising said polynucleotide and a recombinant host cell comprising said polynucleotide or said vector. Further, it relates to a method for producing said antibody or antigen-binding fragment. Further, it relates to a composition comprising said antibody or antigen-binding fragment, said polynucleotide, said vector and/or said host cell. Further, it relates to the said antibody or antigen-binding fragment, said polynucleotide, said vector, said host cell and/or said composition for use in medicine and/or for use in the prevention and/or treatment and/or alleviation and/or detection and/or diagnosis of a disease or disorder susceptible to treatment with an inhibitor of IL-1α, IL-1β, IL-33, IL-36α, IL-36β and/or IL-36γ signaling, and/or wherein the disease or disorder is associated with cells expressing IL1RAP.

28 Claims, 54 Drawing Sheets

Specification includes a Sequence Listing.

(56) References Cited

OTHER PUBLICATIONS

Binz et al: "High-affinity binders selected from designed ankyrin repeat protein libraries", Nature Biotechnology, vol. 22, No. 5, May 2004, pp. 575-582.
Borghouts et al: "Peptide aptamers: recent developments for cancer therapy", Expert Opinion, Biol. Ther. (2005) 5(6) pp. 783-797, ISSN 1471-2598, doi: 10.1517/14712598.5.6.783.
Bruhns et al: "Specificity and affinity of human Fcγ receptors and their polymorphic variants for human IgG subclasses", Immunobiology, Blood, Apr. 16, 2009, vol. 113, No. 16, pp. 3716-3725.
Busfield et al: "Targeting of acute myeloid leukemia in vitro and in vivo with an anti-CD123 mAb engineered for optimal ADCC", Leukemia (2014), 28, pp. 2213-2221.
Cole et al: "Human monoclonal antibodies", Molecular and Cellular Biochemistry 62, 109-120 (1984).
Cote et al: "Generation of human monoclonal antibodies reactive with cellular antigens", Immunology, Proc. Natl. Acad. Sci. USA, vol. 80, pp. 2026-2030, Apr. 1983.
Datta-Mannan et al: "Humanized IgG1 Variants with Differential Binding Properties to the Neonatal Fc Receptor: Relationship to Pharmacokinetics in Mice and Primates", Drug Metabolism and Disposition, vol. 35, No. 1 (2007), doi:10.1124/dmd.106.011734.
Dinarello et al: "Treating inflammation by blocking interleukin-1 in a broad spectrum of diseases", Nat Rev Drug Discov. Aug. 2012; 11(8):633-652. doi: 10.1038/nrd3800.
Dinarello, Charles A.: "An Expanding role for interleukin-2 blockade from gout to cancer", Molecular Medicine 20 (supplement 1), S43-S58, 2014.
Dinarello, Charles A.: "Biologic basis for interleukin-1 in disease", Blood, vol. 87, No. 6, Mar. 15, 1996, pp. 2095-2147.
Dinarello, Charles A.: "Proinflammatory Cytokines", Chest, 118; 2; Aug. 2000, pp. 503-508.
Dinarello, Charles A.: "The IL-1 family and inflammatory diseases", Clinical and Experimental Rheumatology 2002; 20 (suppl. 27), pp. S1-S13.
Ding et al: "IL-36 cytokines in autoimmunity and inflammatory disease", Oncotarget, 2018, vol. 9, No. 2, pp. 2895-2901.
Dondelinger et al: "Understanding the significance and implications of antibody numbering and antigen-binding surface/residue definition", Frontiers in Immunology, Review, Oct. 16, 2018, vol. 9, article 2278, pp. 1-15, doi: 10.3389/fimmu.2018.02278.
Garlanda et al: "The Interleukin-1 Family: Back to the future", Immunity 39, Dec. 12, 2013, Elsevier Inc, pp. 1003-1018.
Gebauer et al: "Engineered protein scaffolds as next-generation antibody therapeutics", Science Direct, Current opinion in chemical biology (2009), 13, pp. 245-255.
Groot et al: "Beyond humanization and de-immunization: tolerization as a method for reducing teh immunogenicity of biologies", Expert review of clinical pharmacology 20141101 Expert reviews Ltd, GBR, vol. 6, No. 6, Nov. 1, 2013, pp. 651-662, XP055237741, UK, ISSN: 1751-2433, doi: 10.1586/17512433.2013.835698.
Hey et al: "Artificial, non-antibody binding proteins for pharmaceutical and industrial applications", Trends in Biotechnology, vol. 23, No. 10, Oct. 2005, pp. 514-522.
Hinton et al: "Engineered Human IgG antibodies with longer serum half-lives in primates", Journal of Biological Chemistry, vol. 279, No. 8, Feb. 20, 2004, pp. 6213-6216.
Hurrell, John G.R.: "Monoclonal hybridoma antibodies: Techniques and applications", CRC Press (1982).
Idusogie et al: "Mapping of the C1q binding site on Rituxan, a chimeric antibody with a human IgG1 Fc", Journal of Immunology (2000), 164: pp. 4178 4184.
Jones et al: "Replacing the complementarity-determining regions in a human antibody with those from a mouse", Nature, vol. 321, May 29, 1986, pp. 522-525.
Jones et al: "Therapeutic Antibodies: Methods and Protocols", vol. 525 (2009) pp. 405-423.
Järås et al: "Isolation and killing of candidate chronic myeloid leukemia stem cells by antibody targeting of IL-1 receptor accessory protein", PNAS, Sep. 14, 2010, vol. 107, No. 37, pp. 16280-16285.
Kabat et al: "Sequences of proteins of immunological interest", National Institutes of Health, vol. 1, Fifth edition (1991).
Kivi et al: "HybriFree: a robust and rapid method for the development of monoclonal antibodies from different host species", BMC Biotechnology (2016) 16:2, pp. 1-14.
Kotsiou et al: "IL-33/ST2 axis in organ fibrosis", Frontiers in Immunology, Oct. 24, 2018, vol. 19, article 2432, pp. 1-15.
Kozbor et al: "Specific immunoglobulin production and enhanced tumorigenicity following ascites growth of human hybridomas", Journal of Immunological Methods, 81 (1985), pp. 31-42, Elsevier.
Krause et al: "Grafting of thrombopoietin-mimetic peptides into cystine knot miniproteins yields high-affinity thrombopoietin antagonists and agonists", FEBS Journal 274 (2007), pp. 86-95.
Köhler et al: "Continuous cultures of fused cells secreting antibody of predefined specificity", Nature, vol. 256, Aug. 7, 1975, pp. 495-497.
Labrijn et al: "Therapeutic IgG4 antibodies engage in Fab-arm exchange with endogenous human IgG4 in vivo", Nature Biotechnology, vol. 27, No. 8, Aug. 2009, pp. 767-773, doi:10.1038/nbt.1553.
Lazar et al: "Engineered antibody Fc variants with enhanced effector function", PNAS, Mar. 14, 2006, vol. 103, No. 11, pp. 4005-4010.
Lefranc et al: "IMGT unique numbering for immunolgobulin and T cell receptor constant domains and Ig superfamily C-like domains", Development and Comparative Immunology 29 (2005), pp. 185-203.
Li et al: "Construction strategies for developing expression vectors for recombinant monoclonal antibody production in CHO cells", Molecular Biology Reports (2018) 45: 2907-2912.
Liew et al: "Interleukin-33 in health and disease", Nature, vol. 16, Nov. 2016, pp. 676-689.
Masuda et al: "Enhanced binding affinity foir FryRIIIa of fucose-negative antibody is sufficient to induce maximal antibody-dependent cellular cytotoxicity", Molecular Immunology 44 (2007), pp. 3122-3131.
Nygren, Per-Åke: "Alternative binding proteins: Affibody binding proteins developed from a small three-helix bundle scaffold", FEBS Journal 275 (2008), 2668-2676.
Okazaki et al: "Fucose Depletion from Human IgG1 Oligosaccharide Enhances Binding Enthalpy and Association Rate Between IgG1 and FcγRIIIa", J. Mol. Biol. (2004) 336, pp. 1239-1249.
Orlandi et al: "Cloning immunoglobulin variable domains for expression by the polymerase chain reaction", Proc. Natl. Acad. Sci. USA, vol. 86, pp. 3833-3837, May 1989.
Pule et al: "Artificial T-cell receptors", Cytotherapy (2003), vol. 5, No. 3, pp. 211-226.
Rattik et al: "Blocking IL1, IL33 and IL36 signaling by an anti-IL1RAP antibody is an efficient anti-inflammatory treatment that improves heart function in a model of autoimmune myocarditis", Poster presentation American Association of Immunologists AAI Virtual Immunology 2021.
Richards et al: "Optimization of antibody binding to FcγRIIa enhances macrophage phagocytosis of tumor cells", Molecular Cancer Therapeutics, Aug. 2008, 7(8), pp. 2517-2527.
Ridker et al: Interleukin-inhibition and the prevention of recurrent cardiovascular events: Rationale and design of the Canakinumab Anti-inflammatory Thrombosis Outcomes study (CANTOS), American Heart Journal, Oct. 2011, vol. 162, No. 4, pp. 597-605.
Riechmann et al: "Reshaping human antibodies for therapy", Nature, vol. 332, Mar. 24, 1988, pp. 323-327.
Ryan et al: "Antibody targeting of B-cell maturation antigen on malignant plasma cells", Molecular Cancer Therapeutics 2007, 6(11), pp. 3009-3018.
Schlehuber et al: Lipocalins in drug discovery: from natural ligand-binding proteins to 'anticalins', Drug Discovery Today, vol. 10, No. 1, Jan. 2005, pp. 23-33.
Shields et al: "High Resolution Mapping of the Binding Site on Human IgG1 for FcγRI, FcγRII, FcγRIII, and FcRn and Design of IgG1 Variants with Improved Binding to the FcγR", Journal of Biological Chemistry, vol. 276, No. 9, Issue of Mar. 2, 2001, pp. 6591-6604.

(56) References Cited

OTHER PUBLICATIONS

Silverman et al: "Multivalent avimer proteins evolved by exon shuffling of a family of human receptor domains", Nature Biotechnology, vol. 23, No. 12, Dec. 2005, pp. 1556-1561.

Steurer et al: "Ex Vivo Coating of Islet Cell Allografts with Murine CTLA4/Fc Promotes Graft Tolerance", Journal of Immunology (1995), 155, pp. 1165-1174.

Strohl, William R.: "Optimization of Fc-mediated effector functions of monoclonal antibodies", Current opinion in Biotechnology 2009, 20, pp. 685-691.

Thøgersen et al: "A tetranectin-based platform for protein engineering", Drug Discovery, Innovation Pharmac Technol (2006), pp. 27-31.

Vaccaro et al: "Engineering the Fc region of immunoglobulin G to modulate in vivo antibody levels", Nature Biotechnology, vol. 23, No. 10, Oct. 2005, pp. 1283-1288.

Verhoeyen et al: "Reshaping human antibodies: Grafting an antilysozyme activity", Science, Mar. 25, 1988, vol. 239, No. 4847, pp. 1534-1536.

Visvader et al: "Cancer stem cells in solid tumours: accumulating evidence and unresolved questions", Nature Reviews, Cancer, vol. 8, Oct. 2008, pp. 755-768.

Wang et al: "Structural insights into the assembly and activation of IL-1β with its receptors", Nature Immunology, vol. 11, No. 10, Oct. 2010, pp. 905-912.

Winter et al: "Man-made antibodies", Nature, vol. 349, Jan. 24, 1991, pp. 293-299.

Xu et al: "In vitro characterization of five humanized OKT3 effector function variant antibodies", Cellular Immunology, 200, pp. 16-26 (2000).

Yoon et al: "Antibodies to domains II and III of the IL-1 receptor accessory protein inhibit IL-1 beta activity but not binding: regulation of IL-1 responses is via type I receptor, not the accessory protein", Journal of Immunology, vol. 160, No. 7, Apr. 1, 1998, pp. 3170-3179, XP055191790.

Zalevsky et al: "Enhanced antibody half-life improves in vivo activity", Nature Biotechnology, vol. 28, No. 2, Feb. 2010, pp. 157-159.

Zola, Heddy: "Monoclonal antibodies: A manual of techniques" CRC Press (1987).

Ågerstam et al: "Antibodies targeting human IL1RAP (IL1R3) show therapeutic effects in xenograft models of acute myeloid leukemia", Proceedings of the national Academy of sciences, vol. 112, No. 34, Aug. 10, 2015, pp. 10786-10791, XP055308490, ISSN: 0027-8424, doi: 10.1073/pnas.1422749112.

Ågerstam et al: "IL1RAP antibodies block IL-1-induced expansion of candidate CML stem cells and mediate cell killing in xenograft models", Blood, American Society of Hematology, US, vol. 128, No. 23, Dec. 8, 2016, pp. 2683-2693, XP086510523, ISSN: 0006-4971, doi: 10.1182/blood-2015-11-679985.

International Search Report and Written Opinion issued in PCT/EP2021/087338 dated Apr. 20, 2022.

Rudikoff et al., Single amino acid substitution altering antigen-binding specificity, Proceedings of the National Academy of Sciences USA, Immunology, vol. 79, Mar. 1, 1982, pp. 1979-1983.

\* cited by examiner

C

Masson's trichrome staining

PBS　　　　　Isotype　　　　mCAN10

D　Cardiac fibrosis

C

D

E

F

K

L

SEQUENCE LISTING

```
<160> NUMBER OF SEQ ID NOS: 39

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: CDR-L1 according to IMGT

<400> SEQUENCE: 1

Glu Ser Ile Ser Thr Ala
1               5

<210> SEQ ID NO 2
<211> LENGTH: 329
<212> TYPE: PRT
<213> ORGANISM: Homo sapiens
<220> FEATURE:
<221> NAME/KEY: MISC_FEATURE
<222> LOCATION: (1)..(329)
<223> OTHER INFORMATION: Immunoglobulin IgG1 constant heavy chain with
      LALA mutation

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 3
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: CDR-L3 according to IMGT

<400> SEQUENCE: 3

Gln Gln Gly Phe Ser Ser Gly Asn Val His Asn Ala
1               5                   10

<210> SEQ ID NO 4
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: CDR-H1 according to IMGT

<400> SEQUENCE: 4

Gly Pro Ser Leu Ser His Phe Asp
1               5

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: CDR-H2 according to IMGT

<400> SEQUENCE: 5

Ile Ser Pro Gly Val Ser Thr
1               5
```

<210> SEQ ID NO 6
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR-H3 according to IMGT

<400> SEQUENCE: 6

Ala Arg Gly Gly Val Gly Ser Ser Trp Lys Ala Phe Asp Leu
1               5                   10

<210> SEQ ID NO 7
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: CDR-L1 according to Kabat

<400> SEQUENCE: 7

Gln Ala Ser Glu Ser Ile Ser Thr Ala Leu Ala
1               5                   10

<210> SEQ ID NO 8
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: CDR-L2 according to Kabat

<400> SEQUENCE: 8

Lys Ala Ser Thr Leu Pro Ser
1               5

<210> SEQ ID NO 9
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: CDR-L3 according to Kabat

<400> SEQUENCE: 9

Gln Gln Gly Phe Ser Ser Gly Asn Val His Asn Ala
1               5                   10

<210> SEQ ID NO 10
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR-H1 according to Kabat

<400> SEQUENCE: 10

His Phe Asp Ile Thr
1               5

<210> SEQ ID NO 11
<211> LENGTH: 16
<212> TYPE: PRT

```
<213> ORGANISM: Homo sapiens
<220> FEATURE:
<221> NAME/KEY: MISC_FEATURE
<222> LOCATION: (1)..(16)
<223> OTHER INFORMATION: CDR-H2 according to Kabat

<400> SEQUENCE: 11

Thr Ile Ser Pro Gly Val Ser Thr Tyr Tyr Ala Ser Trp Ala Lys Ser
1               5                   10                  15

<210> SEQ ID NO 12
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: CDR-H3 according to Kabat

<400> SEQUENCE: 12

Gly Gly Val Gly Ser Ser Trp Lys Ala Phe Asp Leu
1               5                   10

<210> SEQ ID NO 13
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: CDR-L1 according to combination of IMGT and
      Kabat

<400> SEQUENCE: 13

Gln Ala Ser Glu Ser Ile Ser Thr Ala Leu Ala
1               5                   10

<210> SEQ ID NO 14
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: CDR-L2 according to combination of IMGT and
      Kabat

<400> SEQUENCE: 14

Lys Ala Ser Thr Leu Pro Ser
1               5

<210> SEQ ID NO 15
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<220> FEATURE:
<221> NAME/KEY: MISC_FEATURE
<222> LOCATION: (1)..(12)
<223> OTHER INFORMATION: CDR-L3 according to combination of IMGT and
      Kabat

<400> SEQUENCE: 15

Gln Gln Gly Phe Ser Ser Gly Asn Val His Asn Ala
1               5                   10

<210> SEQ ID NO 16
```

```
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: CDR-H1 according to combination of IMGT and
      Kabat

<400> SEQUENCE: 16

Gly Pro Ser Leu Ser His Phe Asp Ile Thr
1               5                   10

<210> SEQ ID NO 17
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: CDR-H2 according to combination of IMGT and
      Kabat

<400> SEQUENCE: 17

Thr Ile Ser Pro Gly Val Ser Thr Tyr Tyr Ala Ser Trp Ala Lys Ser
1               5                   10                  15

<210> SEQ ID NO 18
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR-H3 according to combination of IMGT and
      Kabat

<400> SEQUENCE: 18

Ala Arg Gly Gly Val Gly Ser Ser Trp Lys Ala Phe Asp Leu
1               5                   10

<210> SEQ ID NO 19
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: Light chain variable region (non-humanized,
      non-deimmunized)

<400> SEQUENCE: 19

Ala Pro Val Leu Thr Gln Thr Pro Ala Ser Val Glu Val Ala Val Gly
1               5                   10                  15

Gly Thr Val Thr Ile Lys Cys Gln Ala Ser Glu Ser Ile Ser Thr Ala
                20                  25                  30

Leu Ala Trp Tyr Gln Gln Lys Pro Gly Gln Pro Pro Lys Leu Leu Ile
            35                  40                  45

Tyr Lys Ala Ser Thr Leu Pro Ser Gly Val Ser Ser Arg Phe Lys Gly
        50                  55                  60

Ser Gly Ser Gly Thr Glu Phe Ala Leu Thr Ile Ser Asp Leu Glu Cys
65                  70                  75                  80

Asp Asp Ala Ala Thr Tyr Tyr Cys Gln Gln Gly Phe Ser Ser Gly Asn
                85                  90                  95

Val His Asn Ala Phe Gly Gly Gly Thr Glu Val Val Val Lys
            100                 105                 110
```

<210> SEQ ID NO 20
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Heavy chain variable region (non-humanized, non-deimmunized)

<400> SEQUENCE: 20

Gln Glu Gln Leu Glu Glu Ser Gly Gly Gly Leu Val Lys Pro Gly Gly
1               5                   10                  15

Ser Leu Thr Leu Thr Cys Thr Val Ser Gly Pro Ser Leu Ser His Phe
            20                  25                  30

Asp Ile Thr Trp Val Arg Gln Ala Pro Gly Ser Gly Leu Glu Trp Ile
        35                  40                  45

Gly Thr Ile Ser Pro Gly Val Ser Thr Tyr Tyr Ala Ser Trp Ala Lys
    50                  55                  60

Ser Arg Ser Thr Ile Thr Ser Asn Thr Asn Leu Asn Thr Val Thr Leu
65                  70                  75                  80

Lys Met Thr Ser Leu Thr Ala Ala Asp Thr Ala Thr Tyr Phe Cys Ala
                85                  90                  95

Arg Gly Gly Val Gly Ser Ser Trp Lys Ala Phe Asp Leu Trp Gly Pro
            100                 105                 110

Gly Thr Leu Val Thr Ile Ser Ser
        115                 120

<210> SEQ ID NO 21
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: Humanized light chain variable region VL1

<400> SEQUENCE: 21

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Ser Ile Ser Thr Ala
            20                  25                  30

Leu Ala Trp Tyr Gln Gln Lys Pro Gly Lys Ala Pro Lys Leu Leu Ile
        35                  40                  45

Tyr Lys Ala Ser Thr Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Ser Ser Gly Asn
                85                  90                  95

Val His Asn Ala Phe Gly Gly Gly Thr Lys Val Val Ile Lys
            100                 105                 110

<210> SEQ ID NO 22
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)

-continued

<223> OTHER INFORMATION: Humanized light chain variable region VL2

<400> SEQUENCE: 22

Gln Ile Val Leu Thr Gln Ser Pro Ala Thr Leu Ser Ala Ser Val Gly
1               5                   10                  15

Asp Arg Val Thr Ile Thr Cys Gln Ala Ser Glu Ser Ile Ser Thr Ala
            20                  25                  30

Leu Ala Trp Tyr Gln Gln Lys Pro Gly Lys Ala Pro Lys Leu Leu Ile
        35                  40                  45

Tyr Lys Ala Ser Thr Leu Pro Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Gln Gly Phe Ser Ser Gly Asn
                85                  90                  95

Val His Asn Ala Phe Gly Gln Gly Thr Lys Leu Glu Ile Lys
            100                 105                 110

<210> SEQ ID NO 23
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: Humanized light chain variable region VL3

<400> SEQUENCE: 23

Asp Ile Leu Leu Thr Gln Thr Pro Ser Val Val Ser Ala Ser Val Gly
1               5                   10                  15

Asp Arg Val Thr Ile Thr Cys Gln Ala Ser Glu Ser Ile Ser Thr Ala
            20                  25                  30

Leu Ala Trp Tyr Gln Gln Lys Pro Gly Gln Ala Pro Arg Leu Leu Ile
        35                  40                  45

Tyr Lys Ala Ser Thr Leu Pro Ser Gly Val Pro Ser Arg Phe Arg Gly
50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Gly Phe Ser Ser Gly Asn
                85                  90                  95

Val His Asn Ala Phe Gly Gly Gly Thr Arg Leu Glu Ile Lys
            100                 105                 110

<210> SEQ ID NO 24
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: Humanized light chain variable region VL4

<400> SEQUENCE: 24

Glu Leu Val Met Thr Gln Ser Pro Ser Ser Val Ser Ala Ser Val Gly
1               5                   10                  15

Asp Arg Val Thr Ile Thr Cys Gln Ala Ser Glu Ser Ile Ser Thr Ala
            20                  25                  30

Leu Ala Trp Tyr Gln Gln Lys Pro Gly Lys Ala Pro Lys Leu Leu Ile
        35                  40                  45

```
Tyr Lys Ala Ser Thr Leu Pro Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Gly Phe Ser Ser Gly Asn
                 85                  90                  95

Val His Asn Ala Phe Gly Gly Gly Thr Lys Val Glu Ile Lys
            100                 105                 110

<210> SEQ ID NO 25
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: Humanized light chain variable region VL5

<400> SEQUENCE: 25

Ala Pro Val Leu Thr Gln Ser Pro Ala Thr Leu Glu Ala Ser Val Gly
 1               5                  10                  15

Asp Arg Val Thr Ile Thr Cys Gln Ala Ser Glu Ser Ile Ser Thr Ala
                 20                  25                  30

Leu Ala Trp Tyr Gln Gln Lys Pro Gly Gln Pro Pro Lys Leu Leu Ile
            35                  40                  45

Tyr Lys Ala Ser Thr Leu Pro Ser Gly Val Pro Ser Arg Phe Ser Gly
 50                  55                  60

Ser Gly Ser Gly Thr Glu Phe Thr Leu Thr Ile Ser Asp Leu Glu Ser
 65                  70                  75                  80

Asp Asp Ala Ala Thr Tyr Tyr Cys Gln Gln Gly Phe Ser Ser Gly Asn
                 85                  90                  95

Val His Asn Ala Phe Gly Gly Gly Thr Glu Val Val Val Lys
            100                 105                 110

<210> SEQ ID NO 26
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized heavy chain variable region VH1

<400> SEQUENCE: 26

Glu Val Gln Leu Glu Glu Ser Gly Gly Gly Leu Val Lys Pro Gly Gly
 1               5                  10                  15

Ser Leu Arg Leu Ser Cys Ala Ala Ser Gly Pro Ser Leu Ser His Phe
                 20                  25                  30

Asp Ile Thr Trp Val Arg Gln Ala Pro Gly Lys Gly Leu Glu Trp Val
            35                  40                  45

Ser Thr Ile Ser Pro Gly Val Ser Thr Tyr Tyr Ala Ser Trp Ala Lys
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Val Gly Ser Ser Trp Lys Ala Phe Asp Leu Trp Gly Arg
            100                 105                 110

Gly Thr Leu Val Thr Val Ser Ser
```

115             120

<210> SEQ ID NO 27
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized heavy chain variable region VH2

<400> SEQUENCE: 27

Glu Val Gln Leu Val Glu Ser Gly Gly Ala Leu Val Gln Pro Gly Gly
1               5                   10                  15

Ser Leu Arg Leu Ser Cys Ile Val Ser Gly Pro Ser Leu Ser His Phe
            20                  25                  30

Asp Ile Thr Trp Phe Arg Gln Ala Pro Gly Lys Gly Leu Glu Trp Val
        35                  40                  45

Ala Thr Ile Ser Pro Gly Val Ser Thr Tyr Tyr Ala Ser Trp Ala Lys
    50                  55                  60

Ser Arg Phe Thr Ile Ser Thr Asp Thr Ser Lys Asn Thr Leu Phe Leu
65                  70                  75                  80

Gln Met Asp Ser Leu Arg Ala Glu Asp Thr Ala Val Tyr Tyr Cys Ala
                85                  90                  95

Arg Gly Gly Val Gly Ser Ser Trp Lys Ala Phe Asp Leu Trp Gly Pro
            100                 105                 110

Gly Thr Leu Val Thr Val Ser Ser
        115                 120

<210> SEQ ID NO 28
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized heavy chain variable region VH3

<400> SEQUENCE: 28

Glu Val Gln Leu Leu Glu Ser Gly Gly Gly Leu Val Leu Pro Gly Gly
1               5                   10                  15

Ser Leu Arg Leu Ser Cys Ala Ala Ser Gly Pro Ser Leu Ser His Phe
            20                  25                  30

Asp Ile Thr Trp Val Arg Gln Ala Pro Gly Lys Gly Leu Glu Trp Val
        35                  40                  45

Ser Thr Ile Ser Pro Gly Val Ser Thr Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Gly Gly Val Gly Ser Ser Trp Lys Ala Phe Asp Leu Trp Gly Leu
            100                 105                 110

Gly Thr Thr Val Thr Val Ser Ser
        115                 120

<210> SEQ ID NO 29
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized heavy chain variable region VH4

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Pro Ser Leu Ser His Phe
            20                  25                  30

Asp Ile Thr Trp Ile Arg Gln Pro Pro Gly Lys Gly Leu Glu Trp Ile
        35                  40                  45

Gly Thr Ile Ser Pro Gly Val Ser Thr Tyr Tyr Ala Ser Trp Ala Lys
    50                  55                  60

Ser Arg Phe Thr Ile Ser Val Asp Thr Ser Lys Asn Gln Phe Ser Leu
65                  70                  75                  80

Lys Leu Thr Ser Val Thr Ala Ala Asp Thr Ala Thr Tyr Tyr Cys Ala
                85                  90                  95

Arg Gly Gly Val Gly Ser Ser Trp Lys Ala Phe Asp Leu Trp Gly Pro
            100                 105                 110

Gly Thr Leu Val Thr Val Ser Ser
        115                 120

<210> SEQ ID NO 30
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized heavy chain variable region VH5

<400> SEQUENCE: 30

Gln Glu Gln Leu Glu Glu Ser Gly Gly Gly Leu Val Lys Pro Gly Gly
1               5                   10                  15

Thr Leu Ser Leu Thr Cys Thr Val Ser Gly Pro Ser Leu Ser His Phe
            20                  25                  30

Asp Ile Thr Trp Ile Arg Gln Ala Pro Gly Ser Gly Leu Glu Trp Ile
        35                  40                  45

Gly Thr Ile Ser Pro Gly Val Ser Thr Tyr Tyr Ala Ser Trp Ala Lys
    50                  55                  60

Ser Arg Val Thr Ile Ser Val Asp Thr Ser Leu Asn Thr Val Ser Leu
65                  70                  75                  80

Lys Leu Ser Ser Val Thr Ala Ala Asp Thr Ala Thr Tyr Phe Cys Ala
                85                  90                  95

Arg Gly Gly Val Gly Ser Ser Trp Lys Ala Phe Asp Leu Trp Gly Pro
            100                 105                 110

Gly Thr Leu Val Thr Ile Ser Ser
        115                 120

<210> SEQ ID NO 31
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: Humanized and de-immunized VL5.GL

<400> SEQUENCE: 31

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Ser Thr Ala
            20                  25                  30

Leu Ala Trp Tyr Gln Gln Lys Pro Gly Gln Pro Pro Lys Leu Leu Ile
        35                  40                  45

Tyr Lys Ala Ser Thr Leu Pro Ser Gly Val Pro Ser Arg Phe Ser Gly
50                  55                  60

Ser Gly Ser Gly Thr Glu Phe Thr Leu Thr Ile Ser Asp Leu Glu Ser
65                  70                  75                  80

Asp Asp Ala Ala Thr Tyr Tyr Cys Gln Gln Gly Phe Ser Ser Gly Asn
                85                  90                  95

Val His Asn Ala Phe Gly Gly Gly Thr Glu Val Val Val Lys
            100                 105                 110
```

<210> SEQ ID NO 32
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized and de-immunized VH5.AP

<400> SEQUENCE: 32

```
Gln Glu Gln Leu Glu Glu Ser Gly Gly Gly Leu Val Lys Pro Gly Gly
1               5                   10                  15

Thr Leu Ser Leu Thr Cys Thr Val Ser Gly Pro Ser Leu Ser His Phe
            20                  25                  30

Asp Ile Thr Trp Ile Arg Gln Pro Pro Gly Ser Gly Leu Glu Trp Ile
        35                  40                  45

Gly Thr Ile Ser Pro Gly Val Ser Thr Tyr Tyr Ala Ser Trp Ala Lys
    50                  55                  60

Ser Arg Val Thr Ile Ser Val Asp Thr Ser Leu Asn Thr Val Ser Leu
65                  70                  75                  80

Lys Leu Ser Ser Val Thr Ala Ala Asp Thr Ala Thr Tyr Phe Cys Ala
                85                  90                  95

Arg Gly Gly Val Gly Ser Ser Trp Lys Ala Phe Asp Leu Trp Gly Pro
            100                 105                 110

Gly Thr Leu Val Thr Ile Ser Ser
        115                 120
```

<210> SEQ ID NO 33
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized and de-immunized VH5.SK

<400> SEQUENCE: 33

```
Gln Glu Gln Leu Glu Glu Ser Gly Gly Gly Leu Val Lys Pro Gly Gly
1               5                   10                  15

Thr Leu Ser Leu Thr Cys Thr Val Ser Gly Pro Ser Leu Ser His Phe
            20                  25                  30

Asp Ile Thr Trp Ile Arg Gln Ala Pro Gly Lys Gly Leu Glu Trp Ile
        35                  40                  45

Gly Thr Ile Ser Pro Gly Val Ser Thr Tyr Tyr Ala Ser Trp Ala Lys
```

```
                50                  55                  60
Ser Arg Val Thr Ile Ser Val Asp Thr Ser Leu Asn Thr Val Ser Leu
 65                  70                  75                  80

Lys Leu Ser Ser Val Thr Ala Ala Asp Thr Ala Thr Tyr Phe Cys Ala
                 85                  90                  95

Arg Gly Gly Val Gly Ser Ser Trp Lys Ala Phe Asp Leu Trp Gly Pro
                100                 105                 110

Gly Thr Leu Val Thr Ile Ser Ser
            115                 120

<210> SEQ ID NO 34
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized and de-immunized VH5.GL

<400> SEQUENCE: 34

Gln Glu Gln Leu Glu Glu Ser Gly Gly Gly Leu Val Lys Pro Gly Gly
 1               5                  10                  15

Thr Leu Ser Leu Thr Cys Thr Val Ser Gly Pro Ser Leu Ser His Phe
                 20                  25                  30

Asp Ile Thr Trp Ile Arg Gln Pro Pro Gly Lys Gly Leu Glu Trp Ile
             35                  40                  45

Gly Thr Ile Ser Pro Gly Val Ser Thr Tyr Tyr Ala Ser Trp Ala Lys
         50                  55                  60

Ser Arg Val Thr Ile Ser Val Asp Thr Ser Leu Asn Thr Val Ser Leu
 65                  70                  75                  80

Lys Leu Ser Ser Val Thr Ala Ala Asp Thr Ala Thr Tyr Phe Cys Ala
                 85                  90                  95

Arg Gly Gly Val Gly Ser Ser Trp Lys Ala Phe Asp Leu Trp Gly Pro
                100                 105                 110

Gly Thr Leu Val Thr Ile Ser Ser
            115                 120

<210> SEQ ID NO 35
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Immunoglobulin kappa constant light chain

<400> SEQUENCE: 35

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95
```

Pro Val Thr Lys Ser Phe Asn Arg Gly Glu Cys
            100                 105

<210> SEQ ID NO 36
<211> LENGTH: 330
<212> TYPE: PRT
<213> ORGANISM: Homo sapiens
<220> FEATURE:
<221> NAME/KEY: MISC_FEATURE
<222> LOCATION: (1)..(330)
<223> OTHER INFORMATION: Immunoglobulin IgG1 constant heavy chain

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 37
<211> LENGTH: 356
<212> TYPE: PRT
<213> ORGANISM: Homo sapiens
<220> FEATURE:
<221> NAME/KEY: MISC_FEATURE
<222> LOCATION: (1)..(356)
<223> OTHER INFORMATION: Full-length human IL1RAP

<400> SEQUENCE: 37

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Gly Asn
            340                 345                 350

Arg Cys Gly Gln
```

```
<210> SEQ ID NO 38
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: Domain 2 of IL1RAP

<400> SEQUENCE: 38

Lys Asp Ser Cys Phe Asn Ser Pro Met Lys Leu Pro Val His Lys Leu
1               5                   10                  15

Tyr Ile Glu Tyr Gly Ile Gln Arg Ile Thr Cys Pro Asn Val Asp Gly
            20                  25                  30

Tyr Phe Pro Ser Ser Val Lys Pro Thr Ile Thr Trp Tyr Met Gly Cys
        35                  40                  45

Tyr Lys Ile Gln Asn Phe Asn Asn Val Ile Pro Glu Gly Met Asn Leu
    50                  55                  60

Ser Phe Leu Ile Ala Leu Ile Ser Asn Asn Gly Asn Tyr Thr Cys Val
65                  70                  75                  80

Val Thr Tyr Pro Glu Asn Gly Arg Thr Phe His Leu Thr Arg Thr Leu
                85                  90                  95

Thr Val Lys Val Val
            100

<210> SEQ ID NO 39
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: H2 region of domain 2 of human IL1RAP

<400> SEQUENCE: 39

Thr Ile Thr Trp Tyr Met Gly Cys Tyr Lys Ile Gln Asn Phe Asn Asn
1               5                   10                  15

Val Ile
```

ANTI-IL1RAP ANTIBODY

This application claims the benefit of priority to European Patent Application No. 20216926.4, filed 23 Dec. 2020, United Kingdom Patent Application No. 2105933.2, filed 26 Apr. 2021, and European Patent Application No. 21212368.1, filed 3 Dec. 2021, all of which are incorporated by reference in their entirety.

SEQUENCE LISTING

The instant application contains a Sequence Listing which has been submitted electronically in ASCII format and is incorporated herein by reference in its entirety. Said ASCII copy, created on Dec. 21, 2021, is named 2021-12-21_01177-0008-00US-T1_Sequence_listing_ST25 and is 34,761 bytes in size.

TECHNICAL FIELD

The present invention relates to an anti-IL1RAP antibody or fragments thereof with anti-inflammatory, anti-fibrotic and/or anti-neoplastic properties, and to its use in the prevention, treatment, alleviation, detection and/or diagnosis of diseases or disorders associated with IL-1α, IL-1β, IL-33, IL-36α, IL-36β and/or IL-36γ signaling.

BACKGROUND

The interleukin-1 (IL-1) family of cytokine ligands and its receptors is associated with inflammation, autoimmunity, immune regulation, fibrosis, cell proliferation, tumor growth, tumor metastasis and host defense. It contributes to the pathology of inflammatory, autoimmune, immune regulatory, fibrotic and degenerative diseases and disorders, as well as to cell proliferative or neoplastic diseases or disorders, such as cancer (Garlanda C, *The interleukin-1 family: back to the future*. Immunity, 39:1003-1018 (2013)).

All these diseases cause a tremendous burden on the individual and the society and there remains a need for therapies to treat, ameliorate, prevent, diagnose or detect inflammatory, autoimmune, immune regulatory, fibrotic, degenerative, and cell proliferative diseases or disorders associated with the IL-1 family of cytokine ligands and receptors.

The IL-1 family comprises a number of agonist cytokines including IL-1α, IL-1β, IL-33, IL-36α, IL-36β and IL-36γ, and each of these cytokines bind their specific IL-1 family cell membrane receptor. Upon binding to of the cytokine to its cognate receptor, a co-receptor called IL-1 Receptor Accessory Protein (IL1RAP) is recruited to form a receptor complex that triggers intracellular signal transduction and activation of a set of transcription factors, including NF-κB, which triggers an inflammatory response. IL1RAP is the co-receptor for the IL-1 receptor I (IL1R1; binding IL-1α and IL-1β), IL-33 receptor (ST2, IL1RL1; binding IL-33), and the IL-36 receptor (IL1RL2; binding IL-36α, IL-36β and IL-36γ) and is required for signal transduction downstream of the cytokines IL-1α, IL-1β, IL-33, IL-36α, IL-36β and IL-36γ.

Antibodies binding to IL1RAP can block cytokine signaling downstream of IL1RAP-dependent receptors. Interestingly, apart from this blocking function, antibodies binding IL1RAP can also be used with regard to other functions, for example to induce antibody-dependent cell-mediated cytotoxicity (ADCC) and/or antibody-dependent cellular phagocytosis (ADCP), thereby leading to the killing of target cells, such as IL1RAP-expressing tumor cells.

In the past, antibodies have been generated which are capable of decreasing, inhibiting, and/or blocking signaling pathways of cytokine ligands of the IL-1 family, depending on the properties of the respective antibody. For example, WO 2015/132602 discloses an anti IL1RAP antibody inhibiting signaling of IL-1α, IL-1β and IL-33, to varying degrees.

Blocking all six cytokines (IL-1α, IL-1β, IL-33, IL-36α, IL-36β and IL-36γ) is expected to be beneficial with regard to therapeutic approaches targeting IL-1 family of cytokine ligands and receptors. IL-1α and IL-1β are two potent pro-inflammatory cytokines and the involvement of these in acute inflammation have been extensively described. IL-33 is traditionally thought of as a Th2 cytokine that induces production of type 2 cytokines such as IL-5 and IL-13. The function of IL-36 is less well described but several studies suggest that IL-36 is involved in immune cell activation and induces release of pro-inflammatory cytokines. By targeting the pathways of all these cytokines, a more complete down-regulation of the disease-related processes, for example inflammatory processes, would be achieved, which would improve therapy outcome for patients with inflammatory diseases or disorders.

To date, there is a lack of treatment options addressing various aspects of diseases or disorders associated with interleukin-1 (IL-1) family of cytokine ligands and receptors, such as those associated with signaling of IL-1α, IL-1β, IL-33, IL-36α, IL-36β and/or IL-36γ. Current treatments only target separate pathways associated with distinct IL-1 family cytokine ligands, and the simultaneous downregulation of several pathways associated with IL-1 family cytokine ligands, for example in inflammatory and fibrotic aspects, remains a clinical challenge. Consequently, there remains an urgent need for improved therapies targeting the multi-facetted aspects associated with the IL-1 family of cytokine ligands and receptors.

SUMMARY

The inventors of the present invention have generated an antibody, and variants thereof, binding to IL-1RAP domain 2 with the capability of inhibiting the signaling downstream of six IL1RAP dependent ligands; IL-1α, IL-1β, IL-33, IL-36α, IL-36β and/or IL-36γ. Due to this superior property, this antibody can be used for the prevention, treatment, alleviation, detection and/or diagnosis of diseases and disorders associated with signaling of IL-1α, IL-1β, IL-33, IL-36α, IL-36β and/or IL-36γ, thereby simultaneously targeting several downstream pathways associated with these cytokines. Consequently, this antibody can be used in targeting several aspects and processes of diseases and disorders associated with signaling of IL-1α, IL-1β, IL-33, IL-36α, IL-36β and/or IL-36γ, for example inflammatory and fibrotic aspects in inflammatory or fibrotic diseases or disorders, or inflammatory, fibrotic or proliferative aspects in neoplastic diseases or disorders. The antibody described here allows for simultaneous targeting of multiple cytokine pathways, for example targeting pathways of IL-1α, IL-1β, IL-33, IL-36α, IL-36β and IL-36γ, which is a clinical advantage when treating diseases or disorders where blocking only one or a few cytokines would not be effective enough to treat or prevent a disease or disorder. Further disclosed is the optimization of this antibody by humanization and de-immunization procedures, resulting in antibody variants with fine-tuned properties.

A first aspect of the invention relates to an antibody or antigen-binding fragment thereof with binding specificity for interleukin-1 receptor accessory protein (IL1RAP), wherein the antibody or antigen-binding fragment comprises:

a light chain variable region comprising
a) a CDR-L1 comprising or consisting of an amino acid sequence selected from the group consisting of ESISTA (SEQ ID NO: 1), QASESISTALA (SEQ ID NO: 7) and QASESISTALA (SEQ ID NO: 13);
b) a CDR-L2 comprising or consisting of an amino acid sequence selected from the group consisting of KAS, KASTLPS (SEQ ID NO: 8) and KASTLPS (SEQ ID NO: 14); and
c) a CDR-L3 comprising or consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15);
and/or
a heavy chain variable region comprising
d) a CDR-H1 comprising or consisting of an amino acid sequence selected from the group consisting of GPSLSHFD (SEQ ID NO: 4), HFDIT (SEQ ID NO: 10) and GPSLSHFDIT (SEQ ID NO: 16);
e) a CDR-H2 comprising or consisting of an amino acid sequence selected from the group consisting of ISPGVST (SEQ ID NO: 5), TISPGVSTYYASWAKS (SEQ ID NO: 11) and TISPGVSTYYASWAKS (SEQ ID NO: 17); and
f) a CDR-H3 comprising or consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

A second aspect of the invention relates to a polynucleotide encoding the antibody or antigen-binding fragment of the first aspect of the invention, or a component polypeptide chain thereof.

A third aspect of the invention relates to a vector comprising the polynucleotide according to the second aspect of the invention.

A fourth aspect of the invention relates to a recombinant host cell comprising the polynucleotide according to the second aspect of the invention or a vector according to the third aspect of the invention.

A fifth aspect of the invention relates to a method for producing the antibody or antigen-binding fragment of the first aspect of the invention, the method comprising culturing the host cell of the fourth aspect of the invention, comprising the polynucleotide of the second aspect of the invention or the vector of the third aspect of the invention, under conditions which permit expression of the encoded antibody or antigen-binding fragment thereof.

A sixth aspect of the invention relates to a pharmaceutical composition comprising
the antibody or antigen-binding fragment of the first aspect of the invention,
the polynucleotide of the second aspect of the invention,
the vector of the third aspect of the invention, and/or
the host cell of the fourth aspect of the invention,
in a pharmaceutical composition, wherein the composition further comprises a pharmaceutically-acceptable diluent, carrier or excipient.

A seventh aspect of the invention relates to
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention,
for use in medicine.

An eighth aspect of the invention relates to
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention,
for use in the prevention and/or treatment and/or alleviation and/or detection and/or diagnosis of a disease or disorder susceptible to treatment with an inhibitor of IL-1α, IL-1β, IL-33, IL-36α, IL-36β and/or IL-36γ signaling, and/or wherein the disease or disorder is associated with cells expressing IL1RAP.

A ninth aspect of the invention relates to
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention,
for use in inducing cell death and/or inhibiting the growth and/or proliferation of pathological cells associated with a neoplastic disorder in a subject, or stem cells or progenitor cells thereof, wherein the cells express IL1RAP.

A tenth aspect of the invention relates to the use of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention,
in the preparation of a medicament for the prevention, treatment, alleviation, detection and/or diagnosis of a disease or disorder susceptible to treatment with an inhibitor of IL-1α, IL-1β, IL-33, IL-36α, IL-36β and/or IL-36γ signaling,
and/or wherein the disease or disorder is associated with cells expressing IL1RAP.

An eleventh aspect of the invention relates to the use of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention,
in the preparation of a medicament for the detection and/or diagnosis of a disease or disorder associated with cells expressing IL1RAP.

A twelfth aspect of the invention relates to a method for the prevention and/or treatment and/or alleviation and/or detection and/or diagnosis of a disease or disorder susceptible to treatment with an inhibitor of IL-1α, IL-1R, IL-33, IL-36α, IL-36β and/or IL-36γ signaling and/or wherein the disease or disorder is associated with cells expressing IL1RAP in a subject, comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A thirteenth aspect of the invention relates to an in vitro method for the detection of cells expressing IL1RAP in a subject, the method comprising:
(a) providing a sample of cells from a subject to be tested, such as biopsy tissue or blood sample;
(b) optionally, extracting and/or purifying the cells present in the sample;
(c) contacting the antibody or antigen-binding fragment of the first aspect of the invention with cells present in the sample;
(d) determining whether the antibody or antigen-binding fragment thereof binds to the cells
wherein the binding of the antibody or antigen-binding fragment thereof to the cells is indicative of the presence of a disease or disorder associated with cells expressing IL1RAP in the tissue of a subject.

A fourteenth aspect of the invention relates to an in vitro method for identifying a patient with a disease or disorder associated with cells expressing IL1RAP who would benefit from treatment with the antibody or antigen-binding fragment of the first aspect of the invention, the method comprising:
(a) providing a sample of cells, such as biopsy tissue or blood sample from a patient to be tested;
(b) optionally, extracting and/or purifying the cells present in the sample;
(c) contacting the antibody or antigen-binding fragment of the first aspect of the invention with cells present in the sample;
(d) determining whether the antibody or antigen-binding fragment thereof binds to the cells
wherein the binding of the antibody or antigen-binding fragment thereof to cells expressing IL1RAP is indicative of a patient who would benefit from treatment with the antibody or antigen-binding fragment of the first aspect of the invention.

A fifteenth aspect of the invention relates to a method for treating a patient with a disease or disorder associated with cells expression IL1RAP, the method comprising:
a) selecting a patient identified as having a disease or disorder associated with cells expressing IL1RAP using a method according to the fourteenth aspect of the invention; and
b) administering to said patient a therapeutic agent effective in the treatment of said disease or disorder.

A sixteenth aspect of the invention relates to a method for the detection of cells expressing IL1RAP, the method comprising:
(a) contacting an antibody or antigen-binding fragment thereof according to the first aspect with cells to be analysed for their expression of IL1RAP;
(b) determining whether the antibody or antigen-binding fragment thereof binds to the cells
wherein the binding of the antibody or antigen-binding fragment thereof to the cells is indicative of the presence of a disease or disorder associated with cells expressing IL1RAP in the tissue of a subject.

A seventeenth aspect of the invention relates to a method for reducing inflammation in a subject with peritonitis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

An eighteenth aspect of the invention relates to a method for reducing disease severity in a subject with psoriasis or psoriatic arthritis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A nineteenth aspect of the invention relates to a method for reducing atherosclerotic plaque inflammation in a subject with atherosclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twentieth aspect of the invention relates to a method for reducing atherosclerotic plaque volume and/or atherosclerotic plaque size in a subject with atherosclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-first aspect of the invention relates to a method for reducing inflammation and/or fibrosis in a subject with myocarditis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-second aspect of the invention relates to a method for counteracting deterioration in cardiac function in a subject with myocarditis or autoimmune myocarditis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-third aspect of the invention relates to a method for reducing dermal fibrosis in a subject with systemic sclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-fourth aspect of the invention relates to a method for reducing pulmonary fibrosis in a subject with systemic sclerosis, the method comprising the step of administering to the subject an effective amount of the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

EAM was induced in BALB/c mice by immunization with α-myosin heavy chain peptide, emulsified in complete Freund's adjuvant, on two occasions. Starting from day 7 after the final immunization, mice were treated with mCAN10, isotype control antibody (Isotype) or PBS only, biweekly for 4 wks. At the end of the experiment, mice were sacrificed, hearts collected, and heart sections stained with H&E staining to assess the degree of inflammation (A and B), or by Masson's trichrome staining to assess the degree of fibrosis (C and D).

Figure 6:
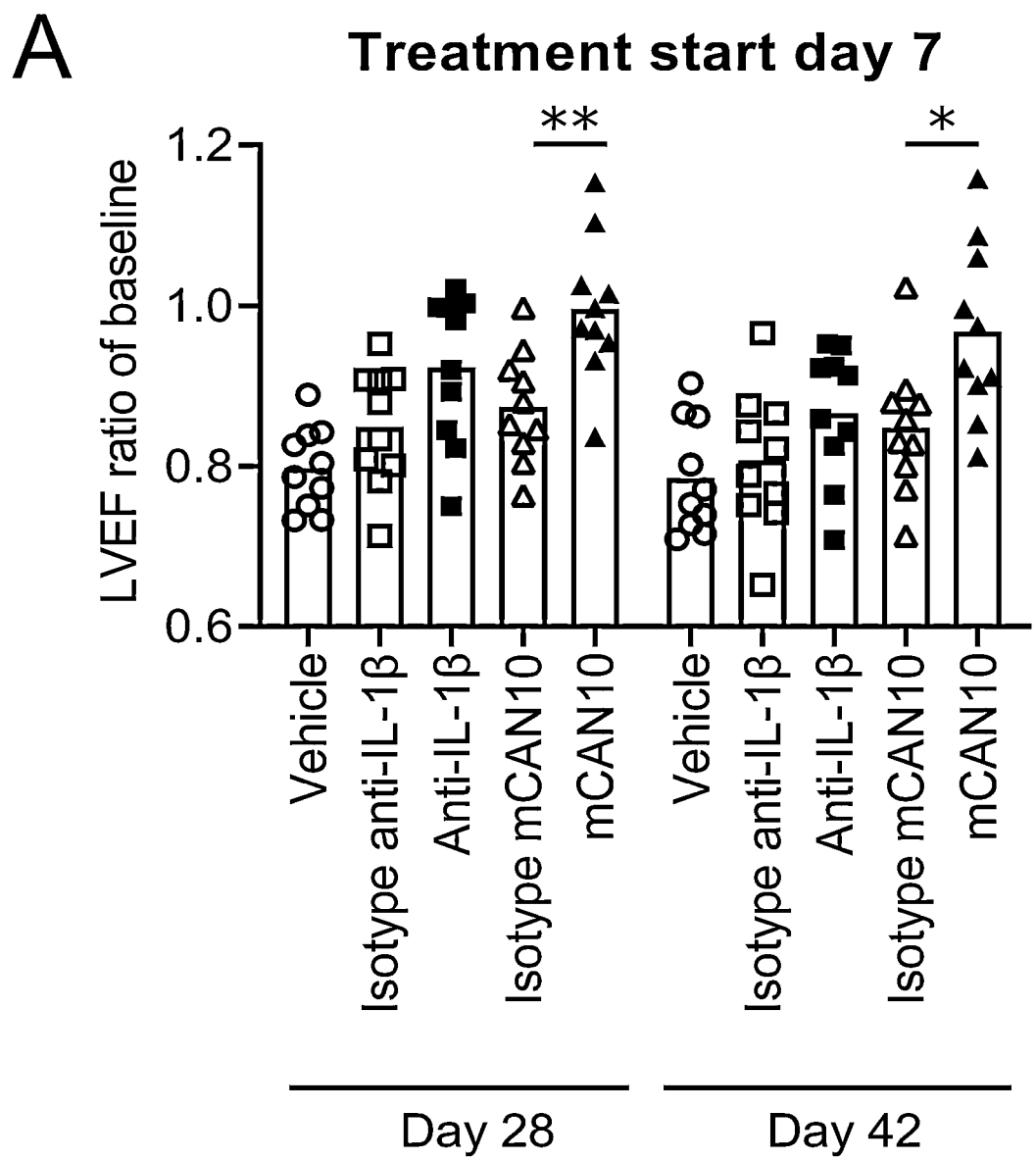
Figure 6:
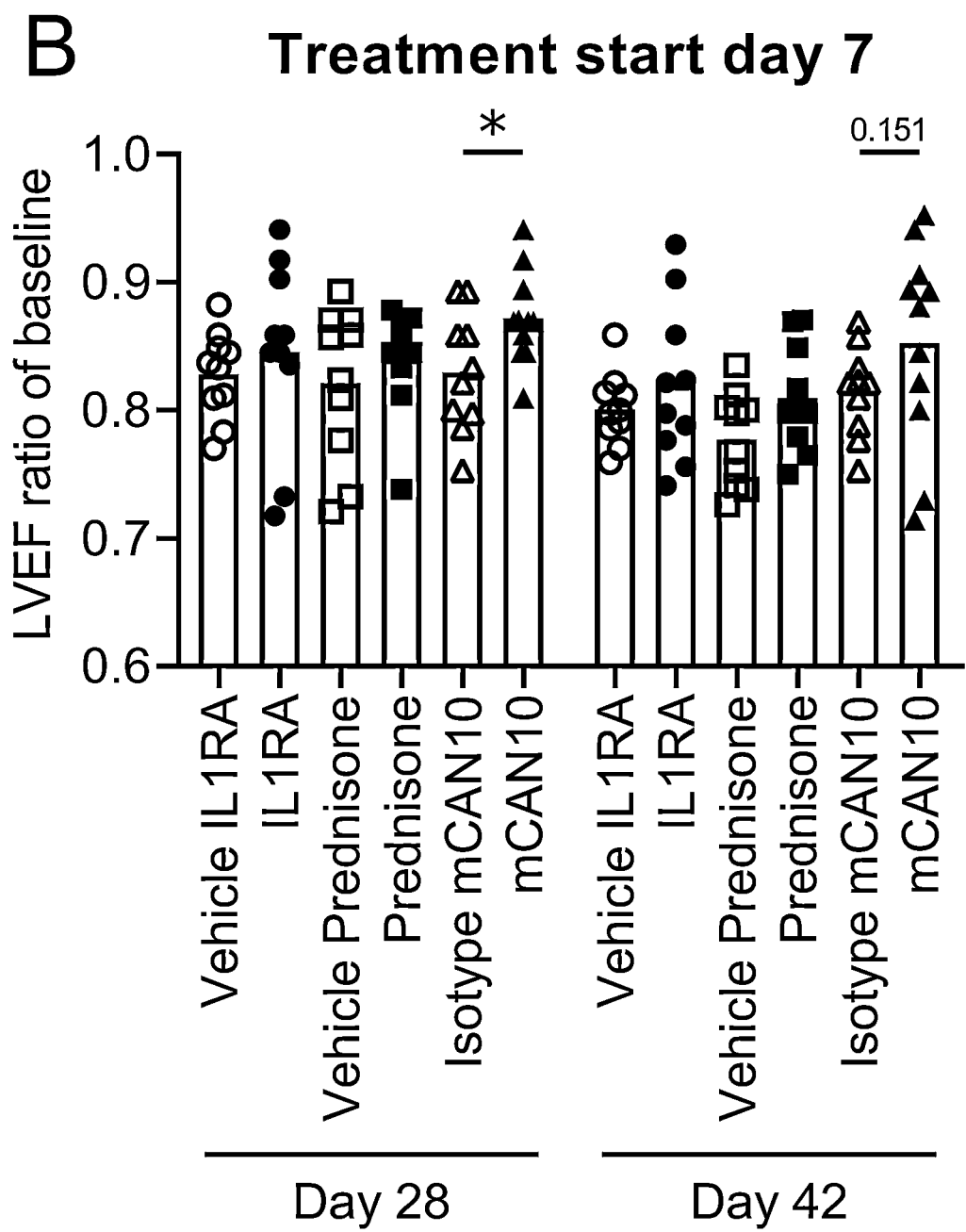
Figure 6:
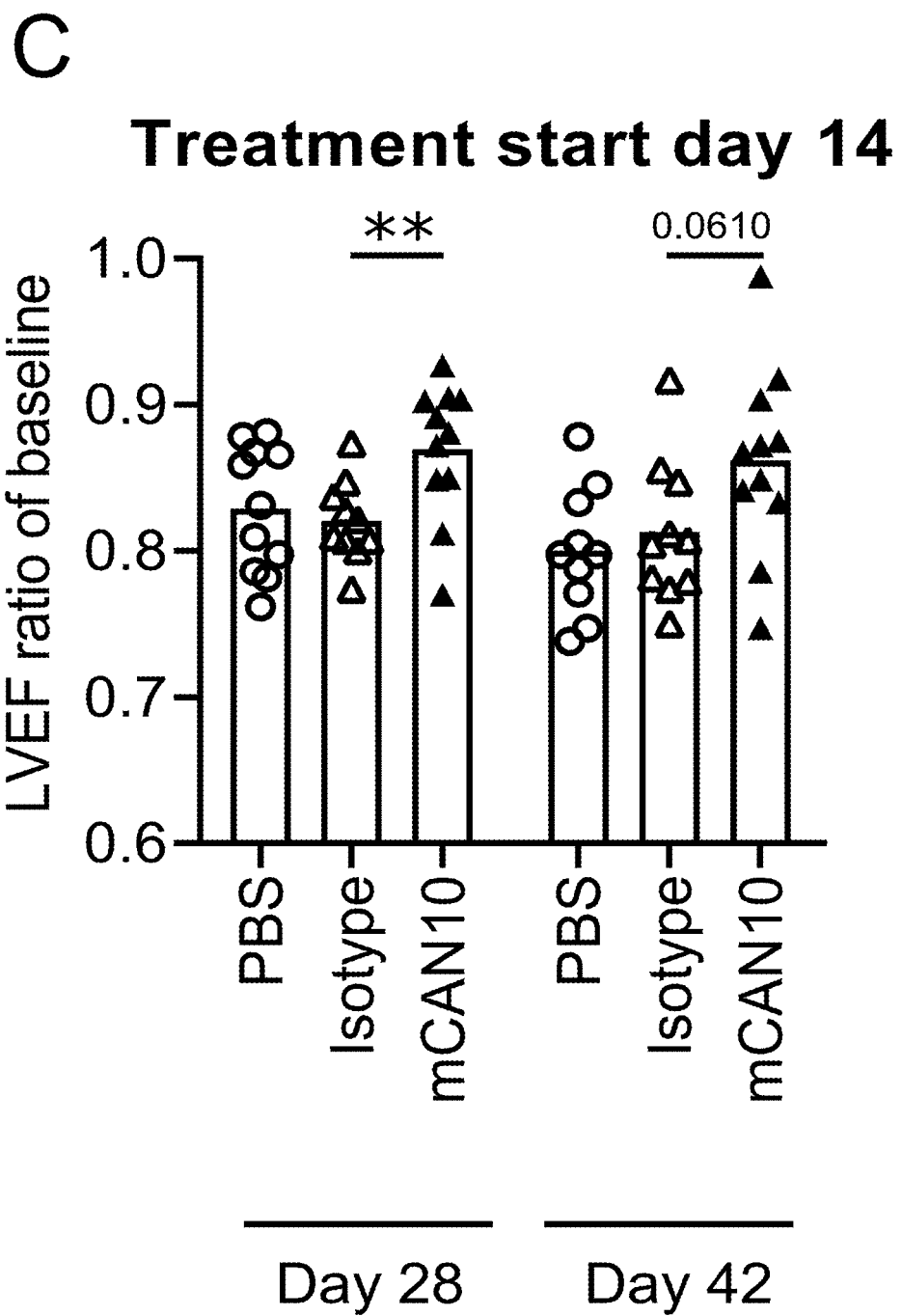

FIG. 6: The anti-IL1RAP antibody mCAN10 counteracts deterioration in cardiac function in experimental autoimmune myocarditis EAM was induced in BALB/c mice by immunization with α-myosin heavy chain peptide, emulsified in complete Freund's adjuvant, on two occasions. Starting from the day of the final immunization (day 7), mice were treated with mCAN10, anti-IL-1β antibody (Anti-IL-1β) or isotype control antibodies (Isotype anti-IL-1β, Isotype mCAN10) biweekly for 5 wks (A). Alternatively, mice were treated with mCAN10, isotype control antibody (Isotype mCAN10), IL1RA, prednisone or vehicle controls (Vehicle IL1RA, Vehicle Prednisone) daily for 5 wks (B). Optionally, mice received mCAN10, isotype control antibody (Isotype), or vehicle control (PBS) as in A, but with treatment starting from day 7 after the final immunization (day 14) (C). Cardiac function was assessed by transthoracic echocardiography at the start of the study, and on day 28 and 42.

Figure 7:
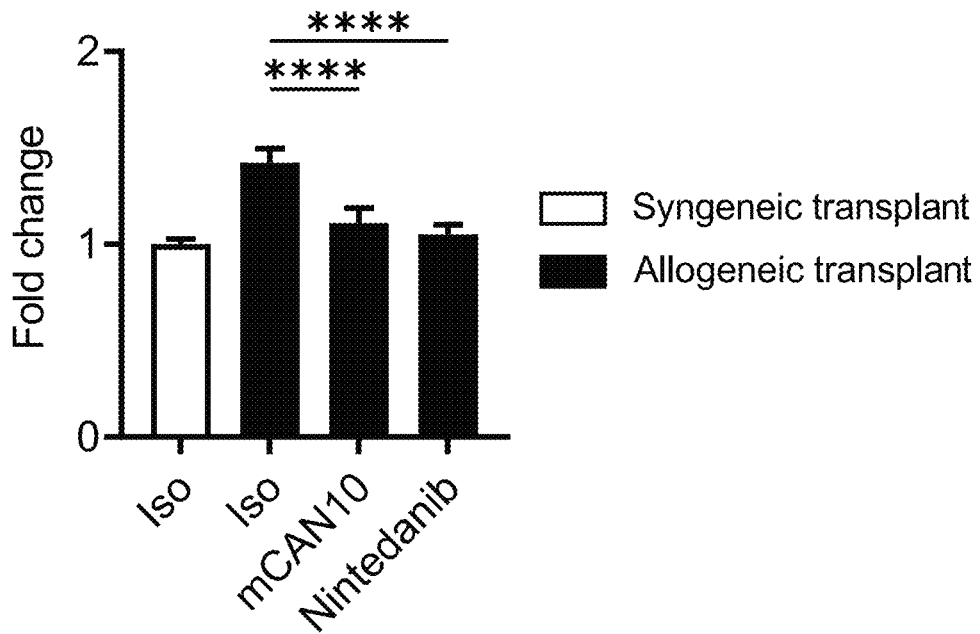
Figure 7:
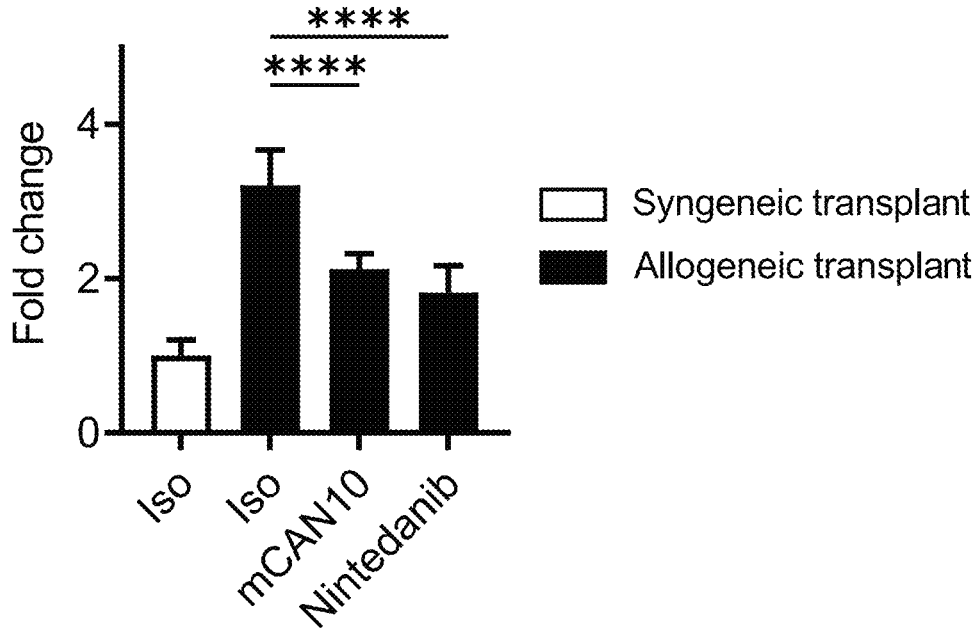
Figure 7:
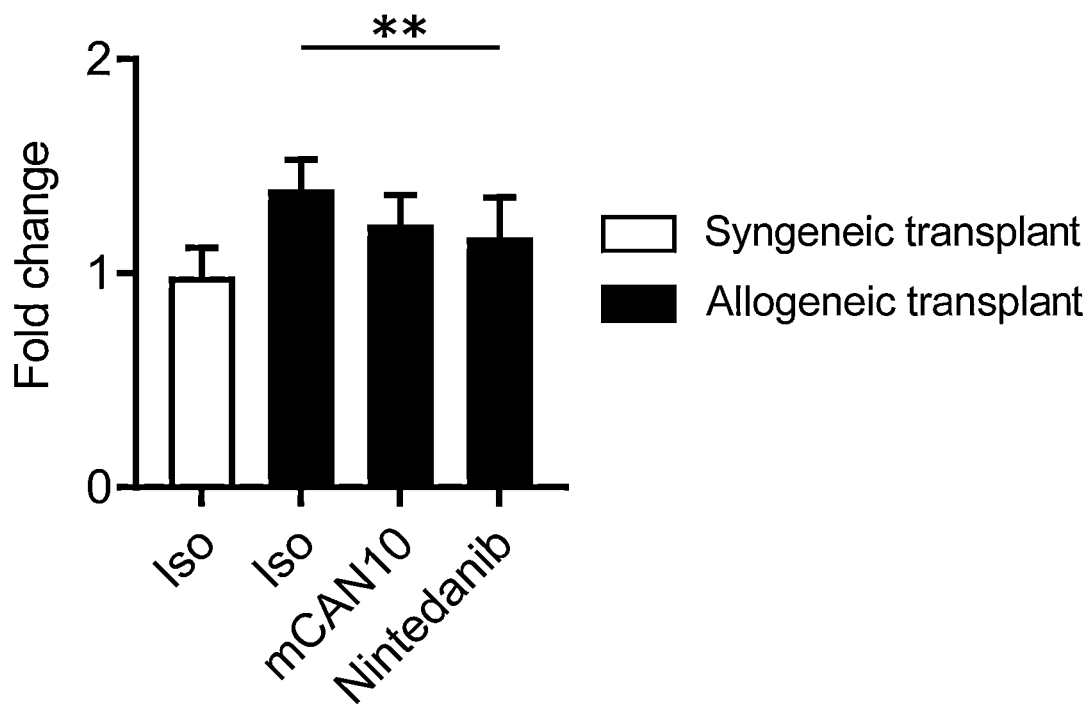

FIG. 7: mCAN10 ameliorates dermal fibrosis in a mouse model for sclerodermatous chronic graft-versus-host disease (scl cGvHD)

Female BALB/c ($H-2^d$) recipient mice received bone marrow from male B10.D2 donor mice ($H-2^d$) in an allogeneic transplantation manner to create an MHC mismatch model which would develop scl cGvHD. As control, the same recipient mice received bone marrow from female BALB/c ($H-2^d$) donor mice in a syngeneic transplantation manner resulting in no disease development. Treatment was initiated 21 days post transplantation and mice received mCAN10 (20 mg/kg at first dose; 10 mg/kg at subsequent doses), or the same doses of isotype control antibody (Iso) i.p. biweekly for 4 wks. Alternatively, these mice were treated with nintedanib at 50 mg/kg p.o. daily for 4 wks. Mice receiving syngeneic transplants were treated with isotype control antibody (Iso) only. Mice were sacrificed on day 49, and skin samples from the upper back collected for histological evaluation to analyze dermal thickness (A) and number of fibroblasts (B), or for quantification of hydroxyproline content (C).

Figure 8:
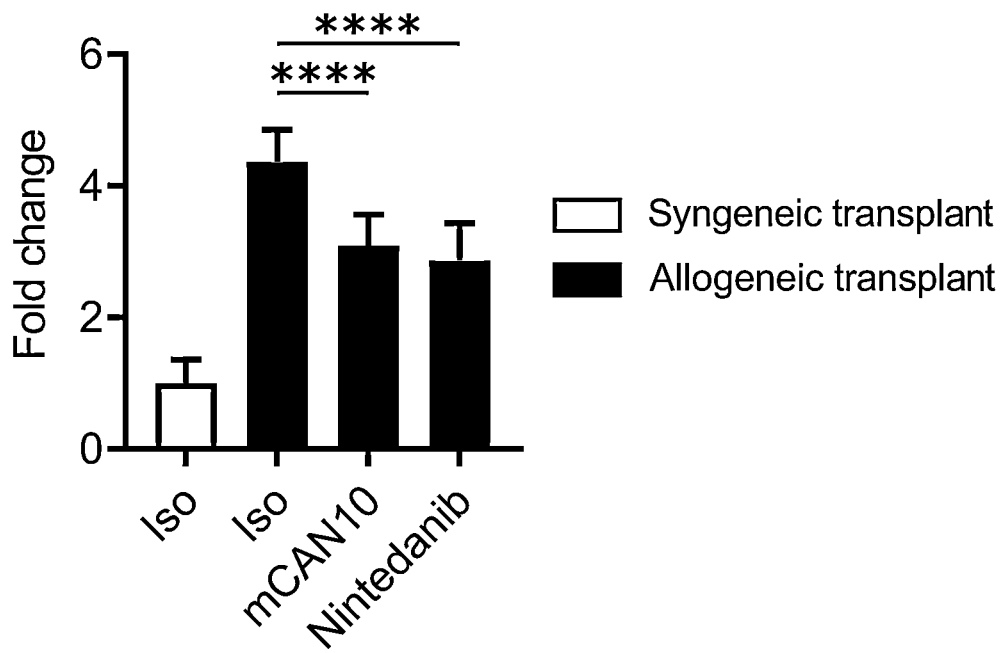
Figure 8:
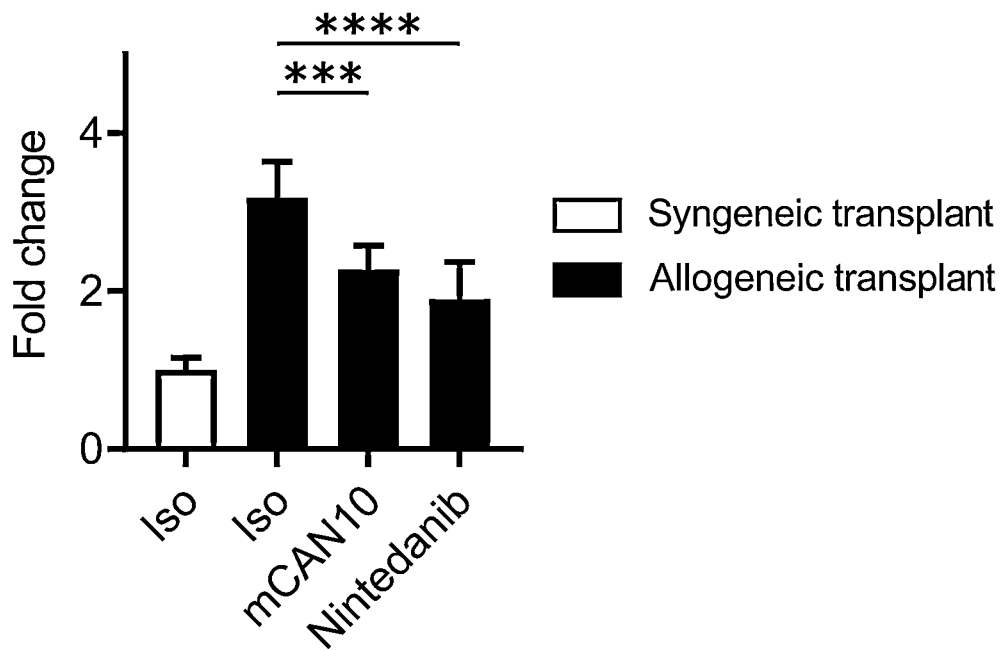
Figure 8:
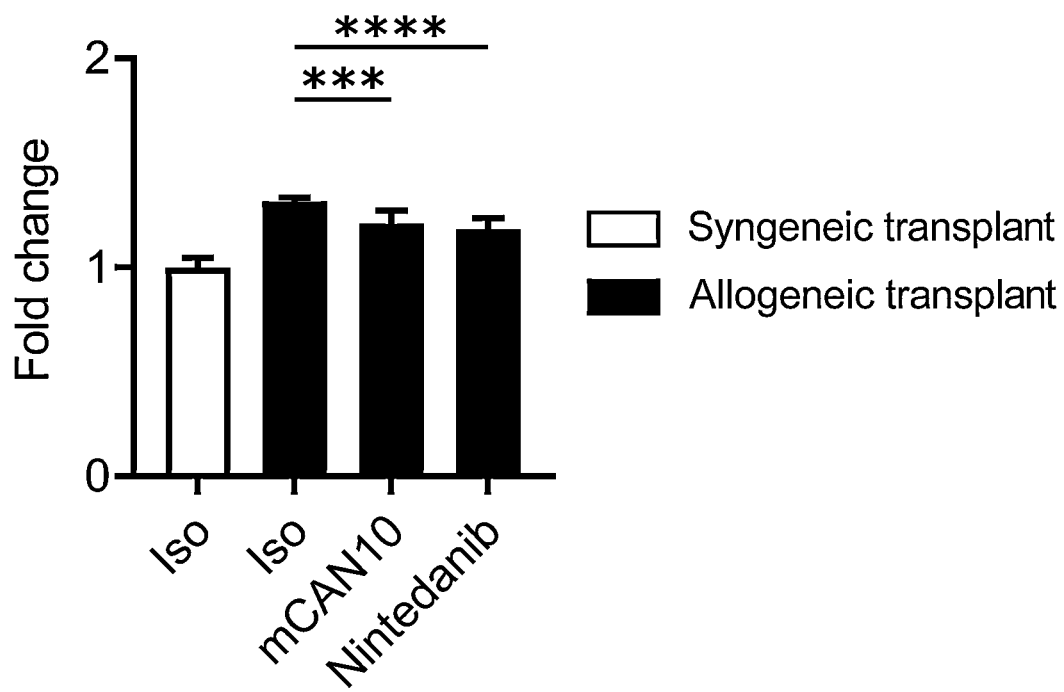

FIG. 8: mCAN10 ameliorates pulmonary fibrosis in a mouse model for scl cGvHD

Mice were treated as described for FIG. 7. After sacrifice of mice on day 49 post transplantation, lungs were collected for histological evaluation to determine Ashcroft score (A) and area stained by Sirius Red (B), or for quantification of hydroxyproline content (C).

Figure 9:
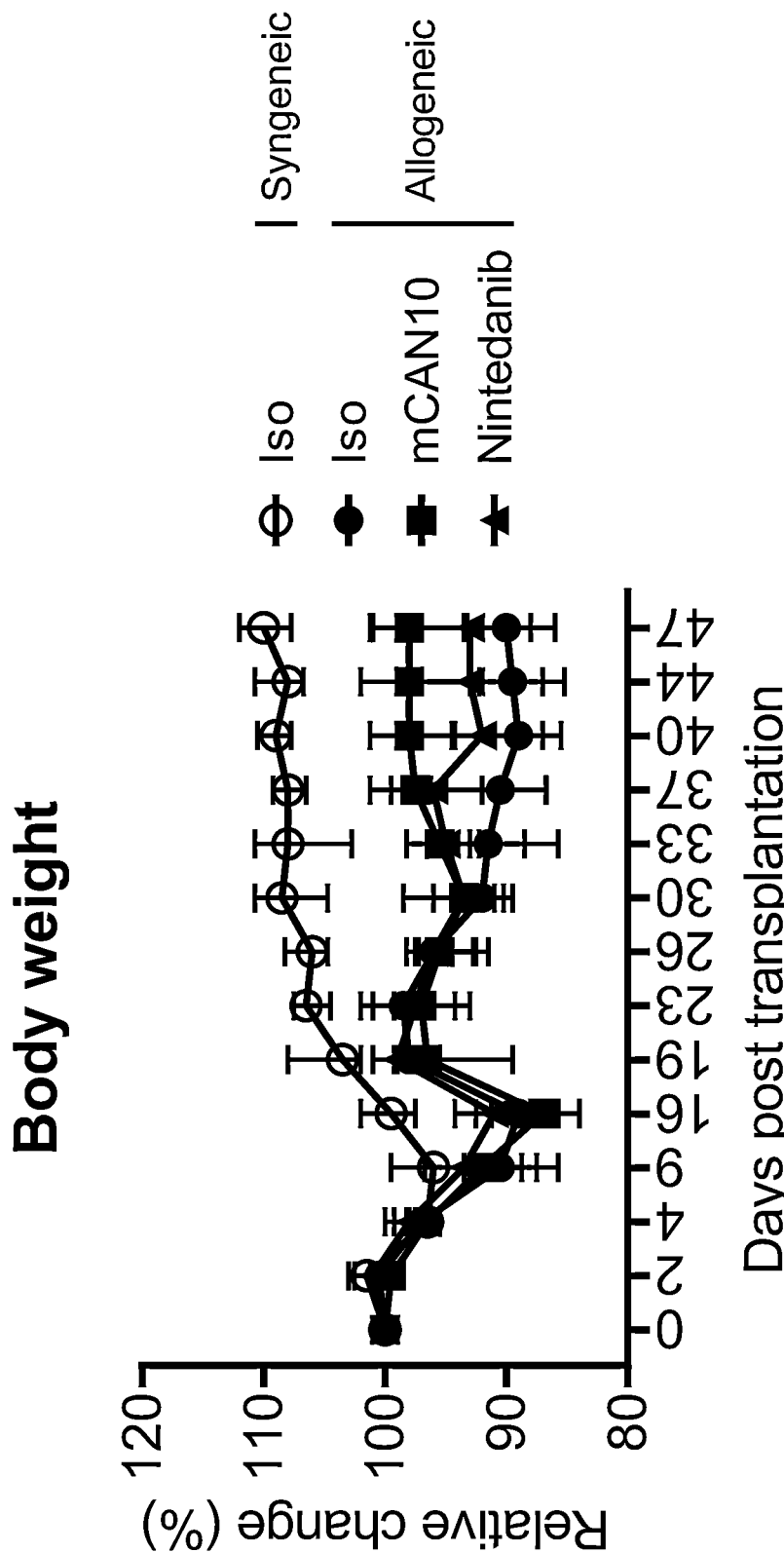

FIG. 9: mCAN10 ameliorates weight loss in a mouse model for scl cGvHD

Mice were treated as described for FIG. 7. Following transplantation, the mice were continuously weighed for the duration of the study, which was finalized 49 days post transplantation.

Figure 10:
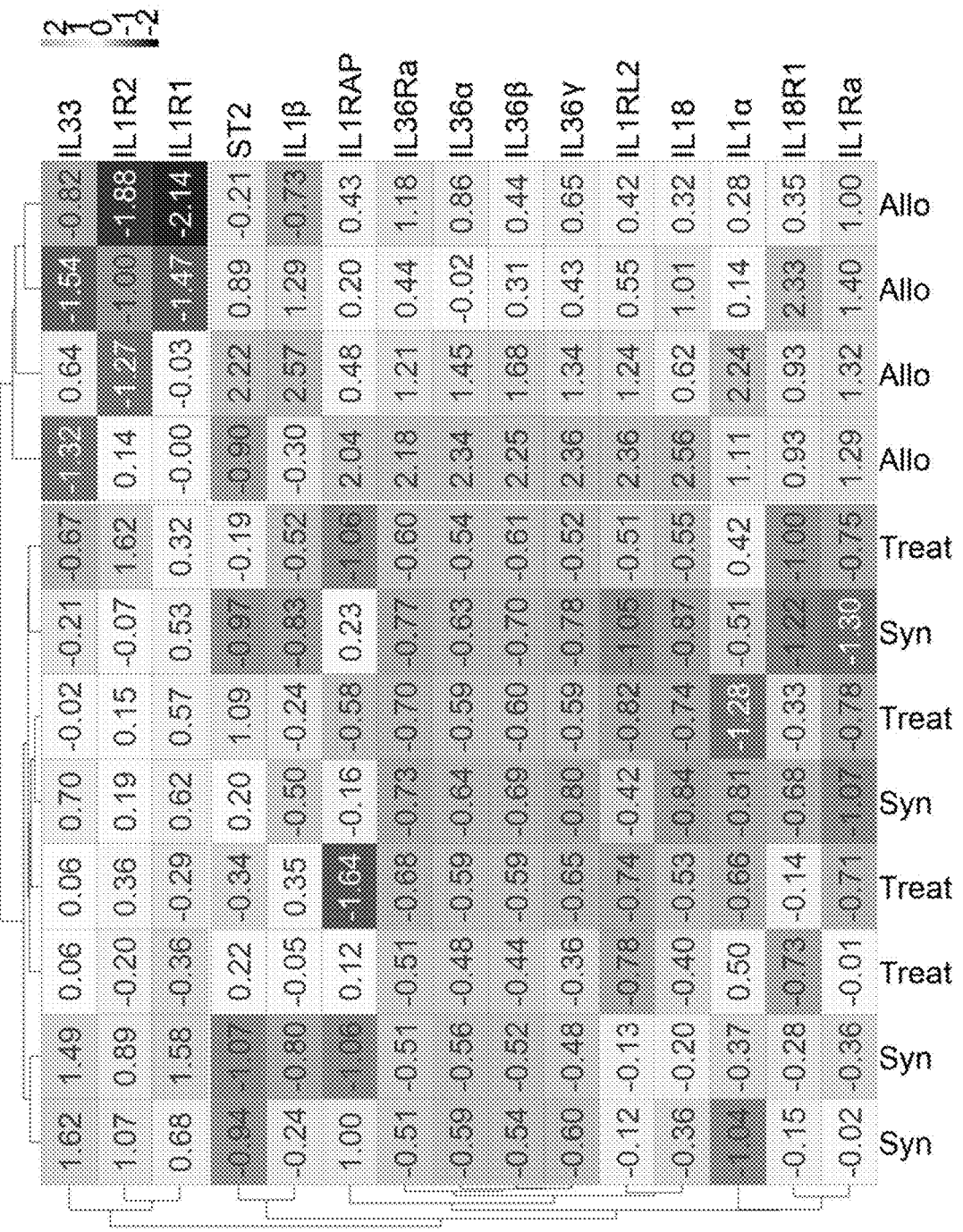

FIG. 10: mCAN10 alters the IL-1 family gene expression profile in a mouse model for scl cGvHD Mice were treated as described for FIG. 7. After sacrifice of mice on day 49 post transplantation, skin samples from the upper back were used for RNA sequencing to generate a heatmap visualizing the changes in gene expression level for the indicated IL-1 family members. Results from four samples from each group, allogeneically-transplanted mice (Allo), syngeneically-transplanted mice (Syn) and allogeneically-transplanted mice treated with mCAN10 (Treat), are shown.

Figure 11:
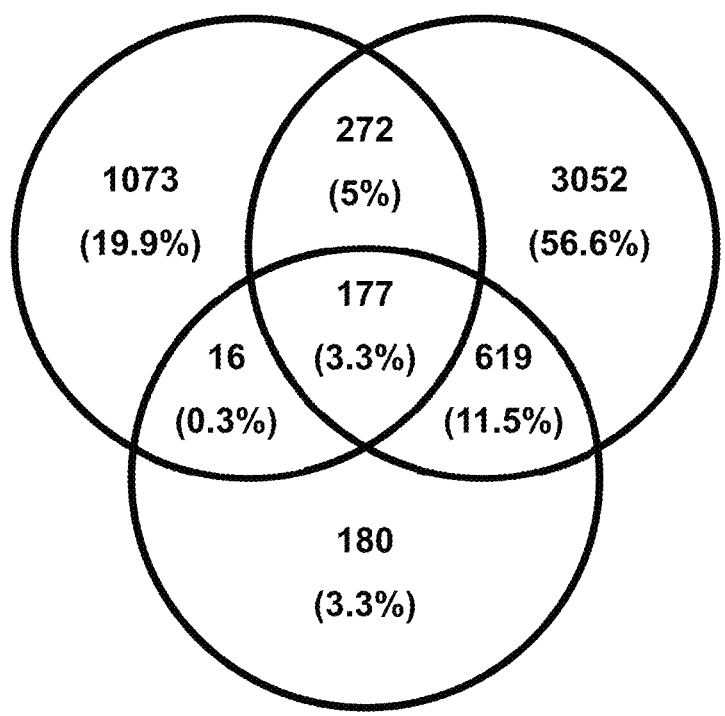

FIG. 11: In a mouse model for scl cGvHD, mCAN10 alters the expression of genes which are also differentially expressed in systemic sclerosis patients Mice were treated as described for FIG. 7. After sacrifice of mice on day 49 post transplantation, skin samples from the upper back were used for RNA sequencing analysis. The transcriptomic profile of systemic sclerosis (SSc) patients was retrieved from a patient cohort, NCBI/GEO/GSE130955, which includes 143 patients and 22 healthy individuals. Number of overlapping genes were visualized by Venn diagrams.

Figure 12:
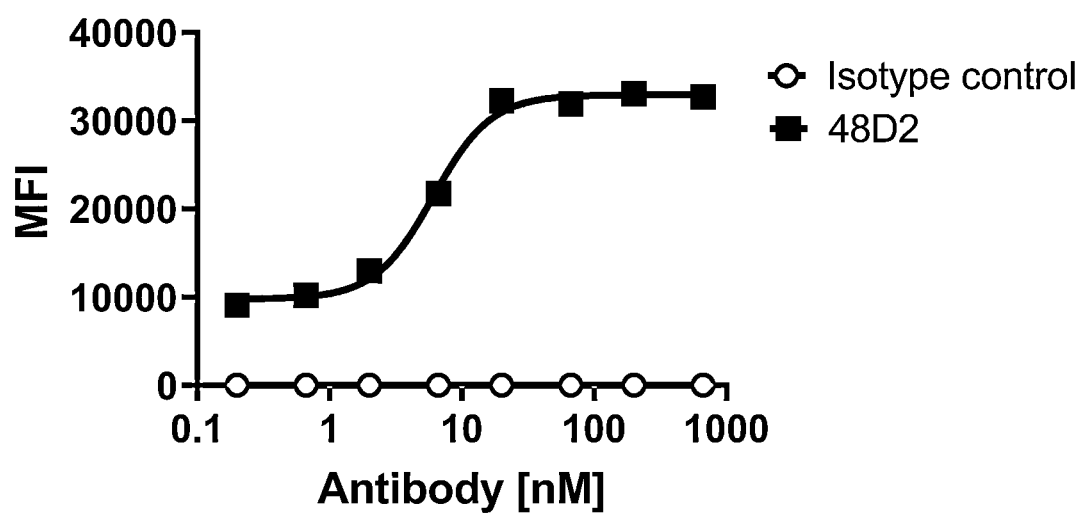

FIG. 12: Dose-dependent binding of chimeric 48D2 to cell membrane IL1RAP

Chimeric 48D2 or hIgG1 (hIg=human immunoglobulin) isotype control antibody was added to SKMEL-5 cells in increasing concentrations and extracellular binding was analyzed by flow cytometry. Chimeric 48D2 specifically bound IL1RAP on the cell membrane in a dose-dependent manner and with higher mean fluorescent intensity (MFI) compared to the hIgG1 isotype control antibody.

Figure 13:
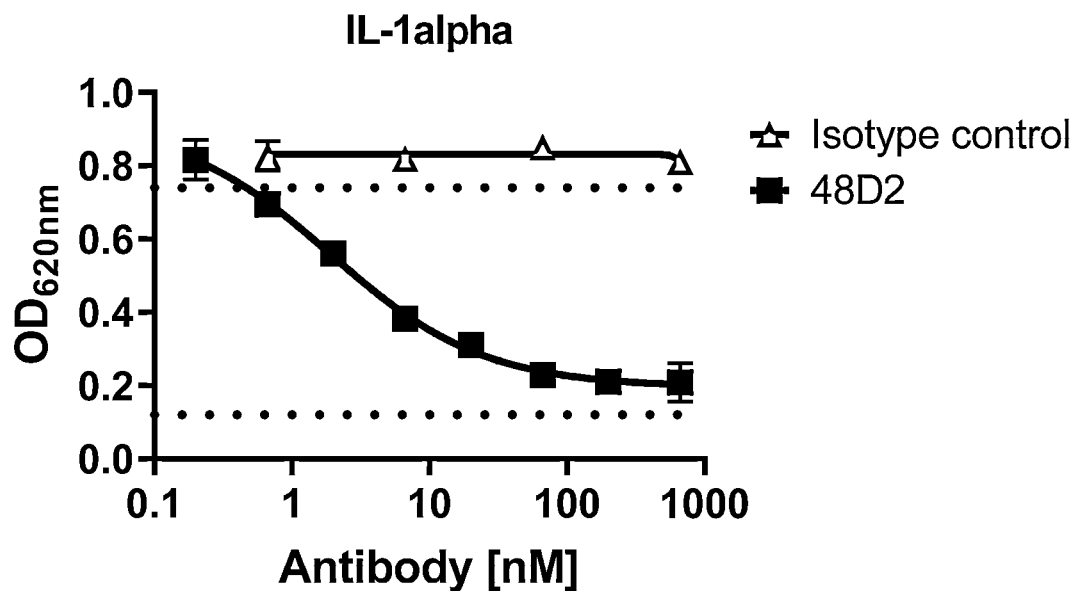
Figure 13:
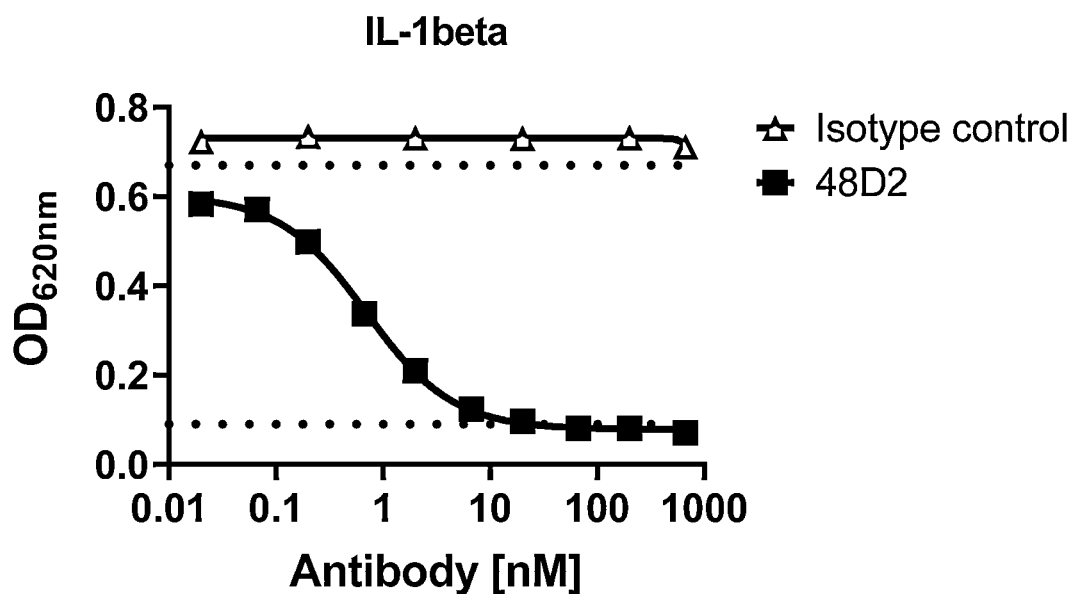
Figure 13:
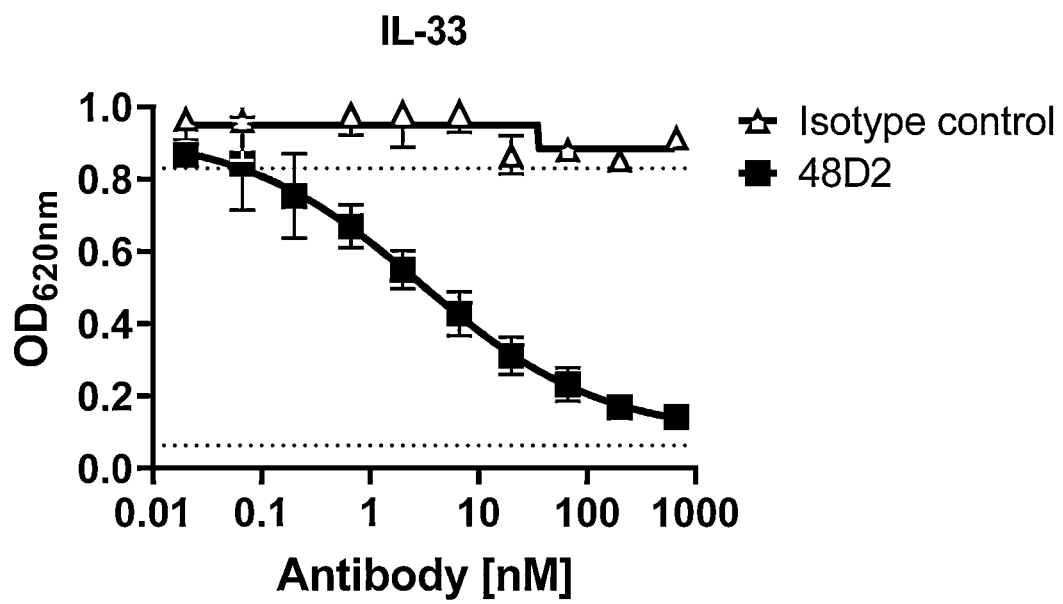
Figure 13:
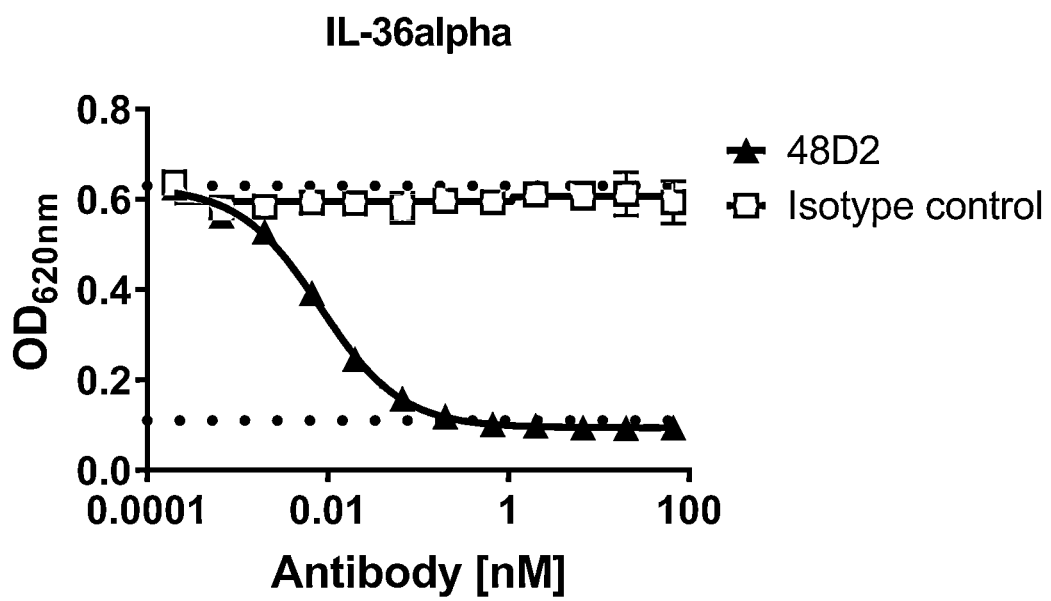
Figure 13:
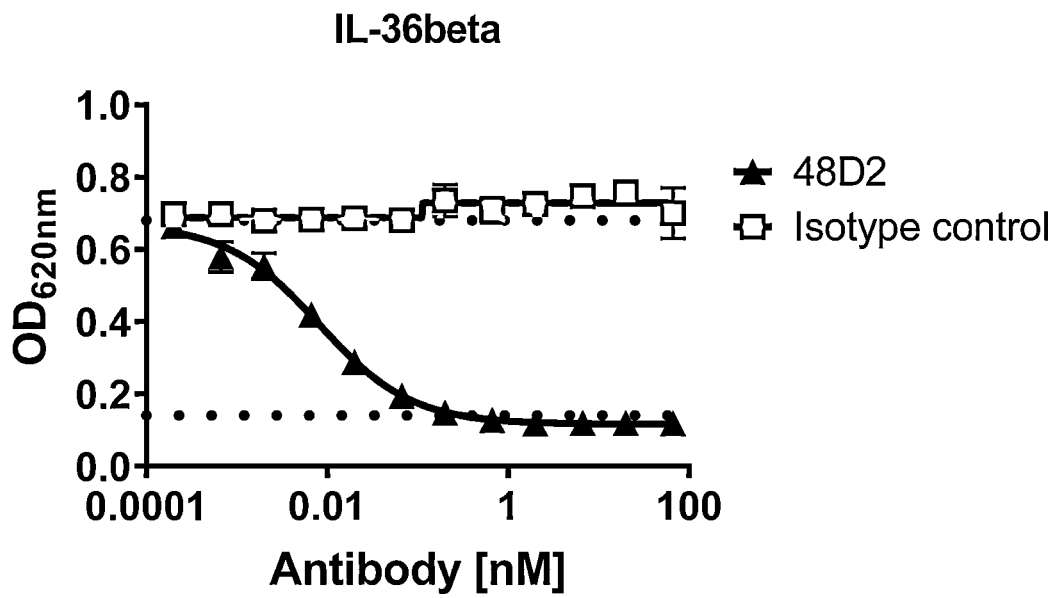
Figure 13:
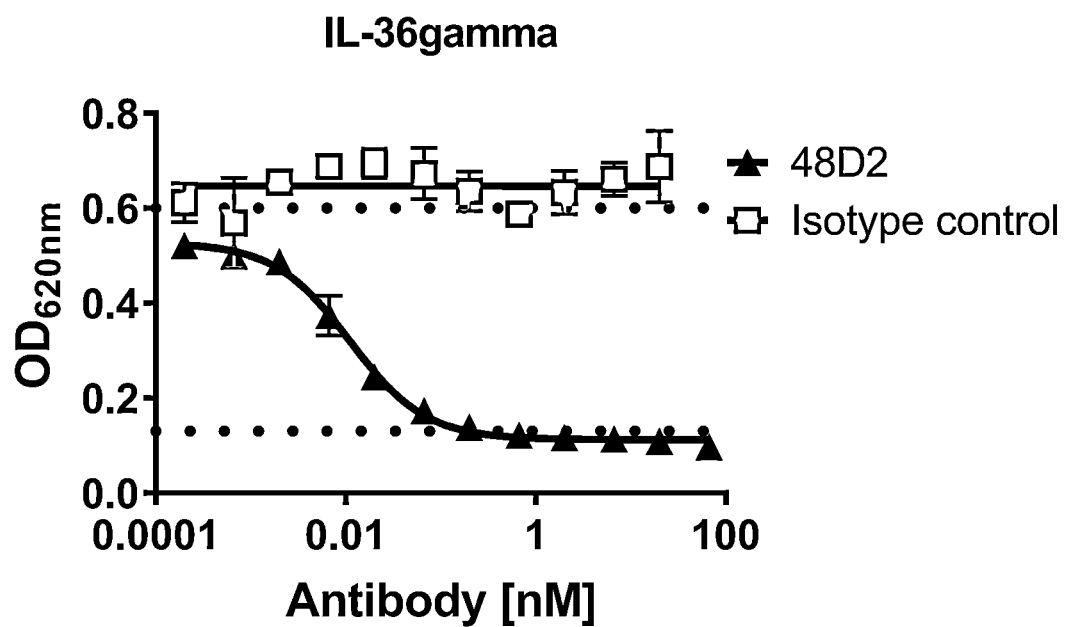

FIG. 13: Inhibition of interleukin signaling by chimeric 48D2

The ability of chimeric 48D2 to block IL-1alpha (A), IL-1beta (B), IL-33 (C), IL-36alpha (D), IL-36beta (E) and IL-36gamma (F) signaling was investigated in a HEK-Blue™ assay. hIgG1 isotype antibody was included as a control. Dotted lines show positive (cells stimulated with cytokine) and negative (cells only) controls to illustrate the window of inhibition. Chimeric 48D2 blocks the signaling downstream of all six cytokines.

Figure 14:
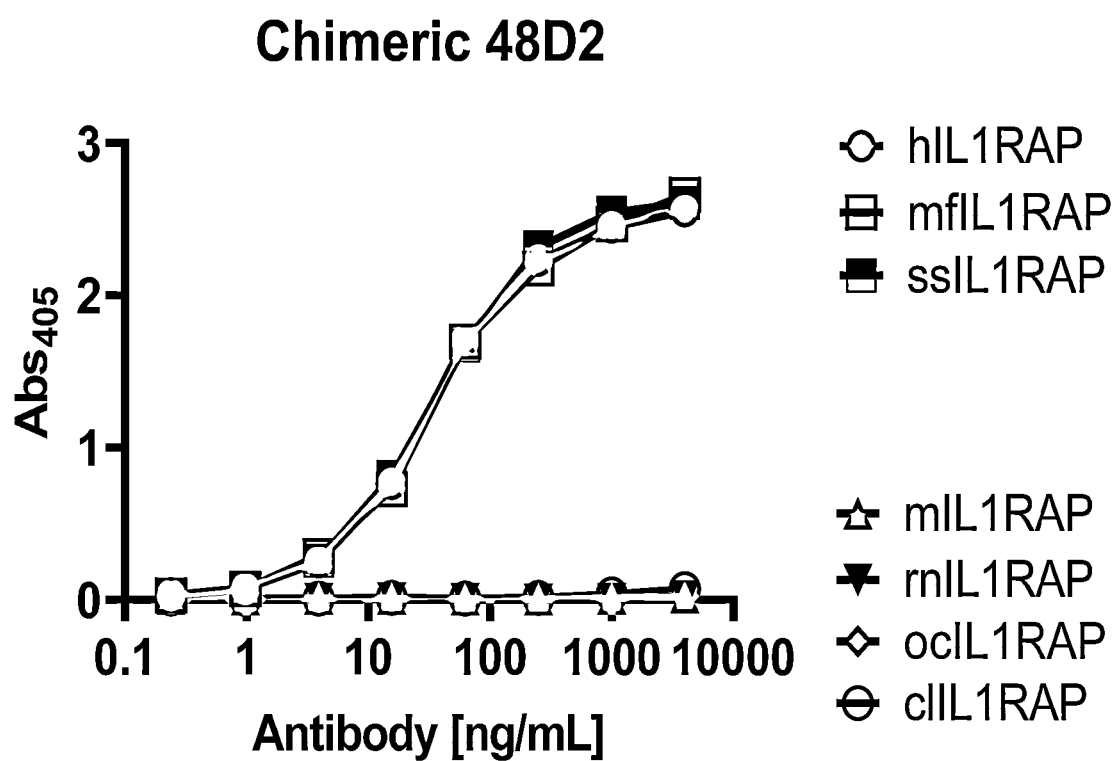

FIG. 14: Chimeric 48D2 binds human, cynomolgus monkey and pig IL1RAP

Cross reactivity of chimeric 48D2 with the IL1RAP orthologues was measured by ELISA. Chimeric 48D2 cross reacts with human (hIL1RAP), cynomolgus monkey (mfIL1RAP) and pig (ssIL1RAP) IL1RAP, but not with mouse (mIL1RAP), rat (rnIL1RAP), rabbit (ocIL1RAP) or dog (clIL1RAP) IL1RAP.

Figure 15:
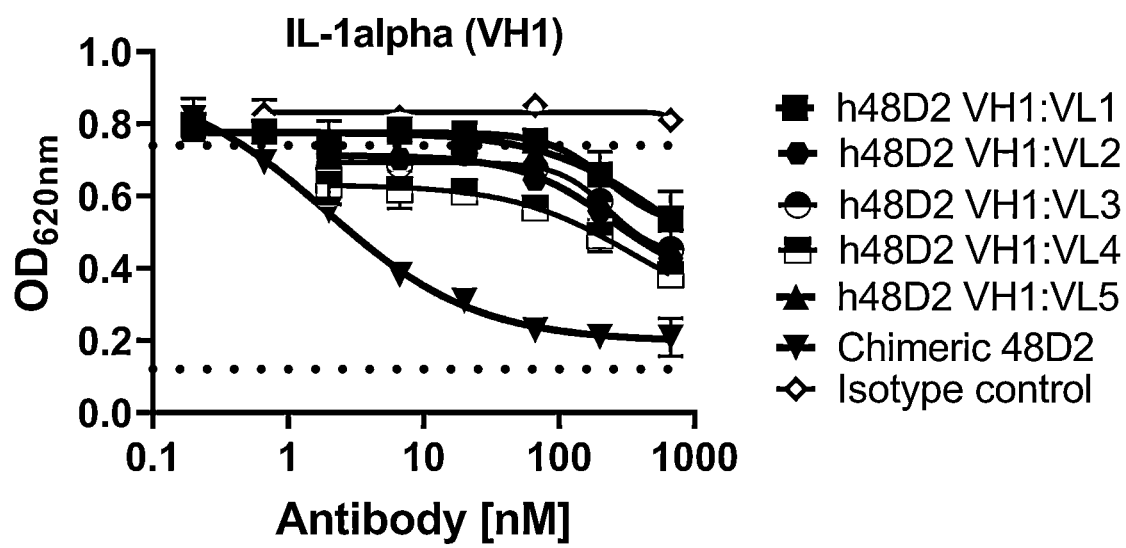
Figure 15:
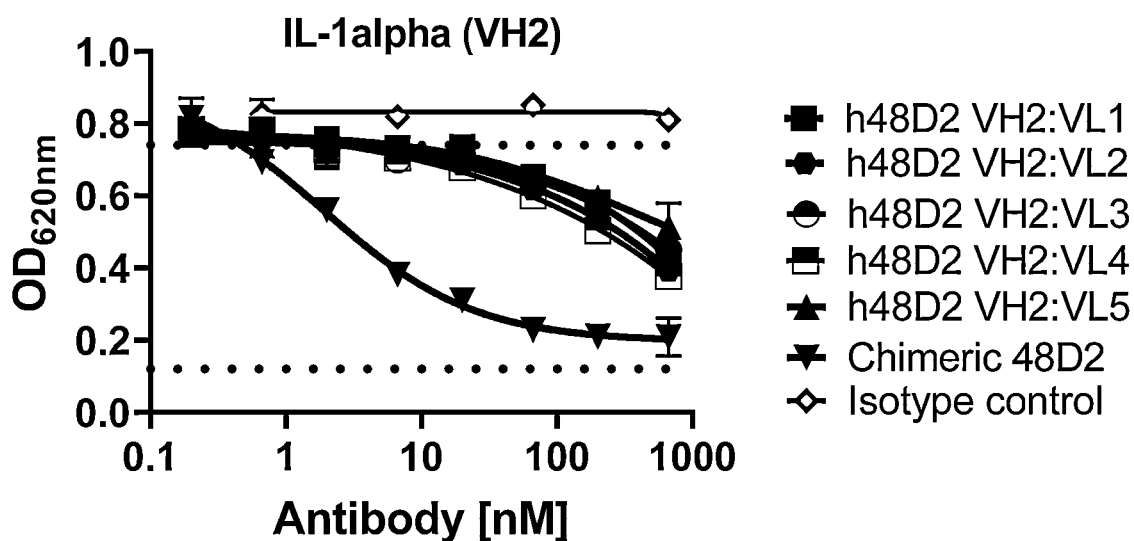
Figure 15:
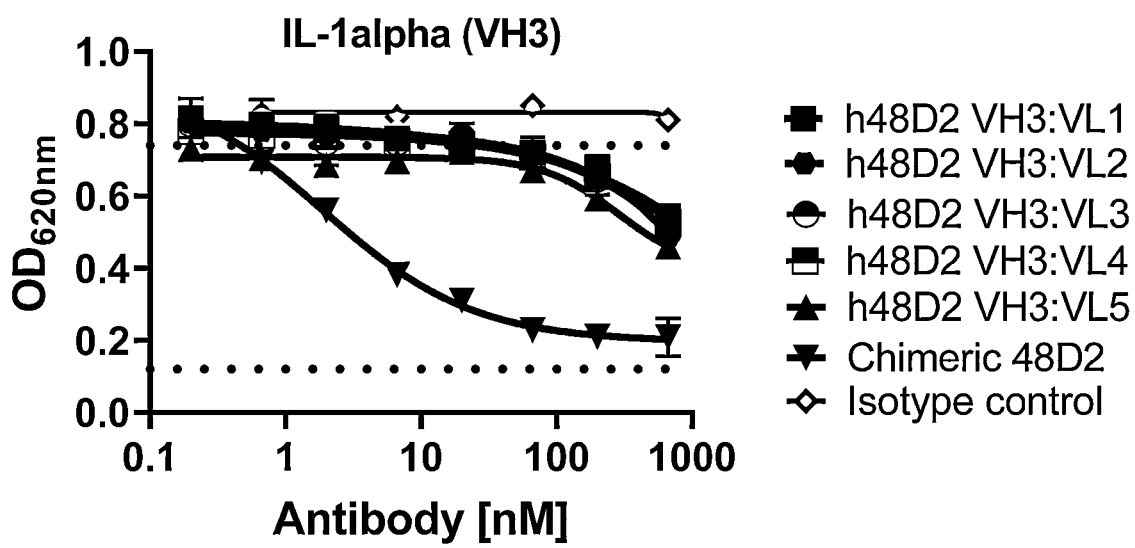
Figure 15:
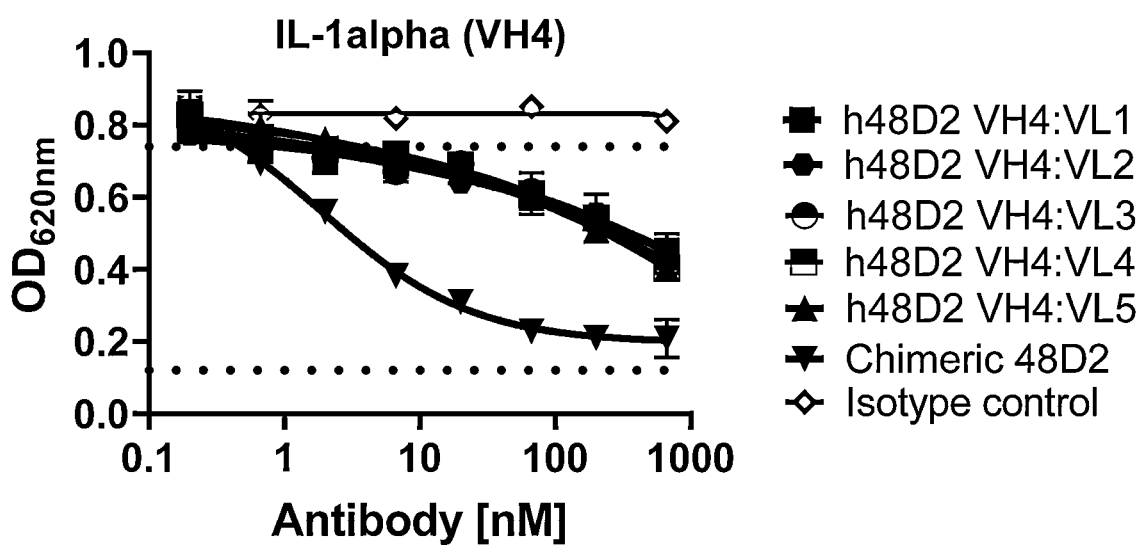
Figure 15:
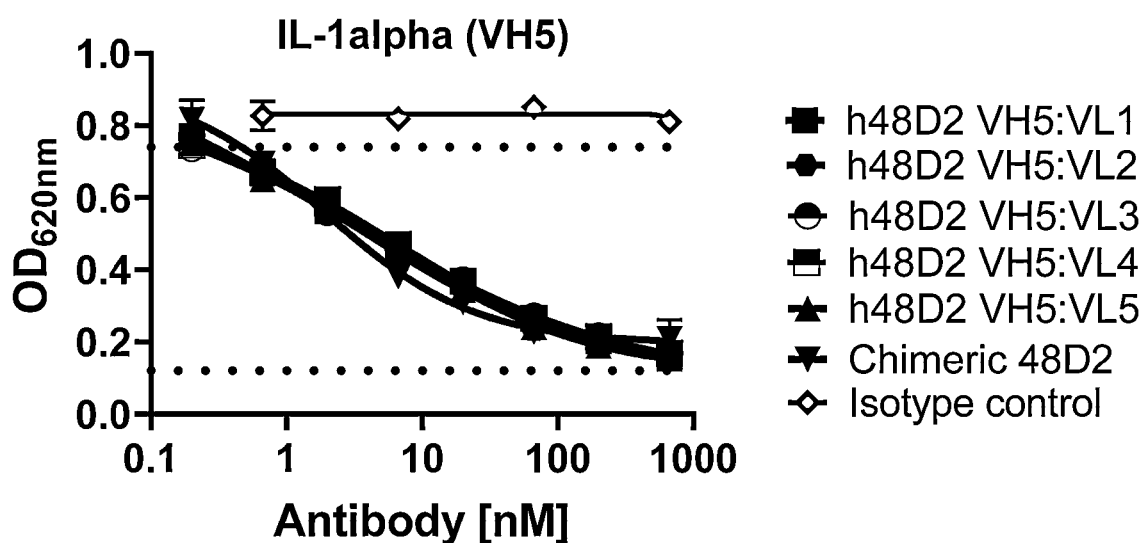
Figure 15:
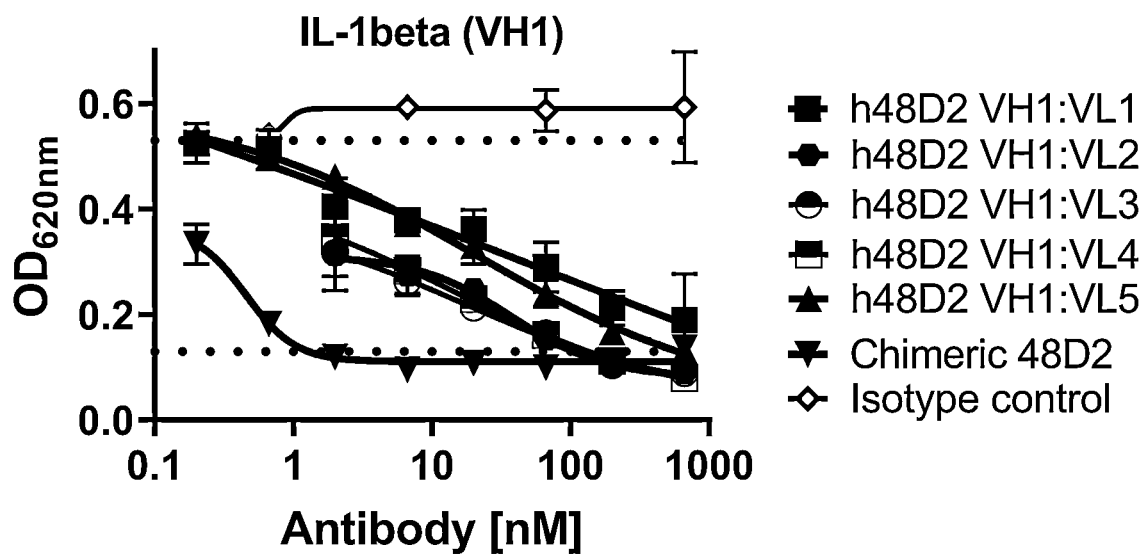
Figure 15:
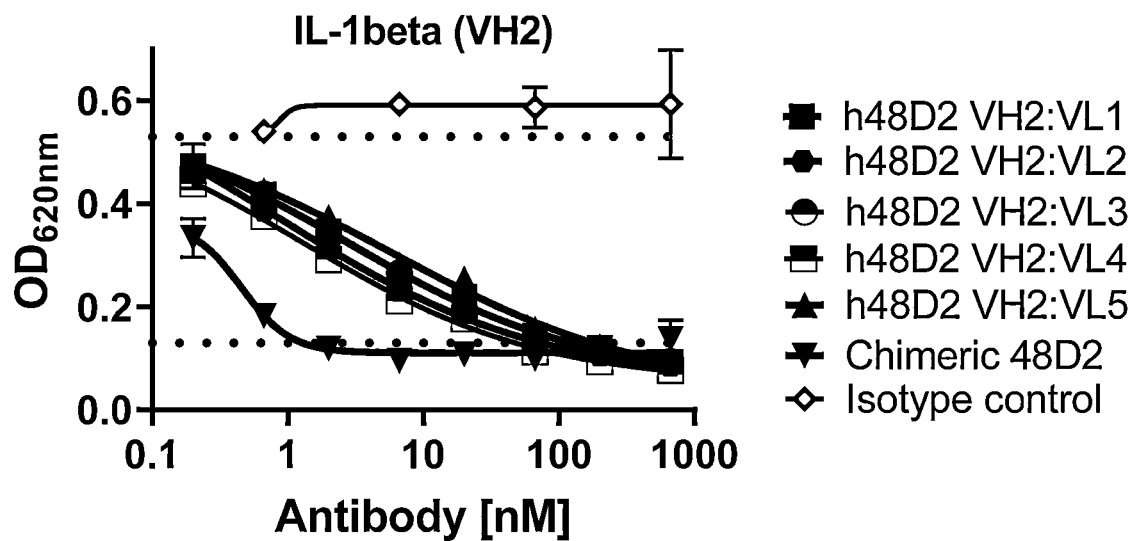
Figure 15:
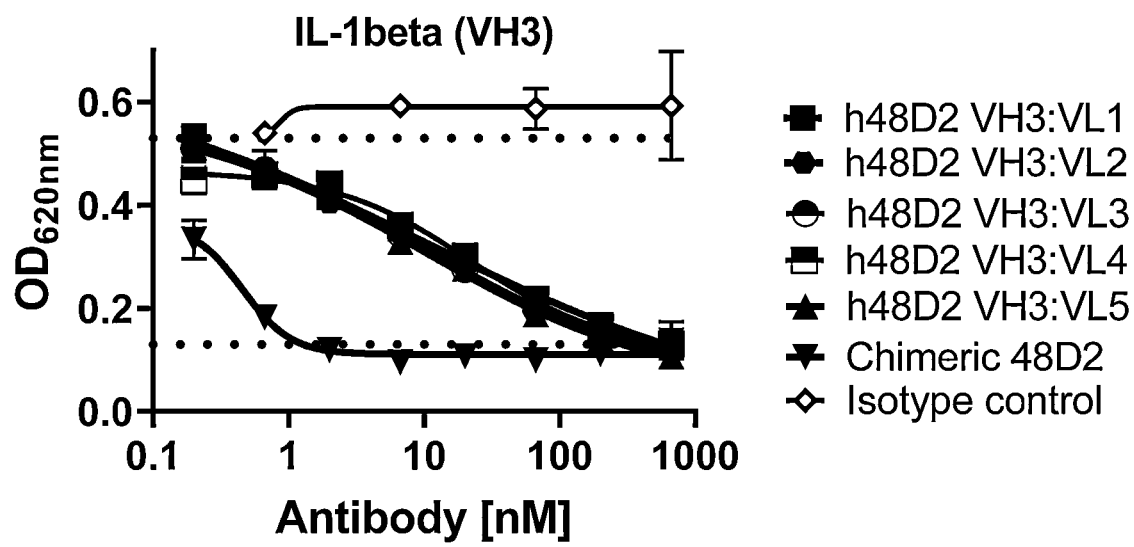
Figure 15:
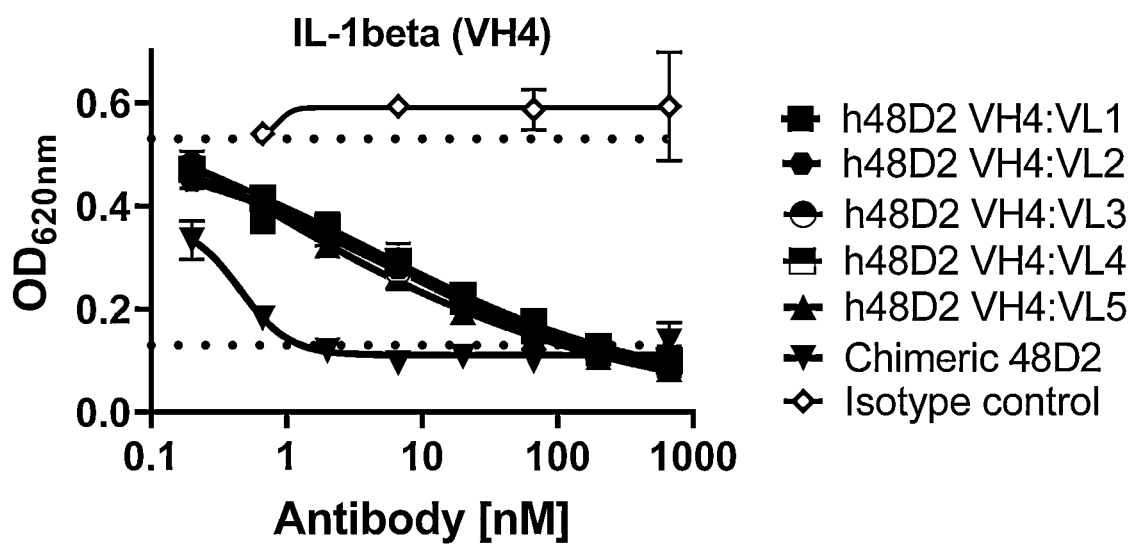
Figure 15:
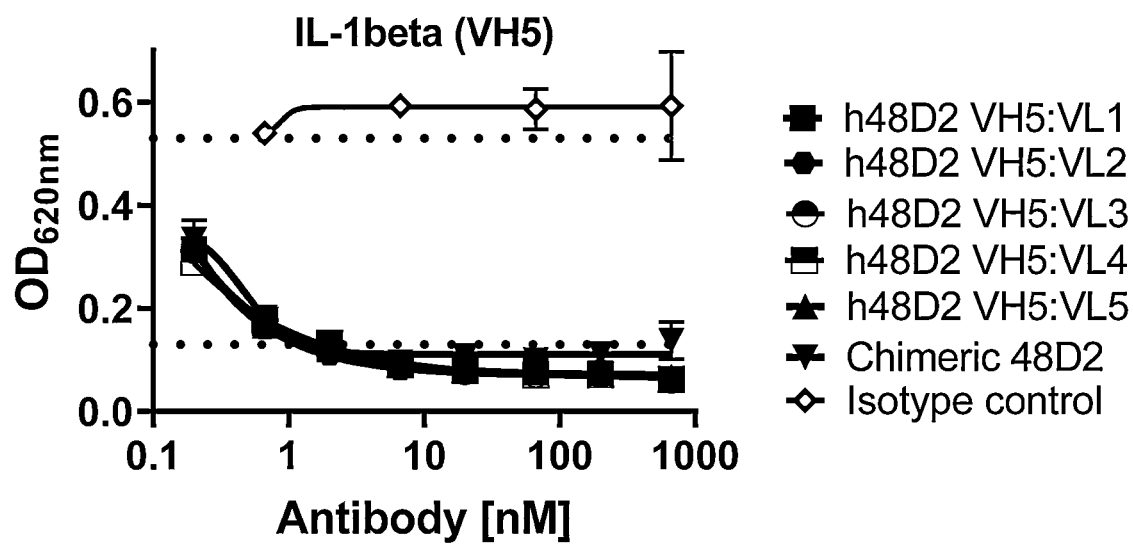
Figure 15:
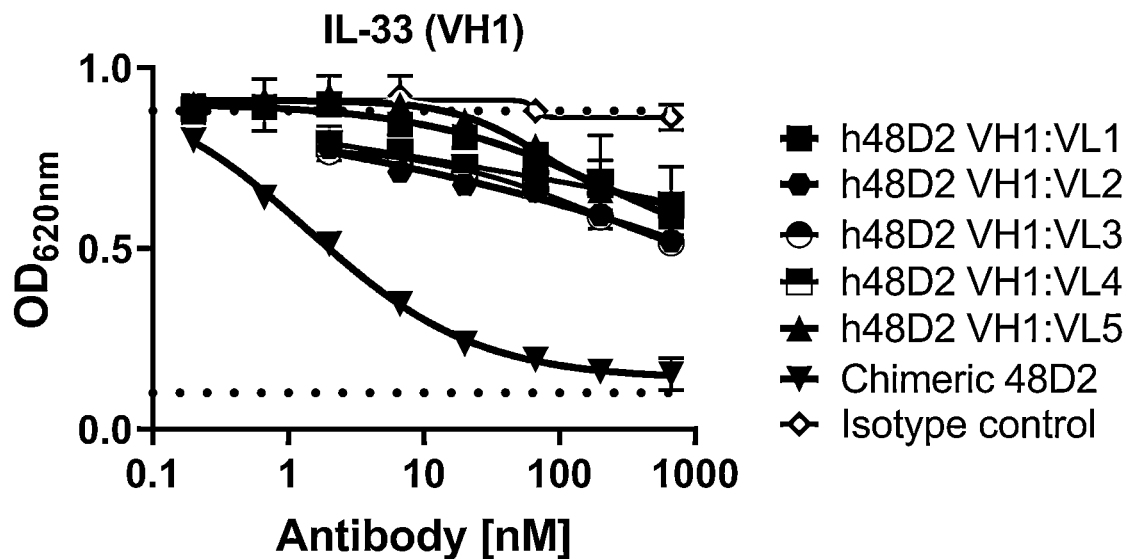
Figure 15:
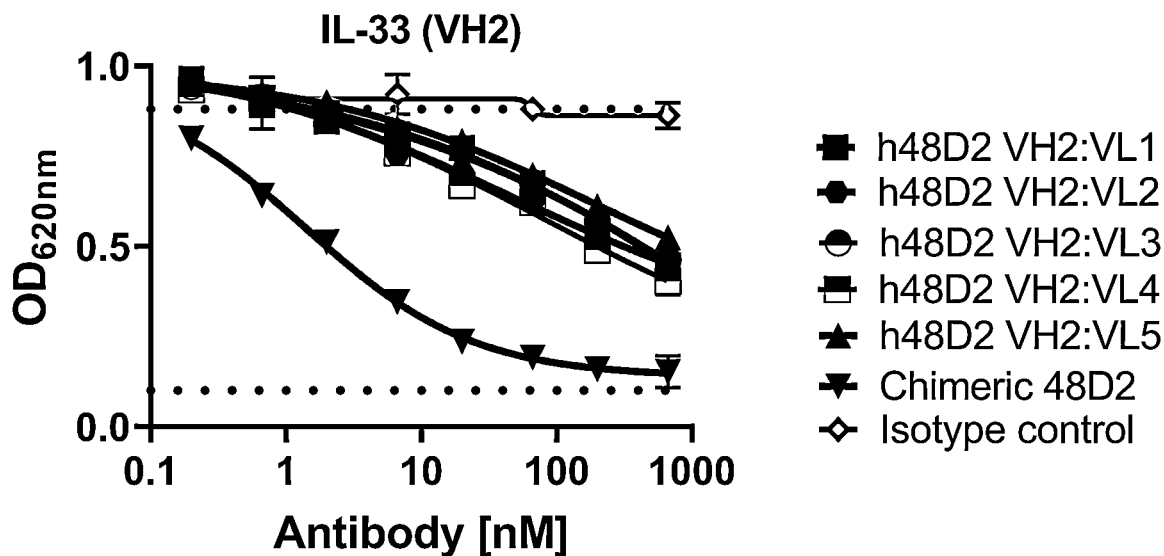
Figure 15:
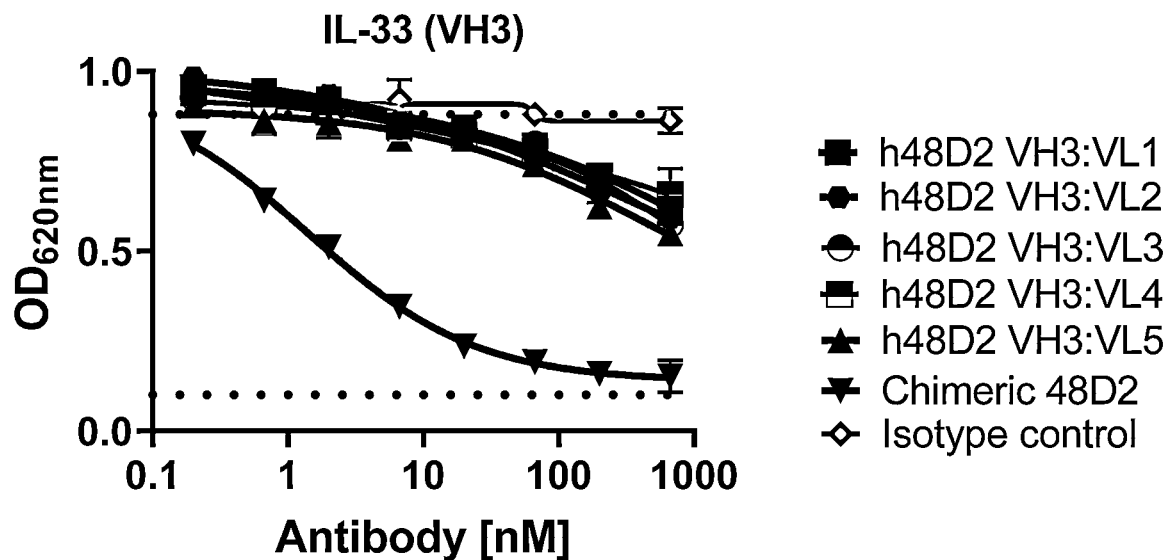
Figure 15:
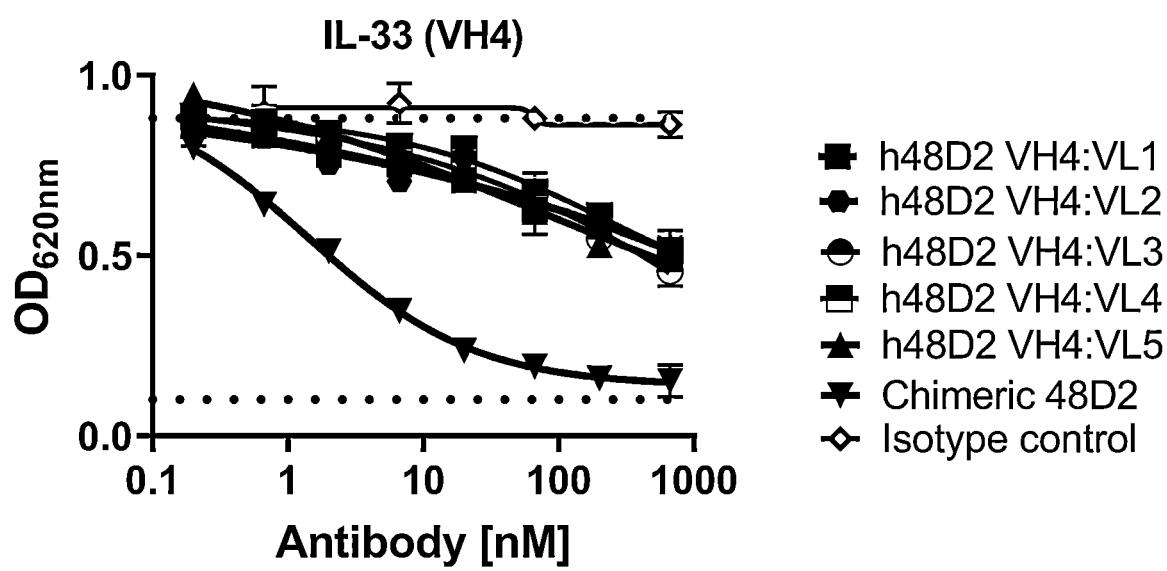
Figure 15:
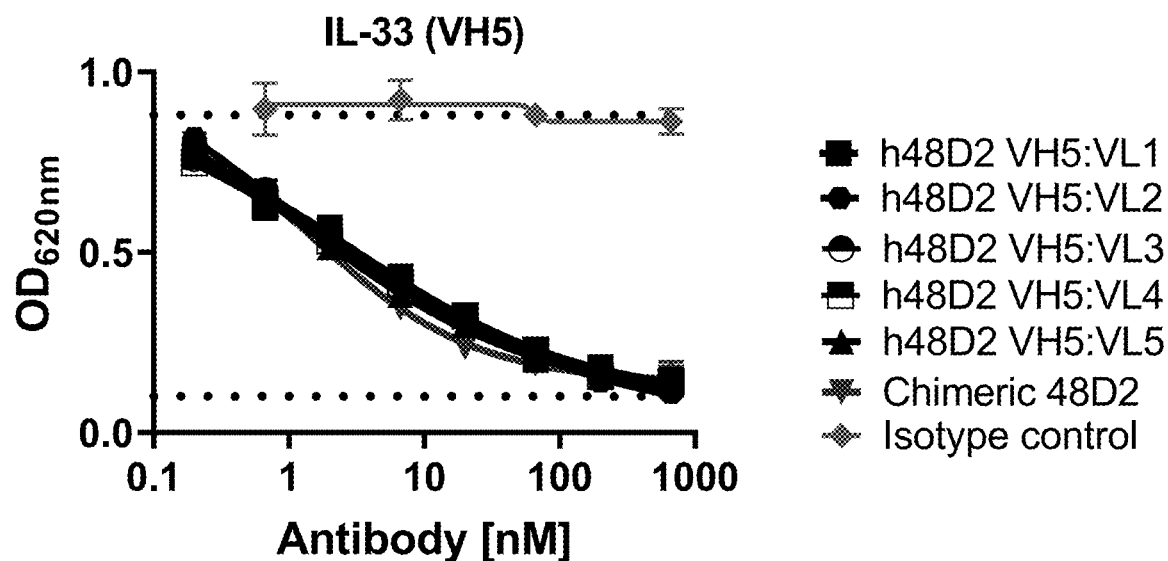
Figure 15:
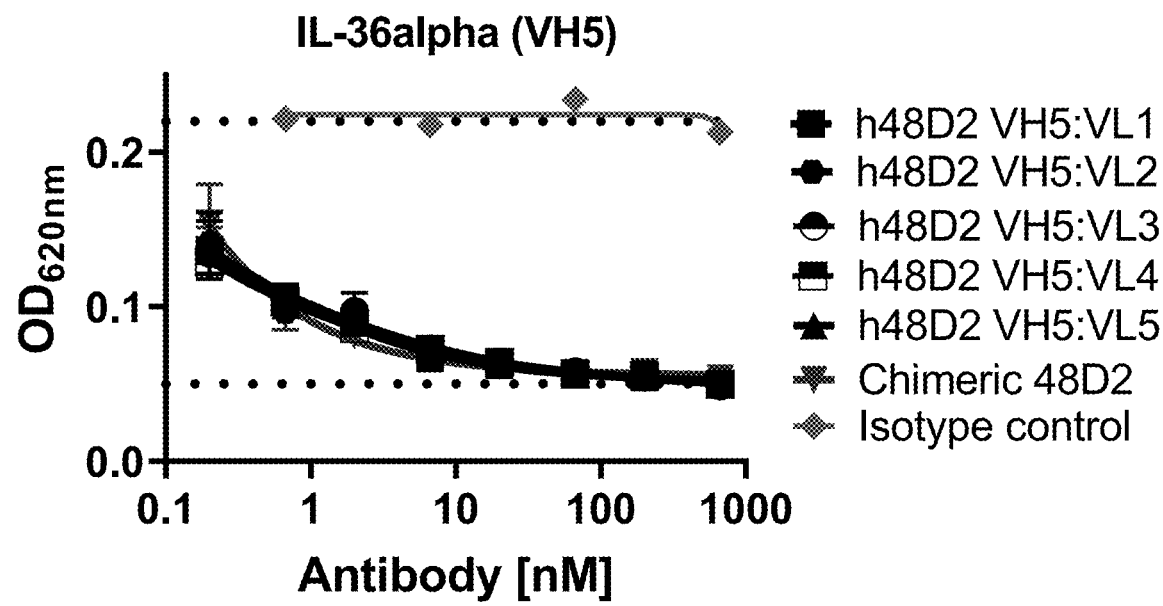
Figure 15:
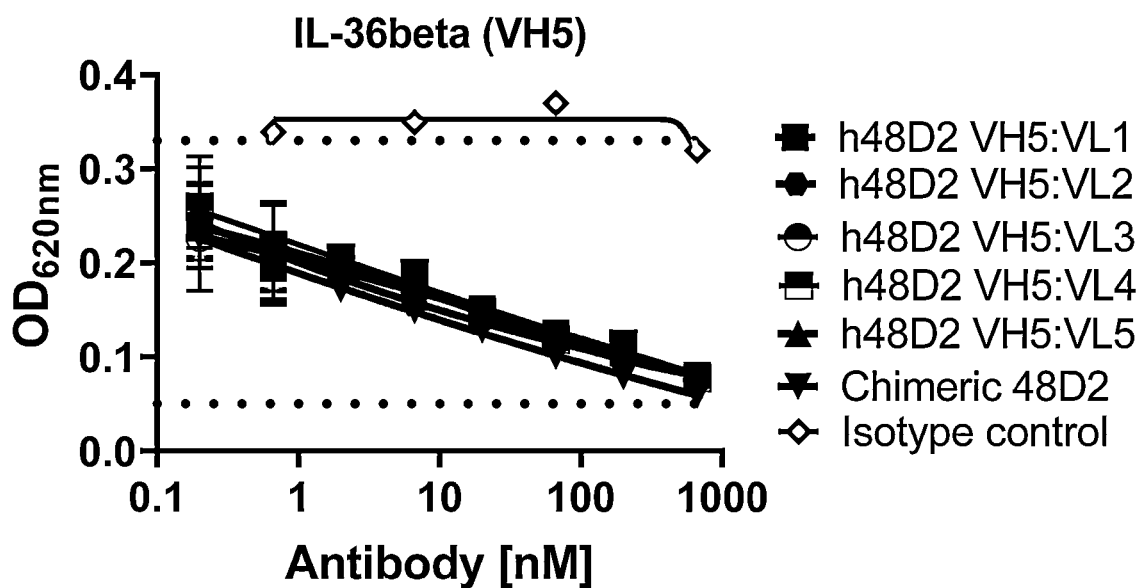
Figure 15:
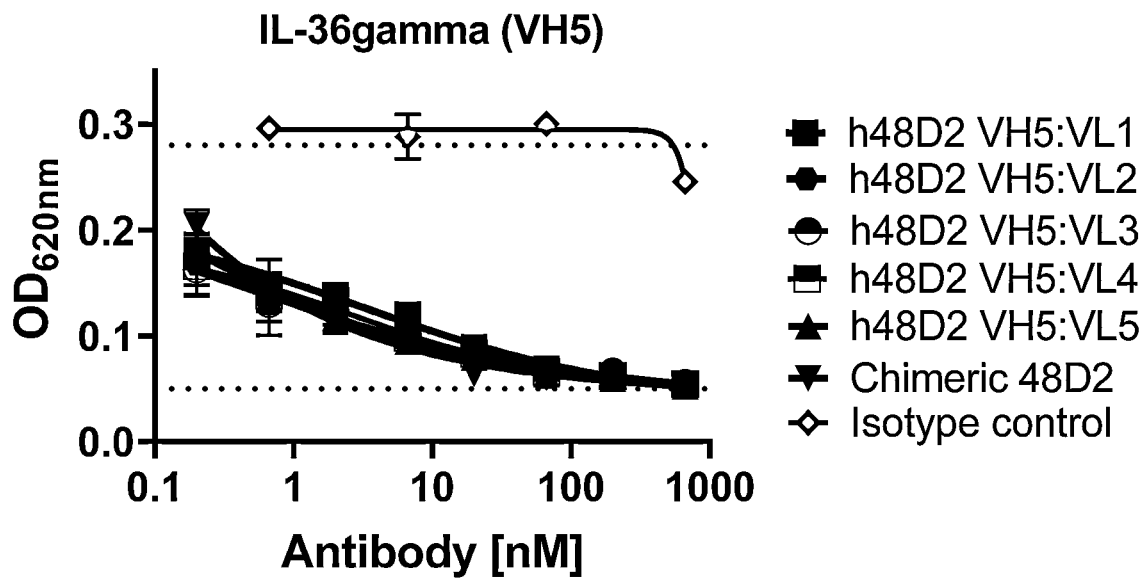

FIG. 15: Inhibition of interleukin signaling by the humanized 48D2 variants

The ability of humanized (h) 48D2 VH variants VH1, VH2, VH3, VH4, and VH5 in combination with VL variants VL1, VL2, VL3, VL4 and VL5 to block IL-1alpha (A-E), IL-1beta (F-J), and IL-33 (K-O) signaling was investigated in a HEK-Blue™ assay. Variants of h48D2 harboring VH5 block the downstream signaling to a similar degree as chimeric 48D2 and were further investigated for inhibition of IL-36alpha (P), IL-36beta (Q), and IL-36gamma (R). Variants of h48D2 harboring VH1, VH2, VH3 or VH4 inhibited signaling of IL-1alpha, IL-1beta and IL-33 to varying degrees. hIgG1 isotype antibody and chimeric 48D2 were included as controls. Dotted lines show positive (cells stimulated with cytokine) and negative (only cells) controls to illustrate the window of inhibition. Variants of h48D2 harboring VH5 in combination with any VL variant (VL1-VL5) block the downstream signaling of all six interleukins to a similar degree as chimeric 48D2.

Figure 16:
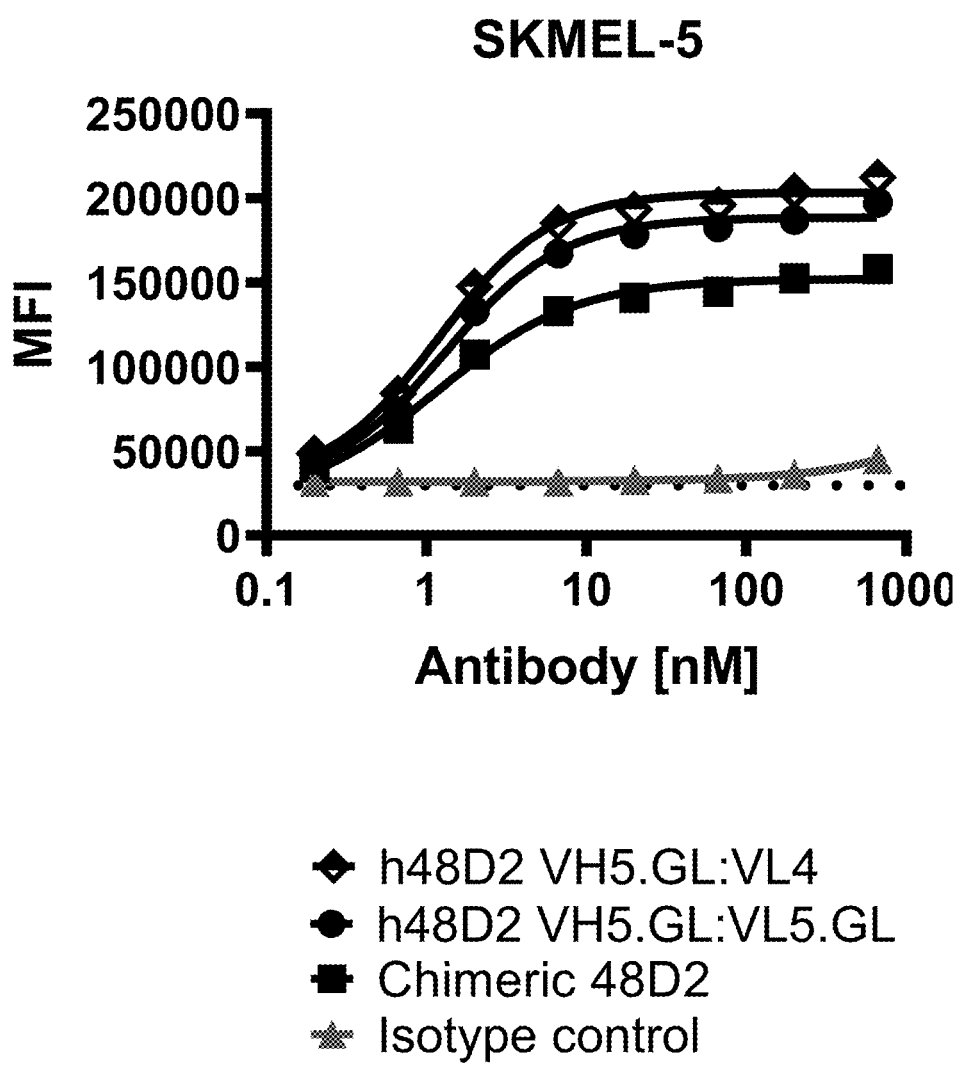

FIG. 16: Dose-dependent binding of two humanized and de-immunized clones to cell membrane IL1RAP Two of the humanized and de-immunized 48D2 clones, h48D2 VH5.GL:VL4 and h48D2 VH5.GL:VL5.GL were added to SKMEL-5 cells in increasing concentrations and extracellular binding was analyzed by flow cytometry. Chimeric 48D2 and hIgG1 isotype antibody were included as controls. h48D2 VH5.GL:VL4 and h48D2 VH5.GL:VL5.GL specifically bound IL1RAP on the cell membrane in a dose-dependent manner and with higher mean fluorescent intensity (MFI) compared to the hIgG1 isotype control antibody and the chimeric 48D2 antibody.

Figure 17:
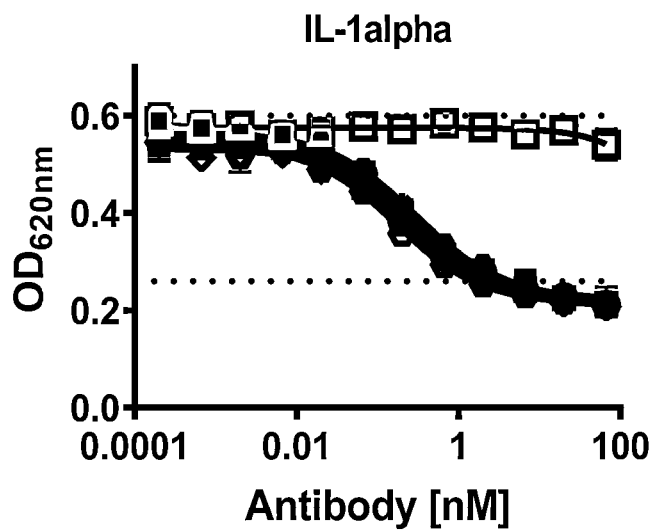
Figure 17:
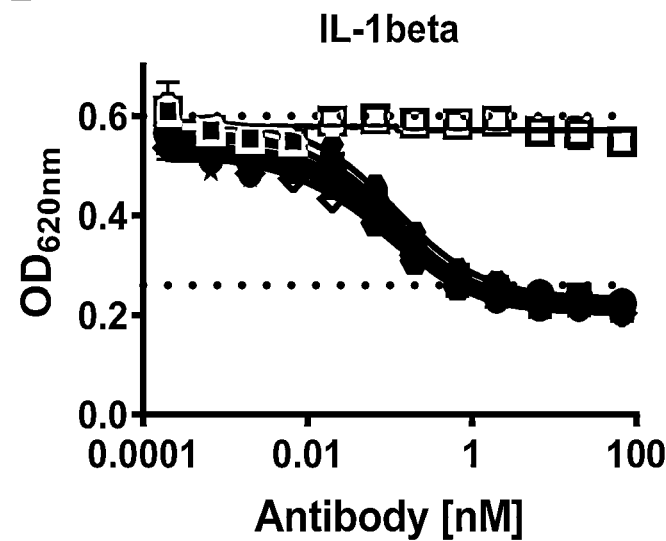
Figure 17:
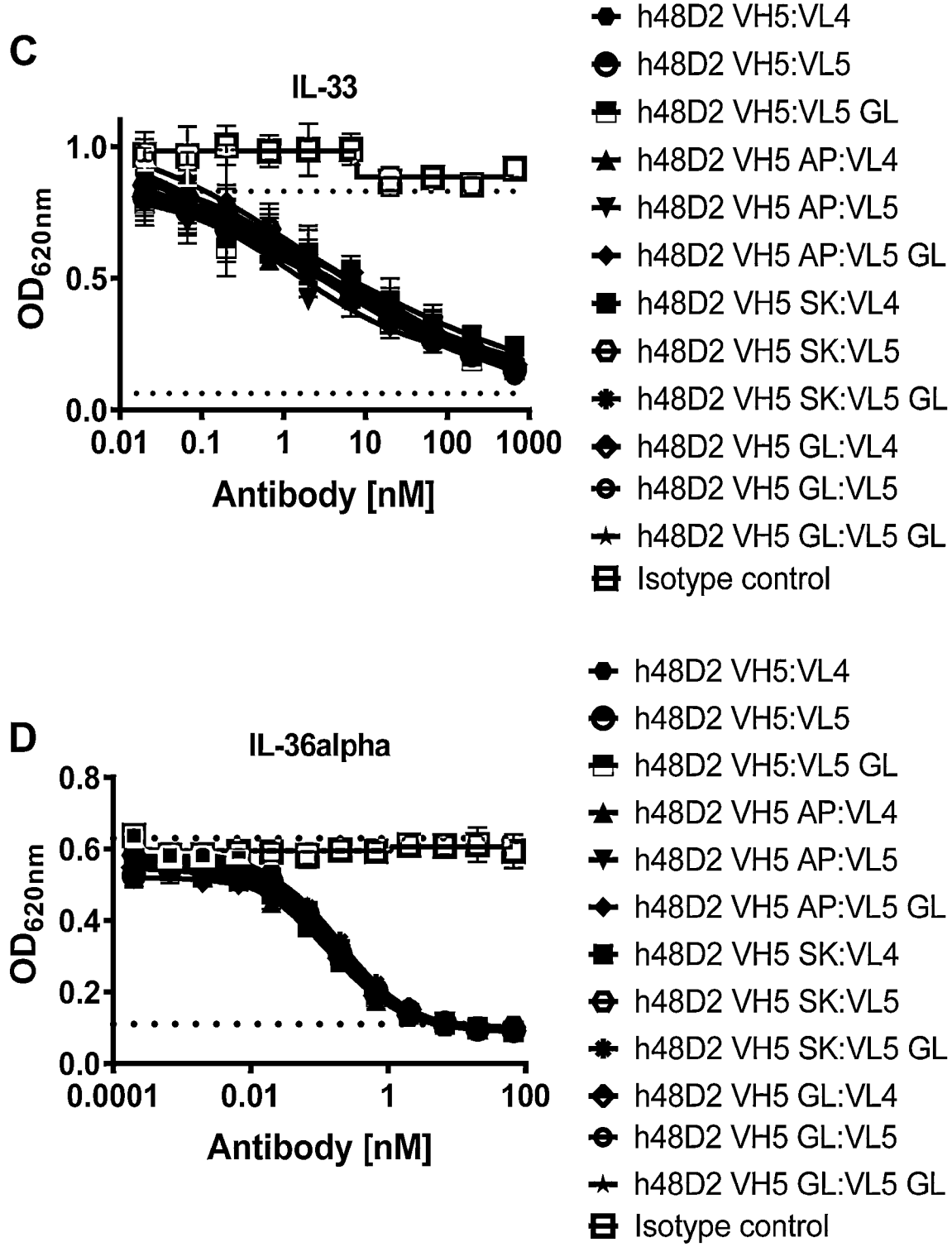
Figure 17:
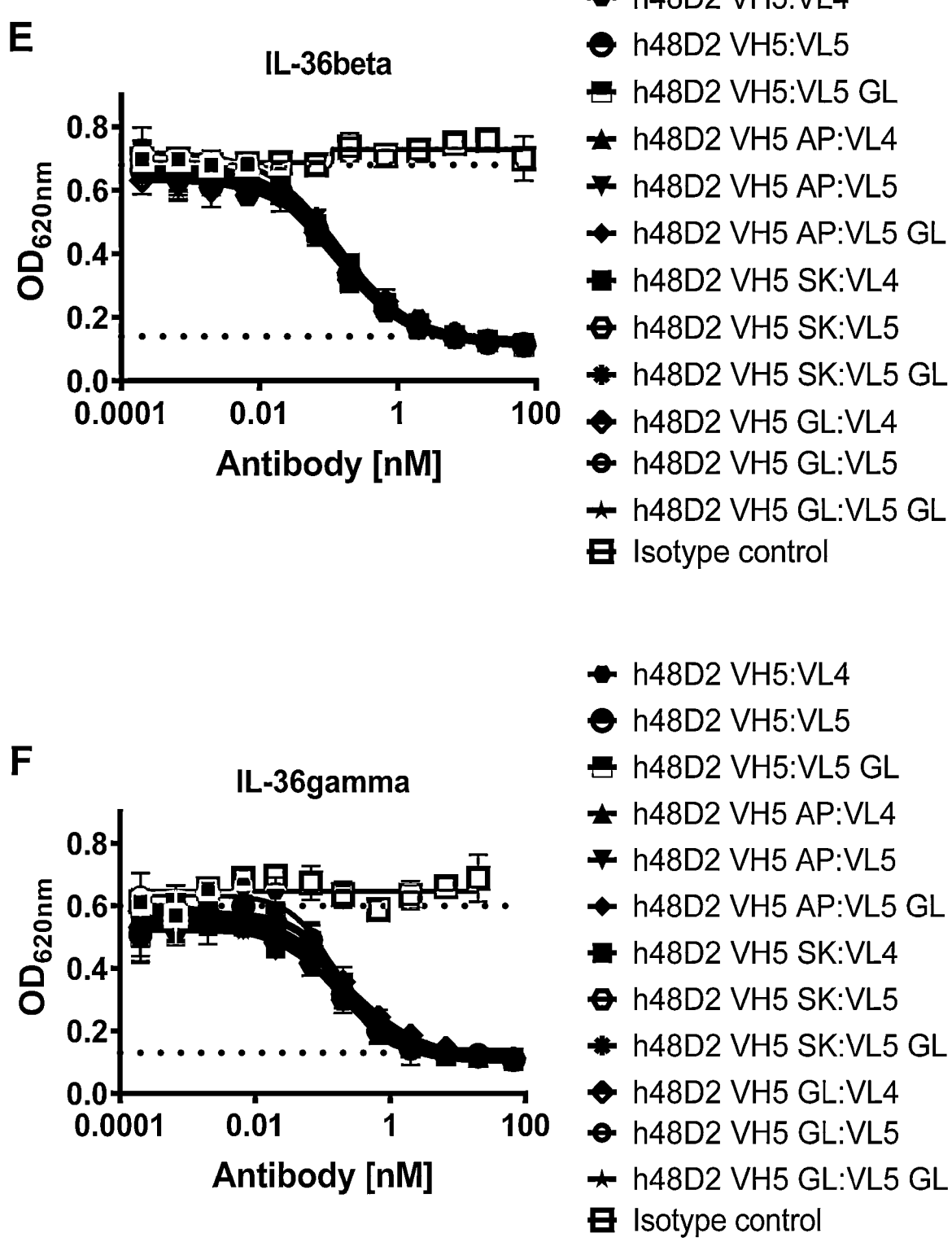
Figure 17:
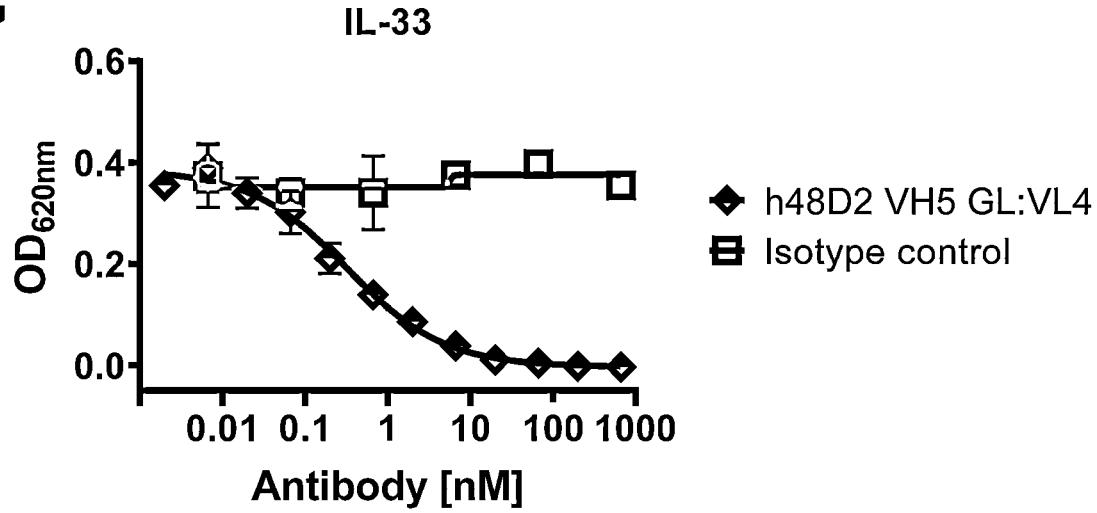
Figure 17:
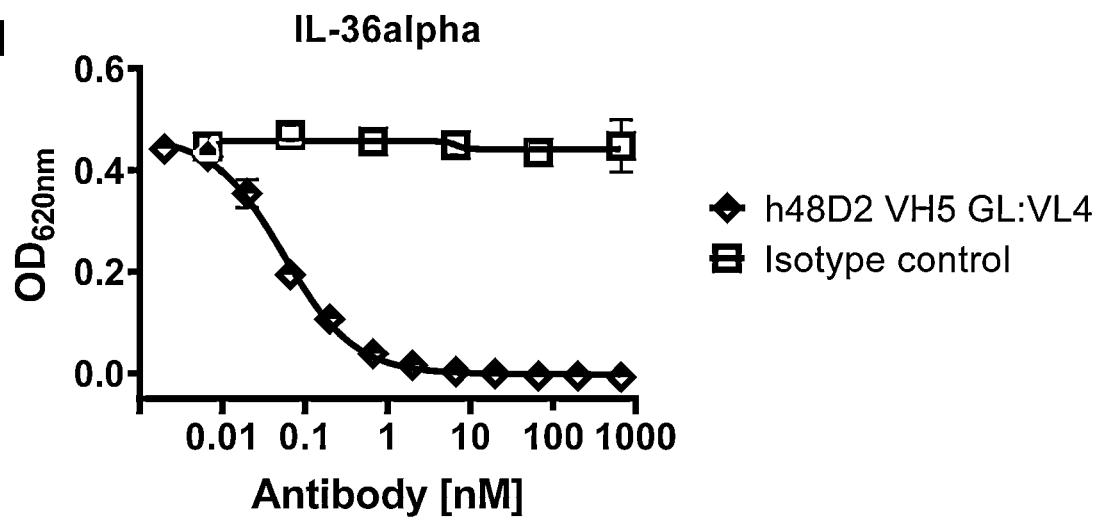
Figure 17:
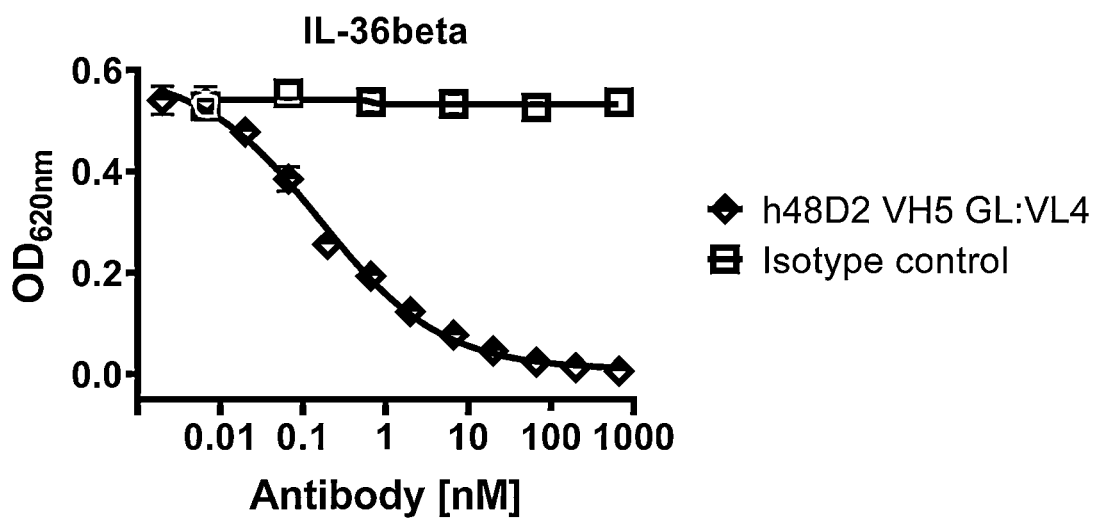
Figure 17:
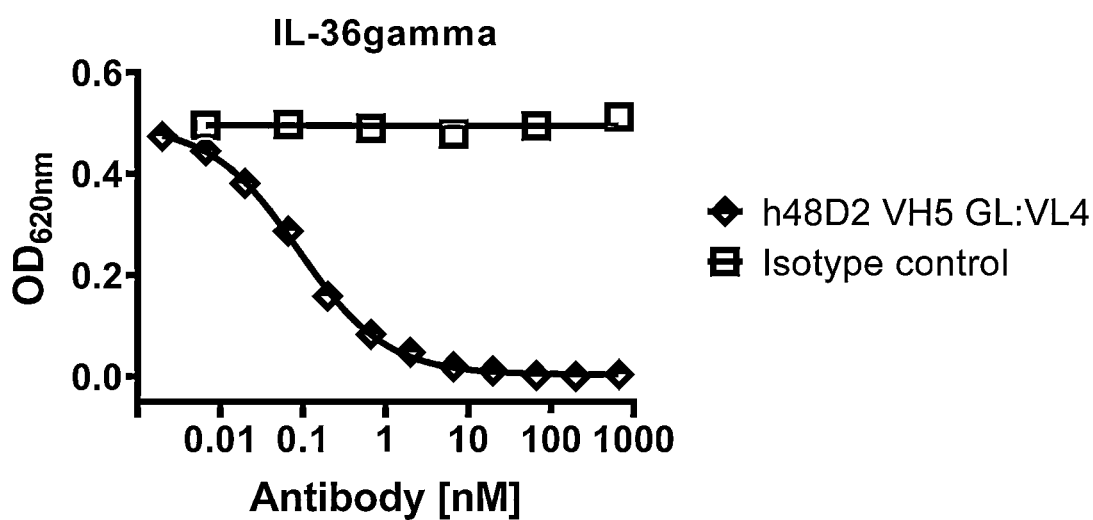

FIG. 17: De-immunized h48D2 clones have preserved inhibitory activity on all six interleukin pathways Inhibitory activity of the de-immunized h48D2 clones on IL-1alpha (A), IL-1beta (B), IL-33 (C), IL-36alpha (D), IL-36beta (E) and IL-36gamma (F) signaling was assessed in a HEK-Blue™ assay. hIgG1 isotype antibody and h48D2 VH5:VL4 and h48D2 VH5:VL5 were included as controls. Dotted lines show positive (cells stimulated with cytokine) and negative (only cells) controls to illustrate the window of inhibition. All six de-immunized clones had similar inhibitory activity as h48D2 VH5:VL4 and VH5:VL5. The inhibitory activity of h48D2 variant VH5.GL:VL4 on IL-33 (G), IL-36alpha (H), IL-36beta (I), IL-36gamma (J) was further evaluated in HEK-Blue™ with stable expression of the IL-36 receptor.

Figure 18:
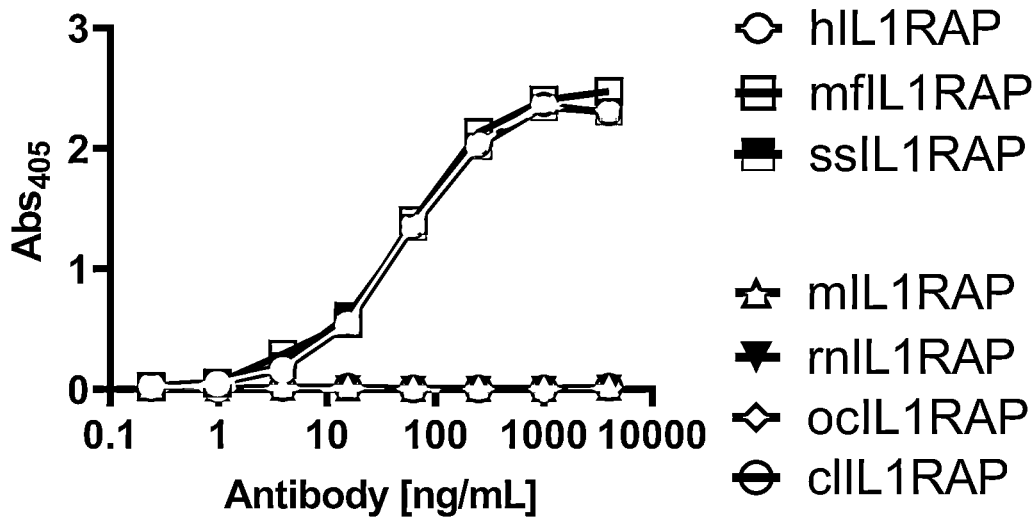
Figure 18:
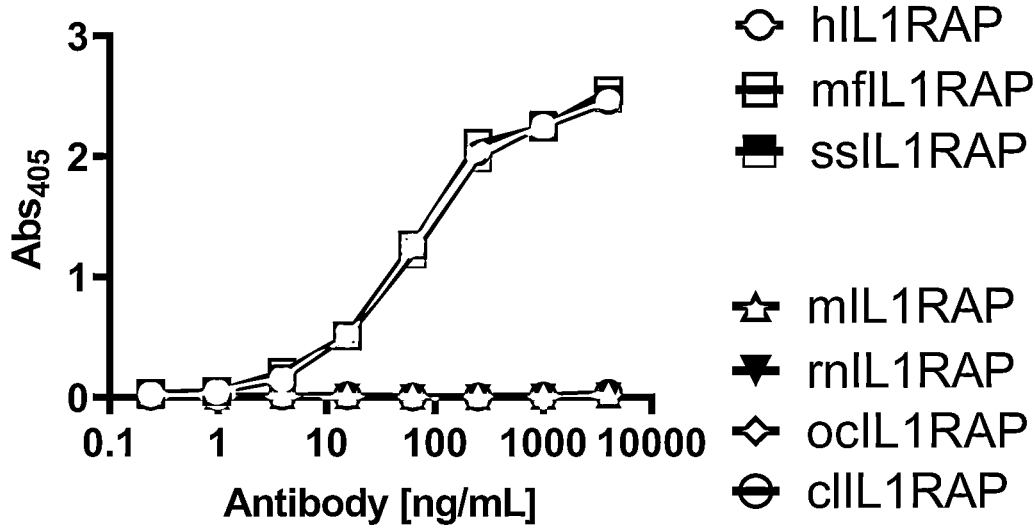

FIG. 18: De-immunized h48D2 clones bind human, cynomolgus monkey and pig IL1RAP

Cross reactivity was measured by ELISA. h48D2 VH5.GL:VL4 (A) and VH5.GL:VL5.GL (B) cross react with human (hIL1RAP), cynomolgus monkey (mfIL1RAP) and pig (ssIL1RAP) IL1RAP, but not with mouse (mIL1RAP), rat (rnIL1RAP), rabbit (ocIL1RAP) or dog (clIL1RAP) IL1RAP.

Figure 19:
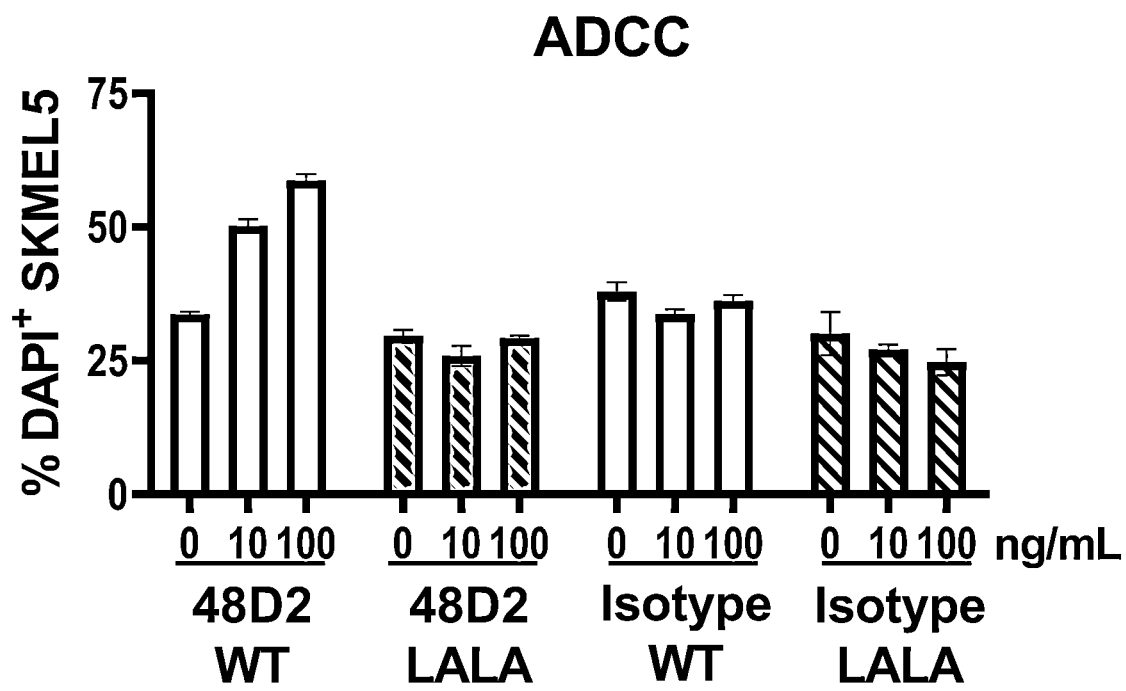

FIG. 19: 48D2 in hIgG1 format induces ADCC of IL1RAP expressing SKMEL-5 cells

ADCC assay was performed in vitro with IL1RAP expressing SKMEL-5 cells and human NK cells and the number of dying SKMEL-5 cells was analyzed by flow cytometry and shown as % dead (DAPI positive) cells. 48D2 in hIgG1 format can direct NK cells to kill SKMEL-5 cells in a dose-dependent manner. When 48D2 is expressed in a hIgG1-LALA format, no dose-dependent ADCC was induced. Isotype hIgG1 and Isotype-LALA did not induce ADCC greater than the background cell death observed in untreated cells.

Figure 20:
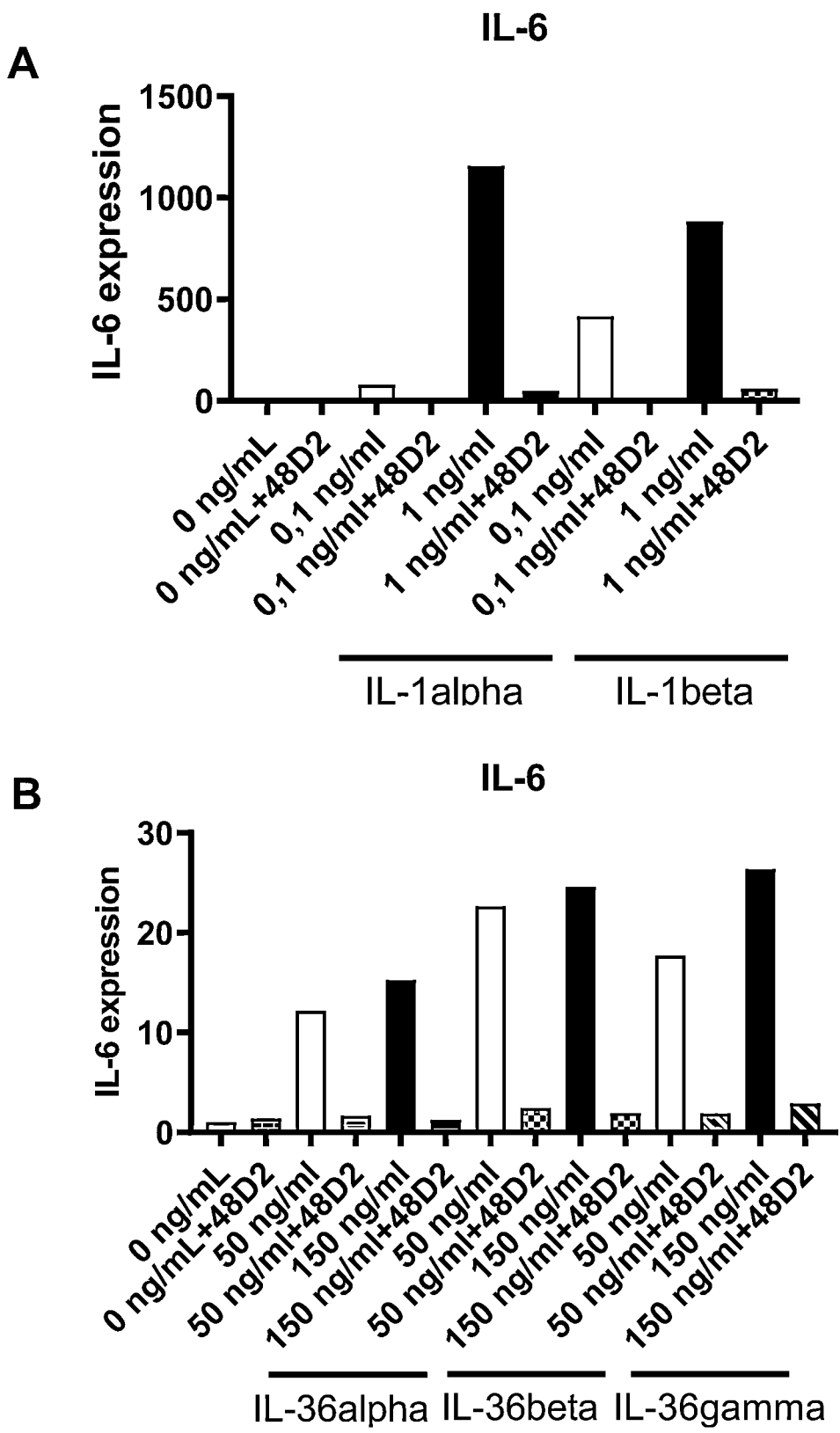

FIG. 20: 48D2 inhibits cytokine-induced IL-6 mRNA expression in human dermal fibroblasts Primary human dermal fibroblasts were cultured in vitro and stimulated with IL-1alpha or IL-1beta (A) or IL-36alpha, IL-36beta or IL-36gamma (B), with or without the addition of chimeric 48D2. Data is shown as fold change ($2^{-ddcT}$) compared to unstimulated control (0 ng/mL). All cytokines induced IL-6 mRNA expression in a dose-dependent manner and 48D2 inhibited the increase down to levels comparable with the unstimulated control.

Figure 21:
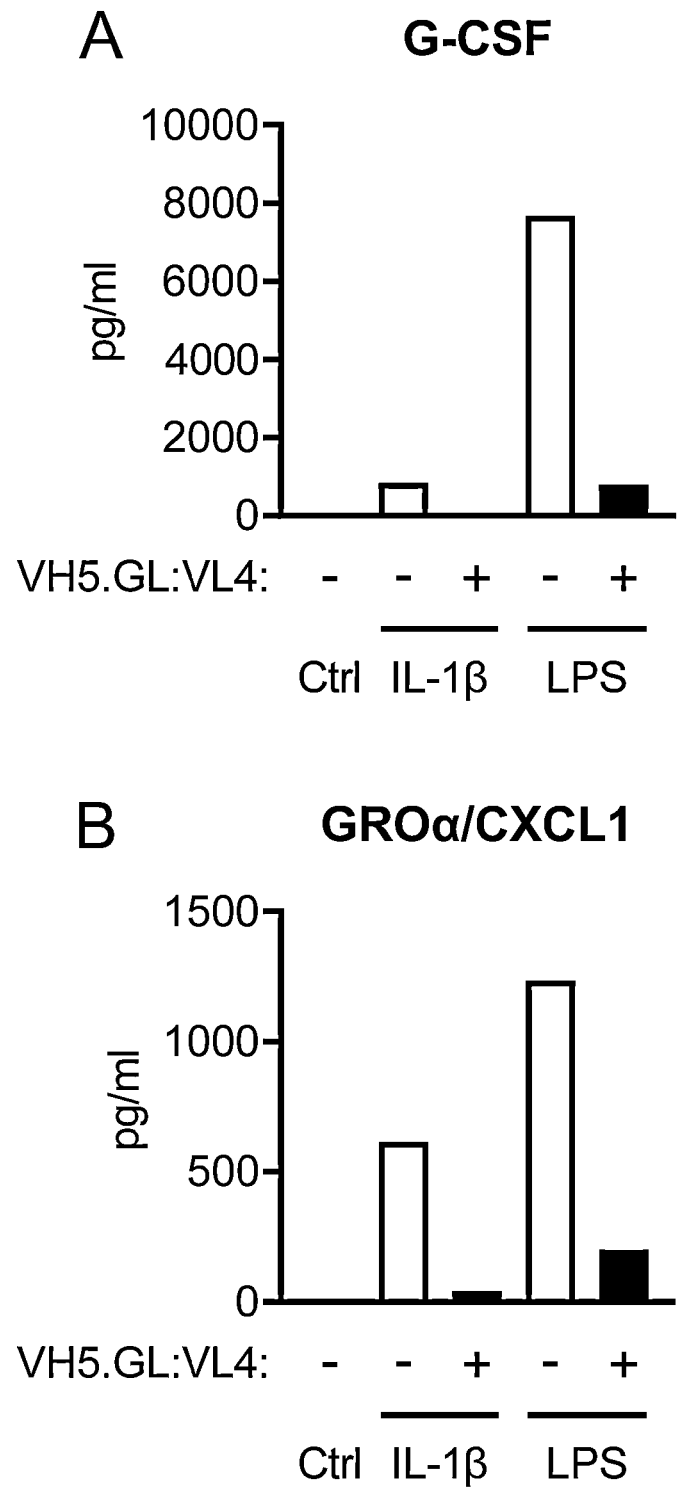
Figure 21:
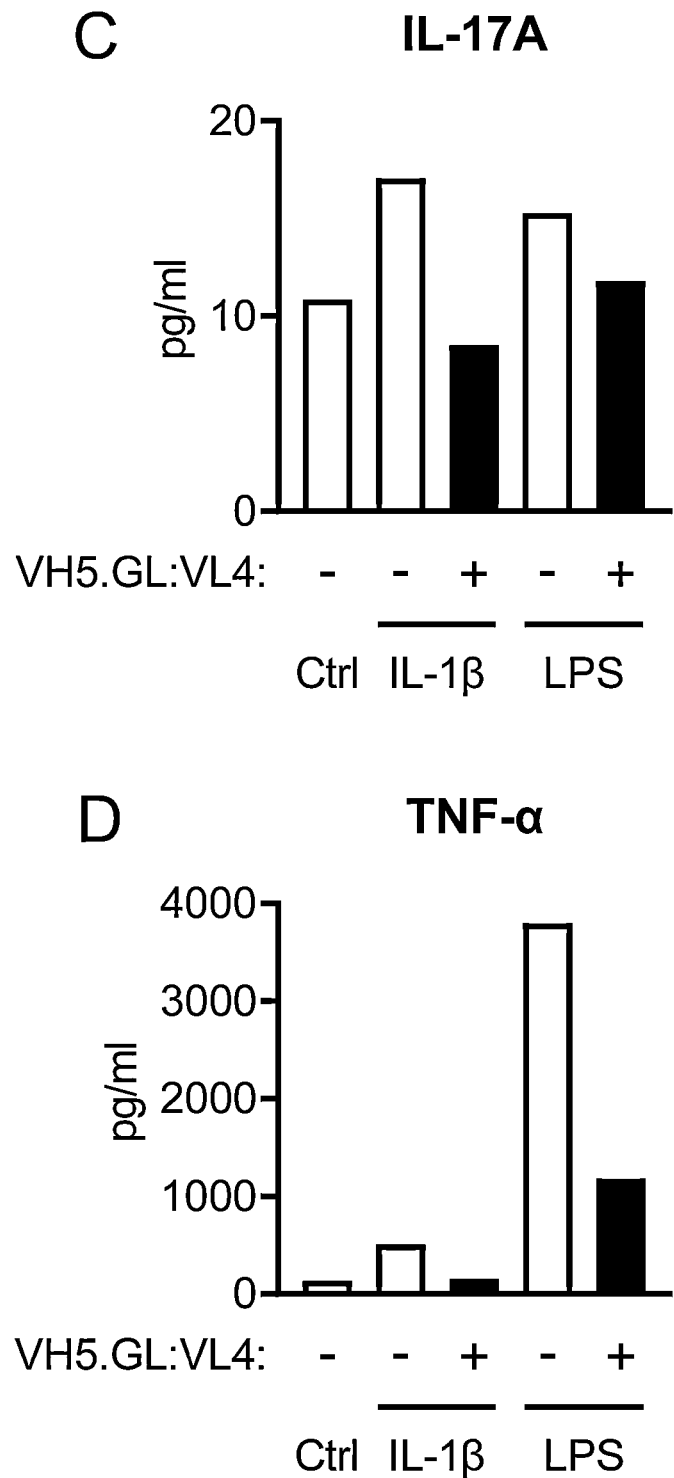

FIG. 21: VH5.GL:VL4 inhibits IL-1β-induced cytokine and chemokine release in human whole blood Blood was collected from two human donors and incubated with VH5.GL:VL4 for 30 min. The blood was subsequently stimulated with either IL-1p or lipopolysaccharide (LPS) for 20 hrs. The plate was centrifuged, and plasma layer collected for analysis by the Human Cytokine/Chemokine 71-Plex Discovery Assay Array. Levels of G-CSF (A), GROα/CXCL1 (B), IL-17A (C) and TNF-α (D) are shown for one of the two donors.

Figure 22:
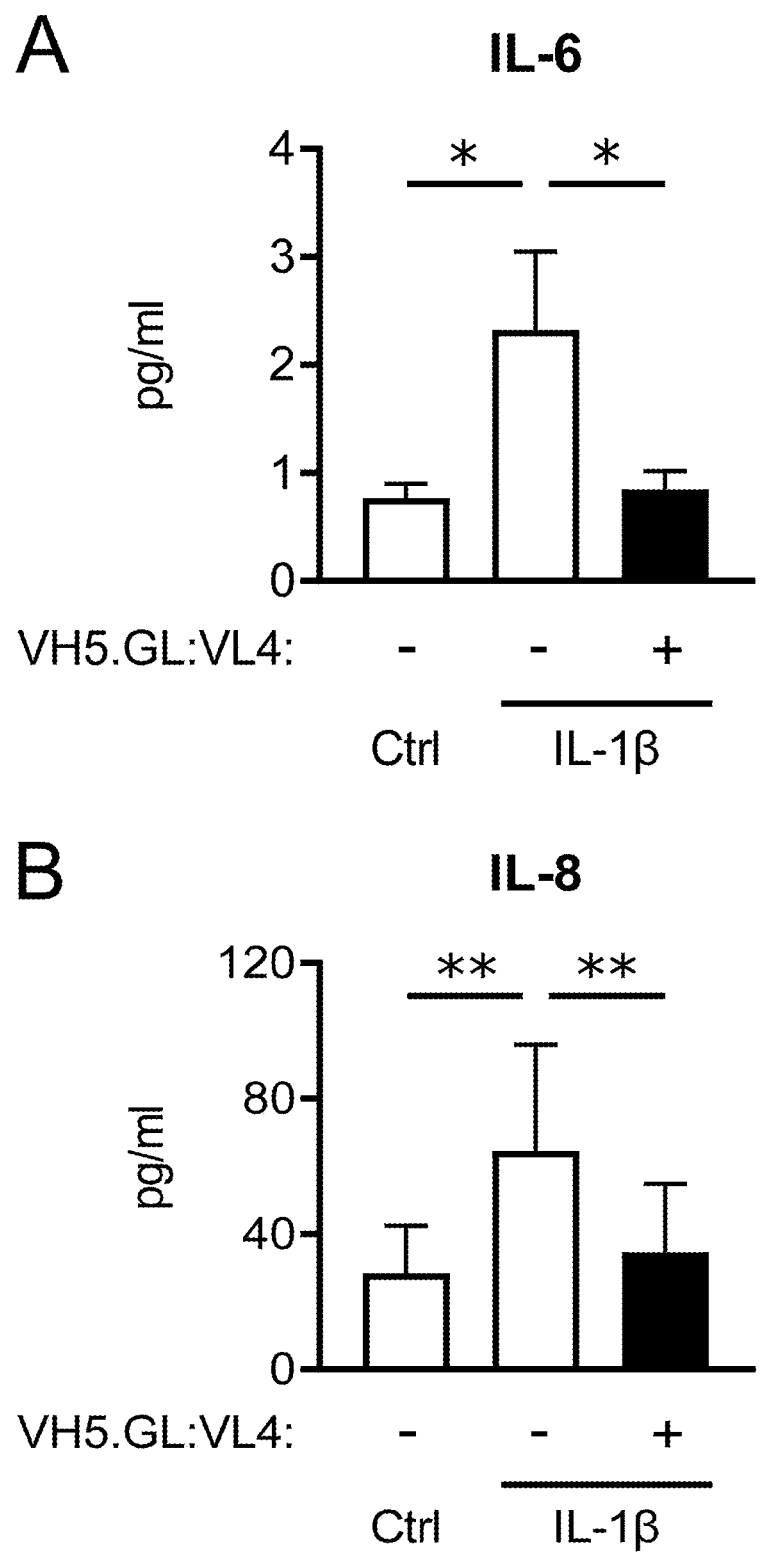

FIG. 22: VH5.GL:VL4 inhibits IL-1β-induced cytokine release in a blood-loop system Blood was collected from ten human donors and transferred to a blood-loop system. VH5.GL:VL4 was administered to the blood at 32 μg/ml and IL-1p at 1 ng/ml was added 15 mins later. The loops were run for 4 hrs. Plasma was obtained from the blood samples and levels of IL-6 (A) and IL-8 (B) measured using the MULTI-ARRAY® technology from MSD.

Figure 23:
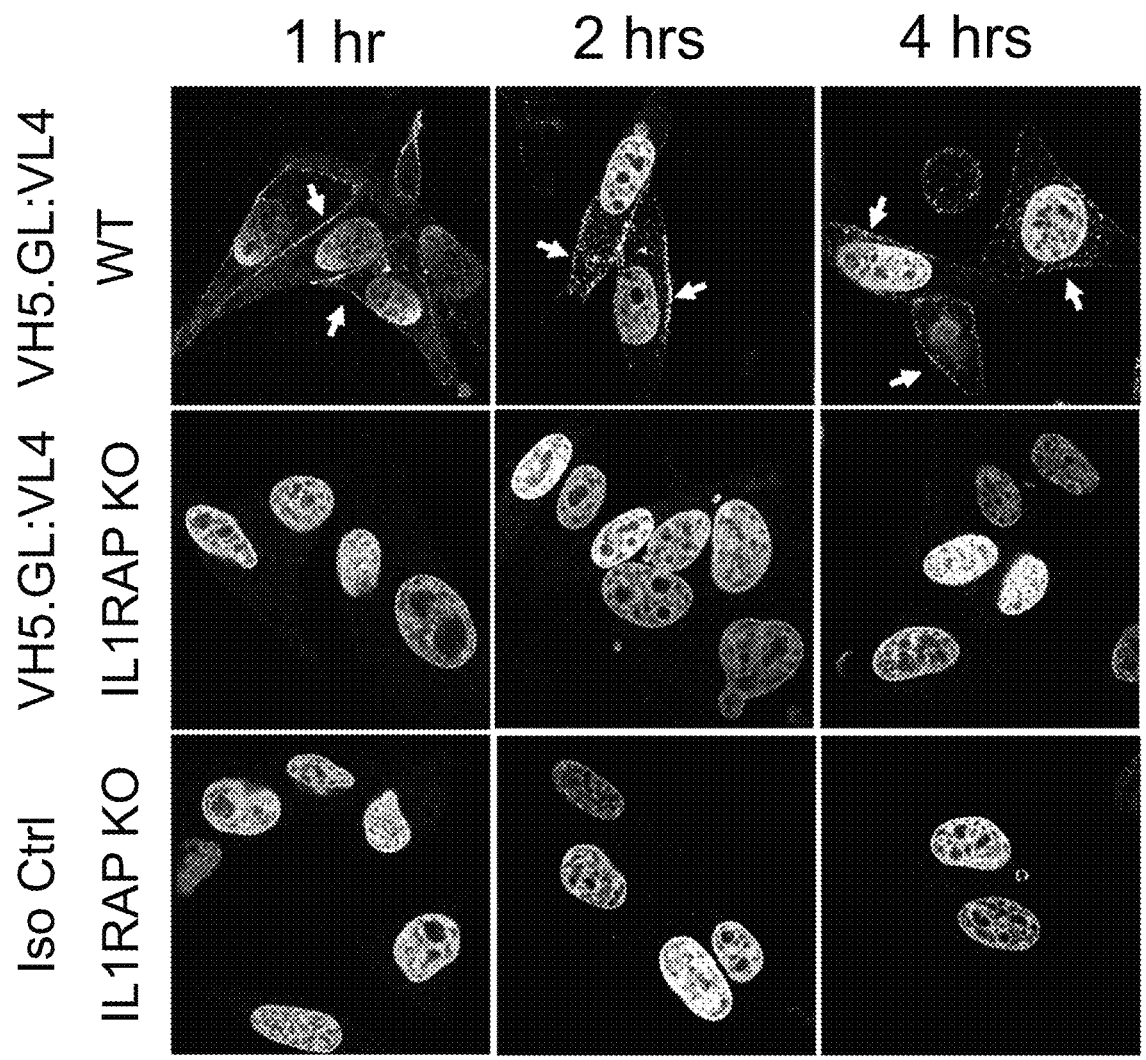

FIG. 23: VH5.GL:VL4 is internalized by IL1RAP-expressing cells

WT and IL1RAP KO SKMEL cells were incubated with fluorescently-conjugated VH5.GL:VL4 or isotype control (Iso Ctrl) for 1, 2 or 4 hrs in Ibidi-treat microscope chamber slides. Cell nuclei were stained by DAPI. Interactive visual analyses were performed of scanned optical sections through the cells, and representative images captured to evaluate membrane binding and internalization of VH5.GL:VL4 (indicated by arrows).

Figure 24:
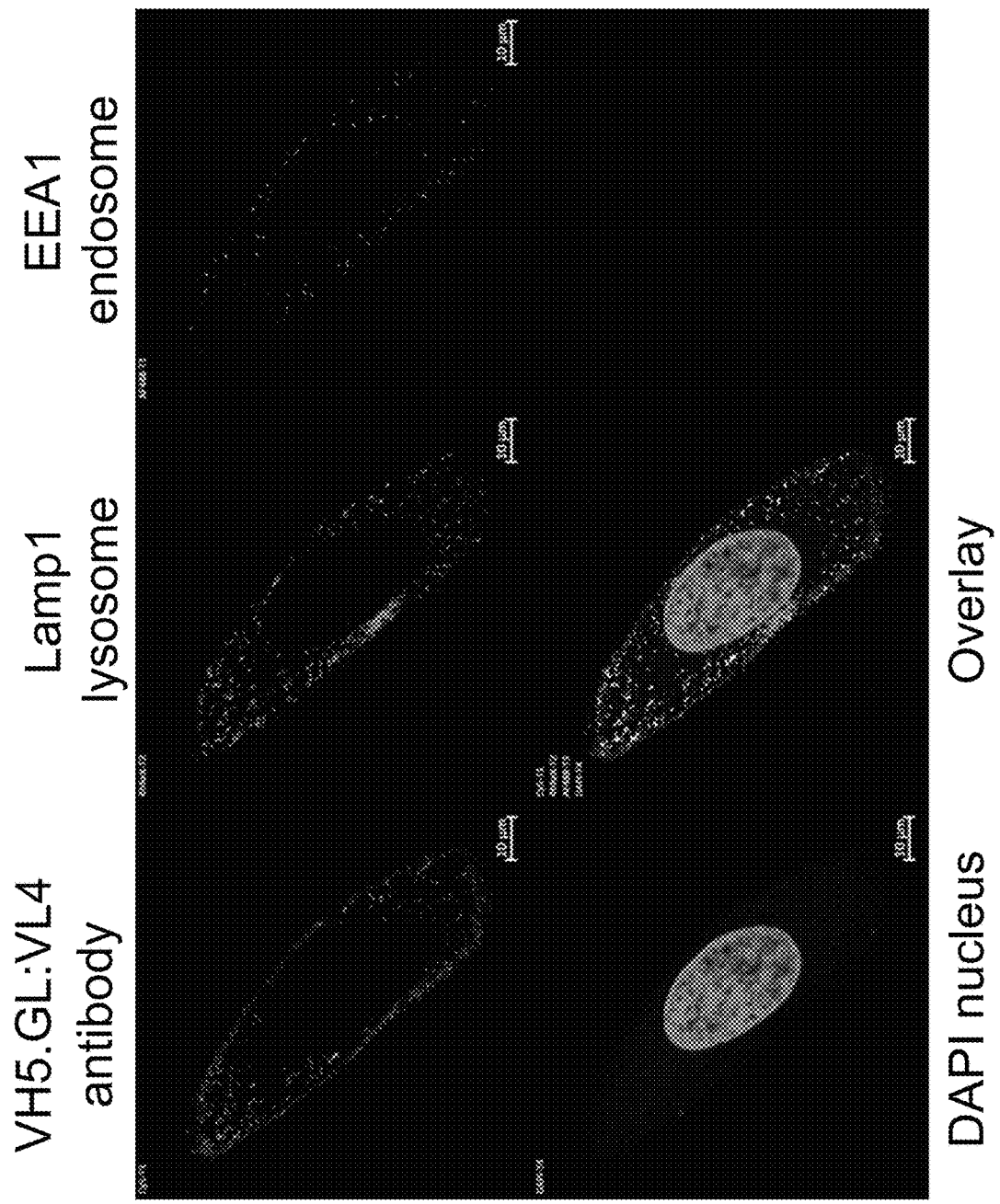

FIG. 24: VH5.GL:VL4 localizes to lysosomes or endosomes upon internalization by IL1RAP-expressing cells WT SKMEL cells were incubated with fluorescently-conjugated VH5.GL:VL4 for 1, 2 or 4 hrs in Ibidi-treat microscope chamber slides. The cells were additionally stained for the markers EEA1 and Lamp1 to detect endosomes and lysosomes, respectively. Cell nuclei were stained by DAPI. Interactive visual analyses were performed of scanned optical sections through the cells, and representative images captured to evaluate overlap of VH5.GL:VL4 staining with EEA1 and Lamp1 staining.

Figure 25:
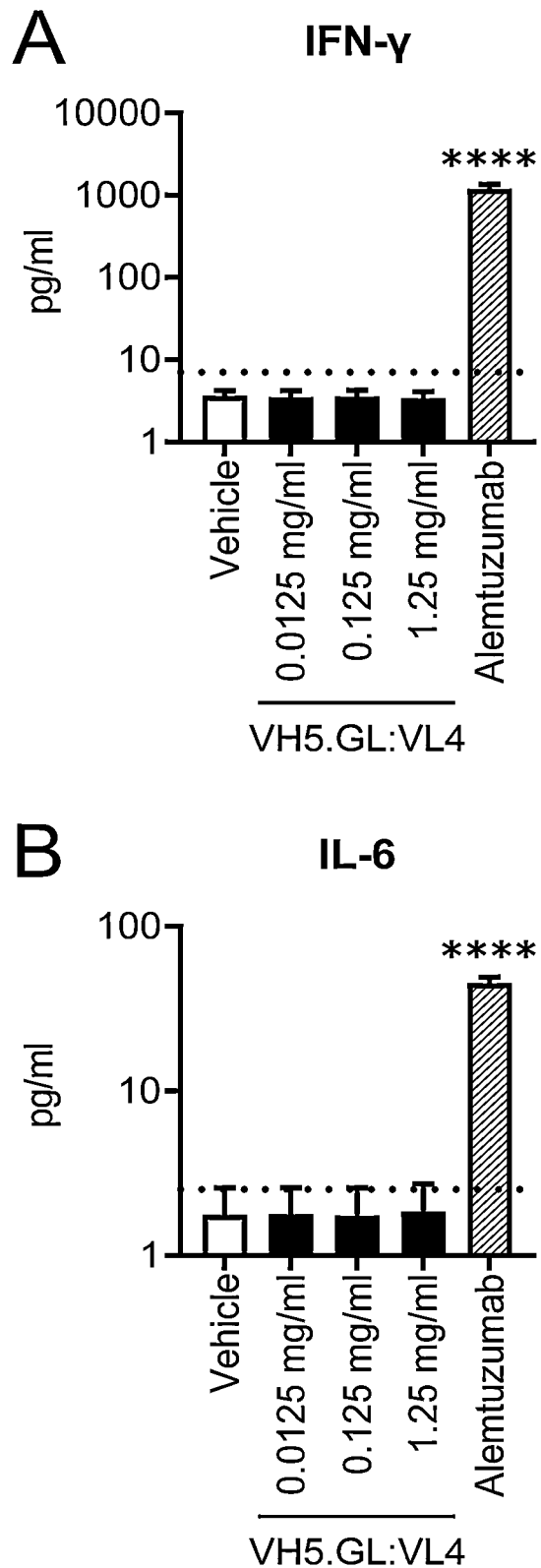
Figure 25:
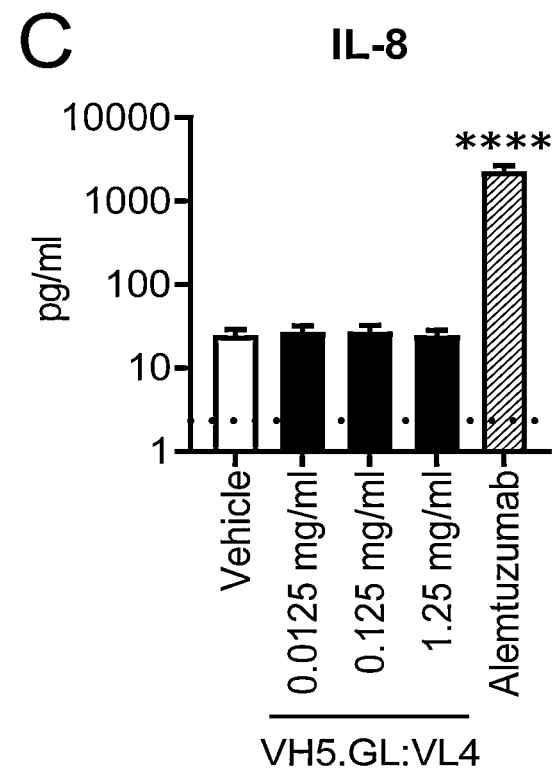
Figure 25:
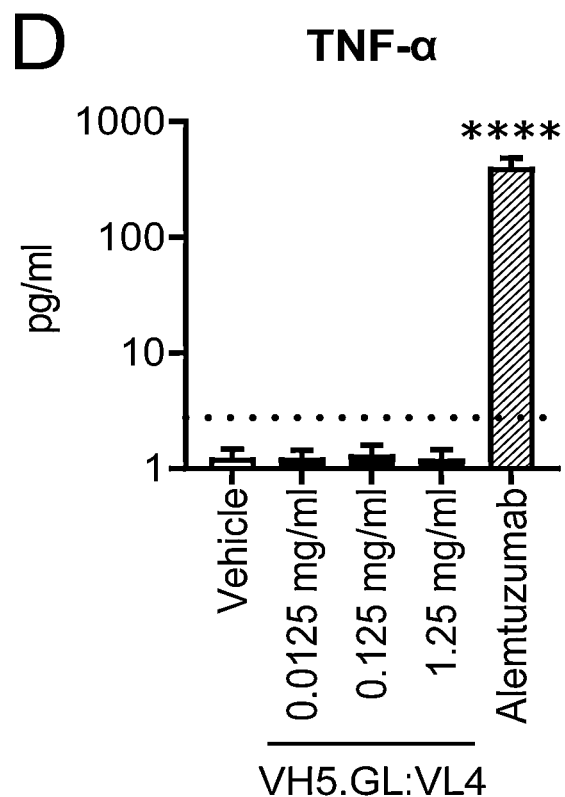

FIG. 25: VH5.GL:VL4 in hIgG1-LALA format does not induce Fc-mediated cytokine release Blood was collected from ten human donors and transferred to a blood-loop system. VH5.GL:VL4 was added to the blood at increasing concentrations as indicated. Alternatively, the anti-CD52 antibody alemtuzumab was added. The loops were run for 4 hrs. Plasma was obtained from the blood samples and levels of IFN-γ (A), IL-6 (B), IL-8 (C) and TNF-α (D) measured using the MULTI-ARRAY® technology from MSD.

Figure 26:
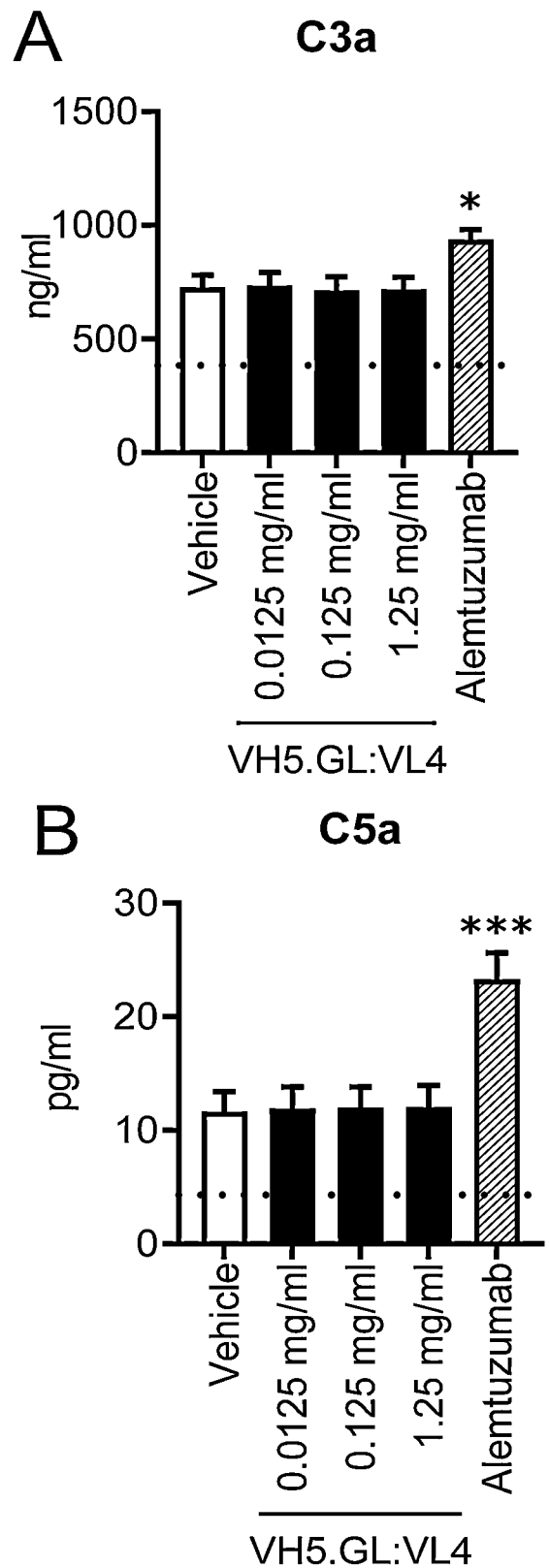

FIG. 26: VH5.GL:VL4 in hIgG1-LALA format does not induce Fc-mediated complement activation Blood was collected from ten human donors and transferred to a blood loop system. VH5.GL:VL4 was added to the blood at increasing concentrations as indicated. Alternatively, the anti-CD52 antibody alemtuzumab was added. The loops were run for 15 min. Plasma was obtained from the blood samples and complement activation was analyzed by measurement of the complement split products C3a (A) and C5a (B) using the ELISA kit from RayBiotech.

Figure 27:
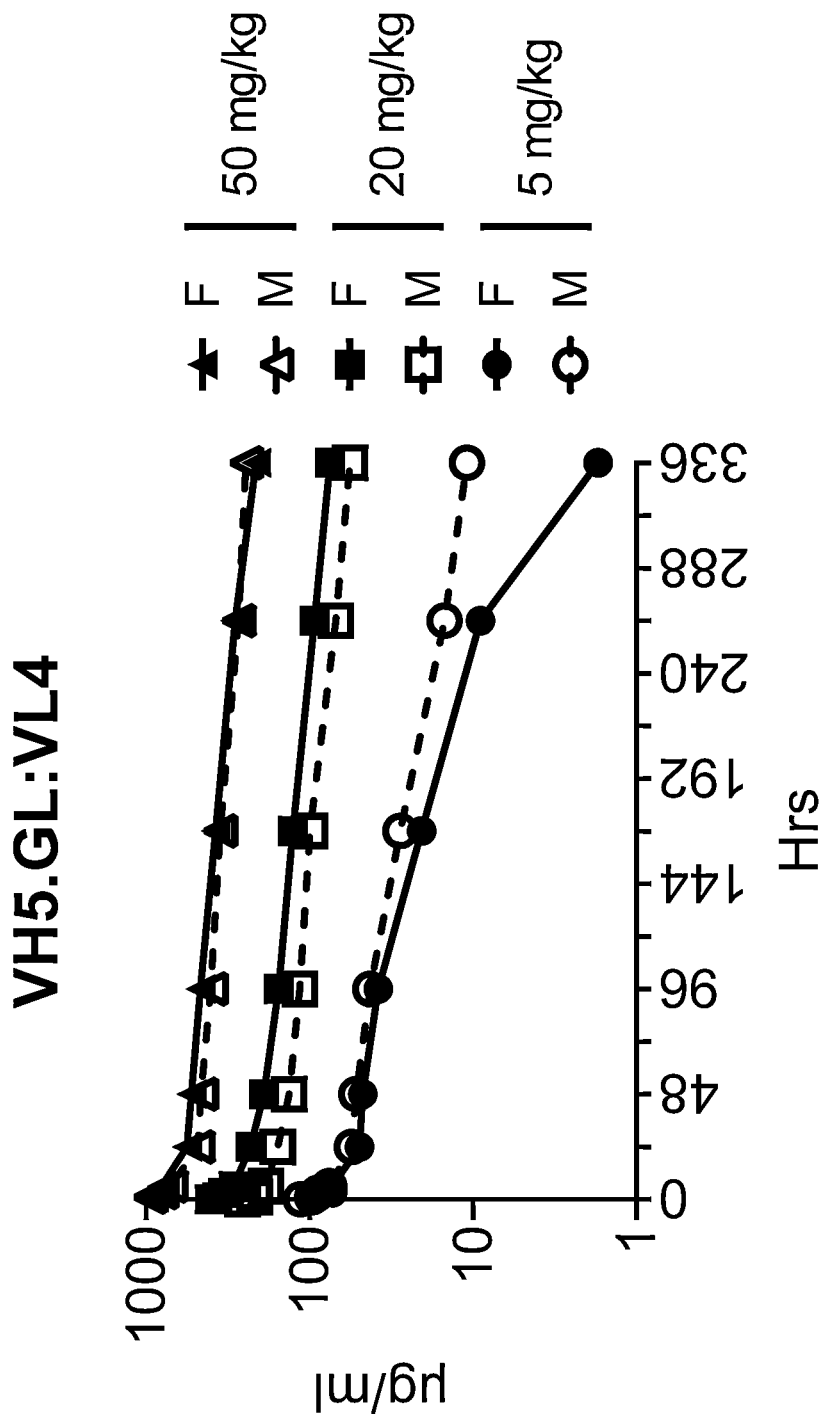

FIG. 27: Serum concentrations of VH5.GL:VL4 after single intravenous administration to cynomolgus monkeys VH5.GL:VL4 was administered intravenously at 5, 20 or 50 mg/kg as a single dose to one male (M) and one female (F) cynomolgus monkey for each dose level evaluated. Blood samples were collected at 0.083, 1, 3, 6, 24, 48, 96, 168, 264 and 336 hrs after administration and serum obtained. The serum samples were transferred to IL1RAP-coated MSD plates and VH5.GL:VL4 in the samples detected by adding an anti-human IgG antibody conjugated to an electrochemiluminescent label and measuring the intensity of emitted light.

Figure 28:
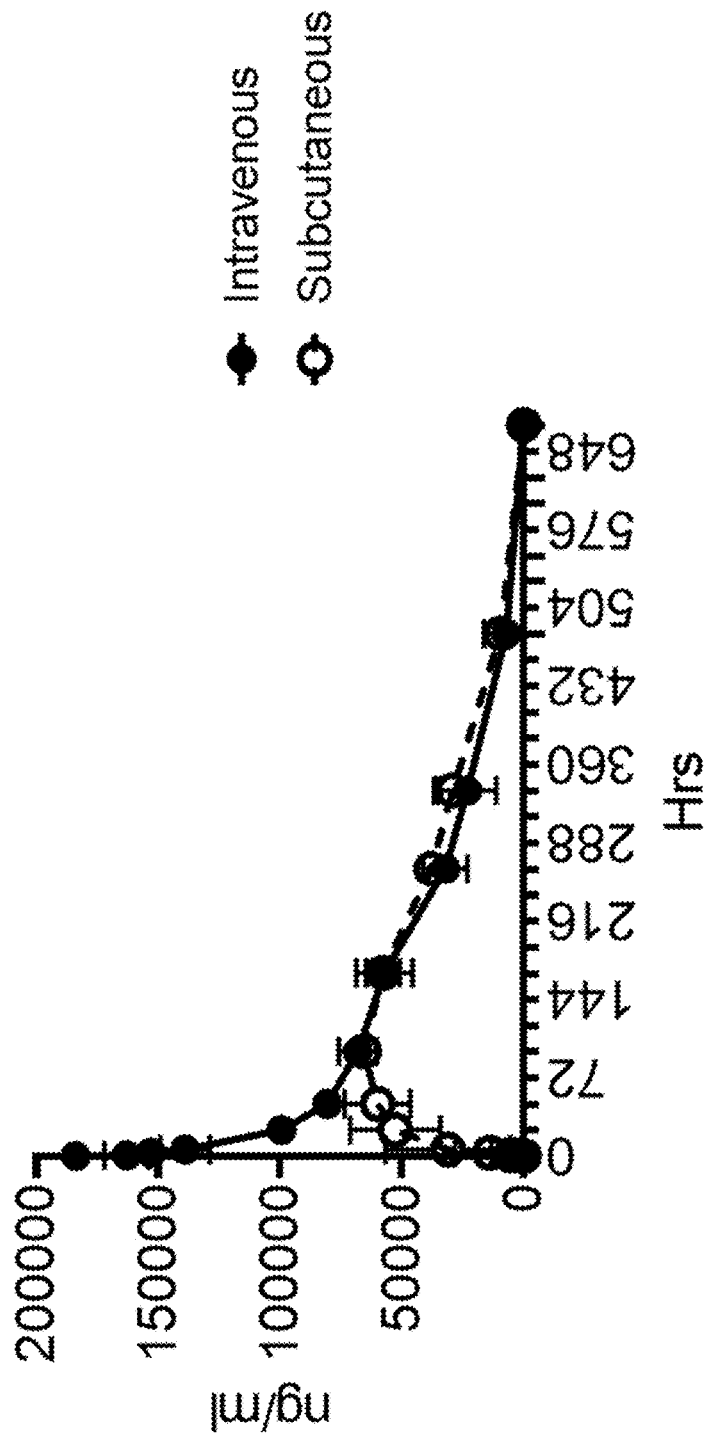

FIG. 28: Serum concentrations of VH5.GL:VL4 after single intravenous or subcutaneous administration to cynomolgus monkeys VH5.GL:VL4 was administered intravenously or subcutaneously at 10 mg/kg as a single dose to two female cynomolgus monkeys. Blood samples were collected at 0.083, 0.5, 1, 3, 6, 24, 48, 96, 168, 264, 336, 480 and 672 hrs after administration and serum obtained. The serum samples were transferred to IL1RAP-coated MSD plates and VH5.GL:VL4 in the samples detected by adding an anti-human IgG antibody conjugated to an electrochemiluminescent label and measuring the intensity of emitted light.

DETAILED DESCRIPTION

As used herein, the singular forms "a", "an" and "the" include plural referents unless the context clearly states otherwise. Thus, for example, reference to "an antibody" includes a plurality of such antibodies, such as one or more antibodies, at least one antibody, or two or more antibodies. Similarly, "an anti-IL1RAP antibody" can also refer to "anti-IL1RAP antibodies", as for example the antibody variants described in Examples 9 to 22.

The term "some embodiments" can include one, or more than one embodiment.

The use of the word "a" or "an" when used throughout the text or in conjunction with the term "comprising" in the claims and/or the specification may mean "one," but it is also consistent with the meaning of "one or more," "at least one," and "one or more than one."

IL1RAP Antibody

A first aspect of the invention relates to an antibody or antigen-binding fragment thereof with binding specificity for interleukin-1 receptor accessory protein (IL1RAP), wherein the antibody or antigen-binding fragment comprises:

a light chain variable region comprising a) a CDR-L1 comprising or consisting of an amino acid sequence selected from the group consisting of ESISTA (SEQ ID NO: 1), QASESISTALA (SEQ ID NO: 7) and QASESISTALA (SEQ ID NO: 13);

b) a CDR-L2 comprising or consisting of an amino acid sequence selected from the group consisting of KAS, KASTLPS (SEQ ID NO: 8) and KASTLPS (SEQ ID NO: 14); and/or c) a CDR-L3 comprising or consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15);

and/or a heavy chain variable region comprising d) a CDR-H1 comprising or consisting of an amino acid sequence selected from the group consisting of GPSLSHFD (SEQ ID NO: 4), HFDIT (SEQ ID NO: 10) and GPSLSHFDIT (SEQ ID NO: 16);

e) a CDR-H2 comprising or consisting of an amino acid sequence selected from the group consisting of ISPGVST (SEQ ID NO: 5), TISPGVSTYYASWAKS (SEQ ID NO: 11) and TISPGVSTYYASWAKS (SEQ ID NO: 17); and f) a CDR-H3 comprising or consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

In some embodiments, the antibody or antigen-binding fragment thereof with binding specificity for IL1RAP comprises:

a light chain variable region comprising a) a CDR-L1 consisting of an amino acid sequence selected from the group consisting of ESISTA (SEQ ID NO: 1), QASESISTALA (SEQ ID NO: 7) and QASESISTALA (SEQ ID NO: 13);

b) a CDR-L2 consisting of an amino acid sequence selected from the group consisting of KAS, KASTLPS (SEQ ID NO: 8) and KASTLPS (SEQ ID NO: 14); and c) a CDR-L3 consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15); and/or
a heavy chain variable region comprising
d) a CDR-H1 consisting of an amino acid sequence selected from the group consisting of GPSLSHFD (SEQ ID NO: 4), HFDIT (SEQ ID NO: 10) and GPSLSHFDIT (SEQ ID NO: 16);
e) a CDR-H2 consisting of an amino acid sequence selected from the group consisting of ISPGVST (SEQ ID NO: 5), TISPGVSTYYASWAKS (SEQ ID NO: 11) and TISPGVSTYYASWAKS (SEQ ID NO: 17); and
f) a CDR-H3 consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

The terms "interleukin-1 receptor accessory protein", "IL1RAP" and "IL1-RAP" as used herein specifically include the human IL1RAP protein, for example as described in GenBank Accession No. AAB84059, NCBI Reference Sequence: NP_002173.1 and UniProtKB/Swiss-Prot Accession No. Q9NPH3-1. IL1RAP is also known in the scientific literature as IL1R3, C3orf13, FLJ37788, IL-1RAcP and EG3556.

The term "mCAN10" (abbreviation for "murine CAN10") as used herein refers to an antibody against murine IL1RAP. This antibody is also denoted as murine surrogate anti-IL1RAP antibody. mCAN10 is capable of blocking signaling by IL-1α, IL-1β, IL-33, IL-36α, IL-36β and/or IL-36γ. mCAN10 can therefore be used for evaluating therapeutic efficacy of IL1RAP blockade in murine disease models as a surrogate to anti-human IL1RAP antibodies that may lack cross-reactivity to mouse IL1RAP, with similar functional properties.

The term "48D2" as used herein refers to an antibody against human IL1RAP, notwithstanding that the antibody may also bind to IL1RAP from other species. For example, it will be understood from Example 10 that 48D2 is cross reactive to IL1RAP from human, cynomolgus monkey and pig. As will be understood from Example 9 and Example 10, the term "48D2" may be used for denoting the chimeric antibody (also referred to as "ch48D2") obtained as described in Example 9 and characterized in Example 10.

The term "h48D2" as used herein refers to the antibody 48D2 that has been humanized as generated in Example 11, and as further characterized in Example 12. As described in Example 12, several variants of h48D2 have been obtained (see for example Table 8). As described in Example 13 several further variants of h48D2 have been obtained by de-immunization.

It will be appreciated that "the antibody or antigen-binding fragment of the invention" can be referred to as "the polypeptide of the invention" or "the antibody polypeptide, or antigen-binding fragment thereof", since an antibody and fragments thereof are polypeptides.

The antibody or antigen-binding fragment of the invention has specificity for IL1RAP. By "specificity" it is meant that the antibody or antigen-binding fragment is capable of binding to IL1RAP in vivo, i.e. under the physiological conditions in which IL1RAP exists within the human body. Preferably, the antibody or antigen-binding fragment does not bind to any other protein in vivo. Alternatively, it is meant that the antibody or antigen-binding fragment is capable of binding to IL1RAP ex vivo or in vitro. Such binding specificity may be determined by methods well known in the art, such as ELISA, immunohistochemistry, immunoprecipitation, Western blots and flow cytometry using transfected cells expressing IL1RAP. Advantageously, the antibody or antigen-binding fragment is capable of binding selectively to IL1RAP, i.e. it binds at least 10-fold more strongly to IL1RAP than to any other proteins.

In some embodiments, the antibody or antigen-binding fragment thereof with binding specificity for IL1RAP binds to human IL1RAP.

In some embodiments, the antibody or antigen-binding fragment thereof with binding specificity for IL1RAP binds to non-human IL1RAP.

In some embodiments, the antibody or antigen-binding fragment thereof with binding specificity for IL1RAP binds to IL1RAP from cynomolgus monkey.

In some embodiments, the antibody or antigen-binding fragment thereof with binding specificity for IL1RAP binds to IL1RAP from pig.

In some embodiments, the antibody or antigen-binding fragment thereof with binding specificity for IL1RAP binds IL1RAP expressed on the surface of a cell.

In some embodiments, the antibody or antigen-binding fragment thereof with binding specificity for IL1RAP binds to an epitope on the extracellular domain of IL1RAP.

In some embodiments, the antibody or antigen-binding fragment thereof with binding specificity for IL1RAP binds to soluble IL1RAP.

In some embodiments, the antibody or antigen-binding fragment thereof with binding specificity for IL1RAP binds to domain 2 of IL1RAP.

In some embodiments, the antibody or antigen-binding fragment thereof with binding specificity for IL1RAP binds IL1RAP at or within the amino acids 135 to 234 of IL1RAP.

Thus, the antibody or antigen-binding fragment may be capable of binding to an epitope located at/within domain 2 of IL1RAP (see Wang et al., 2010, Nature Immunology, 11:905-912, the disclosures of which are incorporated herein by reference), i.e. within amino acids 135 to 234 of IL1RAP (see Accession No. Q9NPH3 within UniProtKB/Swiss-Prot). For example, the epitope to which the antibody or antigen-binding fragment may be located within amino acids 135 to 154, 155 to 174, 175 to 194, 195 to 214 or between amino acids 215 to 234, or between amino acids 174 to 191 of IL1RAP. However, it will be appreciated that the epitope may be non-linear.

In a further embodiment, as discussed above, the antibody or antigen-binding fragment of the invention comprises or consists of an antibody mimic selected from the group comprising or consisting of affibodies, tetranectins (CTLDs), adnectins (monobodies), anticalins, DARPins (ankyrins), avimers, iMabs, microbodies, peptide aptamers, Kunitz domains and affilins.

The term "an antibody or an antigen-binding fragment thereof" includes substantially intact antibodies as well as fragments and derivatives of antibodies. An intact antibody can be regarded as an antibody comprising variable light regions, variable heavy regions, constant light regions and constant heavy regions. The term further includes chimeric antibodies, humanised antibodies, isolated human antibodies, single chain antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include, but are not necessarily limited to, Fv fragments (e.g. single chain Fv and disulphide-bonded Fv), Fab-like fragments (e.g. Fab fragments, Fab' fragments and F(ab)$_2$ fragments), single variable domains (e.g. V$_H$ and V$_L$ domains) and domain antibodies (dAbs, including single and dual formats [i.e. dAb-linker-dAb]). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

The phrase "an antibody or an antigen-binding fragment thereof" is also intended to encompass antibody mimics (for example, non-antibody scaffold structures that have a high degree of stability yet allow variability to be introduced at certain positions). Those skilled in the art of biochemistry will be familiar with many such molecules, as discussed in Gebauer & Skerra, 2009, *Curr Opin Chem Biol* 13(3): 245-255 (the disclosures of which are incorporated herein by reference). Exemplary antibody mimics include: affibodies (also called Trinectins; Nygren, 2008, *FEBS J*, 275, 2668-2676); CTLDs (also called Tetranectins; *Innovations Pharmac. Technol.* (2006), 27-30); adnectins (also called monobodies; *Meth. Mol. Biol.*, 352 (2007), 95-109); anticalins (*Drug Discovery Today* (2005), 10, 23-33); DARPins (ankyrins; *Nat. Biotechnol.* (2004), 22, 575-582); avimers (*Nat. Biotechnol.* (2005), 23, 1556-1561); microbodies (*FEBS J*, (2007), 274, 86-95); peptide aptamers (*Expert. Opin. Biol. Ther.* (2005), 5, 783-797); Kunitz domains (*J. Pharmacol. Exp. Ther.* (2006) 318, 803-809); affilins (*Trends. Biotechnol.* (2005), 23, 514-522); affimers (Avacta Life Sciences, Wetherby, UK).

Also included within the scope of the invention are chimeric T cell receptors (also known as chimeric T cell receptors, chimeric immunoreceptors, and chimeric antigen receptors or CARs) (see Pule et al., 2003, *Cytotherapy* 5(3):211-26, the disclosures of which are incorporated herein by reference). These are engineered receptors, which graft an arbitrary specificity onto an immune effector cell. Typically, CARs are used to graft the specificity of a monoclonal antibody onto a T cell; with transfer of their coding sequence facilitated by retroviral vectors. The most common form of such molecules is fusions comprising a single-chain variable fragment (scFv) derived from a monoclonal antibody fused to CD3-zeta transmembrane and endodomain. When T cells express this fusion molecule, they recognize and kill target cells that express the transferred monoclonal antibody specificity.

Persons skilled in the art will further appreciate that the invention also encompasses modified versions of antibodies and antigen-binding fragments thereof, whether existing now or in the future, e.g. modified by the covalent attachment of polyethylene glycol or another suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299, the disclosures of which are incorporated herein by reference) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120, the disclosures of which are incorporated herein by reference).

Suitable methods for the production of monoclonal antibodies are also disclosed in "*Monoclonal Antibodies: A manual of techniques*", H Zola (CRC Press, 1988, the disclosures of which are incorporated herein by reference) and in "*Monoclonal Hybridoma Antibodies: Techniques and Applications*", J G R Hurrell (CRC Press, 1982, the disclosures of which are incorporated herein by reference).

Likewise, antibody fragments can be obtained using methods well known in the art (see, for example, Harlow & Lane, 1988, "Antibodies: A Laboratory Manual". Cold Spring Harbor Laboratory, New York, the disclosures of which are incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

The term "amino acid" as used herein includes the standard twenty genetically-encoded amino acids and their corresponding stereoisomers in the 'D' form (as compared to the natural 'L' form), omega-amino acids and other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides (the antibody or antigen-binding fragment thereof) of the present invention, as long as the desired functional property is retained by the antibody or antigen-binding fragment. For the amino acid sequences shown, each encoded amino acid residue, where appropriate, is represented by a single letter designation, corresponding to the trivial name of the conventional amino acid.

In some embodiments, the antibody or antigen-binding fragment thereof of the present invention and as defined herein comprises or consists of L-amino acids.

It will be appreciated by persons skilled in the art that for human therapy, human or humanised antibodies are preferably used. Humanised forms of non-human antibodies (e.g. rabbit antibodies as described in Examples 9 and 10) are genetically engineered chimeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat or rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody. As discussed elsewhere herein, humanised antibodies may lack cross-reactivity to mouse IL1RAP. As such, suitable surrogates (e.g. mCAN10) that exhibit similar functional properties to the humanized antibodies can be used in murine disease models, where the surrogate results could be interpreted to reflect the functionality of the humanised antibody.

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed by substituting human complementarity determining regions with corresponding rodent complementarity determining regions. Accordingly, such humanised antibodies are chimeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries.

The optimization of antibodies, for example by humanization (see, for example, Jones et al., 1986, Nature 321: 522-525; Reichmann et al., 1988. Nature 332:323-327; Verhoeyen et al., 1988, Science 239:1534-15361; U.S. Pat. No. 4,816,567, the disclosures of which are incorporated herein by reference) and/or de-immunization, as for example described in Jones et al. (Methods Mol Biol. 2009; 525:405-23) or in Examples 11 and 13, leads to the generation of antibody variants with fine-tuned properties.

CDRs

The antibody of the present invention is defined by its characteristic complementarity-determining region (CDR) sequences. There are several approaches for defining the CDR sequences of an antibody. The CDRs of the antibody of the present invention have been defined using three different and well-known approaches (resulting in three CDR-defining categories): 1) definition according to Kabat, 2) definition according to IMGT or 3) definition according to a combination of IMGT and Kabat.

It is important to note that within each CDR-defining category (Kabat, IMGT or combination of IMGT and Kabat, respectively), the CDR sequences are the same for the chimeric antibody 48D2 and all optimized antibody variants thereof, such as humanized antibody variants or humanized/de-immunized antibody variants (see indicated in the respective sequences in section "Sequences").

The person skilled in the art will appreciate that a set of 6 CDRs (CDR-L1, CDR-L2, CDR-L3, CDR-H1, CDR-H2, CDR-H3) may be defined according to either i) IMGT or ii) Kabat or iii) a combination of Kabat and IMGT.

Further, the person skilled in the art will appreciate that it is possible to define the CDRs of the antibody of the invention by other approaches known in the art, for example by definition of CDRs according to Chothia (Al-Lazikani et al., (1997) JMB 273, 927-948), Martin (Enhanced Chothia), Gelfand or Honneger. Further approaches exist and are known in the art, such as the AbM definition (combination of Kabat definition and Chothia definition used by Oxford Molecular's AbM antibody modelling software) or the contact definition (based on analysis of crystal structures). See, e.g., Kabat et al. (Sequences of Proteins of Immunological Interest, 1987 and 1991, NIH, Bethesda, Md.), Lefranc et al. (IMGT unique numbering for immunoglobulin and T cell receptor constant domains and Ig superfamily C-like domains, Dev Comp Immunol. 2005; 29(3):185-203) and Dondelinger et al. (Understanding the Significance and Implications of Antibody Numbering and Antigen-Binding Surface/Residue Definition, Front. Immunol., 16 Oct. 2018).

The person skilled in the art could, when provided with the IMGT and Kabat CDRs as presented herein, use known information to list other CDR naming conventions or approaches (e.g., Chothia). Thus, all CDR naming conventions or approaches are encompassed.

As shown herein, the numbering systems of IMGT and Kabat identified slightly different residues as CDRs. In certain cases, it can be beneficial to define the CDRs according to one numbering system, such as either IMGT or Kabat. Often, these CDR sequences are short (shorter than, for example, an approach combining numbering systems), thus providing the core sequences critical for binding. In other cases, it can be beneficial to use a combination of, for example, IMGT and Kabat CDR sequences.

In some embodiments, the antibody or antigen-binding fragment thereof with binding specificity for interleukin-1 receptor accessory protein (IL1RAP) comprises: a light chain variable region comprising a) a CDR-L1 comprising or consisting of the amino acid sequence of ESISTA (SEQ ID NO: 1); a CDR-L2 comprising or consisting of the amino acid sequence of KAS; and a CDR-L3 comprising or consisting of the amino acid sequence of QQGFSSGNVHNA (SEQ ID NO: 3); or b) a CDR-L1 comprising or consisting of the amino acid sequence of QASESISTALA (SEQ ID NO: 7); a CDR-L2 comprising or consisting of the amino acid sequence of KASTLPS (SEQ ID NO: 8); and a CDR-L3 comprising or consisting of the amino acid sequence of QQGFSSGNVHNA (SEQ ID NO: 9); or c) a CDR-L1 comprising or consisting of the amino acid sequence of QASESISTALA (SEQ ID NO: 13); a CDR-L2 comprising or consisting of the amino acid sequence of KASTLPS (SEQ ID NO: 14); and a CDR-L3 comprising or consisting of the amino acid sequence of QQGFSSGNVHNA (SEQ ID NO: 15)

and/or a heavy chain variable region comprising d) a CDR-H1 comprising or consisting of the amino acid sequence of GPSLSHFD (SEQ ID NO: 4); a CDR-H2 comprising or consisting of the amino acid sequence of ISPGVST (SEQ ID NO: 5); and a CDR-H3 comprising or consisting of the amino acid sequence of ARGGVGSSWKAFDL (SEQ ID NO: 6); or e) a CDR-H1 comprising or consisting of the amino acid sequence of HFDIT (SEQ ID NO: 10); a CDR-H2 comprising or consisting of the amino acid sequence of TISPGVSTYYASWAKS (SEQ ID NO: 11); and a CDR-H3 comprising or consisting of the amino acid sequence of GGVGSSWKAFDL (SEQ ID NO: 12); or f) a CDR-H1 comprising or consisting of the amino acid sequence of GPSLSHFDIT (SEQ ID NO: 16); a CDR-H2 comprising or consisting of the amino acid sequence of TISPGVSTYYASWAKS (SEQ ID NO: 17); and a CDR-H3 comprising or consisting of the amino acid sequence of ARGGVGSSWKAFDL (SEQ ID NO: 18).

The relation between the differently defined sets of CDR sequences of antibody 48D2 can be described as followed, with CDR residues highlighted in bold that were identified using the IMGT numbering system,
CDR residues highlighted by underlining that were identified using the Kabat numbering system
CDR residues defined by a combination of the IMGT and the Kabat numbering system (combination of bold and underlined sequences)
Variable light chain complementarity-determining region 1 (CDR-L1)
QASESISTALA
(SEQ ID NO: 1, SEQ ID NO: 7, SEQ ID NO: 13, respectively)
Variable light chain complementarity-determining region 2 (CDR-L2)
KASTLPS
(SEQ ID NO: 8, SEQ ID NO: 14, respectively)
Variable light chain complementarity-determining region 3 (CDR-L3)
QQGFSSGNVHNA
(SEQ ID NO: 3, SEQ ID NO: 9, SEQ ID NO: 15, respectively)
Variable heavy chain complementarity-determining region 1 (CDR-H1)
GPSLSHFDIT
(SEQ ID NO: 4, SEQ ID NO: 10, SEQ ID NO: 16, respectively)
Variable heavy chain complementarity-determining region 2 (CDR-H2)
TISPGVSTYYASWAKS
(SEQ ID NO: 5, SEQ ID NO: 11, SEQ ID NO: 17, respectively)
Variable heavy chain complementarity-determining region 3 (CDR-H3)
ARGGVGSSWKAFDL
(SEQ ID NO: 6, SEQ ID NO: 12, SEQ ID NO: 18, respectively)

In some embodiments, the CDR sequences of the antibody or antigen-binding fragment thereof with binding specificity for IL1RAP are defined according to IMGT:
SEQ ID NO: 1
Variable light chain complementarity-determining region 1 (CDR-L1)
ESISTA
Variable light chain complementarity-determining region 2 (CDR-L2)
KAS
SEQ ID NO: 3
Variable light chain complementarity-determining region 3 (CDR-L3)
QQGFSSGNVHNA
SEQ ID NO:4
Variable heavy chain complementarity-determining region 1 (CDR-H1)
GPSLSHFD
SEQ ID NO: 5
Variable heavy chain complementarity-determining region 2 (CDR-H2)
ISPGVST
SEQ ID NO: 6
Variable heavy chain complementarity-determining region 3 (CDR-H3)
ARGGVGSSWKAFDL In some embodiments, the CDR sequences of the antibody or antigen-binding fragment thereof with binding specificity for IL1RAP are defined according to Kabat:
SEQ ID NO: 7
Variable light chain complementarity-determining region 1 (CDR-L1)
QASESISTALA
SEQ ID NO: 8
Variable light chain complementarity-determining region 2 (CDR-L2)
KASTLPS
SEQ ID NO: 9
Variable light chain complementarity-determining region 3 (CDR-L3)
QQGFSSGNVHNA
SEQ ID NO: 10
Variable heavy chain complementarity-determining region 1 (CDR-H1)
HFDIT
SEQ ID NO: 11
Variable heavy chain complementarity-determining region 2 (CDR-H2)
TISPGVSTYYASWAKS
SEQ ID NO: 12
Variable heavy chain complementarity-determining region 3 (CDR-H3)
GGVGSSWKAFDL In some embodiments, the CDR sequences of the antibody or antigen-binding fragment thereof with binding specificity for IL1RAP are defined according to a combination of IMGT and Kabat:
SEQ ID NO: 13
Variable light chain complementarity-determining region 1 (CDR-L1)
QASESISTALA
SEQ ID NO: 14
Variable light chain complementarity-determining region 2 (CDR-L2)
KASTLPS
SEQ ID NO: 15
Variable light chain complementarity-determining region 3 (CDR-L3)
QQGFSSGNVHNA
SEQ ID NO:16
Variable heavy chain complementarity-determining region 1 (CDR-H1)
GPSLSHFDIT
SEQ ID NO: 17
Variable heavy chain complementarity-determining region 2 (CDR-H2)
TISPGVSTYYASWAKS
SEQ ID NO: 18
Variable heavy chain complementarity-determining region 3 (CDR-H3)
ARGGVGSSWKAFDL However, the person skilled in the art will appreciate that a low level of mutation (typically, just one or two amino acids) within a CDR sequence may be tolerated without loss of the specificity of the antibody or antigen-binding fragment for IL1RAP.

In some embodiments, the antibody or antigen-binding fragment thereof with binding specificity for IL1RAP comprises CDRs as described above (comprising or consisting of the amino acid sequence selected from the group consisting of SEQ ID NOs 1 to 18), wherein any one of the amino acids of the CDRs has been altered for another amino acid, for example, with the proviso that no more than 2 amino acids have been so altered, such as 1 amino acid.

Light Chain Variable Regions

As elaborated in Example 9, rabbits were immunized with human and murine IL1RAP. Subsequently, resulting antibodies were analysed for desired properties, such as binding to IL1RAP and capacity to inhibit signaling of IL-1α, IL-1β, IL-33, IL-36α, IL-36β and/or IL-36γ. 48D2 was identified as an antibody with superior properties with regard to these features, and has subsequently been modified and optimized with the aim to improve the antibody for clinical and therapeutic application. This optimization procedure resulted in antibody variants harbouring variable light chain regions and variable heavy chain regions with different amino acid sequences. However, the CDRs are identical for all antibody variants. In other words, within each CDR-defining category (i) Kabat, ii) IMGT or iii) combination of IMGT and Kabat), the CDR sequences (CDR-L1, CDR-L2, CDR-L3, CDR-H1, CDR-H2 or CDR-H3, respectively), are the same for the chimeric antibody 48D2 and all optimized antibody variants thereof.

In some embodiments, the antibody or antigen-binding fragment thereof with binding specificity for IL1RAP comprises a light chain variable region comprising the CDRs comprising or consisting of an amino acid sequence selected from the group consisting of ESISTA (SEQ ID NO: 1), QASESISTALA (SEQ ID NO: 7) and QASESISTALA (SEQ ID NO: 13);

comprising or consisting of an amino acid sequence selected from the group consisting of KAS, KASTLPS (SEQ ID NO: 8) and KASTLPS (SEQ ID NO: 14); and/or comprising or consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15).

In some embodiments, the antibody or antigen-binding fragment thereof with binding specificity for IL1RAP comprises a light chain variable region comprising the CDRs comprising a) a CDR-L1 comprising or consisting of the amino acid sequence of ESISTA (SEQ ID NO: 1); a CDR-L2 comprising or consisting of the amino acid sequence of KAS; and a CDR-L3 comprising or consisting of the amino acid sequence of QQGFSSGNVHNA (SEQ ID NO: 3);

b) a CDR-L1 comprising or consisting of the amino acid sequence of QASESISTALA (SEQ ID NO: 7); a CDR-L2 comprising or consisting of the amino acid sequence of KASTLPS (SEQ ID NO: 8); and a CDR-L3 comprising or consisting of the amino acid sequence of QQGFSSGNVHNA (SEQ ID NO: 9); or c) a CDR-L1 comprising or consisting of the amino acid sequence of QASESISTALA (SEQ ID NO: 13); a CDR-L2 comprising or consisting of the amino acid sequence of KASTLPS (SEQ ID NO: 14); and a CDR-L3 comprising or consisting of the amino acid sequence of QQGFSSGNVHNA (SEQ ID NO: 15).

In some embodiments, the antibody or antigen-binding fragment thereof with binding specificity for IL1RAP comprises a light chain variable region comprising or consisting of the amino acid sequence of SEQ ID NO: 19; or an amino acid sequence having at least 70% sequence identity to SEQ ID NO: 19, for example at least 80%, 85%, 90%, 95%, 98% or 99% sequence identity. This light chain variable region is, for example, part of the chimeric (non-humanized, non-optimized) 48D2 antibody as described in Examples 9 and 10.

In some embodiments, the antibody or antigen-binding fragment thereof with binding specificity for IL1RAP comprises a light chain variable region comprising or consisting of an amino acid sequence selected from the group consisting of SEQ ID NO: 21, SEQ ID NO: 22, SEQ ID NO: 23, SEQ ID NO: 24 and SEQ ID NO: 25;

or an amino acid sequence having at least 70% sequence identity to SEQ ID NO: 21, SEQ ID NO: 22, SEQ ID NO: 23, SEQ ID NO: 24 or SEQ ID NO: 25, for example at least 80%, 85%, 90%, 95%, 98% or 99% sequence identity.

These light chain variable regions are, for example, part of the humanized h48D2 antibody variants as described in Examples 11 and 12.

In some embodiments, the antibody or antigen-binding fragment thereof with binding specificity for IL1RAP comprises a light chain variable region comprising or consisting of the amino acid sequence of SEQ ID NO: 31;

or an amino acid sequence having at least 70% sequence identity to SEQ ID NO: 31, for example at least 80%, 85%, 90%, 95%, 98% or 99% sequence identity.

This light chain variable region is, for example, part of the humanized and de-immunized 48D2 antibody variant as described in Examples 13 and 14.

Percent identity (or sequence identity) can be determined by, for example, the LALIGN program at the Expasy facility site (http://www.ch.embnet.org/software/LALIGN_form-.html) using as parameters the global alignment option, scoring matrix BLOSUM62, opening gap penalty −14, extending gap penalty −4. Alternatively, the percent sequence identity between two polypeptides, such as parts of an antibody, may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program. The parameters used may be as follows:
Fast pair-wise alignment parameters: K-tuple (word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

The person skilled in the art will consider further alterations to the above described light chain variable regions, for example to further optimize the antibody or antigen-binding fragment. For example, the person skilled in the art will, as done during humanization and de-immunization procedures, consider to alter amino acids in the framework regions, i.e. outside the epitope binding CDR regions, thereby not altering the CDR regions.

In some embodiments, the antibody or antigen-binding fragment thereof with binding specificity for IL1RAP comprises a light chain variable region as described above, wherein any one of the amino acids of the framework region of the light chain variable region has been altered for another amino acid, with the proviso that no more than 5 amino acids have been so altered, such as 4 amino acids, no more than 3 amino acids, such as 2 amino acids or no more than 1 amino acid.

Heavy Chain Variable Regions

In some embodiments, the antibody or antigen-binding fragment thereof with binding specificity for IL1RAP comprises a heavy chain variable region comprising the CDRs comprising or consisting of an amino acid sequence selected from the group consisting of GPSLSHFD (SEQ ID NO: 4), HFDIT (SEQ ID NO: 10) and GPSLSHFDIT (SEQ ID NO: 16);

comprising or consisting of an amino acid sequence selected from the group consisting of ISPGVST (SEQ ID NO: 5), TISPGVSTYYASWAKS (SEQ ID NO: 11) and TISPGVSTYYASWAKS (SEQ ID NO: 17); and comprising or consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

In some embodiments, the antibody or antigen-binding fragment thereof with binding specificity for IL1RAP comprises a heavy chain variable region comprising a) a CDR-H1 comprising or consisting of the amino acid sequence of GPSLSHFD (SEQ ID NO: 4); a CDR-H2 comprising or consisting of the amino acid sequence of ISPGVST (SEQ ID NO: 5); and a CDR-H3 comprising or consisting of the amino acid sequence of ARGGVGSSWKAFDL (SEQ ID NO: 6);

b) a CDR-H1 comprising or consisting of the amino acid sequence of HFDIT (SEQ ID NO: 10); a CDR-H2 comprising or consisting of the amino acid sequence of TISPGVSTYYASWAKS (SEQ ID NO: 11); and a CDR-H3 comprising or consisting of the amino acid sequence of GGVGSSWKAFDL (SEQ ID NO: 12); or c) a CDR-H1 comprising or consisting of the amino acid sequence of GPSLSHFDIT (SEQ ID NO: 16); a CDR-H2 comprising or consisting of the amino acid sequence of TISPGVSTYYASWAKS (SEQ ID NO: 17); and a CDR-H3 comprising or consisting of the amino acid sequence of ARGGVGSSWKAFDL (SEQ ID NO: 18).

In some embodiments, the antibody or antigen-binding fragment thereof with binding specificity for IL1RAP comprises a heavy chain variable region comprising or consisting of the amino acid sequence of SEQ ID NO: 20; or an amino acid sequence having at least 70% sequence identity to SEQ ID NO: 20, for example at least 80%, 85%, 90%, 95%, 98% or 99% sequence identity.

This heavy chain variable region is, for example, part of the chimeric (non-humanized, non-optimized) 48D2 antibody as described in Examples 9 and 10.

In some embodiments, the antibody or antigen-binding fragment thereof with binding specificity for IL1RAP comprises a heavy chain variable region comprising or consisting of an amino acid sequence selected from the group consisting of SEQ ID NO: 26, SEQ ID NO: 27, SEQ ID NO: 28, SEQ ID NO: 29 and SEQ ID NO: 30;

or an amino acid sequence having at least 70% sequence identity to SEQ ID NO: 26, SEQ ID NO: 27, SEQ ID NO: 28, SEQ ID NO: 29 or SEQ ID NO: 30, for example at least 80%, 85%, 90%, 95%, 98% or 99% sequence identity.

These heavy chain variable regions are, for example, part of the humanized h48D2 antibody variants as described in Examples 11 and 12.

In some embodiments, the antibody or antigen-binding fragment thereof with binding specificity for IL1RAP comprises a heavy chain variable region comprising or consisting of an amino acid sequence selected from the group consisting of SEQ ID NO: 32, SEQ ID NO: 33 and SEQ ID NO: 34;

or an amino acid sequence having at least 70% sequence identity to SEQ ID NO: 32, SEQ ID NO: 33 or SEQ ID NO: 34, for example at least 80%, 85%, 90%, 95%, 98% or 99% sequence identity.

These heavy chain variable regions are, for example, part of the humanized and de-immunized 48D2 antibody variants as described in Examples 13 and 14.

The person skilled in the art will consider further alterations to the above described heavy chain variable regions, for example to further optimize the antibody or antigen-binding fragment. For example, the person skilled in the art will, as done during humanization and de-immunization procedures, consider to alter amino acids in the framework regions, i.e. outside the epitope binding CDR regions, thereby not altering the CDR regions.

In some embodiments, the antibody or antigen-binding fragment thereof with binding specificity for IL1RAP comprises a heavy chain variable region as described above, wherein any one of the amino acids of the framework region of the heavy chain variable region has been altered for another amino acid, with the proviso that no more than 5 amino acids have been so altered, such as 4 amino acids, no more than 3 amino acids, such as 2 amino acids or no more than 1 amino acid.

Combination of Variable Light and Variable Heavy Chains

The person skilled in the art will appreciate that any of the above described variants of light chain variable regions can be combined with any of the above described variants of heavy chain variable regions.

In some embodiments, the antibody or antigen-binding fragment thereof with binding specificity for IL1RAP comprises a light chain variable region which comprises or consists of the amino acid sequence of SEQ ID NO: 19 and a heavy chain variable region which comprises or consists of the amino acid sequence of SEQ ID NO: 20, or an amino acid sequence having at least 70% sequence identity to SEQ ID NO: 19 or SEQ ID NO: 20, for example at least 80%, 85%, 90%, 95%, 98% or 99% sequence identity.

This combination of light and heavy chain variable regions is, for example, part of the chimeric (non-humanized, non-optimized) 48D2 antibody as described in Examples 9 and 10.

In some embodiments, the antibody or antigen-binding fragment thereof with binding specificity for IL1RAP comprises:

a) a light chain variable region which comprises or consists of the amino acid sequence of SEQ ID NO: 21 and a heavy chain variable region which comprises or consists of the amino acid sequence of SEQ ID NO: 26;

b) a light chain variable region which comprises or consists of the amino acid sequence of SEQ ID NO: 21 and a heavy chain variable region which comprises or consists of the amino acid sequence of SEQ ID NO: 27;

c) a light chain variable region which comprises or consists of the amino acid sequence of SEQ ID NO: 21 and a heavy chain variable region which comprises or consists of the amino acid sequence of SEQ ID NO: 28;

d) a light chain variable region which comprises or consists of the amino acid sequence of SEQ ID NO: 21 and a heavy chain variable region which comprises or consists of the amino acid sequence of SEQ ID NO: 29;

e) a light chain variable region which comprises or consists of the amino acid sequence of SEQ ID NO: 21 and a heavy chain variable region which comprises or consists of the amino acid sequence of SEQ ID NO: 30;

f) a light chain variable region which comprises or consists of the amino acid sequence of SEQ ID NO: 22 and a heavy chain variable region which comprises or consists of the amino acid sequence of SEQ ID NO: 26;

g) a light chain variable region which comprises or consists of the amino acid sequence of SEQ ID NO: 22 and a heavy chain variable region which comprises or consists of the amino acid sequence of SEQ ID NO: 27;
h) a light chain variable region which comprises or consists of the amino acid sequence of SEQ ID NO: 22 and a heavy chain variable region which comprises or consists of the amino acid sequence of SEQ ID NO: 28;
i) a light chain variable region which comprises or consists of the amino acid sequence of SEQ ID NO: 22 and a heavy chain variable region which comprises or consists of the amino acid sequence of SEQ ID NO: 29;
j) a light chain variable region which comprises or consists of the amino acid sequence of SEQ ID NO: 22 and a heavy chain variable region which comprises or consists of the amino acid sequence of SEQ ID NO: 30;
k) a light chain variable region which comprises or consists of the amino acid sequence of SEQ ID NO: 23 and a heavy chain variable region which comprises or consists of the amino acid sequence of SEQ ID NO: 26;
l) a light chain variable region which comprises or consists of the amino acid sequence of SEQ ID NO: 23 and a heavy chain variable region which comprises or consists of the amino acid sequence of SEQ ID NO: 27;
m) a light chain variable region which comprises or consists of the amino acid sequence of SEQ ID NO: 23 and a heavy chain variable region which comprises or consists of the amino acid sequence of SEQ ID NO: 28;
n) a light chain variable region which comprises or consists of the amino acid sequence of SEQ ID NO: 23 and a heavy chain variable region which comprises or consists of the amino acid sequence of SEQ ID NO: 29;
o) a light chain variable region which comprises or consists of the amino acid sequence of SEQ ID NO: 23 and a heavy chain variable region which comprises or consists of the amino acid sequence of SEQ ID NO: 30;
p) a light chain variable region which comprises or consists of the amino acid sequence of SEQ ID NO: 24 and a heavy chain variable region which comprises or consists of the amino acid sequence of SEQ ID NO: 26;
q) a light chain variable region which comprises or consists of the amino acid sequence of SEQ ID NO: 24 and a heavy chain variable region which comprises or consists of the amino acid sequence of SEQ ID NO: 27;
r) a light chain variable region which comprises or consists of the amino acid sequence of SEQ ID NO: 24 and a heavy chain variable region which comprises or consists of the amino acid sequence of SEQ ID NO: 28;
s) a light chain variable region which comprises or consists of the amino acid sequence of SEQ ID NO: 24 and a heavy chain variable region which comprises or consists of the amino acid sequence of SEQ ID NO: 29;
t) a light chain variable region which comprises or consists of the amino acid sequence of SEQ ID NO: 24 and a heavy chain variable region which comprises or consists of the amino acid sequence of SEQ ID NO: 30;
u) a light chain variable region which comprises or consists of the amino acid sequence of SEQ ID NO: 25 and a heavy chain variable region which comprises or consists of the amino acid sequence of SEQ ID NO: 26;
v) a light chain variable region which comprises or consists of the amino acid sequence of SEQ ID NO: 25 and a heavy chain variable region which comprises or consists of the amino acid sequence of SEQ ID NO: 27;
w) a light chain variable region which comprises or consists of the amino acid sequence of SEQ ID NO: 25 and a heavy chain variable region which comprises or consists of the amino acid sequence of SEQ ID NO: 28;
x) a light chain variable region which comprises or consists of the amino acid sequence of SEQ ID NO: 25 and a heavy chain variable region which comprises or consists of the amino acid sequence of SEQ ID NO: 29; or
y) a light chain variable region which comprises or consists of the amino acid sequence of SEQ ID NO: 25 and a heavy chain variable region which comprises or consists of the amino acid sequence of SEQ ID NO: 30;
or an amino acid sequence having at least 70% sequence identity to any one of SEQ ID NO: 21 to SEQ ID NO: 30, for example at least 80%, 85%, 90%, 95%, 98% or 99% sequence identity.

These combinations of light and heavy chain variable regions are, for example, part of the humanized h48D2 antibody variants as described in Examples 11 and 12.

The following table is an alternative way to depict exemplary combinations of humanized light and heavy chain variable regions:

| Variable light/heavy regions | VH1 SEQ ID NO: 26 | VH2 SEQ ID NO: 27 | VH3 SEQ ID NO: 28 | VH4 SEQ ID NO: 29 | VH5 SEQ ID NO: 30 |
|---|---|---|---|---|---|
| VL1 SEQ ID NO: 21 | VL1:VH1 SEQ ID NOs: 21:26 | VL1:VH2 SEQ ID NOs: 21:27 | VL1:VH3 SEQ ID NOs: 21:28 | VL1:VH4 SEQ ID NOs: 21:29 | VL1:VH5 SEQ ID NOs: 21:30 |
| VL2 SEQ ID NO: 22 | VL2:VH1 SEQ ID NOs: 22:26 | VL2:VH2 SEQ ID NOs: 22:27 | VL2:VH3 SEQ ID NOs: 22:28 | VL2:VH4 SEQ ID NOs: 22:29 | VL2:VH5 SEQ ID NOs: 22:30 |
| VL3 SEQ ID NO: 23 | VL3:VH1 SEQ ID NOs: 23:26 | VL3:VH2 SEQ ID NOs: 23:27 | VL3:VH3 SEQ ID NOs: 23:28 | VL3:VH4 SEQ ID NOs: 23:29 | VL3: SEQ ID NOs: 23:30 |
| VL4 SEQ ID NO: 24 | VL4:VH1 SEQ ID NOs: 24:26 | VL4:VH2 SEQ ID NOs: 24:27 | VL4:VH3 SEQ ID NOs: 24:28 | VL4:VH4 SEQ ID NOs: 24:29 | VL4:VH5 SEQ ID NOs: 24:30 |
| VL5 SEQ ID NO: 25 | VL5:VH1 SEQ ID NOs: 25:26 | VL5:VH2 SEQ ID NOs: 25:27 | VL5:VH3 SEQ ID NOs: 25:28 | VL5:VH4 SEQ ID NOs: 25:29 | VL5:VH5 SEQ ID NOs: 25:30 |

In some embodiments, the antibody or antigen-binding fragment thereof with binding specificity for IL1RAP comprises:
a) a light chain variable region which comprises or consists of the amino acid sequence of SEQ ID NO: 24 and a heavy chain variable region which comprises or consists of the amino acid sequence of SEQ ID NO: 30;
b) a light chain variable region which comprises or consists of the amino acid sequence of SEQ ID NO: 24 and a heavy chain variable region which comprises or consists of the amino acid sequence of SEQ ID NO: 32;

c) a light chain variable region which comprises or consists of the amino acid sequence of SEQ ID NO: 24 and a heavy chain variable region which comprises or consists of the amino acid sequence of SEQ ID NO: 33;

d) a light chain variable region which comprises or consists of the amino acid sequence of SEQ ID NO: 24 and a heavy chain variable region which comprises or consists of the amino acid sequence of SEQ ID NO: 34;

e) a light chain variable region which comprises or consists of the amino acid sequence of SEQ ID NO: 25 and a heavy chain variable region which comprises or consists of the amino acid sequence of SEQ ID NO: 30;

f) a light chain variable region which comprises or consists of the amino acid sequence of SEQ ID NO: 25 and a heavy chain variable region which comprises or consists of the amino acid sequence of SEQ ID NO: 32;

g) a light chain variable region which comprises or consists of the amino acid sequence of SEQ ID NO: 25 and a heavy chain variable region which comprises or consists of the amino acid sequence of SEQ ID NO: 33;

h) a light chain variable region which comprises or consists of the amino acid sequence of SEQ ID NO: 25 and a heavy chain variable region which comprises or consists of the amino acid sequence of SEQ ID NO: 34;

i) a light chain variable region which comprises or consists of SEQ ID NO: 31 and a heavy chain variable region which comprises or consists of the amino acid sequence of SEQ ID NO: 30;

j) a light chain variable region which comprises or consists of the amino acid sequence of SEQ ID NO: 31 and a heavy chain variable region which comprises or consists of the amino acid sequence of SEQ ID NO: 32;

k) a light chain variable region which comprises or consists of the amino acid sequence of SEQ ID NO: 31 and a heavy chain variable region which comprises or consists of the amino acid sequence of SEQ ID NO: 33; or l) a light chain variable region which comprises or consists of the amino acid sequence of SEQ ID NO: 31 and a heavy chain variable region which comprises or consists of the amino acid sequence of SEQ ID NO: 34 or an amino acid sequence having at least 70% sequence identity to SEQ ID NO: 24, SEQ ID NO: 25, SEQ ID NO: 31, SEQ ID NO: 30, SEQ ID NO: 32, SEQ ID NO: 33 or SEQ ID NO: 34, for example at least 80%, 85%, 90%, 95%, 98% or 99% sequence identity.

These combinations of light and heavy chain variable regions are, for example, part of the humanized and/or de-immunized h48D2 antibody variants as described in Examples 13 and 14.

The following table is an alternative way to depict exemplary combinations of humanized and/or humanized and de-immunized light and heavy chain variable regions:

| Variable light/heavy regions | VH5 SEQ ID NO: 30 | VH5.AP SEQ ID NO: 32 | VH5.SK SEQ ID NO: 33 | VH5.GL SEQ ID NO: 34 |
|---|---|---|---|---|
| VL4 SEQ ID NO: 24 | VL4:VH5 SEQ ID NOs: 24:30 | VL4:VH5.AP SEQ ID NOs: 24:32 | VL4:VH5.SK SEQ ID NOs: 24:33 | VL4:VH5.GL SEQ ID NOs: 24:34 |
| VL5 SEQ ID NO: 25 | VL5:VH5 SEQ ID NOs: 25:30 | VL5:VH5.AP SEQ ID NOs: 25:32 | VL5:VH5.SK SEQ ID NOs: 25:33 | VL5:VH5.GL SEQ ID NOs: 25:34 |
| VL5.GL SEQ ID NO 31 | VL5.GL:VH5 SEQ ID NOs 31:30 | VL5.GL:VH5.AP SEQ ID NOs 31:32 | VL5.GL:VH5.SK SEQ ID NOs 31:33 | VL5.GL:VH5.GL SEQ ID NOs 31:34 |

It will be appreciated by persons skilled in the art that the above-defined light chain variable regions, heavy chain variable regions and combinations thereof may further be combined with a light/heavy chain constant regions, or parts thereof (see below).

In some embodiments, the antibody or antigen-binding fragment thereof with binding specificity for IL1RAP comprises a light chain variable region which comprises or consists of SEQ ID NO: 24 and a heavy chain variable region which comprises or consists of SEQ ID NO: 34.

In some embodiments, the antibody or antigen-binding fragment thereof with binding specificity for IL1RAP comprises a light chain variable region which comprises or consists of SEQ ID NO: 31 and a heavy chain variable region which comprises or consists of SEQ ID NO: 34.

In some embodiments, the antibody or antigen-binding fragment thereof with binding specificity for IL1RAP comprises a heavy chain variable region as described above, wherein any one of the amino acids of the framework region of the light chain variable region and/or the heavy chain variable region has been altered for another amino acid, with the proviso that no more than 5 amino acids have been so altered, such as 4 amino acids, no more than 3 amino acids, such as 2 amino acids or no more than 1 amino acid.

Constant Regions and Fc Part

The person skilled in the art will appreciate that any light constant region known in the art can be combined with any of the above described variants of light variable regions, and that any heavy constant region known in the art can be combined with any of the above described variants of heavy variable regions, to form a full antibody.

In some embodiments, the antibody or antigen-binding fragment thereof with binding specificity for IL1RAP comprises a light chain constant region, or part thereof.

In some embodiments, the antibody or antigen-binding fragment thereof with binding specificity for IL1RAP comprises a light chain constant region which is of a kappa or lambda light chain.

In some embodiments, the antibody or antigen-binding fragment thereof with binding specificity for IL1RAP comprises a kappa light chain.

In some embodiments, the antibody or antigen-binding fragment thereof with binding specificity for IL1RAP comprises a lambda light chain.

In some embodiments, the antibody or antigen-binding fragment thereof with binding specificity for IL1RAP comprises a light chain constant region comprising or consisting of the amino acid sequence of SEQ ID NO: 35, or an amino acid sequence having at least 70% sequence identity to SEQ ID NO: 35, for example at least 80%, 85%, 90%, 95%, 98% or 99% sequence identity.

In some embodiments, the antibody or antigen-binding fragment thereof with binding specificity for IL1RAP comprises a heavy chain constant region, or part thereof.

In some embodiments, the antibody or antigen-binding fragment thereof with binding specificity for IL1RAP comprises a heavy chain constant region which is selected from the group consisting of α, δ, γ, ε and μ.

In some embodiments, the antibody or antigen-binding fragment thereof with binding specificity for IL1RAP comprises a heavy chain constant region which is of an immunoglobulin isotype selected from the group consisting of IgA, IgD, IgG, IgE and IgM.

In some embodiments, the antibody or antigen-binding fragment thereof with binding specificity for IL1RAP comprises a heavy chain constant region which is of an IgG immunoglobulin isotype.

In some embodiments, the antibody or antigen-binding fragment thereof with binding specificity for IL1RAP is an IgG antibody.

In some embodiments, the antibody or antigen-binding fragment thereof with binding specificity for IL1RAP comprises a heavy chain constant region which is of an immunoglobulin subclass selected from the group consisting of IgG1, IgG2, IgG3 and IgG4.

In some embodiments, the antibody or antigen-binding fragment thereof with binding specificity for IL1RAP is an IgG1 antibody.

In some embodiments, the antibody or antigen-binding fragment thereof with binding specificity for IL1RAP is an IgG2 antibody.

In some embodiments, the antibody or antigen-binding fragment thereof with binding specificity for IL1RAP is an IgG3 antibody.

In some embodiments, the antibody or antigen-binding fragment thereof with binding specificity for IL1RAP is an IgG4 antibody.

In some embodiments, the antibody or antigen-binding fragment thereof with binding specificity for IL1RAP comprises or consists of a heavy chain constant region comprising or consisting of the amino acid sequence of SEQ ID NO: 36 or SEQ ID NO: 2, or an amino acid sequence having at least 70% sequence identity to SEQ ID NO: 36 or SEQ ID NO: 2, for example at least 80%, 85%, 90%, 95%, 98% or 99% sequence identity.

In some embodiments the antibody or antigen-binding fragment thereof with binding specificity for IL1RAP comprises or consists of a light chain constant region and/or a heavy chain constant region wherein any one of the amino acids of the above mentioned light chain constant region and/or above mentioned heavy chain constant region has been altered for another amino acid, with the proviso that no more than 5 amino acids have been so altered, such as 4 amino acids, no more than 3 amino acids, such as 2 amino acids or no more than 1 amino acid.

In some embodiments, the antibody or antigen-binding fragment of the present invention comprises a CH1, CH2 and/or CH3 region of an IgG heavy chain (such as an IgG1, IgG2, IgG3 or IgG4 heavy chain). Thus, the antibody or antigen-binding fragment may comprise part or all of the constant regions from an IgG1 heavy chain. For example, the antibody or antigen-binding fragment may be a Fab fragment comprising CH1 and CL constant regions, combined with any of the above-defined heavy and light variable regions, respectively.

Likewise, the above-defined antibodies or antigen-binding fragments of the invention may further comprise a light chain constant region, or part thereof. For example, the antibody or antigen-binding fragment may comprise a CL region from a kappa or lambda light chain.

In some embodiments, the antibody or antigen-binding fragment thereof with binding specificity for IL1RAP comprises or consists of
  any one of the above mentioned light chain variable regions; and/or
  any one of the above mentioned heavy chain variable regions; and/or
  any one of the above mentioned light chain constant regions; and/or
  any one of the above mentioned heavy chain constant region.

In some embodiments, the antibody or antigen-binding fragment thereof with binding specificity for IL1RAP comprises
  a light chain variable region comprising or consisting of the amino acid sequence selected from the group consisting of an amino acid sequence of SEQ ID NOs 19, 21, 22, 23, 24, 25 and 31; and/or
  a heavy chain variable region comprising or consisting of an amino acid sequence selected from the group consisting of SEQ ID NOs 20, 26, 27, 28, 29, 30, 32, 33, and 34; and/or
  a light chain constant region comprising or consisting of the amino acid sequence of SEQ ID NO 35; and/or
  a heavy chain constant region comprising or consisting of the amino acid sequences of SEQ ID NOs 36 or 2.

In some embodiments, the antibody or antigen-binding fragment thereof with binding specificity for IL1RAP comprises an Fc region.

Fc region may also be referred to as Fc domain.

In some embodiments, the antibody or antigen-binding fragment thereof with binding specificity for IL1RAP comprises an Fc region which is naturally occurring.

In some embodiments, the antibody or antigen-binding fragment thereof with binding specificity for IL1RAP comprises an Fc region which is non-naturally occurring.

In some embodiments, the antibody or antigen-binding fragment thereof with binding specificity for IL1RAP comprises an Fc region with a modified, for example with a mutated, IgG constant region.

In some embodiments the antibody or antigen-binding fragment thereof with binding specificity for IL1RAP comprises an Fc region wherein the Fc region comprises one or more of the mutations identified in Table 1.

The Fc region may be naturally occurring (e.g. part of an endogenously produced antibody) or may be artificial (e.g. comprising one or more point mutations relative to a naturally-occurring Fc region).

As is well documented in the art, the Fc region of an antibody mediates its serum half-life and effector functions, such as complement-dependent cytotoxicity (CDC), antibody-dependent cellular cytotoxicity (ADCC) and antibody-dependent cell phagocytosis (ADCP).

Engineering the Fc region of a therapeutic monoclonal antibody or Fc fusion protein allows the generation of molecules that are better suited to the pharmacology activity required of them (Strohl, 2009, *Curr Opin Biotechnol* 20(6): 685-91, the disclosures of which are incorporated herein by reference).

(a) Engineered Fc Regions for Increased Half-Life

One approach to improve the efficacy of a therapeutic antibody is to increase its serum persistence, thereby allowing higher circulating levels, less frequent administration and reduced doses.

The half-life of an IgG depends on its pH-dependent binding to the neonatal receptor FcRn. FcRn, which is expressed on the surface of endothelial cells, binds the IgG in a pH-dependent manner and protects it from degradation.

Some antibodies that selectively bind the FcRn at pH 6.0, but not pH 7.4, exhibit a higher half-life in a variety of animal models.

Several mutations located at the interface between the CH2 and CH3 domains, such as T250Q/M428L (Hinton et al., 2004, J Biol Chem. 279(8):6213-6, the disclosures of which are incorporated herein by reference) and M252Y/S254T/T256E+H433K/N434F (Vaccaro et al., 2005, Nat. Biotechnol. 23(10):1283-8, the disclosures of which are incorporated herein by reference), have been shown to increase the binding affinity to FcRn and the half-life of IgG1 in vivo.

(b) Engineered Fc Regions for Altered Effector Function

Depending on the therapeutic antibody or Fc fusion protein application, it may be desired to either reduce or increase the effector function (such as ADCC).

For antibodies that target cell-surface molecules, especially those on immune cells, abrogating effector functions may be required for certain clinical indications.

Conversely, for antibodies intended for oncology use (such as in the treatment of leukemias and solid tumours; see below), increasing effector functions may improve the therapeutic activity.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns et al., 2009, Blood. 113(16):3716-25, the disclosures of which are incorporated herein by reference). Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 of IgG2 residues at positions 233-236 and IgG4 residues at positions 327, 330 and 331 were shown to greatly reduce ADCC and CDC (Armour et al., 1999, Eur J Immunol. 29(8):2613-24; Shields et al., 2001, J Biol Chem. 276(9):6591-604, the disclosures of which are incorporated herein by reference). The 'LALA' mutation, L234A/LL235A, has been introduced in several therapeutic IgG1 antibodies for creation of an effector function silent Fc region, see for example Xu et al., 2000, Cell. Immuno. 200: 16-26. Furthermore, Idusogie et al. demonstrated that alanine substitution at different positions, including K322, significantly reduced complement activation (Idusogie et al., 2000, J Immunol. 164(8):4178-84, the disclosures of which are incorporated herein by reference). Similarly, mutations in the CH2 domain of murine IgG2A were shown to reduce the binding to FcγRI, and C1q (Steurer. et al., 1995. J Immunol. 155(3):1165-74, the disclosures of which are incorporated herein by reference).

Numerous mutations have been made in the CH2 domain of human IgG1 and their effect on ADCC and CDC tested in vitro (see references cited above). Notably, alanine substitution at position 333 was reported to increase both ADCC and CDC (Shields et al., 2001, supra; Steurer et al., 1995, supra). Lazar et al. described a triple mutant (S239D/I332E/A330L) with a higher affinity for FcγRIIIa and a lower affinity for FcγRIIb resulting in enhanced ADCC (Lazar et al., 2006, PNAS 103(11):4005-4010, the disclosures of which are incorporated herein by reference). The same mutations were used to generate an antibody with increased ADCC (Ryan et al., 2007, Mol. Cancer Ther. 6:3009-3018, the disclosures of which are incorporated herein by reference). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards et al., 2008. Mol Cancer Ther. 7(8):2517-27, the disclosures of which are incorporated herein by reference).

Due to their lack of effector functions, IgG4 antibodies represent a preferred IgG subclass for receptor blocking without cell depletion (i.e. inhibition of IL-1 signaling). IgG4 molecules can exchange half-molecules in a dynamic process termed Fab-arm exchange. This phenomenon can also occur in vivo between therapeutic antibodies and endogenous IgG4.

The S228P mutation has been shown to prevent this recombination process allowing the design of less unpredictable therapeutic IgG4 antibodies (Labrijn et al., 2009, Nat Biotechnol. 27(8):767-71, the disclosures of which are incorporated herein by reference).

Examples of engineered Fc regions are shown in Table 1 below.

TABLE 1

Examples of Engineered Fc

| Isotype | Species | Mutations* | FcR/C1q Binding | Effector Function |
|---|---|---|---|---|
| IgG1 | Human | T250Q/M428L [1] | Increased binding to FcRn | Increased half-life |
| IgG1 | Human | M252Y/S254T/T256E + H433K/N434F [2] | Increased binding to FcRn | Increased half-life |
| IgG1 | Human | M428L/N434S [3] | Increased binding to FcRn | Increased half-life |
| IgG1 | Human | E233P/L234V/L235A/?G236 + A327G/A330S/P331S [4,5] | Reduced binding to FcγRI | Reduced ADCC and CDC |
| IgG1 | Human | S239D/S298A/I332E + S239D/A330L/I332E [6] | Increased binding to FcγRIIIa | Increased ADCC |
| IgG1 | Human | S239D/I332E [7] | Increased binding to FcγRIIIa | Increased ADCC |
| IgG1 | Human | S298A/E333A/K334A [8] | Increased binding to FcγRIIIa | Increased ADCC |
| IgG1 | Human | E333A [9] | Increased binding to FcγRIIIa | Increased ADCC and CDC |
| IgG1 | Human | P257I/Q311 [10] | Increased binding to FcRn | Unchanged half-life |
| IgG1 | Human | K326W/E333S [11] | Increased binding to C1q | Increased CDC |
| IgG1 | Human | S239D/I332E/G236A [12] | Increased FcγRIIa/FcγRIIb ratio | Increased macrophage phagocytosis |
| IgG1 | Human | K322A [8] | Reduced binding to C1q | Reduced CDC |
| | | N297S | | Reduced (abrogated) ADCC |
| | | N297Q | | Reduced (abrogated) ADCC |
| | | R292P + V305I +/− F243L [13] | | Increased ADCC |
| | | P247I/A339Q [14] | | Increased ADCC |
| IgG4 | Human | S228P [15] | — | Reduced Fab-arm exchange |

TABLE 1-continued

Examples of Engineered Fc

| Isotype | Species | Mutations* | FcR/C1q Binding | Effector Function |
|---|---|---|---|---|
| IgG2a | Mouse | L235E + E318A/K320A/ K322A [11] | Reduced binding to FcγRI and C1q | Reduced ADCC and CDC |

*The position of the Fc amino acid mutations is defined using the EU Numbering Scheme (see Edelman et al., 1969, Proc. Natl. Acad. Sci. USA, 63:78-85), which may differ from the actual numbering in SEQ ID NOS: 36 and 2, for example, see further elaborations on the numbering of mutations below.

References to Table 1
[1] Hinton et al 2004 J. Biol. Chem. 279(8):6213-6)
[2] Vaccaro et al. 2005 Nat Biotechnol. 23(10):1283-8)
[3] Zalevsky et al 2010 Nat. Biotechnology 28(2):157-159
[4] Armour KL. et al., 1999. Eur J Immunol. 29(8):2613-24
[5] Shields RL. et al., 2001. J Biol Chem. 276(9):6591-604
[6] Masuda et al. 2007, Mol Immunol. 44(12):3122-31
[7] Bushfield et al 2014, Leukemia 28(11):2213-21
[8] Okazaki et al. 2004, J Mol Biol.; 336(5):1239-49
[9] Idusogie et al., 2000. J Immunol. 164(8):4178-84
[10] Datta-Mannan A. et al., 2007. Drug Metab. Dispos. 35: 86-94
[11] Steurer W. et al., 1995. J Immunol. 155(3):1165-74
[12] Richards et al. 2008 Mol Cancer There. 7(8):2517-27
[13] U.S. Pat. No. 7,960,512 B2
[14] EP 2 213 683
[15] Labrijn AF. et al., 2009. Nat Biotechnol. 27(8):767-71

In some embodiments, the antibody or antigen-binding fragment thereof with binding specificity for IL1RAP comprises an Fc region wherein the Fc region comprises one or more of the mutations selected from the group consisting of L234A, L235A, P329G, G237A, P238S, H269A, A330S and P331S as defined by the EU Index.

These mutations may reduce the effector function of the antibody.

The EU Index is conventionally used in the art (see generally, Kabat et al, 1991).

The person skilled in the art will appreciate that the exact position of the herein described Fc mutations may differ in the antibody of the invention. This is due to species variations in chimeric antibodies (and therefrom humanized or humanized/de-immunized antibodies) due to species differences in the variable regions. Varying lengths of regions in the variable heavy region lead to a shift of amino acid positions as compared to the one in the EU Index. However, the relative position of the amino acids in the Fc part is preserved.

For example, the LALA mutation is defined by the EU index to be at position L234A, L235A.

An exemplary antibody of the present invention may comprise a variable heavy chain region of, for example

```
                                    SEQ ID NO: 20
Heavy chain variable region (non-humanized, non-
deimmunized)
QEQLEESGGGLVKPGGSLTLTCTVSGPSLSHFDITWVRQAPGSGLEWIGT

ISPGVSTYYASWAKSRSTITSNTNLNTVTLKMTSLTAADTATYFCARGGV

GSSWKAFDLWGPGTLVTISS
``` and a constant heavy chain (not containing the LALA mutation) of, for example

```
                                    SEQ ID NO: 36
Immunoglobulin IgG1 constant heavy chain (heavy
chain constant region)(za allotype)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

(The Bold and underlined amino-acid residues indicate the residues that are altered when the LALA-mutation is introduced as shown in SEQ ID NO: 2, below.)

Alternatively, an exemplary antibody of the present invention may comprise a variable heavy chain region of, for example

```
                                    SEQ ID NO: 20
Heavy chain variable region (non-humanized, non-
deimmunized)
QEQLEESGGGLVKPGGSLTLTCTVSGPSLSHFDITWVRQAPGSGLEWIGT

ISPGVSTYYASWAKSRSTITSNTNLNTVTLKMTSLTAADTATYFCARGGV

GSSWKAFDLWGPGTLVTISS
``` and a constant heavy chain (containing the LALA mutation) of, for example

```
                                    SEQ ID NO: 2
Immunoglobulin IgG1 constant heavy chain (heavy
chain constant region)(za allotype) with 'LALA'
mutation
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG
```

The amino acid mutations (LL to AA in the above sequences) are at positions 237 and 238 (so L237A, L238A), and are, in the context of the amino acid sequence of the heavy chain constant region, equivalent to the L234A, L235A-mutations according to the EU index.

The person skilled in the art will appreciate that the same reasoning applies to the other named mutations that are known in the art, such as P329G, G237A, P238S, H269A, A330S and P331S as defined by the EU Index.

In some embodiments, the antibody or antigen-binding fragment thereof with binding specificity for IL1RAP comprises an Fc region, wherein the glycan attached to the Fc region is lacking fucose.

In some embodiments, the antibody or antigen-binding fragment thereof with binding specificity for IL1RAP comprises an Fc region which is lacking fucose.

In some embodiments, the antibody or antigen-binding fragment thereof with binding specificity for IL1RAP comprises an Fc region, wherein the glycan attached to the Fc region is low in fucose.

In some embodiments, the antibody or antigen-binding fragment thereof with binding specificity for IL1RAP comprises an Fc region which is low in fucose.

In some embodiments, the antibody or antigen-binding fragment thereof with binding specificity for IL1RAP, wherein the antibody or antigen-binding fragment is produced in a FUT8 negative cell line.

In some embodiments, the antibody is produced in a FUT8 negative cell line.

It is possible to create FUT8 negative cell lines by knocking out the FUT8 gene, which encodes for the a-(1, 6)-fucosyltransferase enzyme, which in turn catalyses fucose transfer. Antibodies comprising reduced fucosylation of the Fc region exhibit enhanced ADCC activity, as described in WO 00/61739 A1. It will be appreciated by a skilled person in the art that FUT8 negative cell lines are useful when producing antibodies with enhanced ADCC activity.

In some embodiments, the antibody or antigen-binding fragment thereof with binding specificity for IL1RAP is an intact antibody, or part of an intact antibody.

In some embodiments, the antibody or antigen-binding fragment thereof with binding specificity for IL1RAP is comprising or consisting of an antigen-binding fragment selected from the group consisting of Fv fragments (e.g. single chain Fv and disulphide-bonded Fv), Fab-like fragments (e.g. Fab fragments, Fab' fragments and F(ab)$_2$ fragments) and domain antibodies (e.g. single $V_H$ variable domains or $V_L$ variable domains).

The section below under "Sequences" provide sequences of certain exemplary embodiments of the antibodies disclosed and claimed herein.

Inhibition of Signaling

Interleukins are implicated in various diseases and disorders.

Interleukins, such as interleukins of the IL-1 family, as are cytokines. Cytokines (including, for example, chemokines, interferons, interleukins, lymphokines, and tumour necrosis factors) are of importance for cell signaling. In other words, cytokines have a signaling function to the cell, for example via binding to the respective receptor. For example, IL-1α, IL-1β, IL-33, IL-36α, IL-36β and/or IL-36γ signaling, as described herein, encompasses the events that these cytokines trigger on the cell surface or in the cell. On the cell surface, these signaling events affect, for example, the confirmation of the receptor, the properties of co-receptors and other molecules, the binding of molecules extracellularly, on the cell surface, in or at the cell membrane or in the cell. These events may be physiological or pathological. These events may be biological pathways, leading for example to a response in the cell as a reaction to the signaling. This response may be physiological or pathological.

As used herein "inhibition of signaling" is defined as a reduction of said signaling event, or of, for example, the activity, confirmation, or production of a receptor or biological pathway or molecule activity. This inhibition is to be understood as comparing the situation where the inhibiting factor (in the case of the present invention the antibody or antigen-binding fragment thereof with binding specificity for IL1RAP) is present compared to the situation where the inhibiting factor is not present. The person skilled in the art will appreciate that the degree of inhibition can be determined by methods well known in the art, depending on the signaling event or pathway or activity to be measured. This method can be, for example, a cell assay, for examples as described in Examples 10, 12 or 14.

It is to be noted that, as used herein, phrases such as "inhibiting signaling of (for example) IL-1α" are used interchangeably with the phrase "inhibiting (for example) IL-1a signaling".

IL-1

Interleukin-1 (IL-1) is a potent pro-inflammatory cytokine that can be produced by a variety of cell types, including mononuclear phagocytes, in response to infection and inflammation. The IL-1 family consists of seven agonists, including IL-1α and IL-1β, and three naturally occurring receptor antagonists, including the IL-1 receptor antagonist (IL-1Ra or IL1RA) (Dinarello, C A, Blood 1996, 87(6): 2095-147). Two IL-1 receptors, IL-1R type I and IL-1R type II, have been identified. Both receptors can interact with all three forms of the IL-1 family molecules. IL-1RI is responsible for mediating IL-1-induced cellular activation. However, the IL-1/IL-1RI complex cannot signal by itself, but is dependent on association with a second receptor chain, IL-1R Accessory Protein (IL1RAP) (Dinarello, C A, Blood 1996, 87(6): 2095-147). In contrast to IL-1RI, IL-1RII does not induce cellular activation upon binding to IL-1 and thus IL-1RII functions as a regulatory decoy receptor, leading to a net decrease in IL-1 available to bind to IL-1RI.

In addition to IL1-signaling, IL1RAP is critical for mediating the effects of IL33, through the ST2/IL1RAP complex, and IL36, through the IL1Rrp2/IL1RAP complex (Garlanda et al, Immunity. 2013 Dec. 12;39(6):1003-18).

IL-1α is also released from damaged cells and can act as an alarmin. IL-1 is a potent pro-inflammatory cytokine, which is induced at sites of local infection or inflammation and is involved in the regulation of a variety of physiological and cellular events (summarised in Dinarello C A, CHEST, 2000, 118: 503-508 and Dinarello, C A, Clin *Exp Rheumatol,* 2002, 20(5 Suppl 27): S1-13). It is capable of activating several cell types including leukocytes and endothelial cells. IL-1 induces and amplifies immunological responses by promoting the production and expression of adhesion molecules, cytokines, chemokines and other inflammatory mediators such as prostaglandin $E_2$ and nitric oxide (NO). As a consequence, local inflammation is amplified and sustained. In addition, the IL-1-induced production of inflammatory mediators results in fever, headache, hypotension and weight loss. Furthermore, IL-1 is a hematopoietic growth factor and has been shown to reduce the nadir of leukocytes and platelets in patients during bone marrow transplantation. IL-1 has also been shown to promote angiogenesis by inducing the production of vascular endothelial growth factor, thereby promoting pannus formation and blood supply in rheumatic joints. IL-1 has been shown to promote the bone and cartilage degradation in rheumatic diseases. Lastly, IL-1 has been implicated as an important player in the inflammatory response in cardiovascular and fibrotic diseases.

IL-33

IL-33 is normally released by damaged or necrotic barrier cells (endothelial and epithelial cells), acting as an alarmin, an endogenous danger signal, to alert the immune system of tissue damage during trauma or infection (Liew F Y, *Interleukin-33 in health and disease.* Nature Reviews Immunology, 16, 676-689 (2016)). IL-33 induces T helper 2 (Th2) cells, mast cells, type 2 innate lymphoid cells, eosinophils, and basophils to produce type 2 cytokines (e.g. IL-5, IL-13). IL-33 is also known to target endothelial cells and induce angiogenesis. As a Th2 inducing cytokine, IL-33 has been implicated in e.g. asthma, allergic diseases, inflammatory bowel disease, and dermatitis. IL-33 can potently stimulate a wide range of cells and its pleiotropic nature is reflected in the role of IL-33 in tissue and metabolic homeostasis, infection, inflammation, cancer and diseases of the central nervous system.

IL-36

The IL-36 cytokines α, β, γ are expressed in a variety of cell types, with abundant expression in e.g. keratinocytes, bronchial epithelium, neuronal cells, dendritic cells, and macrophages. IL-36 is most active in barrier tissues (like the skin, lung, and intestines), suggesting that their main responsibility is to regulate the interaction of the environment and the body. IL-36 is known to activate NF-κB and mitogen-activated protein kinases in target cells expressing the IL-36 receptor, such as keratinocytes, monocytes, dendritic cells and CD4 T cells. Emerging evidence indicates that IL-36 signaling is involved in the activation of innate and adaptive immune responses (Ding L, IL-36 cytokines in autoimmunity and inflammatory disease, Oncotarget, Vol. 9, (No. 2), pp: 2895-2901 (2018)).

Besides its critical role in inflammatory skin diseases such as psoriasis and atopic dermatitis, emerging evidence suggests that aberrant IL-36 activities also promote inflammatory diseases in the lung, kidneys, and intestines, underscoring the potential of IL-36 as a therapeutic target for common inflammatory diseases.

Interestingly, all cytokines described herein (IL-1α, IL-1β, IL-33, IL-36α, IL-36β, IL-36γ) have also been shown to target stromal cells such as fibroblasts and endothelial cells. Consequently, apart from the well-established impact of these cytokines in inflammatory diseases and disorders, these cytokines are also implicated in fibrotic diseases or disorders.

The antibody or antigen-binding fragment thereof, according to the first aspect of the invention, has the capacity to inhibit signaling of the interleukin-1 (IL-1) family of cytokine ligands and/or receptors. The person skilled in the art will appreciate that inhibition occurs upon binding of the antibody or antigen-binding fragment to the epitope on IL1RAP.

In some embodiments, the antibody or antigen-binding fragment thereof with binding specificity for IL1RAP is capable of inhibiting signaling upon binding to IL1RAP.

The person skilled in the art will appreciate that binding of the antibody or antigen-binding fragment thereof to IL1RAP can affect IL1RAP in different ways, for example on a molecular level or on a conformational level. However, the person skilled in the art will understand that it today might not be known completely how binding of the antibody or antigen-binding fragment thereof to IL1RAP affects IL1RAP.

One possibility is that binding of the antibody or antigen-binding fragment thereof to IL1RAP can affect the association of IL1RAP with IL-1 receptor, IL-33 receptor and/or IL-36 receptor, respectively. Consequently, the appropriate receptor complex consisting of IL1RAP as co-receptor and any one of IL-1 receptor, IL-33 receptor or IL-36 receptor, might not be formed. Consequently, when cytokines such as IL-1α, IL-1β, IL-33, IL-36α, IL-36β and IL-36γ bind to their cognate receptor (IL-1 receptor, IL-33 receptor or IL-36 receptor, respectively), signaling of these cytokines might be impaired, such as inhibited, such as blocked, such as essentially completely inhibited, such as partially inhibited.

The person skilled in the art will appreciate that not all IL1RAP binding antibodies, binding to any one epitope of IL1RAP, can disturb the association between IL1RAP with IL-1 receptor, IL-33 receptor and/or IL-36 receptor, respectively, and thereby inhibit signaling. It is an achievement of the present invention to provide such an antibody.

In some embodiments, the antibody or antigen-binding fragment thereof with binding specificity for IL1RAP is capable of inhibiting signaling of interleukin-1 (IL-1) family cytokine ligands and/or receptors.

In some embodiments, the antibody or antigen-binding fragment thereof with binding specificity for IL1RAP is capable of inhibiting signaling of IL1RAP-dependent interleukin-1 (IL-1) family of cytokine ligands and/or receptors.

In some embodiments, the antibody or antigen-binding fragment thereof with binding specificity for IL1RAP is capable of inhibiting signaling of at least one cytokine selected from the group consisting of IL-1α, IL-1β, IL-33, IL-36α, IL-36β and IL-36γ, or any combination thereof.

In some embodiments, the antibody or antigen-binding fragment thereof with binding specificity for IL1RAP thereof is capable of inhibiting signaling of IL-1α, IL-1β, IL-33, IL-36α, IL-36β and IL-36γ.

In some embodiments, the antibody or antigen-binding fragment thereof with binding specificity for IL1RAP is capable of inhibiting signaling of IL-1α.

In some embodiments, the antibody or antigen-binding fragment thereof with binding specificity for IL1RAP is capable of inhibiting signaling of IL-1β.

In some embodiments, the antibody or antigen-binding fragment thereof with binding specificity for IL1RAP is capable of inhibiting signaling of IL-33.

In some embodiments, the antibody or antigen-binding fragment thereof with binding specificity for IL1RAP thereof is capable of inhibiting signaling of IL-36α.

In some embodiments, the antibody or antigen-binding fragment thereof with binding specificity for IL1RAP is capable of inhibiting signaling of IL-36β.

In some embodiments, the antibody or antigen-binding fragment thereof with binding specificity for IL1RAP is capable of inhibiting signaling of IL-36γ.

The person skilled in the art will appreciate that inhibition of signaling can be of a varying degree. Inhibition of signaling can be complete or essentially complete, such as blocking of signaling. Inhibition of signaling can also be partial, such as decreasing the signaling, such as non-complete. "Essentially complete" is to be understood as "complete" given uncertainties of assessing completeness associated with the methodology used to measure the inhibition of signaling.

For example, signaling may be inhibited by at least 10%, 20%, 30%, 50%, 60%, 75%, 80%, 85%, 90%, 95%, 98%, 99% or more relative to signaling in the absence of the antibody or antigen-binding fragment of the invention.

In some embodiments, inhibition of signaling is between 10 to 100% relative to signaling in the absence of the antibody or antigen-binding fragment of the invention.

More preferably, the inhibition of signaling is between 25 to 100%. Even more preferably, the inhibition of signaling is between 50 to 100%.

Signaling may be inhibited by 100% relative to signaling in the absence of the antibody or antigen-binding fragment of the invention.

The degree of inhibition of IL-1, IL-33 and/or IL-36 signaling by the antibody or antigen-binding fragment of the invention may be determined using methods well known in the art, for example by the method used in Examples 10, 12 and 14.

In preferred embodiments, the antibody or antigen-binding fragment thereof with binding specificity for IL1RAP is capable of essentially completely inhibiting signaling.

In preferred embodiments, inhibiting signaling is essentially complete inhibition of signaling.

In preferred embodiments, the antibody or antigen-binding fragment thereof with binding specificity for IL1RAP is capable of essentially completely inhibiting signaling of at least one cytokine selected from the group consisting of IL-1α, IL-1β, IL-33, IL-36α, IL-36β and IL-36γ, or any combination thereof.

In preferred embodiments, the antibody or antigen-binding fragment thereof with binding specificity for IL1RAP is capable of essentially completely inhibiting signaling of IL-1α, IL-1β, IL-33, IL-36α, IL-36β and IL-36γ.

The antibody might further inhibit signaling to a certain degree, meaning not essentially completely, meaning partially. Consequently, inhibition of signaling can be not essentially complete inhibition, meaning partial inhibition.

In some embodiments, the antibody or antigen-binding fragment thereof with binding specificity for IL1RAP is capable of partially inhibiting signaling.

In some embodiments, inhibiting signaling is partial inhibition of signaling.

In some embodiments, the antibody or antigen-binding fragment thereof with binding specificity for IL1RAP is capable of partially inhibiting signaling of at least one cytokine selected from the group consisting of IL-1α, IL-1β, IL-33, IL-36α, IL-36β and IL-36γ, or any combination thereof.

In some embodiments, the antibody or antigen-binding fragment thereof with binding specificity for IL1RAP is capable of partially inhibiting signaling of IL-1α, IL-1β, IL-33, IL-36α, IL-36β and IL-36γ.

In some embodiments, the antibody or antigen-binding fragment thereof with binding specificity for IL1RAP is capable of inhibiting signaling of IL-1α, IL-1β, IL-33, IL-36α, IL-36p and/or IL-36γ by at least 10%, 20%, 30%, 50%, 60%, 75%, 80%, 85%, 90%, 95%, 98%, 99% relative to signaling in the absence of the antibody or antigen-binding fragment of the invention.

The person skilled in the art will appreciate that complete inhibition is desirable in some situations where a process, e.g. a disease process depending on signaling of IL-1α, IL-1β, IL-33, IL-36α, IL-36β and/or IL-36γ, should be affected completely and fast to alleviate or treat the disease. In other situations, partial inhibition is desirable where a process, e.g. a disease process depending on signaling of IL-1α, IL-1β, IL-33, IL-36α, IL-36β and/or IL-36γ, should be modified but not be affected completely, for example to avoid side effects of complete inhibition. The person skilled in the art will further appreciate that biological systems are complex and entail various known or unknown feedback loops, which can make it challenging to assess if a process is inhibited completely. Further, this assessment also depends on the sensitivity of the method with which the process, e.g. signaling, is measured. The person skilled in the art will know which method and cut-off values are established and accepted in the field to use to assess the completeness or essential completeness of inhibition of signaling or to assess the degree of partial inhibition of signaling.

As shown and explained in detail in the Examples below, antibodies can be subjected to modifications to optimize certain properties.

In some embodiments, the antibody or antigen-binding fragment thereof with binding specificity for IL1RAP is humanized.

In some embodiments, the antibody or antigen-binding fragment thereof with binding specificity for IL1RAP is a human antibody.

In some embodiments, the antibody or antigen-binding fragment thereof with binding specificity for IL1RAP is de-immunized.

In some embodiments, the antibody or antigen-binding fragment thereof with binding specificity for IL1RAP is humanized and de-immunized.

In some embodiments, the antibody or antigen-binding fragment thereof is monoclonal.

Properties of the Antibody

The antibodies of the present invention were identified after extensive screening of a large number of anti-IL1RAP antibodies, on the basis of exhibiting properties that make them particularly suitable as diagnostic and therapeutic agents for inflammatory, fibrotic and/or neoplastic diseases or disorders.

Thus, in some embodiments, the antibody or antigen-binding fragment thereof with binding specificity for IL1RAP exhibits one or more of the following properties:
 a) a binding affinity ($K_D$) for IL1RAP characterized by a $K_D$-value of 3 nM or less;
 b) binding to domain 2 of IL1RAP, preferably binding to the H2 region of domain 2, wherein the H2 region comprises or consists of the amino acids of SEQ ID NO: 39;
 c) cross-reactivity with IL1RAP from cynomolgus monkey or pig;
 d) an inhibitory action on IL-1α signaling;
 e) an inhibitory action on IL-1β signaling;
 f) an inhibitory action on IL-33 signaling;
 g) an inhibitory action on IL-36a signaling;
 h) an inhibitory action on IL-36β signaling;
 i) an inhibitory action on IL-36γ signaling;
 j) internalization by IL1RAP-expressing cells.

In some embodiments, the antibody or antigen-binding fragment thereof with binding specificity for IL1RAP exhibits one of the above named properties.

In some embodiments, the antibody or antigen-binding fragment thereof with binding specificity for IL1RAP exhibits two of the above named properties.

In some embodiments, the antibody or antigen-binding fragment thereof with binding specificity for IL1RAP exhibits three of the above named properties.

In some embodiments, the antibody or antigen-binding fragment thereof with binding specificity for IL1RAP exhibits four of the above named properties.

In some embodiments, the antibody or antigen-binding fragment thereof with binding specificity for IL1RAP exhibits five of the above named properties.

In some embodiments, the antibody or antigen-binding fragment thereof with binding specificity for IL1RAP exhibits six of the above named properties.

In some embodiments, the antibody or antigen-binding fragment thereof with binding specificity for IL1RAP exhibits seven of the above named properties.

In some embodiments, the antibody or antigen-binding fragment thereof with binding specificity for IL1RAP exhibits eight of the above named properties.

In some embodiments, the antibody or antigen-binding fragment thereof with binding specificity for IL1RAP exhibits nine of the above named properties.

Advantageously, in some embodiments, the antibody or antigen-binding fragment thereof with binding specificity for IL1RAP exhibits all of the above named properties.

In other embodiments, the antibody or antigen-binding fragment thereof with binding specificity for IL1RAP exhibits all of the following properties:
- a) a binding affinity ($K_D$) for IL1RAP characterized by a $K_D$-value of 3 nM or less;
- b) binding to domain 2 of IL1RAP, preferably binding to the H2 region of domain 2, wherein the H2 region comprises or consists of the amino acids of SEQ ID NO: 39;
- c) cross-reactivity with IL1RAP from cynomolgus monkey or pig;
- d) an inhibitory action on IL-1α signaling;
- e) an inhibitory action on IL-1β signaling;
- f) an inhibitory action on IL-33 signaling;
- g) an inhibitory action on IL-36a signaling;
- h) an inhibitory action on IL-36β signaling;
- i) an inhibitory action on IL-36γ signaling;
- j) internalization by IL1RAP-expressing cells.

The H2 region corresponds to amino acids 174-191 based on the IL1RAP amino acid sequence from Uniprot ID Q9NPH3.

In some embodiments, the binding affinity ($K_D$) of the antibody or antigen-binding fragment thereof for IL1RAP is 3 nM or less, such as 2.75 nM, for example 2.5 nM, such as 2 nM, for example 1.75 nM, such as 1.5 nM, for example 1.25 nM, such as 1 nM, for example 0.75 nM, such as 0.5 nM or for example 0.5 nM.

In some embodiments, the binding affinity ($K_D$) of the antibody or antigen-binding fragment thereof for IL1RAP is 3000 pM or less, such as 2750 pM, for example 2500 pM, such as 2000 pM, for example 1750 pM, such as 1500 pM, for example 1250 pM, such as 1000 pM, for example 750 pM, such as 700 pM, for example 650 pM, such as 600 pM, for example 550 pM, such as 500 pM, for example 450 pM, such as 400 pM, for example 350 pM, such as 300 pM, for example 250 pM, such as 200 pM, for example 150 pM, such as 100 pM, for example 50 pM.

The person skilled in the art will appreciate that the determination of the binding affinity of an antibody or antigen-binding fragment depends on the method for determining that binding affinity.

The person skilled in the art will appreciate that an IL1RAP antibody, apart from being able to inhibit cytokine signaling (for example of IL-1α, IL-1β, IL-33, IL-36α, IL-36p, and/or IL-36γ), can exhibit one or more further functions. These functions can be conveyed by the constant region of the antibody or the Fc region. Examples of these functions are antibody-dependent cell-mediated cytotoxicity (ADCC) and/or antibody-dependent cellular phagocytosis (ADCP), thereby leading to the killing of target cells, such as IL1RAP-expressing tumor cells.

In some embodiments, the antibody or antigen-binding fragment thereof with binding specificity for IL1RAP is capable of inducing ADCC of cells expressing IL1RAP.

In some embodiments, the antibody or antigen-binding fragment thereof with binding specificity for IL1RAP is not capable of inducing ADCC of cells expressing IL1RAP.

In some embodiments, the antibody or antigen-binding fragment thereof with binding specificity for IL1RAP is capable of inducing ADCP of cells expressing IL1RAP.

In some embodiments, the antibody or antigen-binding fragment thereof with binding specificity for IL1RAP is not capable of inducing ADCP of cells expressing IL1RAP.

In some embodiments, the antibody or antigen-binding fragment thereof with binding specificity for IL1RAP is capable of inducing ADCC and ADCP of cells expressing IL1RAP.

Modifications of the Antibody

In some embodiments, the antibody or antigen-binding fragment thereof with binding specificity for IL1RAP further comprises a moiety for increasing the in vivo half-life of the agent.

In some embodiments, the antibody or antigen-binding fragment thereof with binding specificity for IL1RAP further comprises a moiety for increasing the in vivo half-life of the agent, wherein the moiety for increasing the in vivo half-life is selected from the group consisting of polyethylene glycol (PEG), human serum albumin, glycosylation groups, fatty acids and dextran.

In some embodiments, the antibody or antigen-binding fragment thereof with binding specificity for IL1RAP is PEGylated.

In some embodiments, the antibody or antigen-binding fragment thereof with binding specificity for IL1RAP fragment is covalently bound, directly or indirectly (e.g. via a chelator), to a functional moiety such as a cytotoxic or detectable moiety.

In some embodiments, the antibody or antigen-binding fragment thereof with binding specificity for IL1RAP comprises a cytotoxic moiety.

In some embodiments, the antibody or antigen-binding fragment thereof with binding specificity for IL1RAP comprising a cytotoxic moiety, wherein the cytotoxic moiety comprises or consists of a radioisotope.

In some embodiments, the antibody or antigen-binding fragment thereof with binding specificity for IL1RAP comprising a cytotoxic moiety which comprises or consists of a radioisotope wherein the radioisotope is selected from the group consisting of beta-emitters, auger-emitters, conversion electron-emitters, alpha-emitters, and low photon energy-emitters.

In some embodiments, the antibody or antigen-binding fragment thereof with binding specificity for IL1RAP comprising a cytotoxic moiety which comprises or consists of a radioisotope, wherein the radioisotope has an emission pattern of locally absorbed energy that creates a high dose absorbance in the vicinity of the agent.

In some embodiments, the antibody or antigen-binding fragment thereof with binding specificity for IL1RAP comprising a cytotoxic moiety which comprises or consists of a radioisotope, wherein the radioisotope is selected from the group consisting of long-range beta-emitters, such as $^{90}$Y, $^{32}$P, $^{186}$Re/$^{186}$Re; $^{166}$Ho, $^{76}$As/$^{77}$As, $^{153}$Sm; medium range beta-emitters, such as $^{131}$I, $^{177}$Lu, $^{67}$Cu, $^{161}$Tb; low-energy beta-emitters, such as $^{45}$Ca, $^{35}$S or $^{14}$C; conversion or auger-emitters, such as $^{51}$Cr, $^{67}$Ga, $^{99}$Tc$^m$, $^{111}$In, $^{123}$I, $^{125}$I, $^{201}$Tl; and alpha-emitters, such as $^{212}$Bi, $^{213}$Bi, $^{223}$Ac, and $^{221}$At.

In some embodiments, the antibody or antigen-binding fragment thereof with binding specificity for IL1RAP comprising a cytotoxic moiety which comprises or consists of a radioisotope, wherein the radioisotope is $^{177}$Lu.

In some embodiments, the antibody or antigen-binding fragment thereof with binding specificity for IL1RAP comprises a cytotoxic moiety, wherein the cytotoxic moiety comprises or consists of a cytotoxic drug.

In some embodiments, the antibody or antigen-binding fragment thereof with binding specificity for IL1RAP comprising a cytotoxic moiety which comprises or consists of a cytotoxic drug, wherein the cytotoxic drug is selected from the group consisting of a cytostatic drug; an anti-androgen drug; cortisone and derivatives thereof; a phosphonate; a testosterone-5-α-reductase inhibitor; a boron addend; a cytokine; thapsigargin and its metabolites; a toxin (such as saporin or calicheamicin); a chemotherapeutic agent (such as an antimetabolite); or any other cytotoxic drug useful in the treatment of neoplastic disorders.

In some embodiments, the antibody or antigen-binding fragment thereof with binding specificity for IL1RAP comprising a cytotoxic moiety which comprises or consists of a cytotoxic drug, wherein the cytotoxic drug is suitable for use in activation therapy, such as photon activation therapy, neutron activation therapy, neutron induced Auger electron therapy, synchrotron irradiation therapy, or low energy X-ray photon activation therapy.

In some embodiments, the antibody or antigen-binding fragment thereof with binding specificity for IL1RAP comprises a detectable moiety.

In some embodiments, the antibody or antigen-binding fragment thereof with binding specificity for IL1RAP comprises a detectable moiety, wherein the detectable moiety comprises or consists of a radioisotope.

In some embodiments, the antibody or antigen-binding fragment thereof with binding specificity for IL1RAP comprises a detectable moiety comprising or consisting of a radioisotope, wherein the radioisotope is selected from the group consisting of $^{99m}Tc$, $^{111}In$, $^{67}Ga$, $^{68}Ga$, $^{72}As$, $^{89}Zr$, $^{123}I$ and $^{201}Tl$.

In some embodiments, the antibody or antigen-binding fragment thereof with binding specificity for IL1RAP comprises a detectable moiety comprising or consisting of a radioisotope, wherein the radioisotope is $^{89}Zr$.

In some embodiments, the antibody or antigen-binding fragment thereof with binding specificity for IL1RAP comprises a pair of detectable and cytotoxic radioisotopes, such as $^{86}Y/^{90}Y$ or $^{124}I/^{211}At$.

In some embodiments, the antibody or antigen-binding fragment thereof with binding specificity for IL1RAP comprises a radioisotope which is capable of simultaneously acting in a multi-modal manner as a detectable moiety and as a cytotoxic moiety.

In some embodiments, the antibody or antigen-binding fragment thereof with binding specificity for IL1RAP comprises a detectable moiety which comprises or consists of a paramagnetic isotope.

In some embodiments, the antibody or antigen-binding fragment thereof with binding specificity for IL1RAP comprises a detectable moiety which comprises or consists of a paramagnetic isotope, wherein the paramagnetic isotope is selected from the group consisting of $^{157}Gd$, $^{55}Mn$, $^{162}Dy$, $^{52}Cr$ and $^{56}Fe$.

In some embodiments, the antibody or antigen-binding fragment thereof with binding specificity for IL1RAP comprises a detectable moiety, wherein the detectable moiety is detectable by an imaging technique such as SPECT, PET, MRI, optical or ultrasound imaging.

In some embodiments, the antibody or antigen-binding fragment thereof with binding specificity for IL1RAP comprises a cytotoxic moiety and/or detectable moiety, wherein the cytotoxic moiety and/or detectable moiety is joined to the antibody or antigen-binding fragment thereof indirectly, via a linking moiety.

In some embodiments, the antibody or antigen-binding fragment thereof with binding specificity for IL1RAP comprises a cytotoxic moiety and/or detectable moiety, wherein the cytotoxic moiety and/or detectable moiety is joined to the antibody or antigen-binding fragment thereof indirectly, via a linking moiety, wherein the linking moiety is a chelator.

In some embodiments, the antibody or antigen-binding fragment thereof with binding specificity for IL1RAP comprises a cytotoxic moiety and/or detectable moiety, wherein the cytotoxic moiety and/or detectable moiety is joined to the antibody or antigen-binding fragment thereof indirectly, via a linking moiety, wherein the linking moiety is a chelator, and wherein the chelator is selected from the group consisting of derivatives of 1,4,7,10-tetraazacyclododecane-1,4,7,10,tetraacetic acid (DOTA), deferoxamine (DFO), derivatives of diethylenetriaminepentaacetic acid (DTPA), derivatives of S-2-(4-Isothiocyanatobenzyl)-1,4,7-triazacyclononane-1,4,7-triacetic acid (NOTA) and derivatives of 1,4,8,11-tetraazacyclododecan-1,4,8,11-tetraacetic acid (TETA).

In some embodiments, the antibody or antigen-binding fragment thereof with binding specificity for IL1RAP does not comprise a cytotoxic moiety or a detectable moiety.

The invention further includes an antibody or antigen-binding fragment thereof with binding specificity for human interleukin-1 receptor accessory protein (IL1RAP), wherein the antibody or antigen-binding fragment is capable of inhibiting the binding of the herein disclosed antibody 48D2 to IL1RAP.

As used herein, the term "capable of inhibiting the binding of antibody 48D2 to IL1RAP" means that the presence of another antibody inhibits, in whole or in part, the binding of 48D2 to IL1RAP. Such competitive binding inhibition can be determined using assays and methods well known in the art, for example using BIAcore chips with immobilised IL1RAP and incubating with the 48D2 with and without an antibody to be tested. Alternatively, a pair-wise mapping approach can be used, in which the antibody 48D2 is immobilised to the surface of the BIAcore chip, IL1RAP antigen is bound to the immobilised antibody, and then a second antibody is tested for simultaneous IL1RAP-binding ability (see 'BIAcore Assay Handbook', GE Healthcare Life Sciences, 29-0194-00 AA 05/2012; the disclosures of which are incorporated herein by reference).

In a further alternative, competitive binding inhibition can be determined using flow cytometry. For example, to test whether a test antibody is able to inhibit the binding of the 48D2 antibody to a cell surface antigen, cells expressing the antigen can be pre-incubated with the test antibody for 20 min before cells are washed and incubated with the 48D2 antibody conjugated to a fluorophore, which can be detected by flow cytometry. If the pre-incubation with the test antibody reduces the detection of the 48D2 antibody in flow cytometry, the test antibody inhibits the binding of the reference antibody to the cell surface antigen. If the antibody to be tested exhibits high affinity for IL1RAP, then a reduced pre-incubation period may be used (or even no pre-incubation at all).

Production of the Antibody

A second aspect of the invention relates to a polynucleotide encoding the antibody or antigen-binding fragment of the first aspect of the invention, or a component polypeptide chain thereof.

The term "polynucleotide" as used herein includes DNA (e.g. genomic DNA or complementary DNA) and mRNA molecules, which may be single- or double-stranded.

In some embodiments, the polynucleotide is an isolated polynucleotide.

In some embodiments, the polynucleotide is a cDNA molecule.

It will be appreciated by persons skilled in the art that the polynucleotide may be codon-optimised for expression of the antibody or antigen-binding fragment in a particular host cell, e.g. for expression in human cells (for example, see Angov, 2011, *Biotechnol. J.* 6(6):650-659, the disclosures of which are incorporated herein by reference).

In some embodiments, the polynucleotide encoding the antibody or antigen-binding fragment of the invention is encoding an antibody light chain or variable region thereof.

In some embodiments, the polynucleotide encoding the antibody or antigen-binding fragment of the invention is encoding an antibody heavy chain or variable region thereof.

A third aspect of the invention relates to a vector comprising the polynucleotide according to the second aspect of the invention.

In some embodiments, the vector is an expression vector.

The term "expression vector" is defined herein as a DNA molecule, for example linear or circular, that comprises a polynucleotide encoding a polypeptide of the present invention (the antibody or antigen-binding fragment thereof) and is operably linked to additional nucleotides that provide for its expression. The terms "plasmid", "expression vector" and "vector" are used interchangeably as the plasmid is generally the most commonly used form of vector at present. However, the invention is intended to include such other forms of expression vectors that serve equivalent functions that are known in the art. As used herein "expression vector" or "vector" refers to a DNA construct containing a DNA sequence that is operably linked to a suitable control sequence capable of effecting the expression of the DNA in a suitable host. Such control sequences may, e.g., include a promoter to effect transcription, an optional operator sequence to control such transcription, a sequence encoding suitable mRNA ribosome binding sites and sequences which control termination of transcription and translation. The vector may, e.g., be a plasmid, a phage or simply a potential genomic insert. Once transformed into a suitable host, the vector may, e.g., replicate and function independently of the host genome, or may, in some instances, integrate into the genome itself. Expression vectors are designed, for example, as described in Li et al. (Construction strategies for developing expression vectors for recombinant monoclonal antibody production in CHO cells, Mol Biol Rep. 2018 December; 45(6):2907-2912).

A fourth aspect of the invention relates to a recombinant host cell comprising the polynucleotide according to the second aspect of the invention or a vector according to the third aspect of the invention.

In some embodiments, the recombinant host cell is a bacterial cell.

In some embodiments, the recombinant host cell is a yeast cell.

In some embodiments, the recombinant host cell is a mammalian cell.

In some embodiments, the recombinant host cell is a human cell.

A fifth aspect of the invention relates to a method for producing the antibody or antigen-binding fragment of the first aspect of the invention, the method comprising culturing the host cell of the fourth aspect of the invention comprising the polynucleotide of the second aspect of the invention or the vector of the third aspect of the invention, under conditions which permit expression of the encoded antibody or antigen-binding fragment thereof.

Pharmaceutical Composition

A sixth aspect of the invention relates to a pharmaceutical composition comprising
the antibody or antigen-binding fragment of the first aspect of the invention,
the polynucleotide of the second aspect of the invention,
the vector of the third aspect of the invention, and/or
the host cell of the fourth aspect of the invention,
in a pharmaceutical composition, wherein the composition further comprises a pharmaceutically-acceptable diluent, carrier or excipient.

In some embodiments, the composition comprises an effective amount of
the antibody or antigen-binding fragment of the first aspect of the invention,
the polynucleotide of the second aspect of the invention,
the vector of the third aspect of the invention, and/or
the host cell of the fourth aspect of the invention.

It will be appreciated by persons skilled in the art that additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g. through freeze drying, spray drying, spray cooling, or through use of particle formation from supercritical particle formation.

The term "pharmaceutically acceptable" is intended to mean a non-toxic material that does not decrease the effectiveness of the IL1RAP-binding activity of the antibody or antigen-binding fragment of the invention. Pharmaceutically acceptable buffers, carriers, diluents or excipients, for example, are well-known in the art.

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the antibody or antigen-binding fragment in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the antibody or antigen-binding fragment of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carrageenans, hyaluronic acid and derivatives thereof, polyacrylic acid, polysulphonate, polyethyleneglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The antibody or antigen-binding fragment of the invention may be formulated into any type of pharmaceutical composition known in the art to be suitable for the delivery thereof.

In some embodiments, the pharmaceutical compositions of the invention may be in the form of a liposome, in which the antibody or antigen-binding fragment is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carrageenans, hyaluronic acid and derivatives thereof, polyacrylic acid, polyvinyl imidazole, polysulphonate, polyethyleneglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the antibody or antigen-binding fragment may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active antibody or antigen-binding fragment. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also, administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. Preferably, the pharmaceutical compositions are administered intravenously. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active antibody or antigen-binding fragment, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the antibody or antigen-binding fragment of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the antibody or antigen-binding fragment of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the antibody or antigen-binding fragment of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The pharmaceutical compositions will be administered to a patient in a pharmaceutically effective dose. A "therapeutically effective amount", or "effective amount", or "therapeutically effective", as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity.

Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

In the context of diagnostic use of the antibody or antigen-binding fragment of the invention, a "pharmaceutically effective amount", or "effective amount", or "diagnostically effective", as used herein, refers to that amount which provides a detectable signal for diagnosis, e.g. for in vivo imaging purposes.

The antibody or antigen-binding fragment can be formulated at various concentrations, depending on the efficacy/toxicity of the antibody or antigen-binding fragment being used. For example, the formulation may comprise the active antibody or antigen-binding fragment at a concentration of between 0.1 μM and 1 mM, more preferably between 1 μM and 500 μM, between 500 μM and 1 mM, between 300 μM and 700 μM, between 1 μM and 100 μM, between 100 μM and 200 μM, between 200 μM and 300 μM, between 300 μM and 400 μM, between 400 μM and 500 μM, between 500 μM and 600 μM, between 600 μM and 700 μM, between 800 μM and 900 μM or between 900 μM and 1 mM. Typically, the formulation comprises the active antibody or antigen-binding fragment at a concentration of between 300 μM and 700 μM.

Typically, the therapeutic dose of the antibody or antigen-binding fragment (with or without a therapeutic moiety) in a human patient will be in the range of 100 μg to 1 g per administration (based on a body weight of 70 kg, e.g. between 300 μg to 700 mg per administration). For example, the maximum therapeutic dose may be in the range of 0.1 to 10 mg/kg per administration, e.g. between 0.1 and 5 mg/kg or between 1 and 5 mg/kg or between 0.1 and 2 mg/kg. In some embodiments, the therapeutic dose may be 5, 20 or 50 mg/kg, or any range formed from these values. For example, the therapeutic dose may be from 5 to 50 mg/kg, from 5 to 20 mg/kg, or from 20 to 50 mg/kg. It will be appreciated that such a dose may be administered at different intervals, as determined by the oncologist/physician; for example, a dose may be administered daily, twice-weekly, weekly, bi-weekly or monthly.

It will be appreciated by persons skilled in the art that the pharmaceutical compositions of the invention may be administered alone or in combination with other therapeutic agents used in the treatment of inflammatory, fibrotic and/or neoplastic disorders or diseases.

In some embodiments, said composition is adapted for parenteral delivery.

In some embodiments, said composition is adapted for intravenous delivery.

In some embodiments, said composition is adapted for topical delivery.

In some embodiments, said composition is adapted for subcutaneous delivery.

In some embodiments, said composition is adapted for intramuscular delivery.

It will be further appreciated by persons skilled in the art that the antibody or antigen-binding fragment and pharmaceutical compositions or formulations of the present invention have utility in both the medical and veterinary fields. Thus, the methods of the invention may be used in the treatment of both human and non-human animals (such as horses, dogs and cats). Preferably, however, the patient is human.

Indications and Use of the Antibody

A seventh aspect of the invention relates to the antibody or antigen-binding fragment of the first aspect of the invention, the polynucleotide of the second aspect of the invention, the vector of the third aspect of the invention, the host cell of the fourth aspect of the invention, and/or the composition of the sixth aspect of the invention, for use in medicine.

An eighth aspect of the invention relates to the antibody or antigen-binding fragment of the first aspect of the invention, the polynucleotide of the second aspect of the invention, the vector of the third aspect of the invention, the host cell of the fourth aspect of the invention, and/or the composition of the sixth aspect of the invention, for use in the prevention and/or treatment and/or alleviation and/or detection and/or diagnosis of a disease or disorder susceptible to treatment with an inhibitor of IL-1α, IL-1β, IL-33, IL-36α, IL-36β and/or IL-36γ signaling, and/or wherein the disease or disorder is associated with cells expressing IL1RAP.

In an alternative aspect to the eighth aspect of the invention, the invention relates to the antibody or antigen-binding fragment of the first aspect of the invention, the polynucleotide of the second aspect of the invention, the vector of the third aspect of the invention, the host cell of the fourth aspect of the invention, and/or the composition of the sixth aspect of the invention, for use in the prevention and/or treatment and/or alleviation and/or detection and/or diagnosis of a disease or disorder susceptible to treatment with an inhibitor of IL-1α, IL-1β, IL-33, IL-36α, IL-36β and/or IL-36γ signaling.

In another alternative aspect to the eighth aspect of the invention, the invention relates to the antibody or antigen-binding fragment of the first aspect of the invention, the polynucleotide of the second aspect of the invention, the vector of the third aspect of the invention, the host cell of the fourth aspect of the invention, and/or the composition of the sixth aspect of the invention, for use in the prevention and/or treatment and/or alleviation and/or detection and/or diagnosis of a disease or disorder, wherein the disease or disorder is associated with cells expressing IL1RAP.

In some embodiments, said disease or disorder is associated with IL-1α, IL-1β, IL-33, IL-36α, IL-36β and/or IL-36γ signaling.

In some embodiments, said disease or disorder is associated with cells expressing IL1RAP.

By "treatment" we include both therapeutic and prophylactic or preventive treatment of the patient. The terms "preventive" or "prophylactic" are used to encompass the use of an antibody or antigen-binding fragment thereof, or formulation thereof, as described herein which either prevents or reduces the likelihood of an inflammatory disease or disorder, a fibrotic disease or disorder, a neoplastic disorder or disorder, which also includes the prevention or reduction of the spread, dissemination, or metastasis of neoplastic cells in a patient or subject. The term "prophylactic" also encompasses the use of an antibody or antigen-binding fragment thereof, or formulation thereof, as described herein to prevent recurrence of an inflammatory, fibrotic and/or neoplastic disease or disorder in a patient who has previously been treated for any of these diseases or disorders.

By "diagnosis" or "detection" we include the detection of cells which are associated with an inflammatory, fibrotic and/or neoplastic disease or disorder, either in vivo (i.e. within the body of a patient) or ex vivo (i.e. within a tissue or cell sample removed from the body of a patient).

By "alleviation" we mean, without being limited by it, decreased symptoms or processes associated with a disease or disorder, i.e. resulting in a milder disease or disorder.

By "an inflammatory, fibrotic and/or neoplastic disease or disorder associated with cells expressing IL1RAP" we include such diseases or disorders wherein the pathological cells which are responsible, directly or indirectly, for the disorder express IL1RAP on the cell surface. It will be appreciated that the cells expressing IL1RAP may be immune cells, cells of the connective tissue such as fibroblasts or neoplastic cells (cancer cells), e.g. tumour cells, per se. In addition, such cells include pathological stem cells (i.e. cancer stem cells, or CSCs) and progenitor cells which are responsible, directly or indirectly, for the development of an inflammatory, fibrotic and/or neoplastic disease or disorder in an individual. Examples of CSCs are disclosed in Visvader & Lindeman, 2008, *Nat Rev Cancer* 8:755-768, the disclosures of which are incorporated herein by reference. Alternatively, or in addition, the cells expressing IL1RAP may be associated indirectly with an inflammatory, fibrotic and/or neoplastic disease or disorder, for example, they may mediate cellular processes required for the cells to survive. The antibody or antigen-binding fragment thereof of the invention may in this event target cells essential for the maintenance of inflammatory and/or fibrotic processes, or, for example, blood supply of the tumour (angiogenesis) or cells inhibiting a beneficial immune response directed against the malignant cells (e.g. suppressive macrophages or T cells).

Depending upon whether it is therapeutically desirable to kill the target cells expressing IL1RAP, for example in the case of neoplastic cells, an antibody or antigen-binding fragment according to the first aspect of the invention may be used that it capable of inducing ADCC. For example, where the target cells expressing IL1RAP are cancer cells (such as CML, AML, ALL, melanoma, lung cancer cells, etc), it may be advantageous for the antibody or antigen-binding fragment to be capable of inducing ADCC in order to eliminate such cells. However, it will be appreciated that a therapeutic benefit may also be achieved using an antibody or antigen-binding fragment that lacks ADCC activity, for example through inhibition of IL-1α, IL-1β, IL-33, IL-36α, IL-36β and/or IL-36γ signaling leading to reduced angiogenesis in the vicinity of a cancer or tumour. Similarly, in the case of inflammatory and/or fibrotic diseases or disorders, it might be beneficial to affect cellular behaviour but not to kill the cells.

Conditions or disease states susceptible to treatment with an inhibitor of IL-1 and/or which may constitute an inflammatory, fibrotic and/or neoplastic disease or disorder associated with cells expressing IL1RAP, are well known in the art (see Dinarello et al., 2012, *Nature Reviews* 11:633-652 and Dinarello, 2014, *Mol. Med.* 20(suppl. 1):S43-S58, the disclosures of which are incorporated herein by reference) and include, but are not limited to, the following:

Rheumatoid arthritis, all types of arthritis, psoriatic arthritis, all types of juvenile arthritis, including systemic onset juvenile idiopathic arthritis (SOJIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, psoriasis, asthma, allergy, atherosclerosis, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease (including ulcerative colitis and Crohn's disease), hepatitis, hepatitis C, ischaemia-reperfusion injury, multiple sclerosis, Neisserial or pneumococcal meningitis, tuberculosis, Behcet's syndrome, septic shock, graft versus host disease, adult T cell leukaemia, multiple myeloma, periodontitis, obesity and obesity-related diseases (for example, metabolic syndrome, cardiomegaly, congestive heart failure, myocardial infarction, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis, acne inversa, Behcet's disease, cardiac fibrosis, cardiovascular diseases, cryopyin-associated periodic syndromes, cystic fibrosis, Goodpasture's syndrome, Guillain-Barre syndrome, kidney fibrosis, liver fibrosis, lung fibrosis (pulmonary fibrosis), skin fibrosis (dermal fibrosis), myocarditis, autoimmune myocarditis, organ dysfunction associated with organ transplantation, pancreatitis, peritonitis, uveitis, vasculitis, pneumonia, pulmonary hypertension, sclerodermatous chronic graft-versus-host disease, sepsis, Sjögren's syndrome, systemic sclerosis, Takayasu's arteritis and gout.

Blockade of IL-1 signaling is also believed to be beneficial in the treatment of myocardial infarction. An extensive clinical trial is sought to confirm the efficacy of anti-IL-1p antibody blockade (using Canakinumab) following myocardial infarction (the CANTOS trail; see Ridker et al., 2011, *Am Heart Journal* 162(4):597-605, the disclosures of which are incorporated herein by reference).

For such indications, it will be appreciated that a therapeutic benefit may also be achieved using an antibody or antigen-binding fragment that binds IL1RAP and thereby blocking IL-1 and/or IL-33 and/or IL-36 signaling associated with immune cells. Such antibody could be modified to lack ADCC activity.

In some embodiments, said disease or disorder is an inflammatory and/or fibrotic and/or neoplastic disease or disorder.

In relation to the therapeutic and prophylactic aspects of the invention, it will be appreciated by persons skilled in the art that binding of the antibody, or antigen-binding fragment thereof, to IL1RAP present on the surface of the cells associated with the inflammatory, fibrotic and/or neoplastic disease or disorder may lead to a modulation (i.e. an increase or decrease) of a biological activity of IL1RAP. However, such a modulatory effect is not essential; for example, the antibody or antigen-binding fragment thereof of the invention may elicit a therapeutic and prophylactic effect simply by virtue of binding to IL1RAP on the surface of the cells associated with the disease or disorder, which in turn may trigger the immune system to induce processes, such as cell death (e.g. by ADCC and/or by the presence within the agent of a cytotoxic/radioactive moiety).

In some embodiments, the antibody or antigen-binding fragment thereof with binding specificity for IL1RAP inhibits the biological activity of IL1RAP.

By "biological activity of IL1RAP" we include any interaction or signaling event which involves IL1RAP on the cells associated with the inflammatory, fibrotic and/or neoplastic disease or disorder. For example, in one embodiment the antibody or antigen-binding fragment thereof is capable of blocking binding of one or more co-receptors to IL1RAP (such as IL1R1, ST2, C-KIT and/or IL1RL2). Further, as elaborated above, in some embodiments, the antibody or antigen-binding fragment thereof with binding specificity for IL1RAP inhibits signaling of IL-1α, IL-1β, IL-33, IL-36α, IL-36β and/or IL-36γ.

The person skilled in the art will understand that "inhibiting signaling of cytokines" (such as cytokines of the IL-1 family, such as inhibiting signaling of IL-1α, IL-1β, IL-33, IL-36α, IL-36β and/or IL-36γ) leads to an inhibition of the biological activity of IL1RAP.

Such inhibition of the biological activity of IL1RAP by an antibody or antigen binding fragment thereof of the invention may be in whole or in part. For example, the antibody or antigen binding fragment thereof may inhibit the biological activity of IL1RAP by at least 10%, preferably at least 20%, 30%, 40%, 50%, 60%, 70%, 80% or 90%, and most preferably by 100% compared to the biological activity of IL1RAP in cells associated with the inflammatory, fibrotic and/or neoplastic disease or disorder which have not been exposed to the antibody or antigen-binding fragment thereof. In a preferred embodiment, the antibody or antigen-binding fragment thereof is capable of inhibiting the biological activity of IL1RAP by 50% or more compared to the biological activity of IL1RAP in cells associated with the inflammatory, fibrotic and/or neoplastic disease or disorder which have not been exposed to the antibody or antigen-binding fragment.

Likewise, it will be appreciated that inhibition of growth and/or proliferation of the cells associated with the neoplastic disease or disorder may be in whole or in part. For example, the antibody or antigen-binding fragment thereof may inhibit the growth and/or proliferation of the cells associated with the neoplastic disease or disorder by at least 10%, preferably at least 20%, 30%, 40%, 50%, 60%, 70%, 80% or 90%, and most preferably by 100% compared to the growth and/or proliferation of cells associated with the neoplastic disease or disorder which have not been exposed to the antibody or antigen binding fragment thereof.

IL-1, IL-33 and IL-36 in Disease

IL-1 is implicated in a wide range of diseases and conditions ranging from gout to cancer (for reviews, see Dinarello et al., 2012, *Nature Reviews* 11:633-652 and Dinarello, 2014, *Mol. Med.* 20(suppl. 1):S43-S58; the disclosures of which are incorporated herein by reference), including:

Joint, bone and muscle diseases, such as rheumatoid arthritis and osteoarthritis;
Hereditary systemic autoinflammatory diseases, such as familial Mediterranean fever;
Systemic autoinflammatory diseases, such as systemic juvenile idiopathic arthritis and adult-onset Still's disease;
Common inflammatory diseases, such as gout and type 2 diabetes;
Acute-onset ischemic diseases, such as myocardial infarction; and
Cancer.

A number of therapies for blocking IL-1 activity are approved and in development. Targeting IL-1 began in 1993 with the introduction of anakinra (Kineret; Amgen), a recombinant form of the naturally occurring IL-1 receptor antagonist (IL-1Ra or IL1RA), which blocks the activity of both IL-1α and IL-1β; this therapeutic has since been used to demonstrate a role for IL-1 in numerous diseases (see above). Anakinra currently dominates the field of IL-1 therapeutics owing to its good safety record, short half-life and multiple routes of administration. Neutralising IL-1 with antibodies or soluble receptors has also proved to be effective, and the soluble decoy receptor rilonacept (Arcalyst; Regeneron) and the anti-IL-1β neutralizing monoclonal antibody canakinumab (Ilaris; Novartis) have now been approved. Other therapeutic approaches, including IL-1α neutralisation, a therapeutic vaccine targeting IL-1β and a chimeric IL-1Ra, are in early clinical trials. In addition, orally active small-molecule inhibitors of IL-1 production, such as caspase 1 inhibitors, have been developed and are being tested.

Similarly, as elaborated above, there is emerging evidence of the implication of IL-33 in disease. As elaborated above, IL-33 has been implicated in e.g. asthma, allergic diseases, inflammatory bowel disease, and dermatitis. Importantly, IL-33 is implicated in fibrosis and inflammation (Kotsiou et al. 2018, IL-33/ST2 Axis in Organ Fibrosis, Front Immunol. 2018 Oct. 24; 9:2432). IL-33 can potently stimulate a wide range of cells and its pleiotropic nature is reflected in the role of IL-33 in tissue and metabolic homeostasis, infection, inflammation, cancer and diseases of the central nervous system.

Similarly, as elaborated above, there is emerging evidence of the implication of IL-36 in disease, even though this field is still evolving and, compared to IL-1, the knowledge relating to IL-36 is still limited. As elaborated above, emerging evidence indicates that IL-36 signaling is involved in the activation of innate and adaptive immune responses (Ding L, IL-36 cytokines in autoimmunity and inflammatory disease, Oncotarget, Vol. 9, (No. 2), pp: 2895-2901 (2018)). Besides its role in inflammatory skin diseases such as psoriasis and atopic dermatitis, emerging evidence suggests that aberrant IL-36 activities also promote inflammatory diseases in the lung, kidneys, and intestines, underscoring the potential of IL-36 as a therapeutic target for common inflammatory diseases.

The person skilled in the art will appreciate that the antibody or antigen-binding fragment thereof of the present invention may have or is expected to have profound effects on inflammatory and/or fibrotic diseases or disorders, for example due to the ability to inhibit signaling of IL-1α, IL-1β, IL-33, IL-36α, IL-36β and/or IL-36γ, thereby targeting several IL-dependent pathways at the same time.

In some embodiments, said disease or disorder is an inflammatory and/or fibrotic disease or disorder.

In some embodiments, said disease or disorder is an inflammatory and/or fibrotic disease or disorder, wherein the inflammatory and/or fibrotic disease or disorder is selected from the group consisting of rheumatoid arthritis, all types of arthritis, psoriatic arthritis, all types of juvenile arthritis, including systemic onset juvenile idiopathic arthritis (SOJIA), osteoarthritis, familial cold autoinflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, psoriasis, asthma, allergy, atherosclerosis, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease (including ulcerative colitis and Crohn's disease), hepatitis, hepatitis C, ischaemia-reperfusion injury, multiple sclerosis, Neisserial or pneumococcal meningitis, tuberculosis, Behcet's syndrome, septic shock, graft versus host disease, adult T cell leukaemia, multiple myeloma, periodontitis, obesity and obesity-related diseases (for example, metabolic syndrome, cardiomegaly, congestive heart failure, myocardial infarction, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis, acne inversa, Behcet's disease, cardiac fibrosis, cardiovascular diseases, cryopyin-associated periodic syndromes, cystic fibrosis, Goodpasture's syndrome, Guillain-Barre syndrome, kidney fibrosis, liver fibrosis, lung fibrosis (pulmonary fibrosis), skin fibrosis (dermal fibrosis), myocarditis, autoimmune myocarditis, organ dysfunction associated with organ transplantation, pancreatitis, peritonitis, uveitis, vasculitis, pneumonia, pulmonary hypertension, sclerodermatous chronic graft-versus-host disease, sepsis, Sjögren's syndrome, systemic sclerosis, Takayasu's arteritis and gout.

In some embodiments, said disease or disorder is systemic sclerosis, also called scleroderma or systemic scleroderma.

In some embodiments, said disease or disorder is peritonitis, such as acute peritonitis.

In some embodiments, said disease or disorder is psoriasis. In some embodiments, said disease or disorder is psoriatic arthritis. In one embodiment said disease or disorder is psoriasis and psoriatic arthritis.

In some embodiments, said disease or disorder is atherosclerosis. In some embodiments, the use of the herein disclosed invention in the prevention, treatment, alleviation, detection and/or diagnosis of atherosclerosis comprises the reduction of atherosclerosis, for example the reduction of clinical signs, symptoms or pathophysiological correlates of atherosclerosis, for example reduction of atherosclerotic plaque inflammation, such as aortic plaque inflammation, and/or a reduction in plaque size (for example, plaque volume and/or plaque area).

Plaque inflammation can be assessed based on a cellular count of $CD45^+$ leukocytes using flow cytometric analyses of an aorta (for example, as shown in Example 4). A higher count of $CD45^+$ leukocytes in a test aorta (for example, an aorta suspected of being or diagnosed as an atherosclerotic aorta) relative to a healthy control aorta indicates atherosclerotic plaque inflammation. In some embodiments, the leukocyte count may be assessed based on myeloid $CD11b^+$ cells (including $Ly6G^+$ neutrophils) and/or $TCR-\beta^+$ cells (including $CD4^+$ and/or $CD8^+$ cells).

Plaque size may be assessed based on plaque volume and/or plaque area. An increase in plaque size (e.g. plaque volume and/or plaque area) in a test aorta (for example, an aorta suspected of being or diagnosed as an atherosclerotic aorta) relative to a healthy control aorta (which may have an absence of plaques) indicates presence of an atherosclerotic plaque.

In some embodiments, said disease or disorder is lung fibrosis, also known as pulmonary fibrosis.

Fibrosis is the hallmark of a multitude of diseases. In some cases, fibrosis may be an integral part of the disease, meaning that fibrosis may be the consequence of aberrant or pathologic cellular behaviour leading to a pathological deposition of extracellular matrix proteins. In other cases, fibrosis may be a secondary event occurring in diseased tissue, in parallel to the primary disease or in the course of the healing process. For example, fibrosis may be scar formation. Any type of fibrosis may be targeted, for example treated or prevented, by the antibodies as disclosed herein. Fibrosis may be categorized as uncontrolled or dysregulated scar tissue formation, which can be caused by excessive accumulation of extracellular matrix components, such as collagen. Accordingly, the use of the herein disclosed invention in the prevention, treatment, alleviation, detection and/or diagnosis of fibrosis may be upstream of the prevention, treatment, alleviation, detection and/or diagnosis of a disease for which fibrosis is a hallmark. Alternatively, or additionally, the use of the herein disclosed invention in the prevention, treatment, alleviation, detection and/or diagnosis of fibrosis may be downstream of a disease for which fibrosis is a secondary event in said disease.

In some embodiments, said disease or disorder is myocarditis.

In some embodiments, said disease or disorder is autoimmune myocarditis.

In some embodiments, the use of the herein disclosed invention in the prevention, treatment, alleviation, detection and/or diagnosis of myocarditis, such as autoimmune myocarditis, comprises the reduction of myocarditis, such as autoimmune myocarditis, for example the reduction of clinical signs, symptoms or pathophysiological correlates of myocarditis, such as autoimmune myocarditis, for example reduction of deterioration in cardiac function, reduction in inflammation and/or reduction fibrosis.

In some embodiments, said disease or disorder is graft-versus-host disease, including chronic graft-versus-host disease and sclerodermatous chronic graft-versus-host disease. In one embodiment, said disease or disorder is dermal fibrosis and/or pulmonary fibrosis in graft-versus-host disease. In a particular embodiment, the graft-versus-host disease is caused by a syngeneic transplantation. In an alternative embodiment, the graft-versus-host disease is caused by an allogeneic transplantation.

In some embodiments, said disease or disorder is an acute inflammatory disease or disorder.

In some embodiments, said disease or disorder is a chronic inflammatory disease or disorder.

The person skilled in the art will appreciate that diseases or disorders are grouped in different ways. While a disease or disorder may not be explicitly labelled as an inflammatory or fibrotic disease, it may still have an inflammatory and/or fibrotic components, for example inflammatory and/or fibrotic processes which form part or contribute to the disease or disorder.

In some embodiments, said disease or disorder has an inflammatory and/or fibrotic component.

In some embodiments, said disease or disorder is an autoimmune disease or disorder.

In some embodiments, the antibody or antigen-binding fragment of the first aspect of the invention inhibits inflammatory processes.

In some embodiments, the antibody or antigen-binding fragment of the first aspect of the invention inhibits fibrotic processes.

In some embodiments, the antibody or antigen-binding fragment of the first aspect of the invention inhibits proliferative processes.

IL1RAP as a Biomarker for Neoplastic Diseases or Disorders

A neoplasm, indicative of neoplastic diseases or disorders (i.e. cancer), is a type of abnormal and excessive growth (also called neoplasia) of tissue or cells, for example tumours.

Tumour biomarkers or biomarkers of neoplastic diseases or disorders are endogenous proteins or metabolites whose amounts or modifications are indicative of tumour state, progression characteristics, and response to therapies. They are present in tumour tissues or body fluids and encompass a wide variety of molecules, including transcription factors, cell surface receptors, and secreted proteins. Effective tumour markers are in great demand since they have the potential to reduce cancer mortality rates by facilitating diagnosis of cancers at early stages and by helping to individualize treatments. During the last decade, improved understanding of carcinogenesis and tumour progression has revealed a large number of potential tumour markers. It is predicted that even more will be discovered in the near future with the application of current technologies such as tissue microarrays, antibody arrays, and mass spectrometry.

Interleukin-1 receptor accessory protein (IL1RAP) has previously been identified as cell-surface biomarker associated with haematological neoplastic disorders such as chronic myeloid leukemia (CML), acute myeloid leukemia (AML) and myelodysplatic syndromes (MDS) (for example, see WO 2011/021014 to Cantargia A B, Järås et al., 2010, *Proc Natl Acad Sci USA* 107(37):16280-5, Askmyr et al., 2013, *Blood.* 121(18):3709-13 and Barreyro et al., 2012, *Blood* 120(6):1290-8, the disclosures of which are incorporated herein by reference). More recently, the usefulness of IL1RAP as a diagnostic and therapeutic biomarker for solid tumours, such as melanomas, has also been revealed (see WO 2012/098407 to Cantargia A B, the disclosures of which are incorporated herein by reference).

Therefore, in some embodiments of the above aspects of the invention, said disease or disorder is a neoplastic disease or disorder.

The person skilled in the art will appreciate that the antibody of the present invention may have profound effects on neoplastic diseases or disorders, for example due to the ability to inhibit signaling of IL-1α, IL-1β, IL-33, IL-36α, IL-36β and IL-36γ, thereby targeting several IL-dependent pathways at the same time.

In some embodiments, said disease or disorder is a neoplastic disease or disorder, wherein the neoplastic disease or disorder is a hematologic disease or disorder or a solid tumour.

In some embodiments, said neoplastic disease or disorder is a hematologic disease, wherein the neoplastic hematologic disease or disorder is selected from the group consisting of chronic myeloid leukemia (CML), myeloproliferative disorders (MPD), myelodysplastic syndrome (MDS), acute lymphoblastic leukemia (ALL) and acute myeloid leukemia (AML).

In some embodiments, said neoplastic disease or disorder is a solid tumor, wherein the solid tumour is selected from the group consisting of prostate cancer, breast cancer, lung cancer, colon cancer, colorectal cancer, melanomas, bladder cancer, brain/CNS cancer, cancer of urinary organs, biliary tract cancer (also known as bile duct cancer), cervical cancer, oesophageal cancer, gastric cancer, head/neck cancer, kidney cancer, liver cancer, lymphomas, ovarian cancer, pancreatic cancer, sarcomas, skin cancer and uterus cancer.

The person skilled in the art will appreciate that the antibody of the present invention is expected to have profound effects on neoplastic diseases or disorders, for example due to the ability to inhibit signaling of IL-1α, IL-1β, IL-33, IL-36α, IL-36β and/or IL-36γ, thereby targeting several IL-dependent pathways at the same time.

The person of skill in the art would, for example in the light of the evidence stated above, understand that the antibody of the present invention could be used for the prevention, treatment, alleviation, detection and/or diagnosis of any disease or disorder implicated by activity of IL-1α, IL-1β, IL-33, IL-36α, IL-36β and/or IL-36γ.

A ninth aspect of the invention relates to the antibody or antigen-binding fragment of
 the first aspect of the invention,
 the polynucleotide of the second aspect of the invention,
 the vector of the third aspect of the invention,
 the host cell of the fourth aspect of the invention, and/or
 the composition of the sixth aspect of the invention,
 for use in inducing cell death and/or inhibiting the growth and/or proliferation of
 pathological cells associated with a neoplastic disorder in a subject, or stem cells or
 progenitor cells thereof, wherein the cells express IL1RAP.

A tenth aspect of the invention relates to the use of
 the antibody or antigen-binding fragment of the first aspect of the invention,
 the polynucleotide of the second aspect of the invention,
 the vector of the third aspect of the invention,
 the host cell of the fourth aspect of the invention, and/or
 the composition of the sixth aspect of the invention,
 in the preparation of a medicament for the prevention, treatment, alleviation, detection
 and/or diagnosis of a disease or disorder susceptible to treatment with an inhibitor of IL-1α, IL-1β, IL-33, IL-36α, IL-36β and/or IL-36γ signaling,
 and/or wherein the disease or disorder is associated with cells expressing IL1RAP.

An eleventh aspect of the invention relates to the use of
 the antibody or antigen-binding fragment of the first aspect of the invention,
 the polynucleotide of the second aspect of the invention,
 the vector of the third aspect of the invention,
 the host cell of the fourth aspect of the invention, and/or
 the composition of the sixth aspect of the invention,
 in the preparation of a medicament for the detection and/or diagnosis of a disease or
 disorder associated with cells expressing IL1RAP.

A twelfth aspect of the invention relates to a method for the prevention and/or treatment and/or alleviation and/or detection and/or diagnosis of a disease or disorder susceptible to treatment with an inhibitor of IL-1α, IL-1β, IL-33, IL-36α, IL-36β and/or IL-36γ signaling and/or wherein the disease or disorder is associated with cells expressing IL1RAP in a subject, comprising the step of administering to the subject an effective amount of
 the antibody or antigen-binding fragment of the first aspect of the invention,
 the polynucleotide of the second aspect of the invention,
 the vector of the third aspect of the invention,
 the host cell of the fourth aspect of the invention, and/or
 the composition of the sixth aspect of the invention.

A thirteenth aspect of the invention relates to an in vitro method for the detection of cells expressing IL1RAP in a subject, the method comprising:
 (a) providing a sample of cells from a subject to be tested, such as biopsy tissue or blood sample;
 (b) optionally, extracting and/or purifying the cells present in the sample;
 (c) contacting the antibody or antigen-binding fragment of the first aspect of the invention with cells present in the sample;
 (d) determining whether the antibody or antigen-binding fragment thereof binds to the cells
 wherein the binding of the antibody or antigen-binding fragment thereof to the cells is indicative of the presence of a disease or disorder associated with cells expressing IL1RAP in the tissue of a subject.

A fourteenth aspect of the invention relates to an in vitro method for identifying a patient with a disease or disorder associated with cells expressing IL1RAP who would benefit from treatment with the antibody or antigen-binding fragment of the first aspect of the invention, the method comprising:
 (a) providing a sample of cells, such as biopsy tissue or blood sample from a patient to be tested;
 (b) optionally, extracting and/or purifying the cells present in the sample;
 (c) contacting the antibody or antigen-binding fragment of the first aspect of the invention with cells present in the sample;
 (d) determining whether the antibody or antigen-binding fragment thereof binds to the cells
 wherein the binding of the antibody or antigen-binding fragment thereof to cells expressing IL1RAP is indicative of a patient who would benefit from treatment with the antibody or antigen-binding fragment of the first aspect of the invention.

A fifteenth aspect of the invention relates to a method for treating a patient with a disease or disorder associated with cells expression IL1RAP, the method comprising:
 a) selecting a patient identified as having a disease or disorder associated with cells expressing IL1RAP using a method according to the fourteenth aspect of the invention; and
 b) administering to said patient a therapeutic agent effective in the treatment of said disease or disorder.

A sixteenth aspect of the invention relates to a method for the detection of cells expressing IL1RAP, the method comprising:
 (a) contacting an antibody or antigen-binding fragment thereof according to the first aspect with cells to be analysed for their expression of IL1RAP;
 (b) determining whether the antibody or antigen-binding fragment thereof binds to the cells
 wherein the binding of the antibody or antigen-binding fragment thereof to the cells is indicative of the presence of a disease or disorder associated with cells expressing IL1RAP in the tissue of a subject.

In some embodiments, the method of the sixteenth aspect is an in vitro method.

In some embodiments, the method of the sixteenth aspect is an in vivo method.

The person skilled in the art will understand that, if the method of the sixteenth aspect is applied, the antibody or antigen-binding fragment with binding specificity for IL1RAP is administered to a subject, for example according to the descriptions herein.

A seventeenth aspect of the invention relates to a method for reducing inflammation in a subject with peritonitis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

In some embodiments, said method for reducing inflammation in a subject with peritonitis comprises reducing infiltration of immune cells into the peritoneum, for example neutrophils and monocytes.

In some embodiments, said method for reducing inflammation in a subject with peritonitis comprises reducing the levels of cytokines, for example reducing the levels of Eotaxin, G-CSF, IL-5, MCP-1, MIP-1P, IL-6 and/or KC (also known as CXCL1).

An eighteenth aspect of the invention relates to a method for reducing disease severity in a subject with psoriasis or psoriatic arthritis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

In some embodiments, said method for reducing disease severity in a subject with psoriasis or psoriatic arthritis comprises reducing skin inflammation and/or erythema of the skin.

In some embodiments, said method for reducing disease severity in a subject with psoriasis or psoriatic arthritis comprises reducing the levels of cytokines, for example reducing the level of IL-17.

A nineteenth aspect of the invention relates to a method for reducing atherosclerotic plaque inflammation in a subject with atherosclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

In some embodiments, said method for reducing atherosclerotic plaque inflammation in a patient with atherosclerosis comprises reducing the numbers of CD45+ leukocytes, for example myeloid CD11b+ cells, for example Ly6G+ neutrophils, and/or reducing the numbers of TCR-β+ cells, for example CD4+ and/or CD8+ cells.

A twentieth aspect of the invention relates to a method for reducing atherosclerotic plaque volume and/or atherosclerotic plaque size in a subject with atherosclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-first aspect of the invention relates to a method for reducing inflammation and/or fibrosis in a subject with myocarditis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-second aspect of the invention relates to a method for counteracting deterioration in cardiac function in a subject with myocarditis or autoimmune myocarditis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

A twenty-third aspect of the invention relates to a method for reducing dermal fibrosis in a subject with systemic sclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

In some embodiments, said method for reducing dermal fibrosis in a subject with systemic sclerosis comprises reducing dermal thickness, reducing the number of myofibroblasts and/or reducing the amount of collagen in the skin.

A twenty-fourth aspect of the invention relates to a method for reducing pulmonary fibrosis in a subject with systemic sclerosis, the method comprising the step of administering to the subject an effective amount of
the antibody or antigen-binding fragment of the first aspect of the invention,
the polynucleotide of the second aspect of the invention,
the vector of the third aspect of the invention,
the host cell of the fourth aspect of the invention, and/or
the composition of the sixth aspect of the invention.

In some embodiments, said method for reducing pulmonary fibrosis in a subject with systemic sclerosis comprises reducing the Ashcroft score and/or the amount of collagen in the lungs.

The embodiments and explanations relating to the eighth aspect, for example in relation to the disease or disorder susceptible to treatment with an inhibitor of IL-1α, IL-1β, IL-33, IL-36α, IL-36β and/or IL-36γ signaling, and/or in relation to the disease or disorder associated with cells expressing IL1RAP, shall also apply to the ninth, tenth, eleventh, twelfth, thirteenth, fourteenth, fifteenth and/or sixteenth aspect of the invention. They may also apply to the seventeenth, eighteenth, nineteenth, twentieth, twenty-first, twenty-second, twenty-third or twenty-fourth aspect of the invention.

EMBODIMENTS

Embodiment 1. An antibody or antigen-binding fragment thereof with binding specificity for interleukin-1 receptor accessory protein (IL1RAP), wherein the antibody or antigen-binding fragment comprises:

a light chain variable region comprising
  a) a CDR-L1 comprising or consisting of an amino acid sequence selected from the group consisting of ESISTA (SEQ ID NO: 1), QASESISTALA (SEQ ID NO: 7) and QASESISTALA (SEQ ID NO: 13);
  b) a CDR-L2 comprising or consisting of an amino acid sequence selected from the group consisting of KAS, KASTLPS (SEQ ID NO: 8) and KASTLPS (SEQ ID NO: 14); and
  c) a CDR-L3 comprising or consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15);
and/or
a heavy chain variable region comprising
  d) a CDR-H1 comprising or consisting of an amino acid sequence selected from the group consisting of GPSLSHFD (SEQ ID NO: 4), HFDIT (SEQ ID NO: 10) and GPSLSHFDIT (SEQ ID NO: 16);
  e) a CDR-H2 comprising or consisting of an amino acid sequence selected from the group consisting of ISPGVST (SEQ ID NO: 5), TISPGVSTYYAS-WAKS (SEQ ID NO: 11) and TISPGVSTYYAS-WAKS (SEQ ID NO: 17); and
  f) a CDR-H3 comprising or consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

Embodiment 2. The antibody or antigen-binding fragment thereof according to embodiment 1, wherein the antibody or antigen-binding fragment comprises:
a light chain variable region comprising
  a) a CDR-L1 consisting of an amino acid sequence selected from the group consisting of ESISTA (SEQ ID NO: 1), QASESISTALA (SEQ ID NO: 7) and QASESISTALA (SEQ ID NO: 13);
  b) a CDR-L2 consisting of an amino acid sequence selected from the group consisting of KAS, KASTLPS (SEQ ID NO: 8) and KASTLPS (SEQ ID NO: 14); and
  c) a CDR-L3 consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15);
and/or
a heavy chain variable region comprising
  d) a CDR-H1 consisting of an amino acid sequence selected from the group consisting of GPSLSHFD (SEQ ID NO: 4), HFDIT (SEQ ID NO: 10) and GPSLSHFDIT (SEQ ID NO: 16);
  e) a CDR-H2 consisting of an amino acid sequence selected from the group consisting of ISPGVST (SEQ ID NO: 5), TISPGVSTYYASWAKS (SEQ ID NO: 11) and TISPGVSTYYASWAKS (SEQ ID NO: 17); and
  f) a CDR-H3 consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

Embodiment 3. The antibody or antigen-binding fragment thereof according to any one of the preceding embodiments wherein the IL1RAP is human IL1RAP.

Embodiment 4. The antibody or antigen-binding fragment thereof according to any one of the preceding embodiments wherein the IL1RAP is expressed on the surface of a cell.

Embodiment 5. The antibody or antigen-binding fragment thereof according to any one of the preceding embodiments wherein the antibody or antigen-binding fragment thereof binds to domain 2 of IL1RAP.

Embodiment 6. The antibody or antigen-binding fragment thereof according to any one of the preceding embodiments, wherein the antibody or antigen-binding fragment thereof comprises a light chain variable region comprising the CDRs
  comprising or consisting of an amino acid sequence selected from the group consisting of ESISTA (SEQ ID NO: 1), QASESISTALA (SEQ ID NO: 7) and QASESISTALA (SEQ ID NO: 13);
  comprising or consisting of an amino acid sequence selected from the group consisting of KAS, KASTLPS (SEQ ID NO: 8) and KASTLPS (SEQ ID NO: 14); and/or
  comprising or consisting of an amino acid sequence selected from the group consisting of QQGFSSGNVHNA (SEQ ID NO: 3), QQGFSSGNVHNA (SEQ ID NO: 9) and QQGFSSGNVHNA (SEQ ID NO: 15).

Embodiment 7. The antibody or antigen-binding fragment thereof according to any one of the preceding embodiments, wherein the antibody or antigen-binding fragment thereof comprises a light chain variable region comprising or consisting of the amino acid sequence of SEQ ID NO: 19;
  or an amino acid sequence having at least 70% sequence identity to SEQ ID NO: 19, for example at least 80%, 85%, 90%, 95%, 98% or 99% sequence identity.

Embodiment 8. The antibody or antigen-binding fragment thereof according to any one of the preceding embodiments, wherein the antibody or antigen-binding fragment thereof comprises a light chain variable region comprising or consisting of an amino acid sequence selected from the group consisting of SEQ ID NO: 21, SEQ ID NO: 22, SEQ ID NO: 23, SEQ ID NO: 24 and SEQ ID NO: 25;
  or an amino acid sequence having at least 70% sequence identity to SEQ ID NO: 21, SEQ ID NO: 22, SEQ ID NO: 23, SEQ ID NO: 24 or SEQ ID NO: 25, for example at least 80%, 85%, 90%, 95%, 98% or 99% sequence identity.

Embodiment 9. The antibody or antigen-binding fragment thereof according to any one of the preceding embodiments, wherein the antibody or antigen-binding fragment thereof comprises a light chain variable region comprising or consisting of the amino acid sequence of SEQ ID NO: 31;
  or an amino acid sequence having at least 70% sequence identity to SEQ ID NO: 31, for example at least 80%, 85%, 90%, 95%, 98% or 99% sequence identity.

Embodiment 10. The antibody or antigen-binding fragment thereof according to any one embodiments 7 to 9, wherein any one of the amino acids of the framework region of the light chain variable region has been altered for another amino acid, with the proviso that no more than 5 amino acids have been so altered, such as 4 amino acids, no more than 3 amino acids, such as 2 amino acids or no more than 1 amino acid.

Embodiment 11. The antibody or antigen-binding fragment thereof according to any one of the preceding embodiments, wherein the antibody or antigen-binding fragment thereof comprises a heavy chain variable region comprising the CDRs
- comprising or consisting of an amino acid sequence selected from the group consisting of GPSLSHFD (SEQ ID NO: 4), HFDIT (SEQ ID NO: 10) and GPSLSHFDIT (SEQ ID NO: 16);
- comprising or consisting of an amino acid sequence selected from the group consisting of ISPGVST (SEQ ID NO: 5), TISPGVSTYYASWAKS (SEQ ID NO: 11) and TISPGVSTYYASWAKS (SEQ ID NO: 17); and/or
- comprising or consisting of an amino acid sequence selected from the group consisting of ARGGVGSSWKAFDL (SEQ ID NO: 6), GGVGSSWKAFDL (SEQ ID NO: 12) and ARGGVGSSWKAFDL (SEQ ID NO: 18).

Embodiment 12. The antibody or antigen-binding fragment thereof according to any one of the preceding embodiments, wherein the antibody or antigen-binding fragment thereof comprises a heavy chain variable region comprising or consisting of the amino acid sequence of SEQ ID NO: 20;
- or an amino acid sequence having at least 70% sequence identity to SEQ ID NO: 20, for example at least 80%, 85%, 90%, 95%, 98% or 99% sequence identity.

Embodiment 13. The antibody or antigen-binding fragment thereof according to any one of the preceding embodiments, wherein the antibody or antigen-binding fragment thereof comprises a heavy chain variable region comprising or consisting of an amino acid sequence selected from the group consisting of SEQ ID NO: 26, SEQ ID NO: 27, SEQ ID NO: 28, SEQ ID NO: 29 and SEQ ID NO: 30;
- or an amino acid sequence having at least 70% sequence identity to SEQ ID NO: 26, SEQ ID NO: 27, SEQ ID NO: 28, SEQ ID NO: 29 or SEQ ID NO: 30, for example at least 80%, 85%, 90%, 95%, 98% or 99% sequence identity.

Embodiment 14. The antibody or antigen-binding fragment thereof according to any one of the preceding embodiments, wherein the antibody or antigen-binding fragment thereof comprises a heavy chain variable region comprising or consisting of an amino acid sequence selected from the group consisting of SEQ ID NO: 32, SEQ ID NO: 33 and SEQ ID NO: 34;
- or an amino acid sequence having at least 70% sequence identity to SEQ ID NO: 32, SEQ ID NO: 33 or SEQ ID NO: 34, for example at least 80%, 85%, 90%, 95%, 98% or 99% sequence identity.

Embodiment 15. The antibody or antigen-binding fragment thereof according to any one of embodiments 12 to 14, wherein any one of the amino acids of the framework region of the heavy chain variable region has been altered for another amino acid, with the proviso that no more than 5 amino acids have been so altered, such as 4 amino acids, no more than 3 amino acids, such as 2 amino acids or no more than 1 amino acid.

Embodiment 16. The antibody or antigen-binding fragment thereof according to any one of the preceding embodiments, wherein the antibody or antigen-binding fragment thereof comprises:
- a light chain variable region which comprises or consists of the amino acid sequence of SEQ ID NO: 19 and a heavy chain variable region which comprises or consists of the amino acid sequence of SEQ ID NO: 20,
- or an amino acid sequence having at least 70% sequence identity to SEQ ID NO: 19 or SEQ ID NO: 20, for example at least 80%, 85%, 90%, 95%, 98% or 99% sequence identity.

Embodiment 17. The antibody or antigen-binding fragment thereof according to any one of the preceding embodiments wherein the antibody or antigen-binding fragment thereof comprises:
a) a light chain variable region which comprises or consists of SEQ ID NO: 21 and a heavy chain variable region which comprises or consists of SEQ ID NO: 26;
b) a light chain variable region which comprises or consists of SEQ ID NO: 21 and a heavy chain variable region which comprises or consists of SEQ ID NO: 27;
c) a light chain variable region which comprises or consists of SEQ ID NO: 21 and a heavy chain variable region which comprises or consists of SEQ ID NO: 28;
d) a light chain variable region which comprises or consists of SEQ ID NO: 21 and a heavy chain variable region which comprises or consists of SEQ ID NO: 29;
e) a light chain variable region which comprises or consists of SEQ ID NO: 21 and a heavy chain variable region which comprises or consists of SEQ ID NO: 30;
f) a light chain variable region which comprises or consists of SEQ ID NO: 22 and a heavy chain variable region which comprises or consists of SEQ ID NO: 26;
g) a light chain variable region which comprises or consists of SEQ ID NO: 22 and a heavy chain variable region which comprises or consists of SEQ ID NO: 27;
h) a light chain variable region which comprises or consists of SEQ ID NO: 22 and a heavy chain variable region which comprises or consists of SEQ ID NO: 28;
i) a light chain variable region which comprises or consists of SEQ ID NO: 22 and a heavy chain variable region which comprises or consists of SEQ ID NO: 29;
j) a light chain variable region which comprises or consists of SEQ ID NO: 22 and a heavy chain variable region which comprises or consists of SEQ ID NO: 30;
k) a light chain variable region which comprises or consists of SEQ ID NO: 23 and a heavy chain variable region which comprises or consists of SEQ ID NO: 26;
l) a light chain variable region which comprises or consists of SEQ ID NO: 23 and a heavy chain variable region which comprises or consists of SEQ ID NO: 27;
m) a light chain variable region which comprises or consists of SEQ ID NO: 23 and a heavy chain variable region which comprises or consists of SEQ ID NO: 28;

n) a light chain variable region which comprises or consists of SEQ ID NO: 23 and a heavy chain variable region which comprises or consists of SEQ ID NO: 29;
o) a light chain variable region which comprises or consists of SEQ ID NO: 23 and a heavy chain variable region which comprises or consists of SEQ ID NO: 30;
p) a light chain variable region which comprises or consists of SEQ ID NO: 24 and a heavy chain variable region which comprises or consists of SEQ ID NO: 26;
q) a light chain variable region which comprises or consists of SEQ ID NO: 24 and a heavy chain variable region which comprises or consists of SEQ ID NO: 27;
r) a light chain variable region which comprises or consists of SEQ ID NO: 24 and a heavy chain variable region which comprises or consists of SEQ ID NO: 28;
s) a light chain variable region which comprises or consists of SEQ ID NO: 24 and a heavy chain variable region which comprises or consists of SEQ ID NO: 29;
t) a light chain variable region which comprises or consists of SEQ ID NO: 24 and a heavy chain variable region which comprises or consists of SEQ ID NO: 30;
u) a light chain variable region which comprises or consists of SEQ ID NO: 25 and a heavy chain variable region which comprises or consists of SEQ ID NO: 26;
v) a light chain variable region which comprises or consists of SEQ ID NO: 25 and a heavy chain variable region which comprises or consists of SEQ ID NO: 27;
w) a light chain variable region which comprises or consists of SEQ ID NO: 25 and a heavy chain variable region which comprises or consists of SEQ ID NO: 28;
x) a light chain variable region which comprises or consists of SEQ ID NO: 25 and a heavy chain variable region which comprises or consists of SEQ ID NO: 29; or
y) a light chain variable region which comprises or consists of SEQ ID NO: 25 and a heavy chain variable region which comprises or consists of SEQ ID NO: 30, or an amino acid sequence having at least 70% sequence identity to any one of SEQ ID NO: 21 to SEQ ID NO: 30, for example at least 80%, 85%, 90%, 95%, 98% or 99% sequence identity.

Embodiment 18. The antibody or antigen-binding fragment thereof according to any one of the preceding embodiments, wherein the antibody or antigen-binding fragment thereof comprises:
a) a light chain variable region which comprises or consists of SEQ ID NO: 24 and a heavy chain variable region which comprises or consists of SEQ ID NO: 30;
b) a light chain variable region which comprises or consists of SEQ ID NO: 24 and a heavy chain variable region which comprises or consists of SEQ ID NO: 32;
c) a light chain variable region which comprises or consists of SEQ ID NO: 24 and a heavy chain variable region which comprises or consists of SEQ ID NO: 33;
d) a light chain variable region which comprises or consists of SEQ ID NO: 24 and a heavy chain variable region which comprises or consists of SEQ ID NO: 34;
e) a light chain variable region which comprises or consists of SEQ ID NO: 25 and a heavy chain variable region which comprises or consists of SEQ ID NO: 30;
f) a light chain variable region which comprises or consists of SEQ ID NO: 25 and a heavy chain variable region which comprises or consists of SEQ ID NO: 32;
g) a light chain variable region which comprises or consists of SEQ ID NO: 25 and a heavy chain variable region which comprises or consists of SEQ ID NO: 33;
h) a light chain variable region which comprises or consists of SEQ ID NO: 25 and a heavy chain variable region which comprises or consists of SEQ ID NO: 34;
i) a light chain variable region which comprises or consists of SEQ ID NO: 31 and a heavy chain variable region which comprises or consists of SEQ ID NO: 30;
j) a light chain variable region which comprises or consists of SEQ ID NO: 31 and a heavy chain variable region which comprises or consists of SEQ ID NO: 32;
k) a light chain variable region which comprises or consists of SEQ ID NO: 31 and a heavy chain variable region which comprises or consists of SEQ ID NO: 33; or
l) a light chain variable region which comprises or consists of SEQ ID NO: 31 and a heavy chain variable region which comprises or consists of SEQ ID NO: 34;

or an amino acid sequence having at least 70% sequence identity to SEQ ID NO: 24, SEQ ID NO: 25, SEQ ID NO: 31, SEQ ID NO: 30, SEQ ID NO: 32, SEQ ID NO: 33 or SEQ ID NO: 34, for example at least 80%, 85%, 90%, 95%, 98% or 99% sequence identity.

Embodiment 19. The antibody or antigen-binding fragment thereof according to any one of the preceding embodiments, wherein the antibody or antigen-binding fragment thereof comprises a light chain variable region which comprises or consists of SEQ ID NO: 24 and a heavy chain variable region which comprises or consists of SEQ ID NO: 34.

Embodiment 20. The antibody or antigen-binding fragment thereof according to any one of the preceding embodiments, wherein the antibody or antigen-binding fragment thereof comprises a light chain variable region which comprises or consists of SEQ ID NO: 31 and a heavy chain variable region which comprises or consists of SEQ ID NO: 34.

Embodiment 21. The antibody or antigen-binding fragment thereof according to any one of the preceding embodiments, wherein any one of the amino acids of the framework region of the light chain variable region and/or the heavy chain variable region has been altered for another amino acid, with the proviso that no more than 5 amino acids have been so altered, such as 4 amino acids, no more than 3 amino acids, such as 2 amino acids or no more than 1 amino acid.

Embodiment 22. The antibody or antigen-binding fragment thereof according to any one of the preceding embodiments, wherein the antibody or antigen-binding fragment thereof comprises a light chain constant region, or part thereof.

Embodiment 23. The antibody or antigen-binding fragment thereof according to embodiment 22, wherein the light chain constant region is of a kappa or lambda light chain.

Embodiment 24. The antibody or antigen-binding fragment thereof according to any one of embodiments 22 to 23, wherein the light chain constant region is of a kappa light chain.

Embodiment 25. The antibody or antigen-binding fragment thereof according to any one of the preceding embodiments, wherein the antibody or antigen-binding fragment thereof comprises a light chain constant region comprising or consisting of the amino acid sequence of SEQ ID NO: 35,
or an amino acid sequence having at least 70% sequence identity to SEQ ID NO: 35, for example at least 80%, 85%, 90%, 95%, 98% or 99% sequence identity.

Embodiment 26. The antibody or antigen-binding fragment thereof according to any one of the preceding embodiments, wherein the antibody or antigen-binding fragment thereof comprises a heavy chain constant region, or part thereof.

Embodiment 27. The antibody or antigen-binding fragment thereof according to embodiment 26, wherein the heavy chain constant region is of an immunoglobulin subclass selected from the group consisting of IgG1, IgG2, IgG3 and IgG4.

Embodiment 28. The antibody or antigen-binding fragment thereof according to any one of embodiments 26 to 27, wherein the heavy chain constant region is of an immunoglobulin subclass IgG1.

Embodiment 29. The antibody or antigen-binding fragment thereof according to any one of the preceding embodiments, wherein the antibody or antigen-binding fragment thereof comprises or consists of a heavy chain constant region comprising the amino acid sequence of SEQ ID NO: 36 or SEQ ID NO: 2,
or an amino acid sequence having at least 70% sequence identity to SEQ ID NO: 36 or SEQ ID NO: 2, for example at least 80%, 85%, 90%, 95%, 98% or 99% sequence identity.

Embodiment 30. The antibody or antigen-binding fragment thereof according to any one of the preceding embodiments, wherein any one of the amino acids of the light chain constant region and/or the heavy chain constant region has been altered for another amino acid, with the proviso that no more than 5 amino acids have been so altered, such as 4 amino acids, no more than 3 amino acids, such as 2 amino acids or no more than 1 amino acid.

Embodiment 31. The antibody or antigen-binding fragment thereof according to any one of the preceding embodiments wherein the antibody or antigen-binding fragment thereof comprises or consists of
a light chain variable region according to any one of embodiments 6 to 10; and/or
a heavy chain variable region according to any one of embodiments 11 to 15; and/or
a light chain constant region according to any one of embodiments 22 to 25; and/or
a heavy chain constant region according to any one of embodiments 26 to 30.

Embodiment 32. The antibody or antigen-binding fragment thereof according to any one of the preceding embodiments, wherein the antibody or antigen-binding fragment thereof comprises an Fc region.

Embodiment 33. The antibody or antigen-binding fragment thereof according to embodiment 32, wherein the Fc region is non-naturally occurring.

Embodiment 34. The antibody or antigen-binding fragment thereof according to any one of the preceding embodiments, wherein the antibody comprises an Fc region with a mutated IgG constant region.

Embodiment 35. The antibody or antigen-binding fragment thereof according to any one of embodiments 32 to 34, wherein the Fc region comprises one or more of the mutations affecting the effector function of the antibody or antigen-binding fragment thereof.

Embodiment 36. The antibody or antigen-binding fragment thereof according to any one of embodiments 32 to 35, wherein the Fc region comprises one or more of the mutations selected from the group consisting of L234A, L235A, P329G, G237A, P238S, H269A, A330S and P331S as defined by the EU Index.

Embodiment 37. The antibody or antigen-binding fragment thereof according to any one of embodiments 32 to 36, wherein the glycan attached to the Fc region is lacking fucose.

Embodiment 38. The antibody or antigen-binding fragment thereof according to any one of embodiments 32 to 36, wherein the glycan attached to the Fc region is low in fucose.

Embodiment 39. The antibody or antigen-binding fragment thereof according to any one of the preceding embodiments, wherein the antibody or antigen-binding fragment is produced in a FUT8 negative cell line.

Embodiment 40. The antibody or antigen-binding fragment thereof according to any one of the preceding embodiments comprising or consisting of an intact antibody.

Embodiment 41. The antibody or antigen-binding fragment thereof according to any one of the preceding embodiments comprising or consisting of an antigen-binding fragment selected from the group consisting of Fv fragments (e.g. single chain Fv and disulphide-bonded Fv), Fab-like fragments (e.g. Fab fragments, Fab' fragments and F(ab)$_2$ fragments) and domain antibodies (e.g. single $V_H$ variable domains or $V_L$ variable domains).

Embodiment 42. The antibody or antigen-binding fragment thereof according to any one of the preceding embodiments, wherein the antibody or antigen-binding fragment thereof is capable of inhibiting signaling of interleukin-1 (IL-1) family cytokine ligands and/or receptors.

Embodiment 43. The antibody or antigen-binding fragment thereof according to any one of the preceding embodiments, wherein the antibody or antigen-binding fragment thereof is capable of inhibiting signaling of at least one cytokine selected from the group consisting of IL-1α, IL-1β, IL-33, IL-36α, IL-36β and IL-36γ, or any combination thereof.

Embodiment 44. The antibody or antigen-binding fragment thereof according to any one of the preceding embodiments, wherein the antibody or antigen-binding fragment thereof is capable of inhibiting signaling of IL-1α.

Embodiment 45. The antibody or antigen-binding fragment thereof according to any one of the preceding embodiments, wherein the antibody or antigen-binding fragment thereof is capable of inhibiting signaling of IL-1β.

Embodiment 46. The antibody or antigen-binding fragment thereof according to any one of the preceding embodiments, wherein the antibody or antigen-binding fragment thereof is capable of inhibiting signaling of IL-33.

Embodiment 47. The antibody or antigen-binding fragment thereof according to any one of the preceding embodiments, wherein the antibody or antigen-binding fragment thereof is capable of inhibiting signaling of IL-36α.

Embodiment 48. The antibody or antigen-binding fragment thereof according to any one of the preceding embodiments, wherein the antibody or antigen-binding fragment thereof is capable of inhibiting signaling of IL-36P.

Embodiment 49. The antibody or antigen-binding fragment thereof according to any one of the preceding embodiments, wherein the antibody or antigen-binding fragment thereof is capable of inhibiting signaling of IL-36γ.

Embodiment 50. The antibody or antigen-binding fragment thereof according to any one of the preceding embodiments, wherein the antibody or antigen-binding fragment thereof is capable of inhibiting signaling of IL-1α, IL-1β, IL-33, IL-36α, IL-36β and IL-36γ.

Embodiment 51. The antibody or antigen-binding fragment thereof according to any one of the preceding embodiments, wherein inhibiting signaling is essentially complete inhibition of signaling.

Embodiment 52. The antibody or antigen-binding fragment thereof according to any one of the preceding embodiments, wherein inhibiting signaling is partial inhibition of signaling.

Embodiment 53. The antibody or antigen-binding fragment thereof according to any one of the preceding embodiments, wherein the antibody or antigen-binding fragment exhibits one or more of the following properties:
a) a binding affinity ($K_D$) for IL1RAP characterized by a $K_D$-value of 3 nM or less; b) binding to domain 2 of IL1RAP, preferably binding to the H2 region of domain 2, wherein the H2 region comprises or consists of amino acids of SEQ ID NO: 39;
c) cross-reactivity with IL1RAP from cynomolgus monkey or pig;
d) an inhibitory action on IL-1α signaling;
e) an inhibitory action on IL-1β signaling;
f) an inhibitory action on IL-33 signaling;
g) an inhibitory action on IL-36a signaling;
h) an inhibitory action on IL-36β signaling;
i) an inhibitory action on IL-36γ signaling;
j) internalization by IL1RAP-expressing cells.

Embodiment 54. The antibody or antigen-binding fragment thereof according to any one of the preceding embodiments wherein the antibody or antigen-binding fragment exhibits all of the following properties:
a) a binding affinity ($K_D$) for IL1RAP characterized by a $K_D$-value of 3 nM or less;
b) binding to domain 2 of IL1RAP, preferably binding to the H2 region of domain 2, wherein the H2 region comprises or consists of amino acids of SEQ ID NO: 39;
c) cross-reactivity with IL1RAP from cynomolgus monkey or pig;
d) an inhibitory action on IL-1α signaling;
e) an inhibitory action on IL-1β signaling;
f) an inhibitory action on IL-33 signaling;
g) an inhibitory action on IL-36a signaling;
h) an inhibitory action on IL-36β signaling;
i) an inhibitory action on IL-36γ signaling;
j) internalization by IL1RAP-expressing cells.

Embodiment 55. The antibody or antigen-binding fragment thereof according to any one of the preceding embodiments, wherein the antibody or antigen-binding fragment is capable of inducing ADCC of cells expressing IL1RAP.

Embodiment 56. The antibody or antigen-binding fragment thereof according to any one of embodiments 1 to 54, wherein the antibody or antigen-binding fragment is not capable of inducing ADCC of cells expressing IL1RAP.

Embodiment 57. The antibody or antigen-binding fragment thereof according to any one of the preceding embodiments, wherein the antibody or antigen-binding fragment further comprises a moiety for increasing the in vivo half-life of the agent.

Embodiment 58. The antibody or antigen-binding fragment thereof according to embodiment 57, wherein the moiety for increasing the in vivo half-life is selected from the group consisting of polyethylene glycol (PEG), human serum albumin, glycosylation groups, fatty acids and dextran.

Embodiment 59. The antibody or antigen-binding fragment thereof according to any one of the preceding embodiments, wherein the antibody or antigen-binding fragment thereof is PEGylated.

Embodiment 60. The antibody or antigen-binding fragment thereof according to any one of the preceding embodiments, wherein the antibody or antigen-binding fragment is covalently bound, directly or indirectly, to a functional moiety such as a cytotoxic or detectable moiety.

Embodiment 61. The antibody or antigen-binding fragment thereof according to any one of the preceding embodiments wherein the antibody or antigen-binding fragment comprises a cytotoxic moiety.

Embodiment 62. The antibody or antigen-binding fragment thereof according to any one of embodiments 60 to 61, wherein the cytotoxic moiety comprises or consists of a radioisotope.

Embodiment 63. The antibody or antigen-binding fragment thereof according to embodiment 62, wherein the radioisotope is selected from the group consisting of beta-emitters, auger-emitters, conversion electron-emitters, alpha-emitters, and low photon energy-emitters.

Embodiment 64. The antibody or antigen-binding fragment thereof according any one of embodiments 62 to 63, wherein the radioisotope has an emission pattern of locally absorbed energy that creates a high dose absorbance in the vicinity of the agent.

Embodiment 65. The antibody or antigen-binding fragment thereof according to any one of embodiments 62 to 64, wherein the radioisotope is selected from the group consisting of long-range beta-emitters, such as $^{90}$Y, $^{32}$P, $^{186}$Re/$^{186}$Re; $^{166}$Ho, $^{76}$As/$^{77}$As, $^{153}$Sm; medium range beta-emitters, such as $^{131}$I, $^{177}$Lu, $^{67}$Cu, $^{161}$Tb; low-energy beta-emitters, such as $^{45}$Ca, $^{35}$S or $^{14}$C; conversion or auger-emitters, such as $^{51}$Cr, $^{67}$Ga, $^{99}$Tc$^{m}$, $^{111}$In, $^{123}$I, $^{125}$I, $^{201}$Tl; and alpha-emitters, such as $^{212}$Bi, $^{213}$Bi, $^{223}$Ac, and $^{221}$At.

Embodiment 66. The antibody or antigen-binding fragment thereof according to any one of embodiments 62 to 65 wherein the radioisotope is $^{177}$Lu.

Embodiment 67. The antibody or antigen-binding fragment thereof according to any one of embodiments 60 to 66, wherein the cytotoxic moiety comprises or consists of a cytotoxic drug.

Embodiment 68. The antibody or antigen-binding fragment thereof according to embodiment 67, wherein the cytotoxic drug is selected from the group consisting of a cytostatic drug; an anti-androgen drug; cortisone and derivatives thereof; a phosphonate; a testosterone-5-α-reductase inhibitor; a boron addend; a cytokine; thapsigargin and its metabolites; a toxin (such as saporin or calicheamicin); a chemotherapeutic agent (such as an antimetabolite); or any other cytotoxic drug useful in the treatment of neoplastic disorders.

Embodiment 69. The antibody or antigen-binding fragment thereof according to any one of embodiments 67 or 68, wherein the cytotoxic drug is suitable for use in activation therapy, such as photon activation therapy, neutron activation therapy, neutron induced Auger electron therapy, synchrotron irradiation therapy, or low energy X-ray photon activation therapy.

Embodiment 70. The antibody or antigen-binding fragment thereof according to any one of the preceding embodiments, wherein the antibody or antigen-binding fragment comprises a detectable moiety.

Embodiment 71. The antibody or antigen-binding fragment thereof according to embodiment 70, wherein the detectable moiety comprises or consists of a radioisotope.

Embodiment 72. The antibody or antigen-binding fragment thereof according to embodiment 71 wherein the radioisotope is selected from the group consisting of $^{99m}$Tc, $^{111}$In, $^{67}$Ga, $^{68}$Ga, $^{72}$As, $^{89}$Zr, $^{123}$I, and $^{201}$Tl.

Embodiment 73. The antibody or antigen-binding fragment thereof according to any one of embodiments 71 to 72, wherein the radioisotope is $^{89}$Zr.

Embodiment 74. The antibody or antigen-binding fragment thereof according to any one of the preceding embodiments, wherein the antibody or antigen-binding fragment comprises a pair of detectable and cytotoxic radioisotopes, such as $^{86}$Y/$^{90}$Y or $^{124}$I/$^{211}$At.

Embodiment 75. The antibody or antigen-binding fragment thereof according to any one of embodiments 60 to 74, wherein the radioisotope is capable of simultaneously acting in a multi-modal manner as a detectable moiety and as a cytotoxic moiety.

Embodiment 76. The antibody or antigen-binding fragment thereof according to any one of embodiments 60 to 75, wherein the detectable moiety comprises or consists of a paramagnetic isotope.

Embodiment 77. The antibody or antigen-binding fragment thereof according to embodiment 76 wherein the paramagnetic isotope is selected from the group consisting of $^{157}$Gd, $^{55}$Mn, $^{162}$Dy, $^{52}$Cr and $^{56}$Fe.

Embodiment 78. The antibody or antigen-binding fragment thereof according to any of embodiments 60 to 77, wherein the detectable moiety is detectable by an imaging technique such as SPECT, PET, MRI, optical or ultrasound imaging.

Embodiment 79. The antibody or antigen-binding fragment thereof according to any of embodiments 60 to 78, wherein the cytotoxic moiety and/or detectable moiety is joined to the antibody or antigen-binding fragment thereof indirectly, via a linking moiety.

Embodiment 80. The antibody or antigen-binding fragment thereof according to embodiment 79, wherein the linking moiety is a chelator.

Embodiment 81. The antibody or antigen-binding fragment thereof according to embodiment 80, wherein the chelator is selected from the group consisting of derivatives of 1,4,7,10-tetraazacyclododecane-1,4,7,10,tetraacetic acid (DOTA), deferoxamine (DFO), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA).

Embodiment 82. The antibody or antigen-binding fragment thereof according to any one of the preceding embodiments, wherein the antibody or antigen-binding fragment does not comprise a cytotoxic moiety.

Embodiment 83. A polynucleotide encoding an antibody or antigen-binding fragment thereof according to any one of the preceding embodiments or a component polypeptide chain thereof.

Embodiment 84. The polynucleotide according to embodiment 83, wherein the polynucleotide is a cDNA molecule.

Embodiment 85. The polynucleotide according to any one of embodiments 83 to 84, encoding an antibody light chain or variable region thereof.

Embodiment 86. The polynucleotide according to any one of embodiments 83 to 84 encoding an antibody heavy chain or variable region thereof.

Embodiment 87. A vector comprising a polynucleotide according to any one of embodiments 83 to 86.

Embodiment 88. The vector according to embodiment 87 wherein the vector is an expression vector.

Embodiment 89. A recombinant host cell comprising a polynucleotide according to any one of embodiments 83 to 86 or a vector according to any one of embodiments 87 to 88.

Embodiment 90. The host cell according to embodiment 89, wherein the host cell is a bacterial cell.

Embodiment 91. The host cell according to embodiment 89, wherein the host cell is a yeast cell.

Embodiment 92. The host cell according to embodiment 89, wherein the host cell is a mammalian cell.

Embodiment 93. The host cell according to embodiment 89, wherein the host cell is a human cell.

Embodiment 94. A method for producing an antibody or antigen-binding fragment according to any one of embodiments 1 to 82, the method comprising culturing a host cell according to any of embodiments 89 to 93 comprising the polynucleotide according to any one of embodiments 83 to 86 or the vector according to any one of embodiments 87 to 88, under conditions which permit expression of the encoded antibody or antigen-binding fragment thereof.

Embodiment 95. A pharmaceutical composition comprising the antibody or antigen-binding fragment thereof according to any one of embodiments 1 to 82, the polynucleotide according to any one of embodiments 83 to 86, the vector according to any one of embodiments 87 to 88, and/or the recombinant host cell according to any one of embodiments 89 to 93, in a pharmaceutical composition, wherein the composition further comprises a pharmaceutically-acceptable diluent, carrier or excipient.

Embodiment 96. The composition according to embodiment 95, wherein the composition comprises an effective amount of the antibody or antigen-binding fragment thereof, the polynucleotide, the vector, and/or the recombinant host cell.

Embodiment 97. The composition according to any one of embodiments 95 to 96 adapted for parenteral delivery.

Embodiment 98. The composition according to embodiment 97, wherein the parenteral delivery is intravenous delivery, topical delivery, subcutaneous delivery and/or intramuscular delivery.

Embodiment 99. An antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98, for use in medicine.

Embodiment 100. An antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98, for use in the prevention, treatment, alleviation, detection and/or diagnosis of a disease or disorder susceptible to treatment with an inhibitor of IL-1α, IL-1β, IL-33, IL-36α, IL-36β and/or IL-36γ signaling, and/or wherein the disease or disorder is associated with cells expressing IL1RAP.

Embodiment 101. The antibody, the antigen-binding fragment thereof, the polynucleotide, the vector, the host cell or the composition for use, according to embodiment 100, wherein the disease or disorder is an inflammatory and/or fibrotic disease or disorder.

Embodiment 102. The antibody, the antigen-binding fragment thereof, the polynucleotide, the vector, the host cell or the composition for use, according any one of embodiments 100 to 101, wherein the inflammatory and/or fibrotic disease or disorder is selected from the group consisting of myocarditis, systemic sclerosis, psoriasis, psoriatic arthritis, atherosclerosis, rheumatoid arthritis, all types of arthritis, all types of juvenile arthritis including systemic onset juvenile idiopathic arthritis (SOJIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, asthma, allergy, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease (including ulcerative colitis and Crohn's disease), hepatitis, hepatitis C, ischaemia-reperfusion injury, multiple sclerosis, Neisserial or pneumococcal meningitis, tuberculosis, Bechet's syndrome, septic shock, graft versus host disease, adult T cell leukaemia, multiple myeloma, periodontitis, obesity and obesity-related diseases (for example, metabolic syndrome, cardiomegaly, congestive heart failure, myocardial infarction, varicose veins, polycystic ovarian syndrome, gastroesophageal reflux disease (GERD), fatty liver disease, colorectal cancer, breast cancer, uterine cancer, chronic renal failure, stroke and hyperuricemia), intervertebral disc disease, irritable bowel syndrome, Schnitzler syndrome, allergy/atopic dermatitis, acne inversa, Behcet's disease, cardiac fibrosis, cardiovascular diseases, cryopyin-associated periodic syndromes, cystic fibrosis, Goodpasture's syndrome, Guillain-Barre syndrome, kidney fibrosis, liver fibrosis, lung fibrosis, skin fibrosis, autoimmune myocarditis, organ dysfunction associated with organ transplantation, pancreatitis, peritonitis, uveitis, vasculitis, pneumonia, pulmonary hypertension, sclerodermatous chronic graft-versus-host disease, sepsis, Sjögren's syndrome, Takayasu's arteritis and gout.

Embodiment 103. The antibody, the antigen-binding fragment thereof, the polynucleotide, the vector, the host cell or the composition for use, according to any one of embodiments 100 to 102, wherein the disease or disorder has an inflammatory and/or fibrotic component.

Embodiment 104. The antibody, the antigen-binding fragment thereof, the polynucleotide, the vector, the host cell or the composition for use, according to any one of embodiments 100 to 103, wherein the disease or disorder is an autoimmune disease or disorder.

Embodiment 105. The antibody, the antigen-binding fragment thereof, the polynucleotide, the vector, the host cell or the composition for use, according to embodiment 100, wherein the disease or disorder is a neoplastic disease or disorder.

Embodiment 106. The antibody, the antigen-binding fragment thereof, the polynucleotide, the vector, the host cell or the composition for use according to any one of embodiments 100 or 105, wherein the neoplastic disease or disorder is a hematologic disease or disorder, or a solid tumour.

Embodiment 107. The antibody, the antigen-binding fragment thereof, the polynucleotide, the vector, the host cell or the composition for use, according to any one of embodiments 105 to 106, wherein the neoplastic hematologic disease or disorder is selected from the group consisting of chronic myeloid leukemia (CML), myeloproliferative disorders (MPD), myelodysplastic syndrome (MDS), acute lymphoblastic leukemia (ALL) and acute myeloid leukemia (AML).

Embodiment 108. The antibody, the antigen-binding fragment thereof, the polynucleotide, the vector, the host cell or the composition for use, according to any one of embodiments 105 to 107, wherein the solid tumour is selected from the group consisting of prostate cancer, breast cancer, lung cancer, colon cancer, colorectal cancer, melanomas, bladder cancer, brain/CNS cancer, cancer of urinary organs, biliary tract cancer, cervical cancer, oesophageal cancer, gastric cancer, head/neck cancer, kidney cancer, liver cancer, lymphomas, ovarian cancer, pancreatic cancer, sarcomas, skin cancer and uterus cancer.

Embodiment 109. The antibody, the antigen-binding fragment thereof, the polynucleotide, the vector, the host cell or the composition for use, according to any one of embodiments 100 to 108, wherein the disease or disorder is associated with cells expressing IL1RAP.

Embodiment 110. An antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98, for use in inducing cell death and/or inhibiting the growth and/or proliferation of pathological cells associated with a neoplastic disorder in a subject, or stem cells or progenitor cells thereof, wherein the cells express IL1RAP.

Embodiment 111. Use of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98,
in the preparation of a medicament for the prevention, treatment, alleviation, detection and/or diagnosis of a disease or disorder susceptible to treatment with an inhibitor of IL-1α, IL-1β, IL-33, IL-36α, IL-36β and/or IL-36γ signaling,
and/or wherein the disease or disorder is associated with cells expressing IL1RAP.

Embodiment 112. Use of antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98,
in the preparation of a medicament for the detection and/or diagnosis of a disease or disorder associated with cells expressing IL1RAP.

Embodiment 113. A method for the prevention and/or treatment and/or alleviation and/or detection and/or diagnosis of a disease or disorder susceptible to treatment with an inhibitor of IL-1α, IL-1β, IL-33, IL-36α, IL-36β and/or IL-36γ signaling and/or wherein the disease or disorder is associated with cells expressing IL1RAP in a subject, comprising the step of administering to the subject an effective amount of
an antibody or antigen-binding fragment thereof according to any one of embodiments 1 to 82,
a polynucleotide according to any one of embodiments 83 to 86,
a vector according to any one of embodiments 87 to 88,
a recombinant host cell according to any one of embodiments 89 to 93, and/or a
composition according to any one of embodiments 95 to 98.

Embodiment 114. An in vitro method for the detection of cells expressing IL1RAP in a subject, the method comprising:
(a) providing a sample of cells from a subject to be tested, such as biopsy tissue or blood sample;
(b) optionally, extracting and/or purifying the cells present in the sample; (c) contacting an antibody or antigen-binding fragment thereof according to any one of embodiments 1 to 82 with cells present in the sample;
(d) determining whether the antibody or antigen-binding fragment thereof binds to the cells
wherein the binding of the antibody or antigen-binding fragment thereof to the cells is indicative of the presence of a disease or disorder associated with cells expressing IL1RAP in the tissue of a subject.

Embodiment 115. An in vitro method for identifying a patient with a disease or disorder associated with cells expressing IL1RAP who would benefit from treatment with an antibody or antigen-binding fragment thereof according to any one of embodiments 1 to 82, the method comprising:
(a) providing a sample of cells, such as biopsy tissue or blood sample from a patient to be tested;
(b) optionally, extracting and/or purifying the cells present in the sample;
(c) contacting an antibody or antigen-binding fragment thereof according to any one of embodiments 1 to 82 with cells present in the sample;
(d) determining whether the antibody or antigen-binding fragment thereof binds to the cells
wherein the binding of the antibody or antigen-binding fragment thereof to cells expressing IL1RAP is indicative of a patient who would benefit from treatment with an antibody or antigen-binding fragment thereof according to any one of embodiments 1 to 82.

Embodiment 116. A method for treating a patient with a disease or disorder associated with cells expression IL1RAP, the method comprising:
a) selecting a patient identified as having a disease or disorder associated with cells expressing IL1RAP according to any one of embodiments 114 to 115;
b) administering to said patient a therapeutic agent effective in the treatment of said disease or disorder.

Embodiment 117. A method for the detection of cells expressing IL1RAP, the method comprising:
(a) contacting an antibody or antigen-binding fragment thereof according to any one of embodiments 1 to 82 with cells to be analysed for their expression of IL1RAP;
(b) determining whether the antibody or antigen-binding fragment thereof binds to the cells
wherein the binding of the antibody or antigen-binding fragment thereof to the cells is indicative of the presence of a disease or disorder associated with cells expressing IL1RAP in the tissue of a subject.

Embodiment 118. The method according to embodiment 117, wherein the method is an in vivo method, an ex vivo method or an in vitro method.

Embodiment 119. A method for reducing inflammation in a subject with peritonitis, the method comprising the step of administering to the subject an effective amount of
an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 120. A method for reducing disease severity in a subject with psoriasis or psoriatic arthritis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 121. A method for reducing atherosclerotic plaque inflammation in a subject with atherosclerosis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 122. A method for reducing atherosclerotic plaque volume and/or atherosclerotic plaque size in a subject with atherosclerosis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 123. A method for reducing inflammation and/or fibrosis in a subject with myocarditis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 124. A method for counteracting deterioration in cardiac function in a subject with myocarditis or autoimmune myocarditis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 125. A method for reducing dermal fibrosis in a subject with systemic sclerosis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

Embodiment 126. A method for reducing pulmonary fibrosis in a subject with systemic sclerosis, the method comprising the step of administering to the subject an effective amount of an antibody or antigen-binding fragment thereof according to any one of embodiments 1 to 82, a polynucleotide according to any one of embodiments 83 to 86, a vector according to any one of embodiments 87 to 88, a recombinant host cell according to any one of embodiments 89 to 93, and/or a composition according to any one of embodiments 95 to 98.

EXAMPLES

Example 1: Inhibition of Cytokine Signaling by the Murine Surrogate Anti-IL1RAP Antibody mCAN10, Specific Inhibitor of Mouse IL1RAP Aim This example illustrates the characterization of the murine surrogate anti-IL1RAP antibody mCAN10, specific inhibitor of mouse IL1RAP, with respect to blocking signaling by IL-1α, IL-1β, IL-33, IL-36α, IL-36β and IL-36γ.

Material and Methods

Chickens were immunized with mouse IL1RAP antigen and multiple anti-mouse IL1RAP binders identified. A selection of these were cloned into a mouse IgG2a backbone. One such clone, mCAN10, capable of binding domain 2 of mouse IL1RAP, was evaluated for its capacity to inhibit signaling by IL-1α, IL-1β, IL-33, IL-36α, IL-36β and IL-36γ.

For this evaluation, HEK-Blue™ cells stably transfected with the murine IL-1R were used. Alternatively, to allow for analysis of murine IL-33 and IL-36 signaling as well, HEK-Blue™ cells were transiently transfected with the murine IL-33 and IL-36 receptors the day before the assay. HEK-Blue™ cells were seeded into 96-well plates and allowed to settle for a minimum of 2 hrs before continuing. Cells were then exposed to increasing concentrations of mCAN10 (0, 0.001, 0.003, 0.01, 0.03, 0.1, 0.3, 1, 3, 10, 30 and 100 μg/ml) and incubated for 1 hr at 37° C., 5% $CO_2$, before addition of murine cytokines. The cytokines were added in the following concentrations: 3 pg/ml IL-1α, 30 pg/ml IL-1β, 5 ng/ml IL-33, 4 ng/ml IL-36α, 5 ng/ml IL-36β and 10 ng/ml IL-36γ. As mouse IL-1α and IL-1β may cross-react with human IL-1R, endogenously expressed by HEK-Blue™ cells, an anti-human IL1RAP antibody was used to block signaling via IL-1R, prior to stimulation of these cells with mouse IL-1α and IL-1β. Cells were cultured for 16-18 hrs at 37° C., 5% $CO_2$ and then analyzed for activation of NF-κB and subsequent production of SEAP using QUANTI-Blue™ Solution measured at 620 nm using the SpectraMax i3x spectrophotometer.

Results mCAN10 was added to HEK-Blue™ cells in increasing concentrations and mouse IL-1α, IL-1β, IL-33, IL-36α, IL-36β or IL-36γ added at a constant concentration. Graphs of optical density values at 620 nm were used to calculate the IC50 values shown in Table 2. mCAN10 induced inhibition of IL-1α, IL-1β, IL-33, IL-36α, IL-36β and IL-36γ signaling.

TABLE 2

IC50 values [nM] of mCAN10 on the different signaling pathways, obtained from the HEKBlue ™ assay

| IC50 [nM] | IL-1α | IL-1β | IL-33 | IL-36α | IL-36β | IL-36γ |
|---|---|---|---|---|---|---|
| mCAN10 | 1.79 | 2.59 | 3.74E−15 | 0.0394 | 0.108 | 0.0376 |

Conclusions mCAN10 is a murine surrogate anti-mouse IL1RAP inhibitor capable of blocking signaling by IL-1α, IL-1β, IL-33, IL-36α, IL-36β and IL-36γ. Therefore, mCAN10 provides a useful tool for evaluating therapeutic efficacy of IL1RAP blockade in various murine disease models. As anti-human IL1RAP antibodies may lack cross-reactivity to mouse IL1RAP (such as the anti-human IL1RAP antibodies described in Example 9-22), mCAN10 is a suitable surrogate to anti-human IL1RAP antibodies with similar functional properties. In subsequent in vivo experiments (Example 2-8), mCAN10 in an effector function silent mouse IgG2a format was used.

Example 2: The Murine Surrogate Anti-IL1RAP Antibody mCAN10, Specific Inhibitor of Mouse IL1RAP, Reduces Inflammation in a Model for Acute Peritonitis Aim The aim of these experiments is to evaluate how blockade of IL-1α/p, IL-33 and IL-36α/β/γ signaling with the murine surrogate anti-IL1RAP antibody mCAN10 impacts the inflammatory response in a mouse model for acute peritonitis. An additional aim is to compare the effects of this antibody to recombinant IL-1R antagonist (IL1RA) protein, anakinra, which only blocks IL-1α/β signaling.

Material and Methods

Female C57Bl/6 mice (10-18 wks of age), which were either wildtype (WT) or IL1RAP knock-out (KO), were immunized intraperitoneal (i.p.) with 2.5 mg monosodium urate (MSU) crystals. WT mice which were not immunized with MSU crystals were included as controls (No MSU). All mice were terminated 6 hrs after immunization and peritoneal lavage collected for quantification of infiltrating cells (B cells, T cells, monocytes, neutrophils and eosinophils) by flow cytometry (FIG. 1A).

Alternatively, female C57Bl/6 WT mice (8-9 wks of age) were treated with 20 mg/kg mCAN10 or IL1RA at a molar equivalent dose (2.3 mg/kg). Mice which were treated with isotype control antibody or PBS were included as controls. One hour (hr) following treatment, mice were immunized i.p. with 2.5 mg MSU crystals. Mice which did not receive any treatment and were not immunized with MSU crystals were also included as controls (No MSU). All mice were terminated 6 hrs after immunization and peritoneal lavage collected for quantification of infiltrating cells by flow cytometry (FIG. 1B), or for quantification of various cytokines and chemokines (eotaxin, G-CSF, IL-5, MCP-1, MIP-1β, IL-6 and KC (also known as CXCL1)) by a Luminex assay (FIG. 1C).

Results

Figure 1:
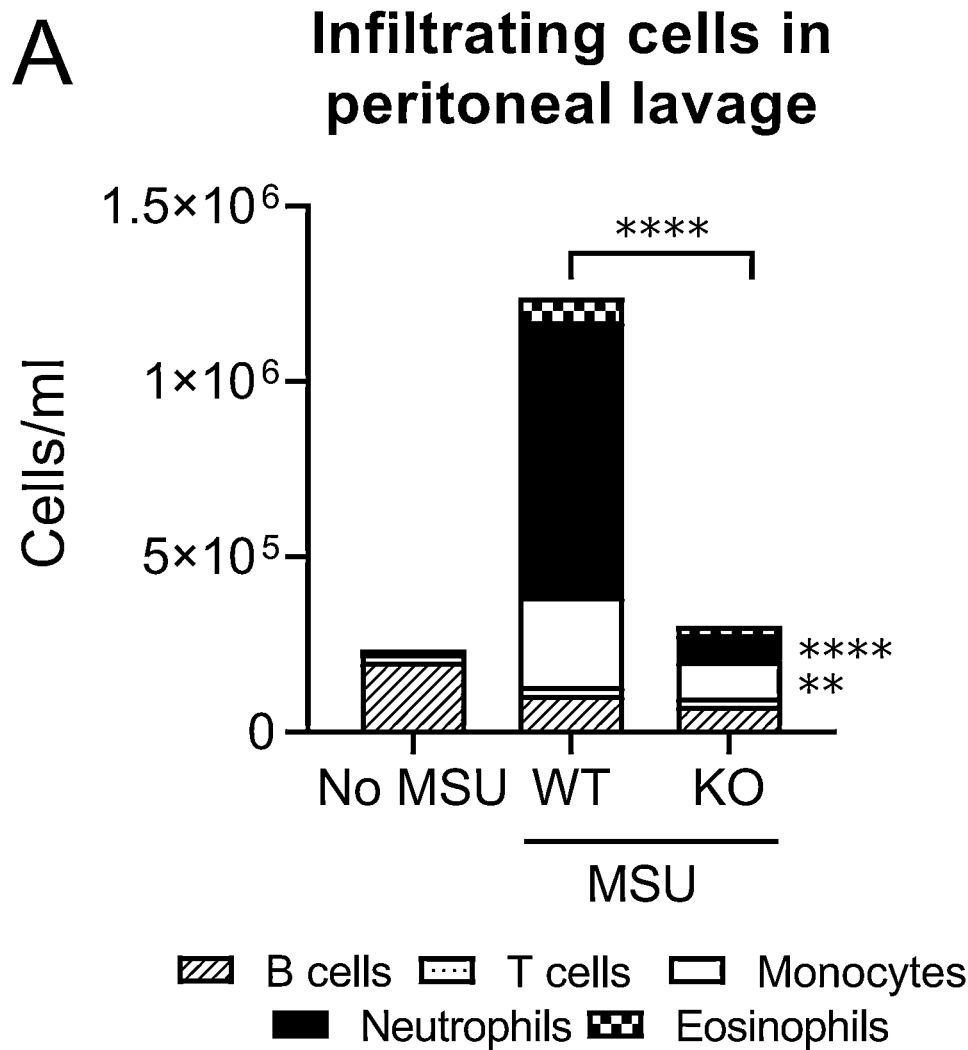
FIG. 1: The anti-IL1RAP antibody mCAN10 reduces inflammation in a model for acute peritonitis WT or KO mice were immunized with MSU crystals and 6 hrs after immunization, flow cytometry was performed on peritoneal lavages for quantification of infiltrating cells (A). WT mice were treated with mCAN10, IL1RA, isotype control antibody (Isotype), or PBS only 1 hr prior to immunization with MSU crystals. Six hrs after immunization, peritoneal lavages were collected for flow cytometry for quantification of infiltrating cells (B), or for quantification of cytokines and chemokines by a Luminex assay (C).
Figure 1:
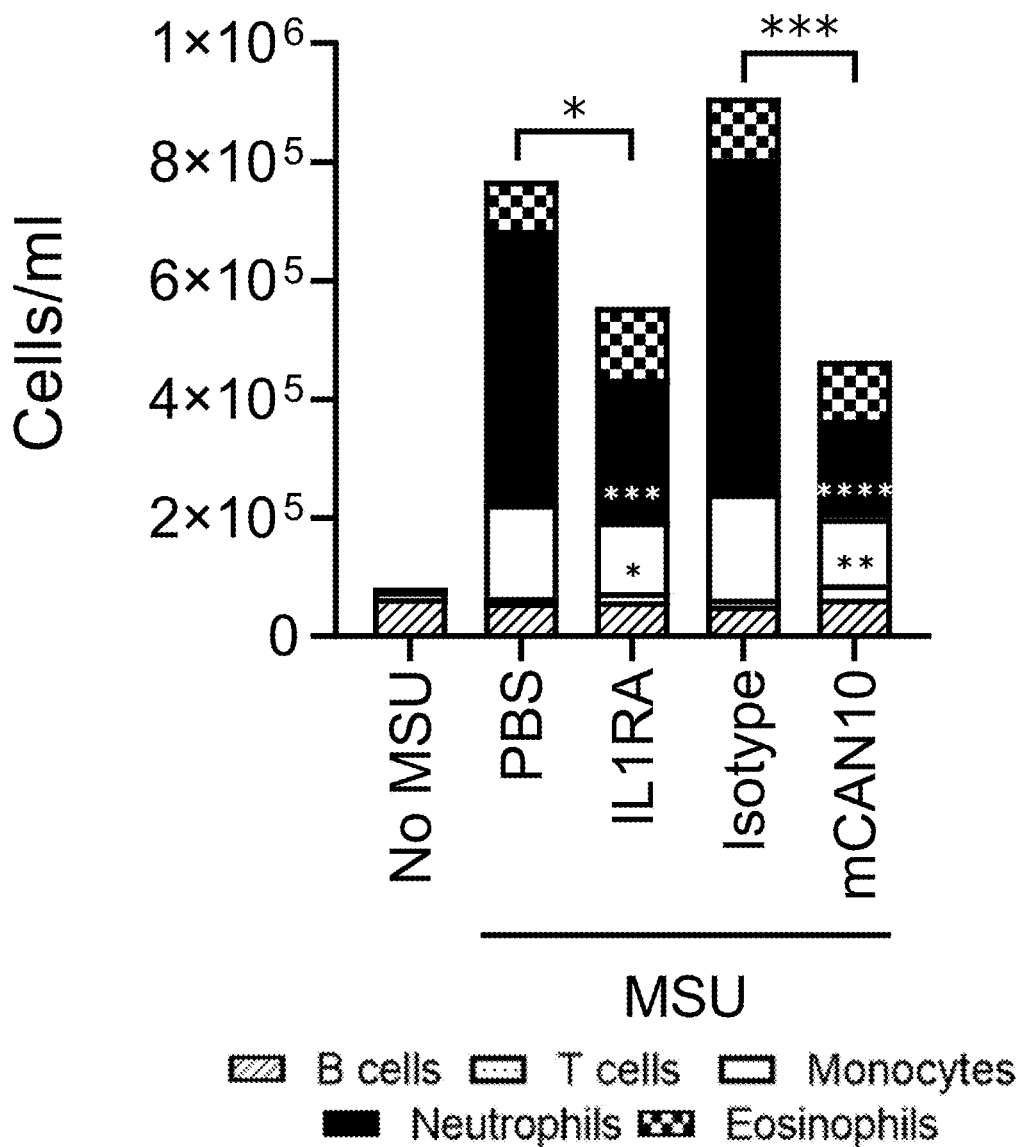
Figure 1:
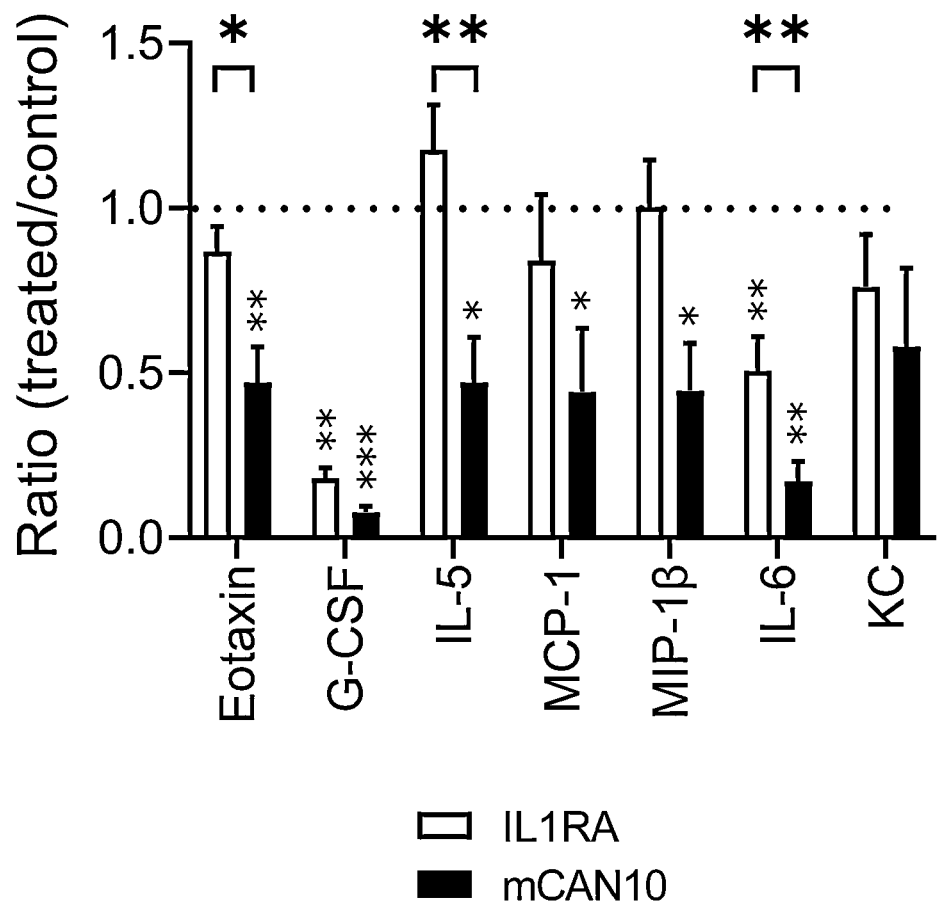

Following immunization with MSU crystals, IL1RAP KO mice displayed a significantly reduced infiltration of cells to the peritoneum compared to WT mice, with the largest effect on infiltrating neutrophils and monocytes (FIG. 1A). Treatment with mCAN10 and IL1RA significantly reduced the number of infiltrating cells, such as neutrophils and monocytes, in the peritoneal cavity in WT mice immunized with MSU crystals, compared to isotype and PBS control, respectively. However, mCAN10 had a more potent anti-inflammatory effect on monocytes and neutrophils than IL1RA (FIG. 1B). mCAN10 and IL1RA also significantly decreased G-CSF and IL-6 compared to isotype and PBS control, respectively. mCAN10 also reduced eotaxin, IL-5, MCP-1 and MIP-1β compared to isotype control, and showed a significantly stronger reduction of IL-6 compared to IL1RA (FIG. 1C).

Conclusions mCAN10 (which blocks IL-1α/p, IL-33 and IL-36α/β/γ signaling) reduces the inflammatory response in a mouse model for acute peritonitis more potently than IL1RA (which only blocks IL-1α/p signaling).

Example 3: The Murine Surrogate Anti-IL1RAP Antibody mCAN10, Specific Inhibitor of Mouse IL1RAP, Reduces Disease Severity in Models for Psoriasis and Psoriatic Arthritis Aim The aim of these experiments is to evaluate how blockade of IL-1α/β, IL-33 and IL-36α/β/γ signaling with the murine surrogate anti-IL1RAP antibody mCAN10 impacts the disease severity in Imiquimod-induced psoriasis and mannan-induced psoriatic arthritis. An additional aim is to compare the effects of this antibody to an anti-IL-1β antibody, which only blocks IL-1β signaling.

Material and Methods

Psoriasis was induced in female BALB/c mice (8-10 wks of age), which received a daily topical administration of Zyclara cream (3.75% Imiquimod; approximately 71.4 mg/day), starting from day 0 until termination on day 7. The cream was applied on the shaved backs of the mice. During this period of disease induction, mice received treatments i.p. on day 0, 3 and 5. The mice were treated with mCAN10 (10 mg/kg), anti-IL-1β antibody (0.5 mg/kg), or the same dose of isotype controls for these antibodies. Mice which were treated with PBS only (Vehicle) or dexamethasone (10 mg/kg) were included as negative and positive controls, respectively. Disease severity was evaluated daily throughout the experiment by scoring the skin inflammation and erythema of the shaved back area using a score ranging from 0-4 (8 total for each mouse) (FIG. 2A-B).

Alternatively, psoriatic arthritis was induced in male and female B6N.Q.NCF1 mice (8-14 wks of age), which received 20 mg mannan from *Saccharomyces cerevisiae* i.p. on day 0. These mice were treated in a similar fashion as above, on day 0, 3 and 5. Disease severity was evaluated by scoring the joint inflammation of the paws and using a macroscopic scoring system of the four limbs ranging from 0-15 (60 total for each mouse) (FIG. 2C-D). At the end of the experiment, blood was collected for analysis of IL-17, a major contributor cytokine in psoriatic arthritis (FIG. 2E).

Figure 2:
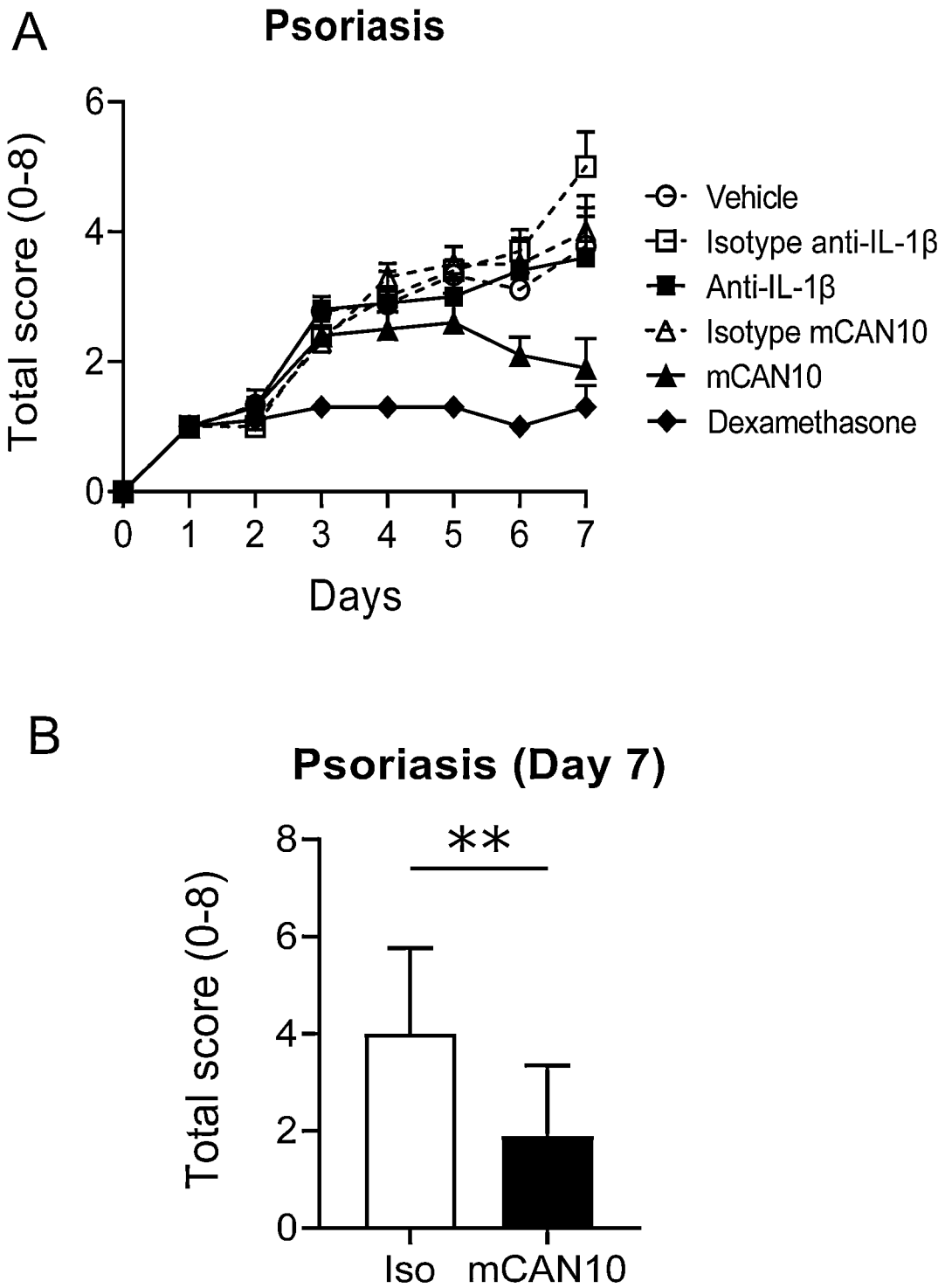
FIG. 2: The anti-IL1RAP antibody mCAN10 reduces disease severity in models for psoriasis and psoriatic arthritis Psoriasis was induced in BALB/c mice by administration of Imiquimod on the shaved backs of mice for 7 days. During this period, mice were treated on three occasions with mCAN10, anti-IL-1p antibody (Anti-IL-1β), isotype control antibodies (Isotype anti-IL-1 β, Isotype mCAN10), dexamethasone, or PBS only (Vehicle). Disease severity was evaluated throughout the 7-day period by scoring of the inflammation and erythema of the back area (A and B). Psoriatic arthritis was induced in B6N.Q.NCF1 mice by administration of mannan from *Saccharomyces cerevisiae*. Mice were treated as in A and B and disease severity evaluated throughout a 7-day period by scoring of the joint inflammation of all paws (C and D). On day 7, mice were sacrificed and blood collected for analysis of IL-17 levels in plasma (E).
Figure 2:
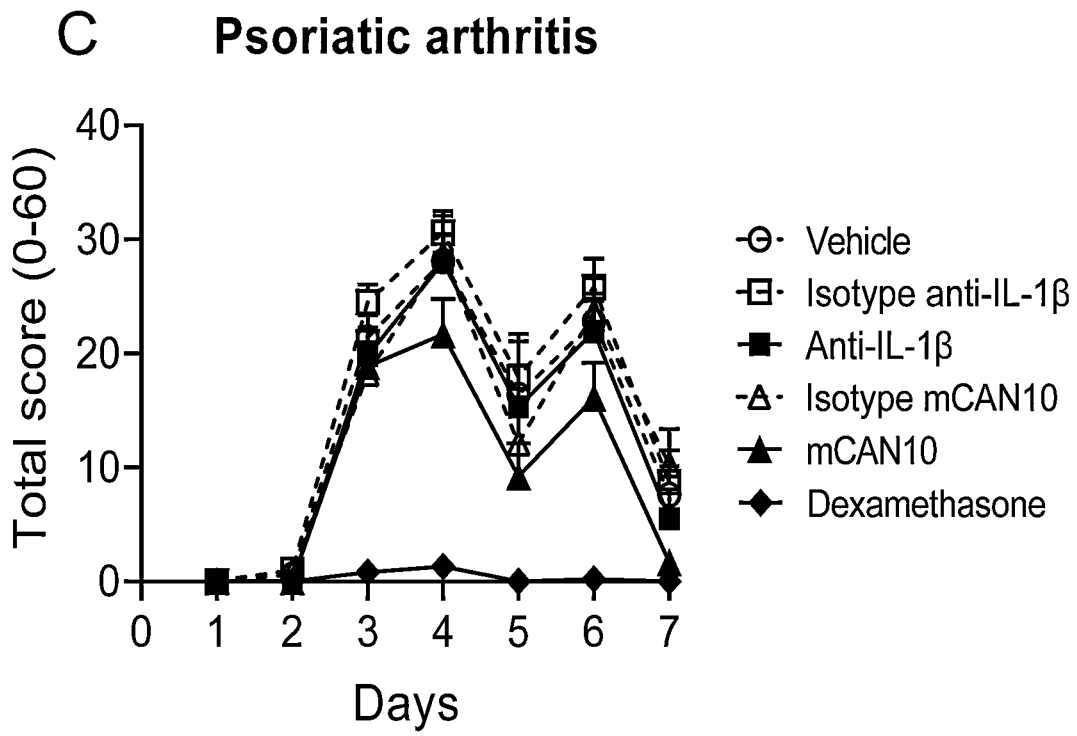
Figure 2:
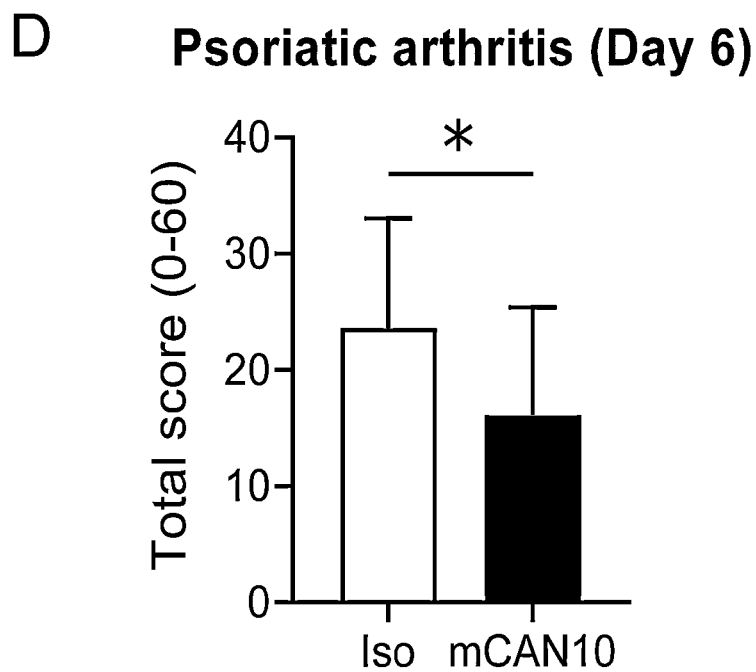
Figure 2:
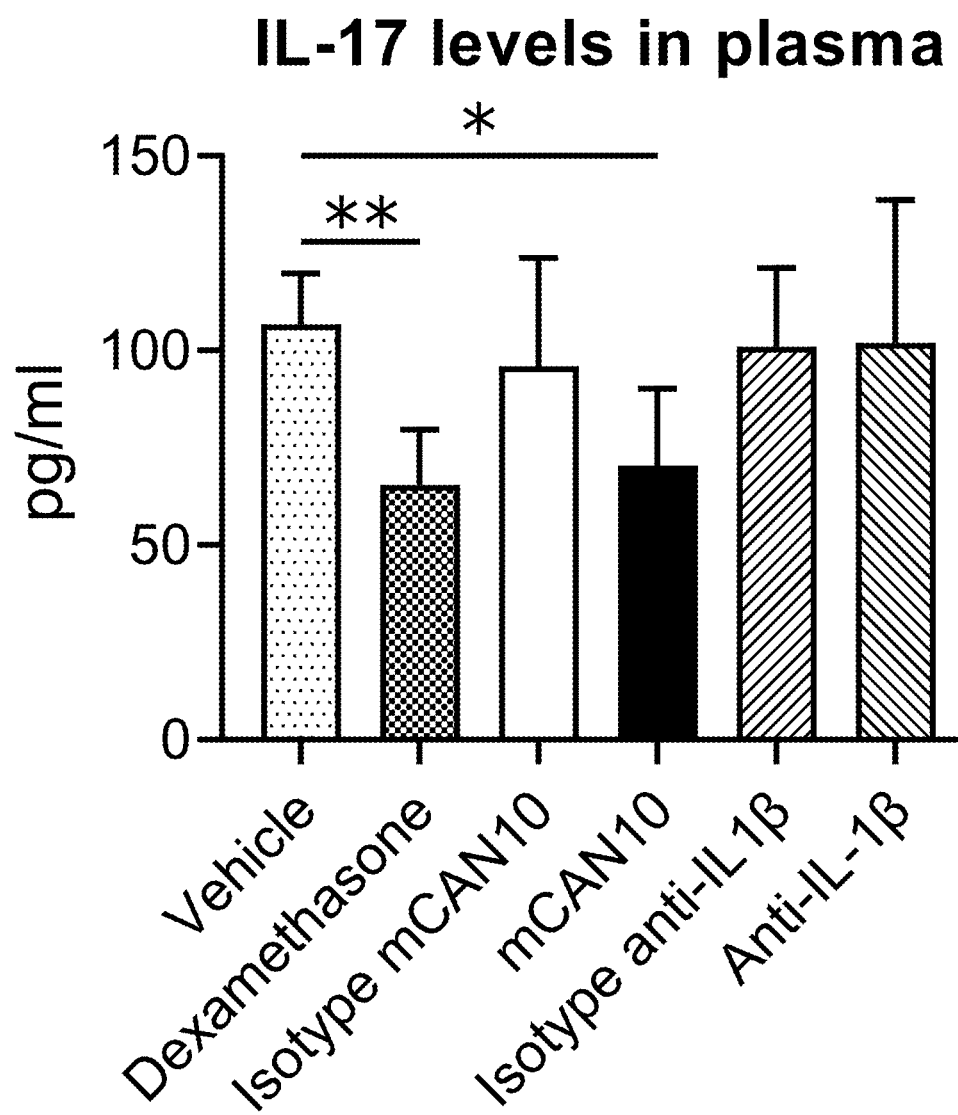

Results mCAN10, but not anti-IL-1β antibody, reduced disease severity in Imiquimod-induced psoriasis (FIG. 2A-B). Similarly, mCAN10, but not anti-IL-1β antibody, reduced disease severity in mannan-induced psoriatic arthritis (FIG. 2C-D), and also reduced circulating IL-17 levels compared to vehicle (FIG. 2E).

Conclusions mCAN10 (which blocks IL-1α/β, IL-33 and IL-36α/β/γ signaling), but not anti-IL-1β antibody (which only blocks IL-1β signaling), reduces disease severity of both Imiquimod-induced psoriasis and mannan-induced psoriatic arthritis.

Example 4: The Murine Surrogate Anti-IL1RAP Antibody mCAN10, Specific Inhibitor of Mouse IL1RAP, Reduces Atherosclerosis and Aortic Plaque Inflammation in Apoe KO Mice Aim The aim of these experiments is to evaluate how blockade of IL-1α/β, IL-33 and IL-36α/β/γ signaling with the murine surrogate anti-IL1RAP antibody mCAN10 impacts the atherosclerosis in apolipoprotein E (Apoe) KO mice.

Material and Methods

Figure 3:
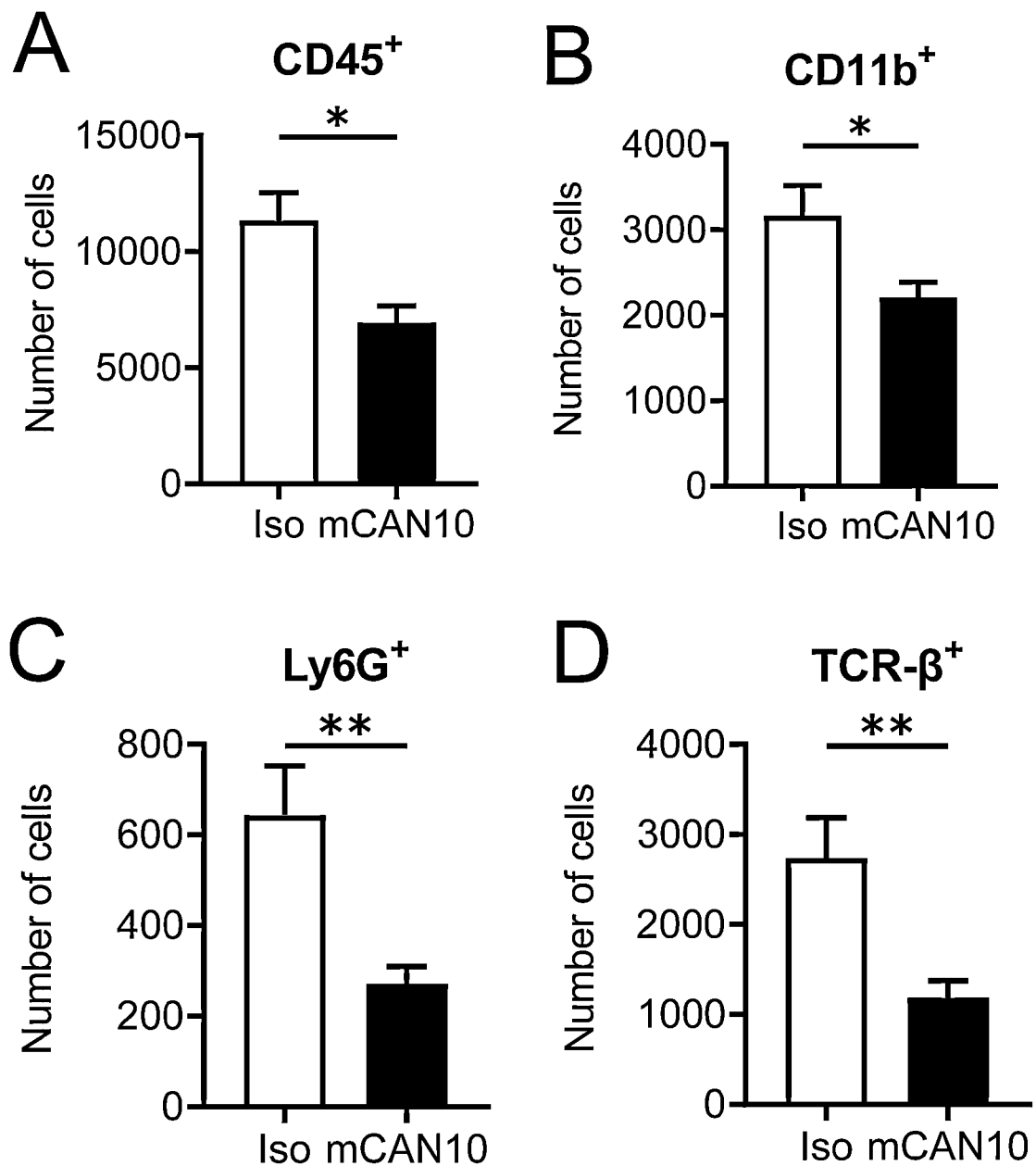
FIG. 3: mCAN10 reduces aortic plaque inflammation in a model for atherosclerosis Development of atherosclerotic lesions was induced in apolipoprotein E (Apoe) KO mice by feeding mice with high cholesterol diet (HCD). After 4 wks on HCD, mice were treated with mCAN10 or isotype control antibody (Iso) biweekly (twice weekly) for 6 wks. During this period, mice were kept on HCD. At the end of the experiment, mice were sacrificed and aortas collected for flow cytometry analyses of total $CD45^+$ cells (A), myeloid cells such as $CD11b^+$ cells and $Ly6G^+$ neutrophils (B and C), and T lymphocytes such as $TCR-\beta^+$ cells, $CD4^+$ cells and $CD8^+$ cells (D-F).
Figure 3:
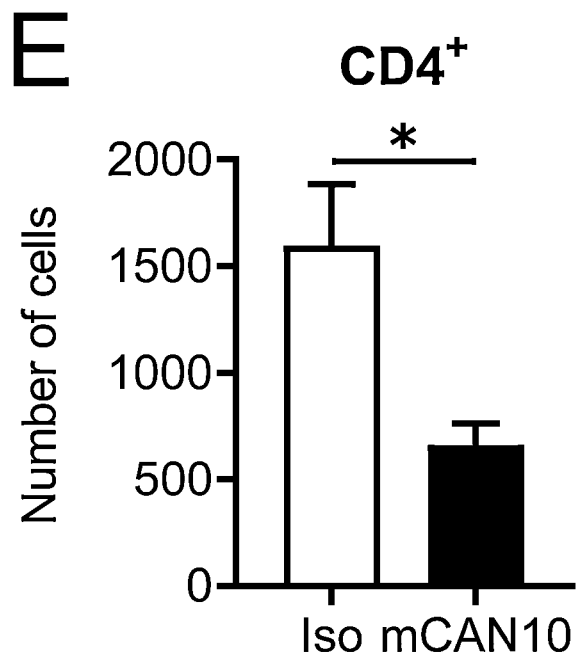
Figure 3:
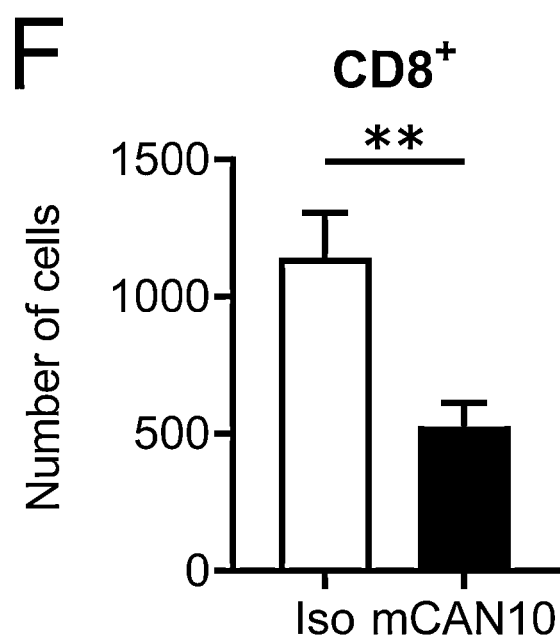
Figure 4:
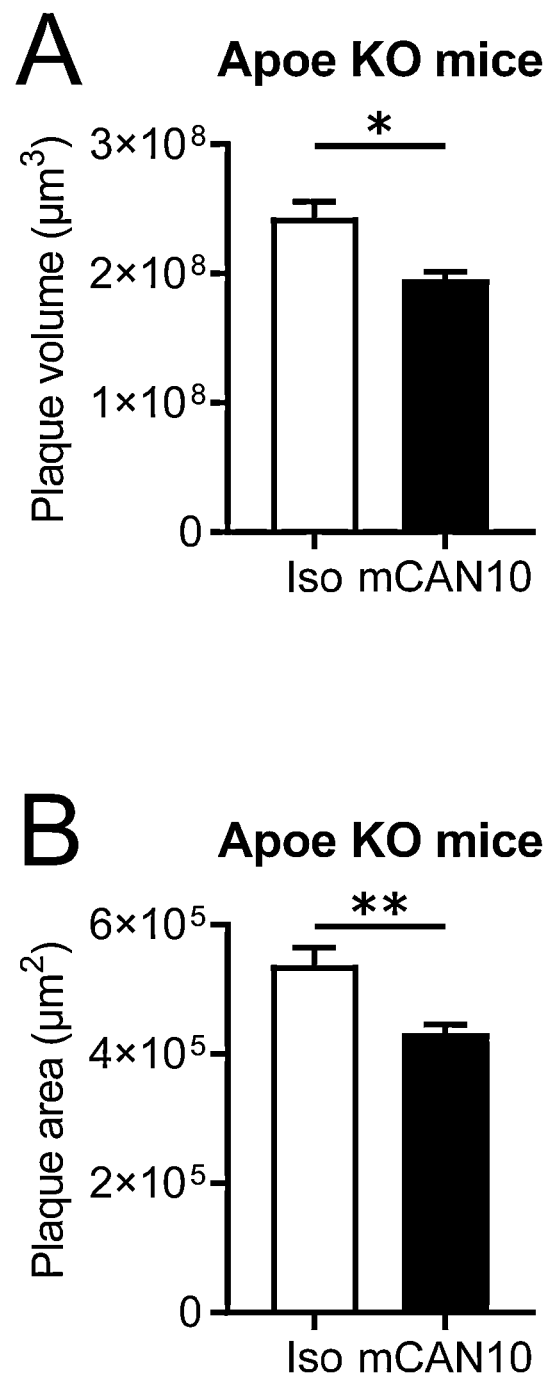
FIG. 4: mCAN10 reduces the size of aortic plaques in a model for atherosclerosis Mice were treated as described for FIG. 3. At the end of the experiment, mice were sacrificed, hearts collected and sections at the aortic root stained for lipid accumulation by Oil-Red O for comparison of both plaque volume (A) and area (B).

Female Apoe KO mice (10-12 wks of age) were fed a high-cholesterol diet (HCD; 21% fat, 0.21% cholesterol) to develop atherosclerotic lesions. After 4 wks on HCD, treatment of mice was initiated and mice were administered either mCAN10 (20 mg/kg at first dose; 10 mg/kg at subsequent doses), or the same doses of isotype control antibody i.p. biweekly (twice weekly) for 6 wks. Throughout these 6 wks, mice were continuously fed HCD. To reduce inter-cage variability, for each cage mice were split between treatment groups. At 48 hrs after the final dosing, mice were anesthetized and sacrificed, whereafter aortas were collected to study changes in immune cell composition by flow cytometry, including myeloid cells (total CD11b$^+$ cells, and the Ly6G$^+$ neutrophil subpopulation thereof) (FIG. 3A-C) and T lymphocytes (total TCR-β$^+$ cells, and CD4$^+$ and CD8$^+$ subpopulations thereof) (FIG. 3D-F). Hearts were harvested, sectioned at the aortic root and sections stained for lipid accumulation by Oil-Red O and plaque size was compared between groups (FIG. 4A-B).

Results

Flow cytometry analyses of the atherosclerotic aorta show that mCAN10 decreases the plaque inflammation. This is observed by reduced numbers of CD45$^+$ leukocytes (FIG. 3A). Among these, myeloid CD11b$^+$ cells were reduced, including Ly6G$^+$ neutrophils (FIG. 3B-C). TCR-β$^+$ cells were also reduced in number, including both CD4$^+$ and CD8$^+$ cells (FIG. 3D-F). Additionally, mCAN10 significantly reduced the aortic plaque volume and area in Apoe KO mice fed HCD, compared to isotype control (FIG. 4A-B).

Conclusions

IL1RAP blockade by mCAN10 reduces atherosclerosis and limits plaque inflammation in Apoe KO mice.

Example 5: The Murine Surrogate Anti-IL1RAP Antibody mCAN10, Specific Inhibitor of Mouse IL1RAP, Reduces Inflammation and Fibrosis in Experimental Autoimmune Myocarditis Aim The aim of these experiments is to evaluate how blockade of IL-1α/β, IL-33 and IL-36α/β/γ signaling with the murine surrogate anti-IL1RAP antibody mCAN10 impacts the development of inflammation and fibrosis in experimental autoimmune myocarditis (EAM).

Material and Methods

Figure 5:
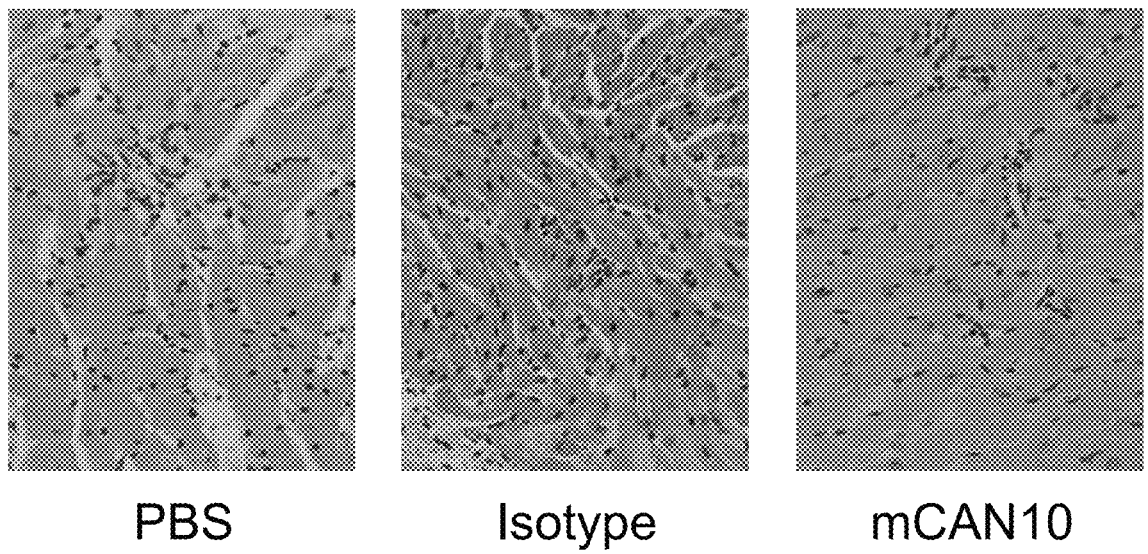
FIG. 5: The anti-IL1RAP antibody mCAN10 reduces inflammation and fibrosis in experimental autoimmune myocarditis (EAM)
Figure 5:
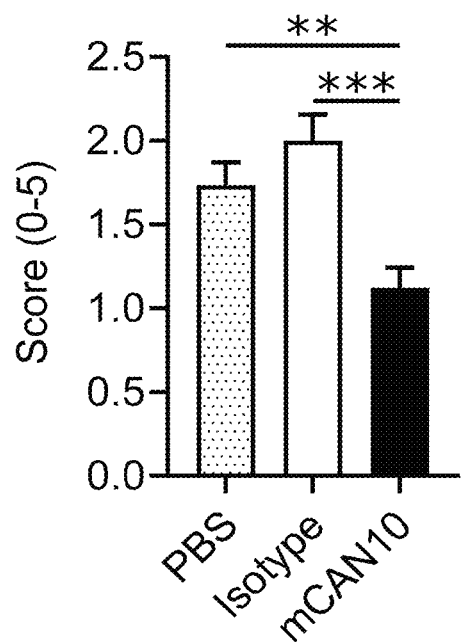
Figure 5:
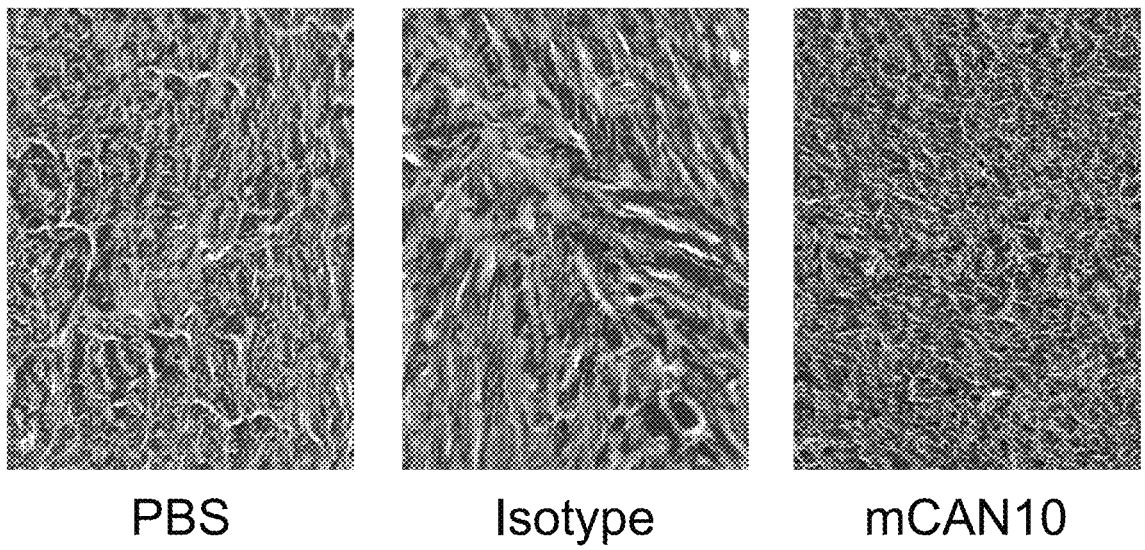
Figure 5:
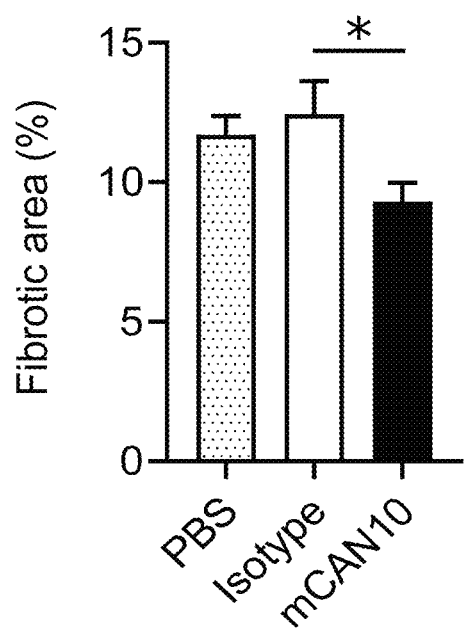

EAM was induced in male BALB/c mice (7-8 wks of age) by immunization of mice with 100 μg mouse α-myosin heavy chain (αMHC) peptide, emulsified in complete Freund's adjuvant, s.c. on day 0 and 7. Mice were treated with mCAN10 (20 mg/kg at first dose; 10 mg/kg at subsequent doses), or the same doses of isotype control antibody i.p., biweekly for 4 wks. Mice treated with PBS were included as controls. The treatments were initiated one wk after the final immunization with αMHC, on day 14. At the end of the experiment, on day 42, mice were sacrificed and hearts were collected. The hearts were fixated with 10% buffered formalin, embedded in paraffin, and sectioned longitudinally. One middle section per heart was stained with hematoxylin and eosin (H&E) to assess the degree of inflammation in the left ventricle (LV), by grading the area infiltrated by hematopoietic cells using a scoring system ranging from 0-5 (FIG. 5A-B). Alternatively, one middle section per heart was stained with Masson's trichrome to detect collagen deposits, as a measure of fibrotic tissue. Fibrotic blue area and whole area was measured using computerized planimetry (ImageJ). The fibrotic area is presented as percentage of the whole area (FIG. 5C-D).

Results mCAN10 significantly decreased the infiltrating inflammatory cells in the myocardium, as assessed by scoring of H&E-stained sections of hearts from EAM-induced mice (FIG. 5A-B). Additionally, mCAN10 also reduced the cardiac fibrosis as determined by analysis of Masson's trichrome-stained heart sections (FIG. 5C-D).

Conclusions mCAN10 is capable of reducing the development of inflammation and fibrosis in EAM.

Example 6: The Murine Surrogate Anti-IL1RAP Antibody mCAN10, Specific Inhibitor of Mouse IL1RAP, Counteracts Deterioration in Cardiac Function in Experimental Autoimmune Myocarditis Aim The aim of these experiments is to evaluate how blockade of IL-1α/β, IL-33 and IL-36α/β/γ signalling with the murine surrogate anti-IL1RAP antibody mCAN10 impacts the cardiac function in experimental autoimmune myocarditis (EAM). An additional aim is to compare the effects of this antibody to an anti-IL-1β antibody, which only blocks IL-1β signalling, recombinant IL-1R antagonist (IL1RA) protein, anakinra, which only blocks IL-1α/p signaling, and prednisone, an anti-inflammatory glucocorticoid.

Material and Methods

EAM was induced in male BALB/c mice (7-8 wks of age) by immunization of mice with 100 μg mouse α-myosin heavy chain (αMHC) peptide, emulsified in complete Freund's adjuvant, s.c. on day 0 and 7. The treatments were initiated on the same day as the final immunization with αMHC, on day 7. Mice were treated with mCAN10 (20 mg/kg at first dose; 10 mg/kg at subsequent doses), anti-IL-1β antibody (0.5 mg/kg), or the same dose of isotype controls for these antibodies i.p., biweekly for 5 wks. Alternatively, mice were treated with IL1RA at 25 mg/kg s.c., prednisone at 5 mg/kg by oral gavage, or relevant vehicle controls, daily for 5 wks. Mice treated with PBS were included as controls. To assess cardiac function, transthoracic echocardiography was performed on mice for measurement of left ventricular ejection fraction (LVEF) at the start of the study, and on day 28 and 42 (FIG. 6A-C).

Results mCAN10 significantly preserved the cardiac function as assessed by measurement of LVEF in EAM-induced mice, compared to isotype and anti-IL-1β antibody (FIG. 6A). However, IL1RA and prednisone did not show significant effects on cardiac function compared to their respective control groups (FIG. 6B). Additionally, mCAN10 preserved cardiac function also when the treatment was initiated on day 14, instead of day 7 (FIG. 6C).

Conclusions mCAN10 has a therapeutic effect on cardiac function in EAM-induced mice, while anti-IL-1β antibody, IL1RA and prednisone do not demonstrate such effects.

Example 7: The Murine Surrogate Anti-IL1RAP Antibody mCAN10, Specific Inhibitor of Mouse IL1RAP, Ameliorates Dermal and Pulmonary Fibrosis in a Model of Sclerodermatous Chronic Graft-Versus-Host Disease Aim The aim of these experiments is to evaluate how blockade of IL-1α/β, IL-33 and IL-36α/β/γ signaling with the murine surrogate anti-IL1RAP antibody mCAN10 impacts the fibrosis in a mouse model of sclerodermatous chronic graft-versus-host disease (scl cGvHD).

Material and Methods

Murine Sclerodermatous Chronic Graft-Versus-Host Disease

Recipient female BALB/c mice (H-$2^d$; 8 wks of age; n=10 per group) received total body irradiation with 700 cGy. Six hrs after irradiation, all BALB/c (H-$2^d$) recipients received bone marrow from either female BALB/c mice (H-$2^d$) in a syngeneic, or male B10.D2 mice (H-$2^d$) in an allogeneic transplantation manner. Due to MHC mismatch, allogeneically transplanted mice develop scl cGvHD, with fibrosis of skin and multiple inner organs. For transplantation, 5×10$^6$ splenocytes and 2×10$^6$ bone marrow cells from donor mice were resuspended in PBS and injected via tail veins. Treatment was initiated 21 days after bone marrow transplantation. Mice receiving allogeneic transplants were treated with mCAN10 (20 mg/kg at first dose; 10 mg/kg at subsequent doses), or the same doses of isotype control antibody (Iso) i.p. biweekly for 4 wks. Alternatively, these mice were treated with the small molecule tyrosine kinase inhibitor nintedanib at 50 mg/kg p.o. daily for 4 wks. Nintedanib is approved for treatment of systemic sclerosis patients with interstitial lung disease and is used here as a positive control. Mice receiving syngeneic transplants were treated with isotype control antibody only. At the end of the experiment, on day 49, mice were sacrificed and skin samples and lungs collected.

Histological Evaluation of Dermal and Pulmonary Fibrosis

Skin samples of defined areas of 1 cm$^2$ on the upper back were fixed in 4% formalin for 6 hrs and embedded in paraffin. Sections were cut at 5 μm and stained with hematoxylin and eosin (H&E). The dermal thickness was quantified on H&E-stained sections using images captured with a light microscope (Nikon Eclipse 80i) at 100-fold magnification by manually measuring the distance between the epidermal-dermal junction and the dermal-subcutaneous fat junction at four sites per mouse. The right lobes of the lung samples were similarly fixed, paraffin-embedded and sectioned and were subsequently stained with Trichrome and Sirius Red. Histologic readouts included evaluation of stained (fibrotic) area as percent of total lung area in Sirius Red-stained sections (two sections per mouse) and quantification of pulmonary changes by Ashcroft score, a numeric scale for determining the degree of fibrosis in lung specimens (four sections per mouse).

Hydroxyproline Quantification

The amount of collagen protein in skin and lung samples was determined by quantification of hydroxyproline. After digestion in 6 M hydrogen chloride for 3 hrs at 120° C., the pH of the samples was adjusted to 6 with 6 M sodium hydroxide. Subsequently, 0.06 M chloramine T was added, and samples incubated for 20 min at room temperature. Next, 3.15 M perchloric acid and 20% p-dimethylaminobenzaldehyde were added and samples were incubated for 20 min at 60° C. The absorbance was determined at 557 nm with a Spectra MAX 190 microplate spectrophotometer. Absolute values were determined using standard curves generated with type I collagen.

Detection of Myofibroblasts

Myofibroblasts positive for α-SMA (smooth muscle actin) were detected by incubation with monoclonal anti-α-SMA antibodies (clone 1A4). The expression was visualized with horseradish peroxidase-labelled secondary antibodies and 3,3-diaminobenzidine tetra hydrochloride (DAB). Monoclonal mouse IgG antibodies were used for controls. Images of sections stained for αSMA were captured on a light microscope (Nikon Eclipse 80i). Images were manually evaluated at four different areas at 200-fold magnification. Myofibroblasts were defined as single, spindle-shaped, αSMA-positive cells in the dermis.

Results

Allogeneic transplantation induced prominent skin fibrosis with increased dermal thickness, myofibroblast count and hydroxyproline content, compared to syngeneic transplantation (FIG. 7A-C). Mice treated with mCAN10 displayed significantly reduced dermal thickening (FIG. 7A) and myofibroblast counts (FIG. 7B), and a decrease in hydroxyproline (FIG. 7C), a measure of collagen content, as compared to allogeneically transplanted mice treated with isotype control antibody. The effects of mCAN10 on these parameters were within the range of those observed with nintedanib (FIG. 7A-C).

Allogeneic bone marrow transplantation induced moderate pulmonary fibrosis with increases in Ashcroft score, area stained by Sirius Red, and hydroxyproline content (FIG. 8A-C). Treatment with mCAN10 significantly reduced the Ashcroft score (FIG. 8A), Sirius Red staining (FIG. 8B), and hydroxyproline content (FIG. 8C), compared to allogeneically transplanted mice treated with isotype control antibody. The effects of mCAN10 on these parameters were again within the range of those observed with nintedanib (FIG. 8A-C).

mCAN10 was well tolerated, without signs of toxicity upon clinical examination, gross necropsy or histology. Additionally, treatment with mCAN10 ameliorated scl cGvHD-induced weight loss more effectively than nintedanib (FIG. 9).

Conclusions

IL1RAP blockade by mCAN10 is an efficient strategy to reduce scl cGvHD-induced dermal and pulmonary fibrosis.

Example 8: The Murine Surrogate Anti-IL1RAP Antibody mCAN10, Specific Inhibitor of Mouse IL1RAP, Alters Gene Expression Profiles Related to Inflammatory Processes Aim The aim of this study is to evaluate molecular pathways affected by IL1RAP blockade using the murine surrogate anti-IL1RAP antibody mCAN10 in a mouse model of sclerodermatous chronic graft-versus-host disease (scl cGvHD). The aim is also to identify disease-related differentially expressed genes (DEG) affected by IL1RAP-inhibition, in skin from scl cGvHD mice, and compare these to disease-related genes in skin biopsies from systemic sclerosis (SSc) patients.

Material and Methods

Mouse Samples

Samples were obtained from mice that had undergone syngeneic or allogeneic transplantation with or without treatment with mCAN10 as reported in Example 7.

RNASeq Preprocessing and Analysis

Raw paired-end reads were aligned to GRCm39 reference genome and mapped reads were counted using Rsubread (v 2.6.4) in R (v 4.1.1). Principal component analysis (PCA) was performed to determine the potential outliers among samples in each batch. Following PCA, three samples (one per condition) were excluded. For each group, four samples resulting in dense group-specific clustering were selected. Median of ratios normalization and differential expression analysis were performed using DESeq2 package (v 1.32.0). The significant DEG list is considered as adjusted p-value≤0.05 and |log2FC|≥1.5 for comparisons.

The transcriptomic profile of SSc patients was retrieved from a North American SSc patient cohort (NCBI/GEO/GSE130955) consisting of 143 SSc patients and 22 healthy individuals. For comparison between mouse and human samples, and detection of reciprocally expressed genes, human orthologs were mapped to murine gene symbols using r package "biomaRt" (v 2.48.3).

Treatment Response Signature

Due to the sample size, a feature selection for a gene combination treatment response signature was performed using logistic regression modeling by applying the R stats package. Logistic regression models allow for classification between two groups (binary outcome system: 1 [=e.g. treatment], 0 [=e.g. healthy]), in which a stepwise feature selection identifies the best gene set combination for group classification. Gene combination models were selected based on the Akaike Information Criteria (AIC) and Area Under the Curve (AUC) values using the MASS and ROCR packages. The AIC value is a quality indicator of how good the statistical gene combination model describes the data considering the number of used features, whereas the AUC describes the model performance.

Results Analysis of RNASeq data shows separation between allogeneically-transplanted mice (Allo), syngeneically-transplanted mice (Syn) and allogeneically-transplanted mice treated with mCAN10 (Treated), in which the Treated group is close to the Syn group. Comparison between Allo vs. Syn identified 2308 DEG (1023 up-, 1285 downregulated; adjusted p-value≤0.05, |log2FC|≥1.5), in which deregulation of processes and pathways related to inflammation and fibrosis were observed. Conversely, comparison between Treated vs. Allo identified 495 DEG (398 up-, 106 downregulated; adjusted p-value≤0.05, |log2FC|≥1.5), in which deregulation of several processes related to inflammation was observed by IL1RAP inhibition with mCAN10. Of interest, mCAN10 altered the gene expression of multiple IL-1 family genes such that the profile was more similar to the Syn group, rather than the Allo group (FIG. 10).

Analysis of the overlap between Allo DEG (Allo vs. Syn), Treated DEG (Treated vs. Allo) and SSc DEG (SSc vs. Healthy; information retrieved from a previously published dataset NCBI/GEO/GSE130955) identified 449 overlapping genes between the mouse model (Allo vs. Syn) and human dataset (SSc vs. Healthy). Of these, 177 (39.4%) genes overlapped between all three groups of DEG (FIG. 11), of which 58 genes (20 up-, 38 downregulated; adjusted p-value≤0.05 and |log2FC|≥0.25) are reciprocally regulated between Treated DEG and SSc DEG.

Conclusions mCAN10 impacts processes and pathways related to inflammation in scl GvHD mice, which supports the observed effects of mCAN10 on disease manifestations in this model. A substantial number of genes influenced by mCAN10 in scl GvHD mice were differentially expressed in SSc patients compared to healthy controls, suggesting that IL1RAP inhibition may influence human disease as well.

Example 9: Immunization with IL1RAP to Generate Anti-IL1RAP Antibodies

Aim

This example illustrates how anti-IL1RAP antibodies were isolated from rabbits immunized with IL1RAP.

Material and Methods

Rabbits were immunized four times followed by a boost using a mixture of recombinantly expressed ectodomains of human and murine IL1RAP, 0.2 mg of antigen per injection. Immunizations were carried out by subscapular injections after every third week. First immunization was performed in Freund's complete adjuvant and second through fourth immunizations in Freund's incomplete adjuvant. For boosting, half the antigen amount was injected subscapularly in Freund's incomplete adjuvant and the other half intravenously.

Immune response of each animal was measured by ELISA using blood serum approximately ten days after the third immunization. The specific antibody titer was measured by ELISA, coating the plates with human and mouse IL1RAP separately for immune response comparison. Two to three weeks after the fourth immunization, the animals were boosted once and spleens were collected four to five days after the boost. Spleens of test animals were homogenized, cells frozen and stored in liquid nitrogen.

Monoclonal antibody sequences were isolated from immunized rabbits using the approach described in Kivi et al. (Kivi G, HybriFree: a robust and rapid method for the development of monoclonal antibodies from different host species. BMC Biotechnology 16:2 (2016)). Streptavidin-coated 96-well plates were coated with biotinylated human or murine IL1RAP, or a mixture of both, at 5 µg/ml. Ten thousand spleen cells were used for each panning. In total 48 panning reactions were performed. After incubation for 45 minutes, wells were washed with PBS to remove unbound cells. RNA was isolated from the bound cells and VH and VL cDNA was synthesized and used for construction of a combinatorial VH-VL library in a human IgG expression plasmid format. Plasmid DNA was purified and transfected into CHO cells for production of chimeric rabbit/human IgG1 pools. Supernatants of antibody pools were analyzed using ELISA 48 hours after transfection and positive pools were identified. Bacteria containing plasmid DNA from the positive pools were plated on LB-ampicillin solid medium and single colonies were isolated and grown in liquid medium. Plasmid DNA was purified from the liquid cultures and transfected into CHO cells for transient antibody production. Supernatants were analyzed by ELISA 48-72 hours after transfection.

Results

Antibodies binding to human and/or murine IL1RAP were identified. The chimeric rabbit/human IgG1 ELISA IL1RAP positive clones were further analyzed by sequencing. The chimeric antibodies were further analyzed in their properties, such as for example the ability to inhibit IL-1, IL-33 or IL-36 signaling. Chimeric antibody 48D2 was selected for further characterization and optimization (see following Examples). The light chain variable region of this antibody comprises a light chain variable region comprising or consisting of the amino acid sequence of SEQ ID NO: 19. The heavy chain variable region of this antibody comprises a heavy chain variable region comprising or consisting of the amino acid sequence of SEQ ID NO: 20. To create a whole antibody, the variable regions were combined with light chain constant regions comprising or consisting of the amino acid sequence of SEQ ID NO: 35, and with IgG1 heavy chain constant regions, either comprising or consisting of the amino acid sequence of SEQ ID NO: 36 or SEQ ID NO: 2.

Conclusions

Monoclonal chimeric rabbit/human IgG1 antibodies directed towards IL1RAP were isolated.

Example 10: Identification and Characterization of an Antibody Binding to IL1RAP and Blocking IL-1, IL-33 and IL-36 Signaling Aim This example illustrates the characterization of the selected antibody, 48D2 chimeric (ch) rabbit/human anti-human IL1RAP, generated as described in Example 9. The goal was to identify an antibody that had high affinity for both cynomolgus monkey and human IL1RAP and completely blocked all IL1RAP regulated signaling pathways.

Material and Methods

Binding of the Antibody to IL1RAP-Expressing Cells

The malignant melanoma (or malign melanoma) cell line SKMEL-5, which expresses IL1RAP on the cell surface, was used for the analysis. SKMEL-5 cells were cultured according to standard procedures. $5 \times 10^4$ SKMEL-5 cells were blocked with human Fc block and then stained with 8-step serial dilutions (100 µg/ml-0.03 µg/ml) of chimeric 48D2 or isotype control antibody. Following secondary staining using Alexa488-conjugated anti-human IgG antibody, 10000 cells/sample were analyzed on a CytoFlex (Beckman Coulter). HTB183 cells expressing low levels of surface IL1RAP were used as negative controls.

Inhibition of Cytokine Signaling

For analysis of IL-1 and IL-33 inhibition, HEK-Blue™ (IL-33/IL-1) cells were used as provided. For IL-36 analysis, HEK-Blue™ (IL-33/IL-1) cells were transiently transfected with the IL-36 receptor the day before the assay or HEK-Blue™ clones with stable expression of the IL-36 receptor (generated in house) were used. Briefly, HEK-Blue™ cells were seeded into 384-well plates and allowed to settle for a minimum of 2 hours before continuing. Cells were then exposed to increasing concentrations of chimeric 48D2 (as depicted in the figures) and incubated for 1 hour at 37° C., 5% $CO_2$, before addition of cytokine. The cytokines were added in the following concentrations: 2 ng/ml IL-1α, 0.1 ng/ml IL-1β, 0.2 ng/ml IL-33, 1 ng/ml IL-36α, 3 ng/ml IL-36β and 0.2 ng/ml IL-36γ. Cells were cultured for 16-18 hours at 37° C., 5% $CO_2$ and then analyzed for activation of NF-κB and subsequent production of SEAP using QUANTI-Blue™ Solution measured at 620 nm using the SpectraMax i3x spectrophotometer.

Expression and Purification of Chimeric 48D2

Chimeric 48D2 was transiently expressed in CHO cells. Purification was performed using protein A affinity chromatography and gel filtration.

Affinity Measurements by Biolayer Interferometry

Affinity measurements were done on BLItz™ Label-Free Protein Analysis System from ForteBio, using the Basic Kinetics module in the BLItz Pro 1.3.1.3 software from Molecular Devices. Protein A biosensors were hydrated in blocking buffer (PBS, 0.5% BSA, 0.05% Tween 20, pH 7.4) for minimum 10 min at room temperature before coating. Protein A biosensors were coated with antibodies by dipping the biosensors in 200 µl of antibody solution (10 µg/ml in blocking buffer) for 30 min at room temperature. The sensors were then incubated in 200 µl blocking buffer for at least 10 min before use. Each antibody was analyzed at four different concentrations of hIL1RAP (21-367) in blocking buffer; 0.8 nM (0.032 µg/ml), 4 nM (0.16 µg/ml), 20 nM (0.8 µg/ml) and 100 nM (4 µg/ml). The baseline was made in blocking buffer with a duration time of 30 sec. Association was made for 120 sec in hIL1RAP followed by 120 sec dissociation in blocking buffer.

Domain Mapping

The IL1RAP ectodomain consists of three domains (domain 1, domain 2, domain 3). In order to understand where 48D2 binds to IL1RAP, a series of IL1RAP constructs were generated corresponding to the different domains and binding to these was tested in an indirect ELISA assay using duplicate samples. Constructs were created using the amino acid sequence for IL RAP given in Uniprot, ID Q9NPH3. Microtiter plates were coated with 100 ng of recombinant hIL1RAP Domain1+2+3 (made up of domain 1, domain 2 and domain 3) (aa21-367) (positive control), recombinant hIL1RAP Domain1+2 (made up of domain 1 and domain 2) (aa21-234), Domain1 (aa21-134) or recombinant hIL1RAP Domain3 (aa235-367) (100 µl/well) diluted in 0.01 M PBS, pH 7.4, and incubated overnight at 4° C. Plates were washed with ELISA washing buffer (0.01 M PBS, 0.05% Tween 20, pH 7.4) followed by a blocking step using 150 µl/well of ELISA blocking solution (PBS, 0.5% BSA, 0.05% Tween 20, pH 7.4). After one hour incubation at room temperature on agitation, the plates were washed again using ELISA washing buffer. A series of 48D2 dilutions in ELISA blocking solution was prepared (ranging from 1 to 10000 ng/ml) and then transferred to the wells at 100 µl/well. Plates were incubated at room temperature for one hour on agitation and then washed with ELISA washing solution. One hundred µl/well of goat anti-human IgG conjugated to alkaline phosphatase was added and incubated one hour at room temperature on agitation. The plates were washed using ELISA washing solution followed by addition of substrate (4-Nitrophenyl phosphate disodium salt hexahydrate, Sigma-Aldrich, 1 mg/ml), 100 µl/well. The plates were thereafter incubated at room temperature on agitation and absorbance at 405 nm was measured consecutively for 30 min. Absorbance at 0 min was taken as background signal. The polyclonal anti-hIL1RAP antibody KMT-1 was used as a control.

Epitope Mapping

Based on the domain mapping and cross reactivity data, two regions in domain 2 of IL1RAP were identified as potential interaction sites for 48D2 (a humanized and de-immunized 48D2 variant VH5.GL:VL4 (see Example 13)), corresponding to aa 141-157 (designated H1) and 174-191 (designated H2) (based on the human IL1RAP amino acid sequence from Uniprot, ID Q9NPH3). Two chimeric constructs of murine/human IL1RAP were created, where the human sequence of the two regions of interest were grafted onto murine IL1RAP: chimeric IL1RAP.H1 and chimeric IL1RAP.H2. Microtiter plates were coated with the chimeric IL1RAP constructs and ELISA measurements were performed as described above for the domain mapping. The polyclonal anti-hIL1RAP antibodies KMT-2 (affinity purified rabbit polyclonal antibodies against human IL1RAP) and KMT-3 (affinity purified rabbit polyclonal antibodies against murine IL1RAP) were used as positive controls.

Cross Reactivity

Microtiter plate wells were coated with IL1RAP orthologs (*Mus musculus, Rattus norvegicus, Macaca fascicularis* (Mf, synonymous to cynomolgus monkey), *Oryctolagus cuniculus, Canis lupus familiaris, Sus scrofa*) and incubated for 1 hour at 37° C. Plates were washed followed by a blocking step. After 1 hour incubation at room temperature on agitation, the plates were washed again. The antibody was diluted in fourfold serial dilution, ranging from 4000 ng/ml to 0.24 ng/ml, in ELISA blocking solution, and then transferred to the ELISA plate. Plates were incubated at 37° C. in 30 min on agitation and then washed. Goat Anti-Human antibody conjugated to Alkaline Phosphatase was added and incubated 30 min at 37° C. on agitation. The plates were washed followed by addition of substrate (4-Nitrophenyl phosphate disodium salt hexahydrate). The plates were thereafter incubated at room temperature on agitation and absorbance at 405 nm measured consecutively for 50 min. Absorbance at 0 min was taken as background signal.

Results

Binding of the Antibody to IL1RAP-Expressing Cells

Flow cytometry analysis of IL1RAP-expressing SKMEL-5 cells stained with chimeric 48D2 or isotype control revealed a higher mean fluorescence intensity (MFI) for 48D2 compared to the isotype control antibody (FIG. 12). 48D2 and the isotype control are added to the cells in increasing concentrations. No binding was observed to HTB183 cells with low surface expression of IL1RAP (data not shown).

Inhibition of Cytokine Signaling

FIG. 13 shows the inhibitory activity of ch48D2 on IL-1α, IL-1β, IL-33, IL-36α, IL-36β and IL-36γ signaling in HEK cells. The antibodies were added in increasing concentrations and then the depicted cytokine was added at a constant concentration. The graph shows optical density (OD) values at 620 nm with a high OD representing signaling downstream of the cytokine receptor. The chimeric antibody 48D2 induced a pronounced inhibition of IL-1α, IL-1β, IL-33, IL-36α, IL-36β and IL-36γ signaling, up to complete inhibition (blocking) of the signaling of these cytokines. The IC50 values are shown in Table 3.

TABLE 3

IC50 values [nM] of chimeric 48D2 on the different signaling pathways, obtained from the HEK-Blue™ assay

| IC50 [nM] | IL-1α | IL-1β | IL-33 | IL-36α | IL-36β | IL-36γ |
|---|---|---|---|---|---|---|
| 48D2 | 1.92 | 0.70 | 2.917 | 0.0083 | 0.0081 | 0.0111 |

Affinity Measurements

Affinity measurement results are shown in Table 4 for chimeric 48D2, as well as for humanized 48D2 variant VH5:VL4 (see Example 11) and for humanized and de-immunized 48D2 variant VH5.GL:VL4 (see Example 13). $k_a$ is the association rate constant, for characterization of the antibody binding to the target, $k_d$ is the dissociation rate constant, for characterization of the antibody dissociation from the target, and $K_D$ is the equilibrium dissociation constant between the antibody and its antigen, the ratio of $k_d/k_a$. $K_D$ corresponds to the antibody concentration at which 50% of the antigen binding sites are occupied at equilibrium. The lower the $K_D$ value (lower concentration), the higher the affinity.

The 48D2 variants displayed fast binding to human (h) IL1RAP and slow dissociation resulting in affinities in the nM range. No loss of affinity for human IL1RAP was seen for the humanized, or the humanized and de-immunized, variants compared to chimeric 48D2.

TABLE 4

Affinity measurements

| Antibody name | $K_D$ (nM) | $k_a$ (1/Ms) | $k_d$ (1/s) |
|---|---|---|---|
| chimeric 48D2 | 2.673 | 6.521E4 | 1.743E-4 |
| h48D2 VH5:VL4 | 2.742 | 6.022E4 | 1.716E-4 |
| h48D2 VH5.GL:VL4 | 2.532 | 7.797E4 | 1.974E-4 |

Domain Mapping

The domain mapping data is summarized in Table 5 below. The control polyclonal antibody KMT-1 bound to all domains, whereas 48D2 only bound to IL1RAP constructs containing domain 2, suggesting that the antibody binds to this domain.

TABLE 5

Domain mapping of chimeric 48D2

| Antibody | Domain1 + 2 + 3 (aa21-367) | Domain1 + 2 (aa21-234) | Domain1 (aa21-134) | Domain3 (aa235-367) | Suggested epitope |
|---|---|---|---|---|---|
| 48D2 | + | + | | | Domain 2 |
| KMT-1 | + | + | + | + | polyclonal |

Epitope Mapping

The epitope mapping results using murine IL1RAP with the grafted human sequences for regions H1 and H2 are shown in Table 6. The h48D2 VH5.GL:VL4 (see Example 13) binding to murine IL1RAP was restored when the human sequence for the H2 region was introduced in murine IL1RAP, suggesting that H2 is involved in the interaction with 48D2 (compare Table 5 and 6). The positive control polyclonal antibodies KMT-2 and KMT-3 bound to both chimeric versions of IL1RAP.

TABLE 6

Epitope mapping of 48D2 using chimeric IL1RAP

| Antibody | Chimeric IL1RAP.H1 | Chimeric IL1RAP.H2 | Suggested epitope |
|---|---|---|---|
| h48D2 VH5.GL:VL4 | − | + | H2 |
| KMT-2 | + | + | Polyclonal |
| KMT-3 | + | + | Polyclonal |

Cross Reactivity

FIG. 14 shows cross reactivity of chimeric 48D2 to IL1RAP from different species. The antibody is added in increasing concentrations and absorbance at 405 nm is used to detect binding of the antibody to IL1RAP orthologues. 48D2 is cross reactive to IL1RAP from human, cynomolgus monkey (cyno) and pig, but has no cross reactivity to IL1RAP from mouse, rat, rabbit or dog (FIG. 14 and Table 7).

TABLE 7

Cross reactivity of chimeric 48D2

| | hIL1 RAP (human) | mIL1 RAP (mouse) | rnIL1 RAP (rat) | mfIL1 RAP (cyno) | ocIL1 RAP (rabbit) | clIL1 RAP (dog) | ssIL1 RAP (pig) |
|---|---|---|---|---|---|---|---|
| ch48D2 | + | − | − | + | − | − | + |

Conclusions

Chimeric 48D2 was found to bind to domain 2 of hIL1RAP, had high affinity for both cynomolgus monkey and human IL1RAP, selectively bound IL1RAP on the cell membrane, and completely inhibited IL-1α, IL-1β, IL-33, IL-36α, IL-36p, and IL-36γ signaling, and was thus selected for humanization. Chimeric 48D2 exhibited superior properties over other antibodies that were generated as described in Example 9.

Example 11: Humanization of Chimeric 48D2

Aim

This example illustrates how humanized variants of 48D2 were obtained.

Material and Methods

In-Silico Humanization

The sequences of the antibody light and heavy variable regions of 48D2 were searched against a database containing mature human antibody sequences and human germline antibody sequences. The CDRs were defined according to the IMGT and the Kabat numbering systems and amino acid residues were included as a combination of both (see SEQ ID NOs 1, and 3 to 18, as well as CDR-L2 with the sequence of KAS). Selection of acceptor frameworks for humanization was based on sequence homology and on subsequent ab initio structure predictions created using the software tool Maestro. Frameworks were chosen to maintain key structural framework residues. Five sequences each were obtained for VL and VH, creating 25 different humanized antibody variants to further characterize (VL1-VL5 to combine with VH1-VH5). For the acceptor frameworks based on human germline antibody sequences, back mutations were introduced to ensure structure and function of the antibody. Part of the humanization was also predictions of immunogenicity (MHC class II binding affinity) and manufacturability. The MHC class II binding affinity prediction was performed using the NetMHCII server.

Results

Five in-silico humanized variants of VL and five of VH were created and verified to the have been humanized in accordance with WHO's definition of humanized antibodies. Immunogenicity was assessed to avoid introducing sequences with potential MHC class II binding affinity. Manufacturability was assessed to avoid introducing glycosylation motifs or sequences prone to deamidation, isomerization or fragmentation. The sequences are depicted in Table 8.

TABLE 8

In-silico humanized variants of VL and VH (48D2)

| SEQ ID NO | Chain | Sequence |
|---|---|---|
| 21 | VL1 | DIVMTQSPSSLSASVGDRVTITCQASESISTALAWYQQKPGKA PKLLIYKASTLPSGVPSRFSGSGSGTDFTLTISSLQPEDFATY YCQQGFSSGNVHNAFGGGTKVVIK |
| 22 | VL2 | QIVLTQSPATLSASVGDRVTITCQASESISTALAWYQQKPGKA PKLLIYKASTLPSGVPSRFSGSGSGTEFTLTISSLQPDDSATY YCQQGFSSGNVHNAFGQGTKLEIK |
| 23 | VL3 | DILLTQTPSVVSASVGDRVTITCQASESISTALAWYQQKPGQA PRLLIYKASTLPSGVPSRFRGSGSGTDFTLTITSLQPEDFATY YCQQGFSSGNVHNAFGGGTRLEIK |
| 24 | VL4 | ELVMTQSPSSVSASVGDRVTITCQASESISTALAWYQQKPGKA PKLLIYKASTLPSGVPSRFSGSGSGTDFTLTINSLQPEDFATY YCQQGFSSGNVHNAFGGGTKVEIK |
| 25 | VL5 | APVLTQSPATLEASVGDRVTITCQASESISTALAWYQQKPGQP PKLLIYKASTLPSGVPSRFSGSGSGTEFTLTISDLESDDAATY YCQQGFSSGNVHNAFGGGTEVVVK |
| 26 | VH1 | EVQLEESGGGLVKPGGSLRLSCAASGPSLSHFDITWVRQAPGK GLEWVSTISPGVSTYYASWAKSRFTISRDNSKNTLYLQMNSLR AEDTAVYYCARGGVGSSWKAFDLWGRGTLVTVSS |
| 27 | VH2 | EVQLVESGGALVQPGGSLRLSCIVSGPSLSHFDITWFRQAPGK GLEWVATISPGVSTYYASWAKSRFTISTDTSKNTLFLQMDSLR AEDTAVYYCARGGVGSSWKAFDLWGPGTLVTVSS |
| 28 | VH3 | EVQLLESGGGLVLPGGSLRLSCAASGPSLSHFDITWVRQAPGK GLEWVSTISPGVSTYYASWAKSRFTISRDNSKNTLYLQMSSLR AEDTAVYYCARGGVGSSWKAFDLWGLGTTVTVSS |
| 29 | VH4 | QVQLQESGPGLVKPSETLSLTCTVSGPSLSHFDITWIRQPPGK GLEWIGTISPGVSTYYASWAKSRFTISVDTSKNQFSLKLTSVT AADTATYYCARGGVGSSWKAFDLWGPGTLVTVSS |
| 30 | VH5 | QEQLEESGGGLVKPGGTLSLTCTVSGPSLSHFDITWIRQAPGS GLEWIGTISPGVSTYYASWAKSRVTISVDTSLNTVSLKLSSVT AADTATYFCARGGVGSSWKAFDLWGPGTLVTISS |

Conclusions

Five in-silico humanized variants of VL and five of VH were created and were to be synthesized in-frame with IgG1 constant domains for production and characterization of 25 humanized antibody variants (see Example 12).

Example 12: Characterization of Humanized 48D2

Aim

This example illustrates how the humanized 48D2 variants (see Example 11) were expressed and characterized with the aim of finding a humanized antibody with retained affinity, cytokine inhibition and optimized biochemical properties.

Material and Methods

Expression, Purification, and Characterization of Humanized Variants

Heavy and light variable domains of 25 humanized variants of 48D2 (see Table 8) were sub-cloned into vectors containing human constant domains:

Kappa constant domain (of the Km3 allotype) is combined with a VL domain forming the entire light chain (SEQ ID NO: 35).

IgG1za (of the za allotype) heavy chain constant domain is combined with a VH domain forming the entire heavy chain. The heavy chain constant domain also contained the LALA mutation (SEQ ID NO: 2) (corresponding to the one described, for example, in Xu et al., 2000, Cell. Immuno. 200: 16-26) in order to avoid Fc-gamma-receptor mediated antibody effector functions.

The humanized antibodies (h48D2) were transiently expressed in HEK-293 cells, Protein A-purified from the harvested medium of 50 ml cultures and buffer-exchanged into PBS pH 7.4.

The antibodies were characterized for A) binding (ELISA analysis, human and cynomolgus monkey IL1RAP), B) inhibition of cytokine signaling (HEK-Blue™ assay), C) affinity (Bio-layer interferometry), D) size heterogeneity (SE-HPLC) and E) yield (concentration, A280). Binding ELISA was performed in a similar manner to the indirect ELISA presented for the domain mapping in Example 10 using recombinant hIL1RAP aa21-367 or recombinant mfIL1RAP aa21-367 as coating reagents. SE-HPLC was performed using standard procedures and PBS as running buffer. Affinity and cytokine inhibition were measured as previously described in Example 10. All 25 humanized clones were analyzed for blocking activity on IL-1α, IL-1β and IL-33 signaling while only the clones that had retained the inhibitory activity similar to chimeric 48D2 were analyzed for IL-36 inhibition.

Results

A) Binding of the Humanized Antibody Clones to IL1RAP (ELISA)

IC50 values obtained using ELISA measurements are shown in Table 9. Using binding ELISA, only small differences in binding can be seen between different clones. Also, for each clone, the binding affinities towards human and cynomolgus monkey (cyno) IL1RAP were similar.

TABLE 9

Binding of the humanized antibody clones to IL1RAP

| h48D2 variant | IC50 human IL1RAP (ng/ml) | IC50 cyno IL1RAP (ng/ml) |
|---|---|---|
| h48D2 VH1:VL1 | 18.07 | 22.60 |
| h48D2 VH1:VL2 | 18.2 | 19.81 |
| h48D2 VH1:VL3 | 20.09 | 17.97 |
| h48D2 VH1:VL4 | 19.04 | 20.02 |
| h48D2 VH1:VL5 | 23.44 | 24.16 |
| h48D2 VH2:VL1 | 23.76 | 27.95 |
| h48D2 VH2:VL2 | 26.15 | 29.22 |

TABLE 9-continued

Binding of the humanized antibody clones to IL1RAP

| h48D2 variant | IC50 human IL1RAP (ng/ml) | IC50 cyno IL1RAP (ng/ml) |
|---|---|---|
| h48D2 VH2:VL3 | 27.35 | 31.41 |
| h48D2 VH2:VL4 | 26.23 | 31.17 |
| h48D2 VH2:VL5 | 24.86 | 27.87 |
| h48D2 VH3:VL1 | 25.68 | 29.35 |
| h48D2 VH3:VL2 | 25.77 | 27.36 |
| h48D2 VH3:VL3 | 28.13 | 27.87 |
| h48D2 VH3:VL4 | 26.27 | 30.35 |
| h48D2 VH3:VL5 | 23.15 | 27.92 |
| h48D2 VH4:VL1 | 30.82 | 31.65 |
| h48D2 VH4:VL2 | 32.16 | 29.11 |
| h48D2 VH4:VL3 | 31.21 | 30.18 |
| h48D2 VH4:VL4 | 24.33 | 25.11 |
| h48D2 VH4:VL5 | 25.81 | 24.44 |
| h48D2 VH5:VL1 | 24.82 | 26.06 |
| h48D2 VH5:VL2 | 23.13 | 21.83 |
| h48D2 VH5:VL3 | 24.89 | 28.78 |
| h48D2 VH5:VL4 | 25.8 | 28.01 |
| h48D2 VH5:VL5 | 27.63 | 31.30 |

B) Inhibition of Cytokine Signaling

FIG. 15A-O shows the inhibitory activity of the humanized 48D2 antibody clones on IL-1α, IL-1β and IL-33 signaling in HEK cells. The antibodies are added in increasing concentrations and then the depicted cytokine is added at a constant concentration. The graph shows optical density (OO) values at 620 nm with a high OO representing signaling downstream of the cytokine receptor. The antibody clones harboring the VH5 variant induced a complete inhibition of IL-1α, IL-1β and IL-33 signaling with a similar potency as the chimeric 48D2 antibody (FIGS. 15E, 15J, 15O). The antibody clones harboring the variants VH1-VH4 inhibited signaling of IL-1α, IL-1β and IL-33 to varying degrees, with varying potency compared to chimeric 48D2. Partial inhibition was achieved by these variants with regard to IL-1α(FIG. 15A-D) and IL-33 (FIG. 15K-N); and complete inhibition was achieved with regard to IL-1β (FIG. 15F-I). The antibody clones harboring the variants VH1-VH4 were not analyzed for IL-36 inhibition. The respective IC50 values are shown in Table 10. FIG. 15P-R shows that antibody clones harboring the VH5 variant also induced a complete inhibition of IL-36α, IL-36β and IL-36γ signaling with a similar potency as the chimeric 48D2 antibody.

TABLE 10

IC50 values [nM] of the humanized antibodies from the HEK-Blue ™ assay

| IC50 [nM] | IL-1α | IL-1β | IL-33 | IL-36α | IL-36β | IL-36γ |
|---|---|---|---|---|---|---|
| h48D2 VH1:VL1 | 226.6 | 51.63 | 254.3 | n/a | n/a | n/a |
| h48D2 VH1:VL2 | 242.0 | 37.63 | 8.105E+13 | n/a | n/a | n/a |
| h48D2 VH1:VL3 | 231.0 | 17.21 | 195.1 | n/a | n/a | n/a |
| h48D2 VH1:VL4 | 346.8 | 14.60 | 2.097E+9 | n/a | n/a | n/a |
| h48D2 VH1:VL5 | 527.9 | 20.24 | 74.66 | n/a | n/a | n/a |
| h48D2 VH2:VL1 | ~43765 | 2.749 | 2.679E+12 | n/a | n/a | n/a |
| h48D2 VH2:VL2 | ~2.54E+7 | 0.882 | 45.81 | n/a | n/a | n/a |
| h48D2 VH2:VL3 | ~3.754E+8 | 3.658 | 1954 | n/a | n/a | n/a |
| h48D2 VH2:VL4 | ~4.126E+6 | 1.359 | 86.40 | n/a | n/a | n/a |

TABLE 10-continued

IC50 values [nM] of the humanized antibodies from the HEK-Blue™ assay

| IC50 [nM] | IL-1α | IL-1β | IL-33 | IL-36α | IL-36β | IL-36γ |
|---|---|---|---|---|---|---|
| h48D2 VH2:VL5 | 400.8 | 5.767 | 182.9 | n/a | n/a | n/a |
| h48D2 VH3:VL1 | ~1.187E+9 | 9.536 | ~87533 | n/a | n/a | n/a |
| h48D2 VH3:VL2 | ~4.250E+7 | 9.106 | 474.0 | n/a | n/a | n/a |
| h48D2 VH3:VL3 | ~3.973E+7 | 10.46 | ~3.400E+6 | n/a | n/a | n/a |
| h48D2 VH3:VL4 | ~2.368E+7 | 22.32 | ~1.864E+11 | n/a | n/a | n/a |
| h48D2 VH3:VL5 | 287.5 | 9.874 | 473.6 | n/a | n/a | n/a |
| h48D2 VH4:VL1 | ~6.986E+10 | 2.948 | ~6.431E+9 | n/a | n/a | n/a |
| h48D2 VH4:VL2 | ~7.412E+12 | 5.549 | ~3.509E+10 | n/a | n/a | n/a |
| h48D2 VH4:VL3 | ~1.563E+13 | 2.967 | 7030 | n/a | n/a | n/a |
| h48D2 VH4:VL4 | ~5.778E+11 | 4.672 | 260.3 | n/a | n/a | n/a |
| h48D2 VH4:VL5 | ~5.454E+10 | 0.2725 | 74.30 | n/a | n/a | n/a |
| h48D2 VH5:VL1 | 2.137 | ~6.142E−6 | 3.140 | 0.286 | ~2.098E+8 | 3.101 |
| h48D2 VH5:VL2 | 3.765 | ~4.156E−5 | 0.647 | ~8.858E−8 | ~9.266E−12 | 0.253 |
| h48D2 VH5:VL3 | 4.452 | ~0.541E−4 | 2.717 | 0.0779 | 17.42 | 0.167 |
| h48D2 VH5:VL4 | 6.470 | ~7.579E−5 | 2.002 | ~0.0025 | ~0.3423 | 2.835 |
| h48D2 VH5:VL5 | 6.304 | ~4.660E−5 | 1.232 | ~2.079E−7 | 11.11 | 0.192 |

C) Affinity Measurements $K_D$ values for affinity towards human IL RAP are shown in Table 11 for the humanized 48D2 variants. Affinity was measured using bio-layer interferometry. All antibody variants exhibited affinity in the nanomolar range. The highest affinities were obtained for the VH5 series with KD values in the range of 1-4 nM. See also Table 4 for a direct comparison of chimeric 48D2, humanized 48D2 variant VH5:VL4, and a humanized and de-immunized 48D2 variant VH5.GL:VL4.

TABLE 11

Affinity measurements of the humanized antibodies

| Name | Affinity human IL1RAP (nM) |
|---|---|
| h48D2 VH1:VL1 | 30.27 |
| h48D2 VH1:VL2 | 33.68 |
| h48D2 VH1:VL3 | 35.04 |
| h48D2 VH1:VL4 | 42.86 |
| h48D2 VH1:VL5 | 31.59 |
| h48D2 VH2:VL1 | 13.15 |
| h48D2 VH2:VL2 | 7.33 |
| h48D2 VH2:VL3 | 12.1 |
| h48D2 VH2:VL4 | 11.17 |
| h48D2 VH2:VL5 | 12.0 |
| h48D2 VH3:VL1 | 28.02 |
| h48D2 VH3:VL2 | 22.41 |
| h48D2 VH3:VL3 | 27.35 |
| h48D2 VH3:VL4 | 29.6 |
| h48D2 VH3:VL5 | 34.39 |
| h48D2 VH4:VL1 | 19.67 |
| h48D2 VH4:VL2 | 13.25 |
| h48D2 VH4:VL3 | 16.66 |
| h48D2 VH4:VL4 | 22.8 |
| h48D2 VH4:VL5 | 14.98 |
| h48D2 VH5:VL1 | 2.75 |
| h48D2 VH5:VL2 | 4.27 |
| h48D2 VH5:VL3 | 2.33 |
| h48D2 VH5:VL4 | 1.67 |
| h48D2 VH5:VL5 | 1.68 |

D) Size Heterogeneity

Size heterogeneity was determined using size-exclusion HPLC (SE-HPLC) (Table 12). The intact monomeric antibody consists of two identical heavy chains and two identical light chains covalently linked together by disulfide bonds. The high-molecular weight (HMW) species potentially contain soluble antibody aggregates, for example dimers. The low-molecular weight (LMW) species potentially contain antibodies where, for example, peptide bonds have been cleaved, i.e. fragmented antibodies. Almost all variants were highly monomeric (≥97%), except for h48D2 VH4:VL3 that contained >5% high-molecular weight species (HMW). For all analyzed variants, no to small amounts of low-molecular weight (LMW) species were detected.

TABLE 12

Size heterogeneity analysis of the humanized antibodies

| Name | HMW (%) | Monomeric (%) | LMW (%) |
|---|---|---|---|
| h48D2 VH1:VL1 | 1.8 | 98.2 | 0 |
| h48D2 VH1:VL2 | 1.6 | 98.4 | 0 |

TABLE 12-continued

Size heterogeneity analysis of the humanized antibodies

| Name | HMW (%) | Monomeric (%) | LMW (%) |
|---|---|---|---|
| h48D2 VH1:VL3 | 1.9 | 98.1 | 0 |
| h48D2 VH1:VL4 | 1.7 | 98.3 | 0 |
| h48D2 VH1:VL5 | 1.8 | 97.4 | 0.8 |
| h48D2 VH2:VL1 | 1.7 | 98.3 | 0 |
| h48D2 VH2:VL2 | 2.2 | 97.8 | 0 |
| h48D2 VH2:VL3 | 1.7 | 98.3 | 0 |
| h48D2 VH2:VL4 | 1.3 | 98.7 | 0 |
| h48D2 VH2:VL5 | 3.3 | 96.7 | 0 |
| h48D2 VH3:VL1 | 1.4 | 98.6 | 0 |
| h48D2 VH3:VL2 | 1.1 | 98.9 | 0 |
| h48D2 VH3:VL3 | 1.6 | 98.4 | 0 |
| h48D2 VH3:VL4 | 1.3 | 98.7 | 0 |
| h48D2 VH3:VL5 | 1.4 | 98.6 | 0 |
| h48D2 VH4:VL1 | 3 | 97 | 0 |
| h48D2 VH4:VL2 | 2.2 | 97.8 | 0 |
| h48D2 VH4:VL3 | 6.4 | 93.6 | 0 |
| h48D2 VH4:VL4 | 2 | 98 | 0 |
| h48D2 VH4:VL5 | 2.8 | 97.2 | 0 |
| h48D2 VH5:VL1 | 2 | 98 | 0 |
| h48D2 VH5:VL2 | 3.1 | 96.9 | 0 |
| h48D2 VH5:VL3 | 2.2 | 97.8 | 0 |
| h48D2 VH5:VL4 | 1.4 | 98.6 | 0 |
| h48D2 VH5:VL5 | 2.1 | 97.9 | 0 |

E) Yield

For the humanized 48D2 variants, protein concentrations were determined using absorbance measurements at 280 nm and yields were calculated for the 50 ml cultures (Table 13). VL affected the yield, with the highest yields obtained with the VL-4 variants and the lowest yields obtained with the VL-3 variants. Thus, the yield was in part dependent on the VL sequence.

TABLE 13

Yields of the humanized antibodies

| h48D2 variant | Yield (mg) |
|---|---|
| h48D2 VH1:VL1 | 7.03 |
| h48D2 VH1:VL2 | 8.17 |
| h48D2 VH1:VL3 | 2.66 |
| h48D2 VH1:VL4 | 8.2 |
| h48D2 VH1:VL5 | 8.74 |
| h48D2 VH2:VL1 | 7.03 |
| h48D2 VH2:VL2 | 9.12 |
| h48D2 VH2:VL3 | 3.00 |
| h48D2 VH2:VL4 | 7.92 |
| h48D2 VH2:VL5 | 7.41 |
| h48D2 VH3:VL1 | 7.98 |
| h48D2 VH3:VL2 | 7.41 |
| h48D2 VH3:VL3 | 2.85 |
| h48D2 VH3:VL4 | 10.45 |
| h48D2 VH3:VL5 | 5.7 |
| h48D2 VH4:VL1 | 6.08 |
| h48D2 VH4:VL2 | 7.98 |
| h48D2 VH4:VL3 | 3.04 |
| h48D2 VH4:VL4 | 8.6 |
| h48D2 VH4:VL5 | 7.03 |
| h48D2 VH5:VL1 | 7.4 |
| h48D2 VH5:VL2 | 7.22 |
| h48D2 VH5:VL3 | 3.42 |
| h48D2 VH5:VL4 | 10.07 |
| h48D2 VH5:VL5 | 7.6 |

Conclusions

The humanized antibody variants harboring the VH5 variant retained full capacity to completely inhibit signaling of IL-1α, IL-1β, IL-33, IL-36α, IL-36β and IL-36γ, with a similar potency as the chimeric 48D2 antibody. The antibody variants harboring the variants VH1-VH4 completely inhibited signaling of IL-1β and partially inhibited signaling of IL-1α and IL-33, with varying potency compared to chimeric 48D2. The affinity towards human IL1RAP was highest for the VH5 series, and within this series the variants h48D2 VH5:VL4 and h48D2 VH5:VL5 both obtained good yields and high monomeric content in SE-HPLC. Thus, further research was pursued using these variants.

Example 13: De-Immunization of Two of the Humanized 48D2 Clones

Aim

This example illustrates how sequences in h48D2 VL5 and VH5 with predicted affinity to MHC class II molecules were de-immunized by germlining.

Material and Methods

Removal of Sequences with Predicted Affinity to MHC Class II Molecules

The humanized 48D2 VL5 and VH5 sequences were created using germline antibody sequences. For these two sequences, a number of back mutations to the original rabbit sequences were introduced to ensure retained antibody structure and function (see Example 11). These introduced back mutations gave rise to sequences with predicted affinity to MHC class II molecules.

For VH5, two back mutations in framework region 2 resulted in potential immunogenicity and for VL5, six back mutations in framework region 1. For de-immunization of VH5, the back mutations were reverted to the germline sequence as single mutations and mutations of both residues (resulting in three different sequence variants). For VL5, all six back mutations were reverted to the germline sequence as one new sequence (resulting in one sequence variant).

This resulted in the following new sequences for de-immunized VH5:
h48D2 VH5.AP (alanine to proline) (SEQ ID No. 32),
h48D2 VH5.SK (serine to lysine) (SEQ ID No. 33),
h48D2.VH5.GL ("germline", both residues reverted to the germline sequence) (SEQ ID No. 34);
and in the following new sequence for de-immunized VL5;
h48D2 VL5.GL ("germline", all six residues reverted to the germline sequence) (SEQ ID No. 31).

Results and Conclusions

De-immunization was performed on VL5 and VH5. The new VL5 and VH5 were combined with the previously obtained sequences for h48D2 VL4, h48D2 VL5 and h48D2 VH5, thus creating ten new, additional variants for expression and characterization:
h48D2 VH5:VL5.GL
h48D2 VH5.AP:VL4
h48D2 VH5.AP:VL5
h48D2 VH5.AP:VL5.GL
h48D2 VH5.SK:VL4
h48D2 VH5.SK:VL5
h48D2 VH5.SK:VL5.GL
h48D2 VH5.GL:VL4
h48D2 VH5.GL:VL5
h48D2 VH5.GL:VL5.GL Example 14: Characterization of the Humanized De-Immunized 48D2 Clones Aim This example illustrates how the humanized and de-immunized 48D2 variants were expressed and characterized with the aim of finding humanized and de-immunized antibodies with retained affinity, cytokine inhibition and optimized biochemical properties.

Material and Methods

Expression, Purification, and Characterization of De-Immunized h48D2

Expression, purification, and characterization were performed as previously described for the chimeric 48D2 and the humanized variants in Examples 10 and 12.

Results

Binding of the Humanized and De-Immunized Antibody Clones to IL1RAP (ELISA)

IC50 values obtained using ELISA measurements are shown in Table 14 for the de-immunized h48D variants. Using binding ELISA, only small differences in binding can be seen between different variants. For each clone, the binding affinities towards human and cynomolgus monkey (cyno) IL1RAP were similar.

TABLE 14

Binding of the humanized and de-immunized antibody clones to IL1RAP

| Name | IC50 human IL1RAP | IC50 cyno IL1RAP |
|---|---|---|
| h48D2 VH5:VL5.GL | 29.91 | 29.78 |
| h48D2 VH5.AP:VL4 | 24.15 | 30.53 |
| h48D2 VH5.AP:VL5 | 28.07 | 35.62 |
| h48D2 VH5.AP:VL5.GL | 25.23 | 35.08 |
| h48D2 VH5.SK:VL4 | 26.26 | 33.93 |
| h48D2 VH5.SK:VL5 | 34.91 | 46.95 |
| h48D2 VH5.SK:VL5.GL | 39.95 | 58.36 |
| h48D2 VH5.GL:VL4 | 36.71 | 57.35 |
| h48D2 VH5.GL:VL5 | 34.57 | 43.95 |
| h48D2 VH5.GL:VL5.GL | 58.52 | 60.06 |

Binding of Humanized and De-Immunized Antibody Clones to IL1RAP Expressing Cells Flow cytometry analysis of IL1RAP-expressing SKMEL-5 cells stained with h48D2 VH5.GL:VL4 and h48D2 VH5.GL:VL5.GL or isotype control reveals a higher mean fluorescence intensity (MFI) for VH5.GL:VL4 and VH5.GL:VL5.GL compared to the isotype control antibody, when the antibodies are added in increasing concentrations (FIG. 16).

Inhibition of Cytokine Signaling

FIG. 17 shows the inhibitory activity of the humanized and de-immunized 48D2 antibody clones on IL-1α, IL-1β, IL-33, IL-36α, IL-36β and IL-36γ signaling in HEK cells. The antibodies were added in increasing concentrations and the depicted cytokine was added at a constant concentration. Humanized variants h48D2 VH5:VL4 and h48D2 VH5:VL5 were included as controls. The graph shows OD values at 620 nm with a high OD representing signaling downstream of the cytokine receptor. All variants exhibited retained inhibitory effect on IL-1α (A), IL-1β (B), IL-33 (C), IL-36a (D), IL-36β (E) and IL-36γ (F). IC50 values are shown in Table 15.

TABLE 15

IC50 values [nM] of the de-immunized antibody clones

| IC50 [nM] | IL-1α | IL-1β | IL-33 | IL-36α | IL-36β | IL-36γ |
|---|---|---|---|---|---|---|
| h48D2 VH5:VL5.GL | 0.236 | 0.105 | 7.833 | 0.158 | 0.165 | 0.217 |
| h48D2 VH5.AP:VL4 | 0.209 | 0.122 | 1.476 | 0.132 | 0.146 | 0.182 |

TABLE 15-continued

IC50 values [nM] of the de-immunized antibody clones

| IC50 [nM] | IL-1α | IL-1β | IL-33 | IL-36α | IL-36β | IL-36γ |
|---|---|---|---|---|---|---|
| h48D2 VH5.AP:VL5 | 0.178 | 0.098 | 1.675 | 0.149 | 0.134 | 0.191 |
| h48D2 VH5.AP:VL5.GL | 0.204 | 0.107 | 2.969 | 0.178 | 0.162 | 0.190 |
| h48D2 VH5.SK:VL4 | 0.213 | 0.099 | 5.440 | 0.143 | 0.108 | 0.170 |
| h48D2 VH5.SK:VL5 | 0.172 | 0.061 | 2.866 | 0.136 | 0.125 | 0.157 |
| h48D2 VH5.SK:VL5.GL | 0.321 | 0.117 | 3.112 | 0.204 | 0.160 | 0.245 |
| h48D2 VH5.GL:VL4 | 0.268 | 0.097 | 7.508 | 0.147 | 0.169 | 0.206 |
| h48D2 VH5.GL:VL5 | 0.214 | 0.0999 | 2.462 | 0.128 | 0.135 | 0.129 |
| h48D2 VH5.GL:VL5.GL | 0.240 | 0.130 | 3.562 | 0.174 | 0.185 | 0.244 |

In the experimental set-up used to obtain the results in FIG. 17A-F, HEK-Blue™ (IL-33/IL-1) cells were transiently transfected with the IL-36 receptor the day before. Subsequently, further evaluation of the inhibition of IL-33 and IL-36 cytokine signaling was performed for h48D2 VH5.GL:VL4 using HEK-Blue™ cells stably transfected with the IL-36 receptor. Results from this evaluation also show inhibitory effect on IL-33 (FIG. 17G) IL-36a (FIG. 17H), IL-36β (FIG. 17I) and IL-36γ (FIG. 17J). I050 values are shown in Table 16.

TABLE 16

IC50 values [nM] of h48D2 variant VH5.GL:VL4

| IC50 [nM] | IL-33 | IL-36α | IL-36β | IL-36γ |
|---|---|---|---|---|
| h48D2 VH5.GL:VL4 | 0.324 | 0.0557 | 0.161 | 0.0880 |

Affinity Measurements

KD values for affinity towards human IL1RAP are shown in Table 17 for the de-immunized h48D2 variants. Affinity was measured using bio-layer interferometry. The affinities were similar for all de-immunized variants with KD values at 1-2 nM. See also Table 4 for a direct comparison of 48D2, humanized 48D2, and de-immunized h48D2.

TABLE 17

Affinity measurements of the de-immunized h48D2 antibodies

| Name | $K_D$ (nM) |
|---|---|
| h48D2 VH5:VL5.GL | 0.752 |
| h48D2 VH5.AP:VL4 | 1.7 |
| h48D2 VH5.AP:VL5 | 1.96 |
| h48D2 VH5.AP:VL5.GL | 1.5 |
| h48D2 VH5.SK:VL4 | 2 |
| h48D2 VH5.SK:VL5 | 2.8 |
| h48D2 VH5.SK:VL5.GL | 2.28 |
| h48D2 VH5.GL:VL4 | 2.53 |
| h48D2 VH5.GL:VL5 | 1.87 |
| h48D2 VH5.GL:VL5.GL | 1.47 |

Size Heterogeneity

Size-heterogeneity was determined using size-exclusion HPLC (SE-HPLC) (Table 18). Almost all variants were highly monomeric (≥98%) with the exception of h48D2 variants with VL5.GL which contained some HMW species. For all analyzed variants, no LMW species were detected.

TABLE 18

Size heterogeneity analysis of the de-immunized h48D2 antibodies

| Name | Aggregates HMW (%) | Monomeric (%) |
|---|---|---|
| h48D2 VH5:VL5.GL | 4.6 | 95.4 |
| h48D2 VH5.AP:VL4 | 0.7 | 99.3 |
| h48D2 VH5.AP:VL5 | 1.2 | 98.8 |
| h48D2 VH5.AP:VL5.GL | 2.6 | 97.4 |
| h48D2 VH5.SK:VL4 | 0.3 | 99.7 |
| h48D2 VH5.SK:VL5 | 0.5 | 99.5 |
| h48D2 VH5.SK:VL5.GL | 3.8 | 96.2 |
| h48D2 VH5.GL:VL4 | 0.6 | 99.4 |
| h48D2 VH5.GL:VL5 | 1.3 | 98.7 |
| h48D2 VH5.GL:VL5.GL | 4.1 | 95.9 |

Yield

For the de-immunized h48D2 variants, protein concentrations were determined using absorbance measurements at 280 nm and yields were calculated for the 50 ml cultures (Table 19). Antibody variants harboring the VL variant VL5.GL exhibited lower obtainable yields compared to the other variants.

TABLE 19

Yields of de-immunized h48D2 antibodies

| Name | Yield (mg) |
|---|---|
| h48D2 VH5:VL5.GL | 1.5 |
| h48D2 VH5.AP:VL4 | 7.8 |
| h48D2 VH5.AP:VL5 | 7.0 |
| h48D2 VH5.AP:VL5.GL | 1.8 |
| h48D2 VH5.SK:VL4 | 6.2 |
| h48D2 VH5.SK:VL5 | 3.8 |
| h48D2 VH5.SK:VL5.GL | 1.5 |
| h48D2 VH5.GL:VL4 | 10.1 |
| h48D2 VH5.GL:VL5 | 10.0 |
| h48D2 VH5.GL:VL5.GL | 1.7 |

Cross Reactivity

FIG. 18 shows cross reactivity of h48D2 VH5.GL:VL4 and h48D2 VH5.GL:VL5.GL to IL1RAP from different species. The antibody is added in increasing concentrations and absorbance at 405 nm is used to detect binding to IL1RAP. As for chimeric 48D2, the humanized and de-immunized variants h48D2 VH5.GL:VL4 and h48D2 VH5.GL:VL5.GL were cross reactive to IL1RAP from cynomolgus monkey (cyno) and pig, but have no cross reactivity to IL1RAP from mouse, rat, rabbit or dog (FIG. 18 and Table 20).

TABLE 20

Cross reactivity of h48D2 VH5.GL:VL4 and VH5 GL.VL5.GL

| | hIL1 RAP (human) | mIL1 RAP (mouse) | rnIL1 RAP (rat) | mfIL1 RAP (cyno) | ocIL1 RAP (rabbit) | clIL1 RAP (dog) | ssIL1 RAP (pig) |
|---|---|---|---|---|---|---|---|
| h48D2 VH5.GL: VL4 | + | − | − | + | − | − | + |
| h48D2 VH5.GL: VL5.GL | + | − | − | + | − | − | + |

Conclusions

All de-immunized variants displayed high affinity with $K_D$ values at 1-3 nM and retained biological function. The variant h48D2 VH5.GL:VL4 excelled with good yield and high monomeric content in SE-HPLC.

Example 15: ADCC Effect of Chimeric 48D2

Aim

This example aimed to investigate the antibody-dependent cellular cytotoxicity (ADCC) effect of chimeric 48D2 when expressed in hIgG1-wild type (WT) or an effector-function silent IgG1-LALA format.

Material and Methods

The malignant melanoma cell line SKMEL-5, expressing IL1RAP on the cell surface, was used as a target for an in vitro ADCC assay. Target cells were seeded into a 96-well plate at a density of 10000 cells per well. Subsequently, 48D2-WT, 48D2-LALA or isotype control antibodies were added to the wells in different concentrations and incubated for 30 min before 100000 NK effector cells were added to each well. NK cells were extracted from Leukocyte Concentrates by using an NK cell negative cell isolation kit according to manufacturer's instructions (Miltenyi Biotech, Bergisch Gladbach, Germany). Non-specific human IgG1-WT and IgG1-LALA antibodies were used as controls in the experiment. The degree of cell death was assessed by detection of DAPI positive cells using a FACS LSR Fortessa flow cytometer (BD) after 18 hours in culture.

Results

The in vitro ADCC assay shows that chimeric 48D2 in hIgG1 format directs NK cells to kill SKMEL-5 cells in an antibody-specific, dose-dependent manner (FIG. 19). There was no increase in the percentage of dead SKMEL-5 cells after treatment with chimeric 48D2 expressed in a hIgG1-LALA format, compared to isotype controls and untreated cells (untreated cells correspond to 0 ng/ml antibody).

The effect was shown to be dose-dependent. When chimeric 48D2 is expressed in a hIgG1-LALA format, the ADCC effect disappears. It can be assumed that antibody variants of the 48D2 antibody (such as the described antibodies in the Examples above, e.g. humanized, or humanized and de-immunized antibody variants) can have similar effects when expressed in a hIgG1-WT or hIgG1 LALA format. Indeed, Example 19 below demonstrates that antibody variant VH5.GL:VL4 in a hIgG1 LALA format does not induce Fc-mediated immune activation in the blood loop assay.

Conclusions

The experiment shows that 48D2 can direct NK cells to specific cell killing of a melanoma cell line, expressing IL1RAP on the surface, and that the cytotoxic effect induced by 48D2 is dose-dependent. Moreover, the ADCC effect can be abolished by expressing 48D2 in an effector function silent hIgG1-LALA format.

Example 16: Inhibition of Cytokine Signaling in Human Fibroblasts by Chimeric 48D2

Aim

The aim of this example is was investigate the inhibitory activities of chimeric 48D2 on IL-1α, IL-1β, IL-33, IL-36α, IL-36β and IL-36γ-stimulated IL-6 gene expression in human fibroblasts in vitro.

Material and Methods

Fibroblasts from healthy human skin were commercially acquired and grown in complete fibroblast growth media. 75000 cells were seeded per well in a 24-well plate. 80% confluent cells were serum starved in fibroblast media containing only 1% FBS overnight. Media was changed to new fibroblast media with 1% FBS and no growth factors and 20 ug/ml chimeric 48D2 was added to the wells 1 hour before stimulating with different concentrations of the cytokines (as depicted in FIG. 20). Cells were stimulated for 24 hours after which RNA was isolated according to the manufacturer's instructions. IL-6 mRNA levels were analyzed using SYBR Green and data were analyzed using the ΔΔCT method and shown as fold change $2^{-\Delta\Delta CT}$ compared to the untreated control.

Results

IL-1α, IL-1β, IL-36α, IL-36β and IL-36γ induced IL-6 gene expression in dermal fibroblasts in a dose-dependent manner (FIG. 20). In this experiment, chimeric 48D2 inhibited the increase in gene expression down to levels comparable with the unstimulated control. IL-33 had no effect on IL-6 expression in these cells (data not shown). It can be assumed that antibody variants of the 48D2 antibody (such as the described antibodies in the Examples above, e.g. humanized, or humanized and de-immunized antibody variants) can have similar effects. Indeed, Example 17 demonstrates that antibody variant VH5.GL:VL4 inhibits IL-1β signaling in human whole blood.

Conclusions

48D2 can block the cytokine-induced increase in IL-6 gene expression in human fibroblasts.

Example 17: Inhibition of IL-1β Signaling in Human Whole Blood by 48D2 Variant VH5.GL:VL4

Aim

The aim of this study is to investigate how blockade of IL-1α/β, IL-33 and IL-36α/β/γ signaling, by pre-incubation of human whole blood with the 48D2 variant VH5.GL:VL4, affects the release of various downstream cytokines and chemokines in response to stimulation with IL-1β.

Material and Methods

Human blood was collected from two different donors in Heparin tubes. The blood was transferred to wells of a 96-well plate and incubated with 150 μg/ml VH5.GL:VL4 at 37° C. and 5% $CO_2$ for 30 min during agitation. IL-1β or LPS were subsequently added to the wells, both at 1 ng/ml, and the blood incubated for 20 hrs at 37° C. and 5% $CO_2$ for 30 min during agitation. Wells where the blood samples were incubated with only formulation buffer were included as negative controls (Ctrl). The plate was centrifuged at 1500 rpm to separate plasma from blood cells. The plasma was diluted 1:2 and levels of 71 different cytokines and chemokines (6CKine, BCA-1, CTACK, EGF, ENA-78, Eotaxin, Eotaxin-2, Eotaxin-3, FGF-2, Flt3L, Fractalkine, G-CSF, GM-CSF, GROα/CXCL1, I-309, IFNα2, IFNγ, IL-1α, IL-1β, IL-1RA, IL-2, IL-3, IL-4, IL-5, IL-6, IL-7, IL-8, IL-9, IL-10, IL-12p40, IL-12p70, IL-13, IL-15, IL-16, IL-17A, IL-17E/IL-25, IL-17F, IL-18, IL-20, IL-21, IL-22, IL-23, IL-27, IL-28, IL-33, IP-10, LIF, MCP-1, MCP-2, MCP-3, MCP-4, M-CSF, MDC, MIG, MIP-1α, MIP-1β, MIP-1δ, PDGF-AA, PDGF-AB/BB, RANTES, sCD40L, SCF, SDF-1α+β, TARC, TGFα, TNFα, TNFβ, TPO, TRAIL, TSLP, VEGF-A) were measured in the plasma samples by use of the Human Cytokine/Chemokine 71-Plex Discovery Assay Array (Eve Technologies; HD71) according to the manufacturer's instructions. Results for four of these, G-CSF, GROα/CXCL1, IL-17A and TNF-α, are discussed below.

Results

Blockade of IL-1α/β, IL-33 and IL-36α/β/γ signaling by VH5.GL:VL4 decreased the release of G-CSF, GROα/ CXCL1, IL-17A and TNF-α in human whole blood in response to stimulation with IL-1β (FIG. 21A-D). A similar effect was observed when the blood was stimulated with LPS, as VH5.GL:VL4 notably decreased the levels of G-CSF, GROα/CXCL1 and TNF-α and slightly decreased level of IL-17A (FIG. 21A-D).

Conclusions

IL1RAP blockade by VH5.GL:VL4 impacts downstream effects of IL-1R signaling mediated by IL-1β and LPS such that the release of multiple cytokines and chemokines is reduced.

Example 18: Inhibition of IL-1β Signaling in a Blood-Loop System by 48D2 Variant VH5.GL:VL4

Aim

The aim of this study is to investigate how blockade of IL-1α/β, IL-33 and IL-36α/β/γ signaling, by pre-incubation of human whole blood with the 48D2 variant VH5.GL:VL4, affects the release of IL-6 and IL-8 in response to stimulation with IL-1β in a blood-loop system, which mimics the human blood circulation.

Material and Methods

Fresh whole blood was collected from ten healthy donors and low amounts of soluble heparin was added. The blood was immediately transferred to pre-coated plastic tubes to form the loops of a blood-loop system. The loops were placed on a rotating wheel and samples were run in parallel. VH5.GL:VL4 was administered to the samples at 32 μg/ml and IL-1β at 1 ng/ml was added 15 mins later. PBS was used for control. Each loop was sampled following 4 hrs and EDTA was added at a concentration of 10 mM to each sample to stop reactions at sampling time points. Plasma samples were prepared by centrifugation, aliquoted and stored at ≤−60° C. until further cytokine analysis. Cytokines IL-6 and IL-8 were measured using the MULTI-ARRAY® technology from Meso Scale Discovery. All samples were diluted 1:4 and samples were run in duplicates according to the manufacturer's instructions.

Results

Blockade of IL-1α/β, IL-33 and IL-36α/β/γ signaling by VH5.GL:VL4 decreased the release of IL-6 and IL-8 in human whole blood circulating in the blood-loop system, in response to stimulation with IL-1β (FIG. 22A-B).

Conclusions

In a blood-loop system, which mimics human blood circulation, IL1RAP blockade by VH5.GL:VL4 impacts downstream effects of IL-1R signaling mediated by IL-1β such that the release of the cytokines IL-6 and IL-8 is reduced.

Example 19: Internalization of 48D2 Variant VH5.GL:VL4 by IL1RAP-Expressing Cells Aim The aim of this experiment is to investigate membrane binding and potential internalization of fluorescently-labelled 48D2 variant VH5.GL:VL4 by IL1RAP-expressing cells.

Material and Methods

WT and IL1RAP KO SKMEL human melanoma cells were grown to 60-80% confluence and subsequently transferred to 8-well Ibidi-treat microscope chamber slides at 12500 cells per well. Cells were incubated with 3 μg/ml AlexaFluor647 (AF647)-conjugated VH5.GL:VL4 at 37° C. for 1, 2 or 4 hrs. Control cells were incubated with AF647-conjugated isotype control antibody. Alternatively, WT SKMEL cells incubated for 2 hrs with A647-conjugated VH5.GL:VL4 were additionally incubated with 5 µg/ml rabbit anti-EEA1 antibody and 10 µg/ml mouse anti-Lamp1 antibody for 3 hrs to stain for endosomal and lysosomal markers, respectively. The cells were washed and incubated with AlexaFluor488 (AF488)-conjugated anti-rabbit antibody and rhodamine (RX)-conjugated anti-mouse antibody for 30 min. Following incubation, cells were washed and fixed with 2% paraformaldehyde. Cells were again washed and subsequently labelled with DAPI to stain cell nuclei. A Zeiss LSM800 confocal microscope was used to analyze the cells with a 63× oil immersion lens. Detection level was set from control cells that had not been incubated with A647-conjugated VH5.GL:VL4, or anti-EEA1 or anti-Lamp1, and the same settings used throughout the analyses. Interactive visual analyses were performed of scanned 500 nm optical sections through the cells, and representative images captured.

Results

Initial membrane binding and cellular internalization of A647-conjugated VH5.GL:VL4 was demonstrated for IL1RAP-expressing WT SKMEL cells, detectable after 1 hr of incubation (FIG. 23; top left image; arrows indicate membrane binding and internalization). Maximum internalization was indicated at around 2 hrs of incubation (FIG. 23; top middle image). Lack of binding and internalization of A647-conjugated VH5.GL:VL4 by IL1RAP KO cells indicates that the effects observed in WT cells are mediated by the interaction with IL1RAP (FIG. 23; middle row; only staining of nuclei by DAPI observed). Moreover, no binding or internalization was observed for isotype control antibody to WT cells (FIG. 23; bottom row; only staining of nuclei by DAPI observed). Additional co-staining for EEA1 and Lamp1, markers for endosomes and lysosomes, respectively, shows an overlap with the signal for A647-labelled VH5.GL:VL4 (FIG. 24). This indicates that VH5.GL:VL4 is localized to these compartments upon internalization.

Conclusions

VH5.GL:VL4 is internalized upon binding to IL1RAP-expressing SKMEL cells. This internalization is dependent on the binding of VH5.GL:VL4 to IL1RAP.

Example 20: Fc-Mediated Immune Activation in a Blood-Loop System by 48D2 Variant VH5.GL:VL4

Aim

The aim of this study is to investigate if, and to what extent, the 48D2 variant VH5.GL:VL4, expressed in an effector function silent hIgG1-LALA format, can induce immune activation in the absence of other stimuli in a blood-loop system, which mimics the human blood circulation. Immune activation will be evaluated by release of proinflammatory cytokines and complement activation in circulating human whole blood.

Material and Methods

Fresh whole blood was collected from ten healthy donors and low amounts of soluble heparin was added to allow for analysis of drug-related effects on complement system. The blood was immediately transferred to pre-coated plastic tubes to form the loops of a blood-loop system, followed by addition of VH5.GL:VL4 at 0.0125 mg/ml, 0.125 mg/ml or 1.25 mg/ml. Samples to which the anti-CD52 antibody alemtuzumab was added at 3 µg/ml, or formulation buffer only (Vehicle), were used as positive and negative control, respectively. The loops were placed on a rotating wheel and samples were run in parallel. Each loop was sampled following 15 min and 4 hrs and EDTA was added at a concentration of 10 mM to each sample to stop reactions at sampling time points. The samples collected at 15 min were processed to plasma for complement analysis, while blood samples collected at 4 hrs were processed to plasma for cytokine analysis. Plasma samples were prepared by centrifugation, aliquoted and stored at ≤−60° C. until analysis.

Cytokines IFNγ, IL-6, IL-8, TNFα were measured using the MULTI-ARRAY® technology from Meso Scale Discovery. All samples were diluted 1:4 and samples were run in duplicates according to the manufacturer's instructions.

Complement activation was analyzed by measurement of the complement split products C3a and C5a using ELISA kit (RayBio® Human C3a ELISA Kit and RayBio® Human C5a ELISA Kit). Plasma samples were diluted 1:500 with sample diluent for C3a analysis and 1:50 with sample diluent for C5a analysis and run in duplicates according to the manufacturer's instructions.

Results

VH5.GL:VL4 displayed no effect on release of IFNγ, IL-6, IL-8 or TNFα (FIG. 25A-D), or on complement activation as measured by levels of C3a and C5a (FIG. 26A-B), in the blood-loop system, at any of the three concentrations evaluated. In contrast, the anti-CD52 antibody alemtuzumab induced cytokine release as well as complement activation.

Conclusions

VH5.GL:VL4 with an effector function silent Fc region does not induce Fc-mediated immune activation.

Example 21: Initial Safety and Pharmaco- and Toxicokinetic Properties of Intravenously Dosed 48D2 Variant VH5.GL:VL4

Aim

The aim of this study is to determine the pharmacokinetics and potential toxicity of VH5.GL:VL4, administered intravenously as a single dose to male and female cynomolgus monkeys at three escalating dose levels, up to maximum tolerated dose.

Material and Methods

VH5.GL:VL4 was administered intravenously via peripheral veins at 5, 20 or 50 mg/kg as a single dose (bolus) to one male and one female cynomolgus monkey for each dose level evaluated. Animals were observed daily for two weeks after administration for mortality, clinical signs and food consumption. Hematology and serum chemistry were performed pre-test and on day 8 of the study. Body weight was recorded pre-test and on day 8 and 15. Samplings for bioanalytical and toxicokinetic evaluation were collected via the femoral vein (at least 0.6 ml blood for each sampling) pre-dose and at 0.083, 1, 3, 6, 24, 48, 96, 168, 264 and 336 hrs after administration. Blood samples were allowed to clot in tubes for serum separation for 30 min at room temperature. The clot was spun down by centrifugation at 1200 g for 10 min at 4° C. The resultant serum was stored at −80° C. until analysis.

Biotinylated human IL1RAP was added to a Meso Scale Discovery (MSD) plate pre-coated with streptavidin and incubated at room temperature. After washing, serum samples were added to the plate followed by incubation at room temperature. The plate was washed and anti-human IgG conjugated to an electrochemiluminescent label (MSD SULFO-TAG) was added to the plate. After a final incubation and wash, read buffer was added. The SULFO-TAG emits light when a voltage in the MSD instrument is applied to the plate electrodes. The instrument measures the intensity of emitted light to provide a quantitative measure of VH5.GL:VL4 in the samples. Serum toxicokinetic analyses were performed according to standard noncompartmental approach using WinNonlin package (v. 8.1, Pharsight Inc, Certara Company, USA).

Results

No abnormal clinical signs and no relevant toxicological changes were present in body weights and at clinical pathology investigations. No toxicologically relevant changes in serum chemistry and hematology were observed.

In the dose range investigated, dose-normalized maximum concentrations of the compound were similar. At each dose level, male and female serum toxicokinetic parameters of VH5.GL:VL4 were similar. Terminal half-life of VH5.GL:VL4 was, on average, 98 hrs (4 days) after the 5 mg/kg dose; after the 20 mg/kg and 50 mg/kg doses the parameter, of the order of 220 hrs (9 days), was two-fold higher than that at 5 mg/kg (Table 21). VH5.GL:VL4 was found to decline in a bi-exponential manner (FIG. 27). After all doses, serum clearance of VH5.GL:VL4 was low and the volumes of distribution of the terminal phase was of the same order of magnitude as monkey total body water (~700 ml/kg).

Sera were analyzed by MSD as described in Example 21. Serum pharmacokinetic analyses for VH5.GL:VL4 were performed using Phoenix-WinNonlin package (Certara Company, USA).

Results

After single intravenous administration of 10 mg/kg of VH5.GL:VL4 to female cynomolgus monkeys, serum concentrations of VH5.GL:VL4 declined with a terminal half-life on average of 86.9 hrs (FIG. 28 and Table 22). Both serum clearance of VH5.GL:VL4 and volume of distributions were low. The volume of distributions accounted for approximately a tenth of the total body water in monkey (Table 22). After subcutaneous dosing of 10 mg/kg dose of VH5.GL:VL4, the absorption of the compound was slow, resulting in a $T_{max}$ of 48-96 hrs post-dosing (FIG. 28 and Table 23). After the $C_{max}$ was reached, serum concentrations of the compound decreased with a mean terminal half-life on average of 112 hrs (Table 23). The subcutaneous bioavailability was high, 93%.

TABLE 21

Toxicokinetic parameters of VH5.GL:VL4 after single intravenous dosing of 5, 20 and 50 mg/kg to cynomolgus monkeys

| Dose | $C_0$ (μg/ml) | | $AUC_{last}$ (μg*h/ml) | | $t_{1/2z}$ (h) | | $AUC_\infty$ (μg*h/ml) | | CL (ml/h/kg) | |
|---|---|---|---|---|---|---|---|---|---|---|
| (mg/kg) | Mean | SD | Mean | SD | Mean | SD | Mean | SD | Mean | SD |
| 5 | 108 | 10.1 | 9780 | 1480 | 97.7 | 41.5 | 10900 | 2780 | 0.476 | 0.122 |
| 20 | 338 | 107 | 40600 | 8980 | 212 | 13.1 | 60600 | 11700 | 0.336 | 0.0651 |
| 50 | 985 | 54.9 | 129000 | 7530 | 226 | N = 1 | 204000 | N = 1 | 0.245 | N = 1 |

Conclusions

After single intravenous dosing of VH5.GL:VL4 to cynomolgus monkeys, the pharmacokinetics of the antibody were characterized by low clearance, low volume of distribution and long half-life. In the dose range investigated, whilst maximum concentrations of the compound increased in direct proportion with the dose, $AUC_{last}$ at 50 mg/kg showed a trend to increase more than in direct proportion with the dose.

Example 22: Pharmacokinetic Properties of Subcutaneously Dosed 48D2 Variant VH5.GL:VL4

Aim

The aim of this study is to determine the pharmacokinetics and bioavailability of VH5.GL:VL4 after single subcutaneous administration of the antibody to female cynomolgus monkeys.

Material and Methods

VH5.GL:VL4 was administered intravenously or subcutaneously in the dorsal area at 10 mg/kg, as a single dose to two female cynomolgus monkeys per route of administration. Samplings for pharmacokinetic evaluation were collected (at least 0.6 ml blood for each sampling) pre-dose and at 1, 3, 6, 24, 48, 96, 168, 264, 336, 480 and 672 hrs following administration. Additionally, a first dose was collected at 0.083 hrs following intravenous administration and at 0.5 hrs following subcutaneous administration. Blood samples were allowed to clot in tubes for serum separation for 30 min at room temperature. The clot was spun down by centrifugation at 1200 g for 10 min at 4° C. The resultant serum was stored at −80° C. until analysis.

TABLE 22

Pharmacokinetic parameters of VH5.GL:VL4 after single intravenous dosing of 10 mg/kg to cynomolgus monkeys

| | $C_0$ (ng/ml) | $AUC\infty$ (h*ng/ml) | $V_{SS}$ (ml/kg) | $V_z$ (ml/kg) | CL (ml/h/kg) | $t_{1/2z}$ (h) |
|---|---|---|---|---|---|---|
| N | 2 | 2 | 2 | 2 | 2 | 2 |
| Mean | 186000 | 22600000 | 68.7 | 55.6 | 0.456 | 86.9 |
| SD | 1290 | 5480000 | 0.544 | 0.712 | 0.111 | 20.0 |
| CV % | 0.696 | 24.3 | 0.792 | 1.28 | 24.3 | 23.0 |

TABLE 23

Pharmacokinetic parameters of VH5.GL:VL4 after single subcutaneous dosing of 10 mg/kg to cynomolgus monkeys

| | $C_{max}$ (ng/ml) | $T_{max}$ (h) | $AUC\infty$ (h*ng/ml) | $V_z/F$ (ml/kg) | CL/F (ml/h/kg) | $t_{1/2z}$ (h) |
|---|---|---|---|---|---|---|
| N | 2 | 2 | 2 | 2 | 2 | 2 |
| Mean | 66300 | 72 | 21100000 | 76.2 | 0.475 | 112 |
| SD | 4630 | 33.9 | 1450000 | 13.1 | 0.0328 | 26.9 |
| CV % | 6.98 | 47.1 | 6.90 | 17.2 | 6.90 | 24 |

Conclusions

After single intravenous dosing of 10 mg/kg VH5.GL:VL4 to cynomolgus monkeys, the pharmacokinetics of the compound were characterized by low clearance and volume of distribution and long half-life. After subcutaneous dosing of 10 mg/kg VH5.GL:VL4, the absorption of the compound was slow. After the $C_{max}$ was reached, serum concentrations of the compound decreased with a mean terminal half-life comparable to that after intravenous administration. The subcutaneous bioavailability was high.

Sequences

CDR Sequences (Defined According to IMGT)

SEQ ID NO: 1
Variable light chain complementarity-determining region 1 (CDR-L1)
ESISTA Variable light chain complementarity-determining region 2 (CDR-L2)
KAS SEQ ID NO: 3
Variable light chain complementarity-determining region 3 (CDR-L3)
QQGFSSGNVHNA SEQ ID NO: 4
Variable heavy chain complementarity-determining region 1 (CDR-H1)
GPSLSHFD SEQ ID NO: 5
Variable heavy chain complementarity-determining region 2 (CDR-H2)
ISPGVST SEQ ID NO: 6
Variable heavy chain complementarity-determining region 3 (CDR-H3)
ARGGVGSSWKAFDL CDR Sequences (Defined According to Kabat)

SEQ ID NO: 7
Variable light chain complementarity-determining region 1 (CDR-L1)
QASESISTALA SEQ ID NO: 8
Variable light chain complementarity-determining region 2 (CDR-L2)
KASTLPS SEQ ID NO: 9
Variable light chain complementarity-determining region 3 (CDR-L3)
QQGFSSGNVHNA SEQ ID NO: 10
Variable heavy chain complementarity-determining region 1 (CDR-H1)
HFDIT SEQ ID NO: 11
Variable heavy chain complementarity-determining region 2 (CDR-H2)
TISPGVSTYYASWAKS SEQ ID NO: 12
Variable heavy chain complementarity-determining region 3 (CDR-H3)
GGVGSSWKAFDL CDR Sequences (Defined According to a Combination of IMGT and Kabat)

SEQ ID NO: 13
Variable light chain complementarity-determining region 1 (CDR-L1)
QASESISTALA SEQ ID NO: 14
Variable light chain complementarity-determining region 2 (CDR-L2)
KASTLPS SEQ ID NO: 15
Variable light chain complementarity-determining region 3 (CDR-L3)
QQGFSSGNVHNA SEQ ID NO: 16
Variable heavy chain complementarity-determining region 1 (CDR-H1)
GPSLSHFDIT SEQ ID NO: 17
Variable heavy chain complementarity-determining region 2 (CDR-H2)
TISPGVSTYYASWAKS SEQ ID NO: 18
Variable heavy chain complementarity-determining region 3 (CDR-H3)
ARGGVGSSWKAFDL It is important to note that within each CDR-defining category (i) Kabat, ii) IMGT or iii) combination of IMGT and Kabat), the CDR sequences (CDR-L1, CDR-L2, CDR-L3, CDR-H1, CDR-H2 or CDR-H3, respectively) are the same for the chimeric antibody 48D2 and all optimized antibody variants thereof, such as humanized antibody variants or humanized/de-immunized antibody variants (see indicated in the sequences of the light chain variable regions and heavy chain variable regions below.

CDR residues highlighted in bold were identified using the IMGT numbering system, CDR residues highlighted by underlining were identified using the Kabat numbering system CDR residues defined by a combination of the IMGT and the Kabat numbering system (combination of bold and underlined sequences)

Variable Chain Regions as in Chimeric 48D2 Antibody (Non-Humanized, Non-Deimmunized) (e.g. In Examples 9 and 10)

```
                                            SEQ ID NO: 19
Light chain variable region (non-humanized, non-
deimmunized)
APVLTQTPASVEVAVGGTVTIKCQASESISTALAWYQQKPGQPPKLLIY

KASTLPSGVSSRFKGSGSGTEFALTISDLECDDAATYYCQQGFSSGNVH

NAFGGGTEVVVK
```

```
                                            SEQ ID NO: 20
Heavy chain variable region (non-humanized, non-
deimmunized)
QEQLEESGGGLVKPGGSLTLTCTVSGPSLSHFDITWVRQAPGSGLEWIG

TISPGVSTYYASWAKSRSTITSNTNLNTVTLKMTSLTAADTATYFCARG

GVGSSWKAFDLWGPGTLVTISS
```

Humanized Variable Chain Regions (e.g. In Examples 11 and 12)

```
                                            SEQ ID NO: 21
Humanized light chain variable region VL1
DIVMTQSPSSLSASVGDRVTITCQASESISTALAWYQQKPGKAPKLLIY

KASTLPSGVPSRFSGSGSGTDFTLTISSLQPEDFATYYCQQGFSSGNVH

NAFGGGTKVVIK
```

```
                                            SEQ ID NO: 22
Humanized light chain variable region VL2
QIVLTQSPATLSASVGDRVTITCQASESISTALAWYQQKPGKAPKLLIY

KASTLPSGVPSRFSGSGSGTEFTLTISSLQPDDSATYYCQQGFSSGNVH

NAFGQGTKLEIK
```

```
                                                     SEQ ID NO: 23
Humanized light chain variable region VL3
DILLTQTPSVVSASVGDRVTITCQASESISTALAWYQQKPGQAPRLLIY

KASTLPSGVPSRFRGSGSGTDFTLTITSLQPEDFATYYCQQGFSSGNVH

NAFGGGTRLEIK
                                                     SEQ ID NO: 24
Humanized light chain variable region VL4
ELVMTQSPSSVSASVGDRVTITCQASESISTALAWYQQKPGKAPKLLIY

KASTLPSGVPSRFSGSGSGTDFTLTINSLQPEDFATYYCQQGFSSGNVH

NAFGGGTKVEIK
                                                     SEQ ID NO: 25
Humanized light chain variable region VL5
APVLTQSPATLEASVGDRVTITCQASESISTALAWYQQKPGQPPKLLIY

KASTLPSGVPSRFSGSGSGTEFTLTISDLESDDAATYYCQQGFSSGNVH

NAFGGGTEVVVK
                                                     SEQ ID NO: 26
Humanized heavy chain variable region VH1
EVQLEESGGGLVKPGGSLRLSCAASGPSLSHFDITWVRQAPGKGLEWVS

TISPGVSTYYASWAKSRFTISRDNSKNTLYLQMNSLRAEDTAVYYCARG

GVGSSWKAFDLWGRGTLVTVSS
                                                     SEQ ID NO: 27
Humanized heavy chain variable region VH2
EVQLVESGGALVQPGGSLRLSCIVSGPSLSHFDITWFRQAPGKGLEWVA

TISPGVSTYYASWAKSRFTISTDTSKNTLFLQMDSLRAEDTAVYYCARG

GVGSSWKAFDLWGPGTLVTVSS
                                                     SEQ ID NO: 28
Humanized heavy chain variable region VH3
EVQLLESGGGLVLPGGSLRLSCAASGPSLSHFDITWVRQAPGKGLEWVS

TISPGVSTYYASWAKSRFTISRDNSKNTLYLQMSSLRAEDTAVYYCARG

GVGSSWKAFDLWGLGTTVTVSS
                                                     SEQ ID NO: 29
Humanized heavy chain variable region VH4
QVQLQESGPGLVKPSETLSLTCTVSGPSLSHFDITWIRQPPGKGLEWIG

TISPGVSTYYASWAKSRFTISVDTSKNQFSLKLTSVTAADTATYYCARG

GVGSSWKAFDLWGPGTLVTVSS
                                                     SEQ ID NO: 30
Humanized heavy chain variable region VH5
QEQLEESGGGLVKPGGTLSLTCTVSGPSLSHFDITWIRQAPGSGLEWIG

TISPGVSTYYASWAKSRVTISVDTSLNTVSLKLSSVTAADTATYFCARG

GVGSSWKAFDLWGPGTLVTISS
```

Humanized and De-Immunized Variable Chain Regions (e.g. in Examples 13 and 14)

Amino-acid residues in bold and italics indicate the residues that are reverted during the de-immunization process.

```
                                                     SEQ ID NO: 31
Humanized and de-immunized VL5.GL
DIQMTQSPSTLSASVGDRVTITCQASESISTALAWYQQKPGQPPKLLIY

KASTLPSGVPSRFSGSGSGTEFTLTISDLESDDAATYYCQQGFSSGNVH

NAFGGGTEVVVK
                                                     SEQ ID NO: 32
Humanized and de-immunized VH5.AP
QEQLEESGGGLVKPGGTLSLTCTVSGPSLSHFDITWIRQPPGSGLEWIG

TISPGVSTYYASWAKSRVTISVDTSLNTVSLKLSSVTAADTATYFCARG

GVGSSWKAFDLWGPGTLVTISS
                                                     SEQ ID NO: 33
Humanized and de-immunized VH5.SK
QEQLEESGGGLVKPGGTLSLTCTVSGPSLSHFDITWWIRQAPGKGLEWIG

TISPGVSTYYASWAKSRVTISVDTSLNTVSLKLSSVTAADTATYFCARGG

VGSSWKAFDLWGPGTLVTISS
                                                     SEQ ID NO: 34
Humanized and de-immunized VH5.GL
QEQLEESGGGLVKPGGTLSLTCTVSGPSLSHFDITWWIRQPPGKGLEWIG

TISPGVSTYYASWAKSRVTISVDTSLNTVSLKLSSVTAADTATYFCARGG

VGSSWKAFDLWGPGTLVTISS
```

Constant Regions

```
                                                     SEQ ID NO: 35
Immunoglobulin kappa constant light chain (light
chain constant region)(Km3 allotype)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC
```

Bold and underlined amino-acid residues indicate the residues that are altered when the LALA-mutation is introduced.

```
                                                     SEQ ID NO: 36
Immunoglobulin IgG1 constant heavy chain (heavy
chain constant region)(za allotype)
ASTKGPSVFPLAPSSKSISGGTAALGCLVKDYFPEPVTVSWNSGALISGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
                                                      SEQ ID NO: 2
Immunoglobulin IgG1 constant heavy chain (heavy
chain constant region)(za allotype) with 'LALA'
mutation
ASTKGPSVFPLAPSSKSISGGTAALGCLVKDYFPEPVTVSWNSGALISGV

HTFPAVLQSSGLYSLSSVVTVPSSSLGTQTYICNVNHKPSNTKVDKKVEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG
```

Human IL1RAP

SEQ ID NO: 37
Full-length human IL1RAP
MTLLWCVVSLYFYGILQSDASERCDDWGLDTMRQIQVFEDEPARIKCPLF
EHFLKFNYSTAHSAGLTLIWYWTRQDRDLEEPINFRLPENRISKEKDVLW
FRPTLLNDTGNYTCMLRNTTYCSKVAFPLEVVQKDSCFNSPMKLPVHKLY
IEYGIQRITCPNVDGYFPSSVKPTITWYMGCYKIQNFNNVIPEGMNLSFL
IALISNNGNYTCVVTYPENGRTFHLTRTLTVKVVGSPKNAVPPVIHSPND
HVVYEKEPGEELLIPCTVYFSFLMDSRNEVWWTIDGKKPDDITIDVTINE
SISHSRTEDETRTQILSIKKVTSEDLKRSYVCHARSAKGEVAKAAKVKQK
GNRCGQ SEQ ID NO: 38
Domain 2 of IL1RAP
KDSCFNSPMKLPVHKLYIEYGIQRITCPNVDGYFPSSVKPTITWYMGCYK
IQNFNNVIPEGMNLSFLIALISNNGNYTCVVTYPENGRTFHLTRTLTVKV
V SEQ ID NO: 39
H2 region of domain 2 of human IL1RAP
TITWYMGCYKIQNFNNVI

The invention claimed is:

1. An antibody or antigen-binding fragment thereof with binding specificity for interleukin-1 receptor accessory protein (IL1RAP) comprising
(a)(i) a CDR-L1 comprising the amino acid sequence of ESISTA (SEQ ID NO: 1); a CDR-L2 comprising the amino acid sequence of KAS; and a CDR-L3 comprising the amino acid sequence of QQGFSSGNVHNA (SEQ ID NO: 3); and
(ii) a CDR-H1 comprising the amino acid sequence of GPSLSHFD (SEQ ID NO: 4); a CDR-H2 comprising the amino acid sequence of ISPGVST (SEQ ID NO: 5); and a CDR-H3 comprising the amino acid sequence of ARGGVGSSWKAFDL (SEQ ID NO: 6); or
(b)(i) a CDR-L1 comprising the amino acid sequence of QASESISTALA (SEQ ID NO: 7); a CDR-L2 comprising the amino acid sequence of KASTLPS (SEQ ID NO: 8); and a CDR-L3 comprising the amino acid sequence of QQGFSSGNVHNA (SEQ ID NO: 9); and
(ii) a CDR-H1 comprising the amino acid sequence of HFDIT (SEQ ID NO: 10); a CDR-H2 comprising the amino acid sequence of TISPGVSTYYASWAKS (SEQ ID NO: 11); and a CDR-H3 comprising the amino acid sequence of GGVGSSWKAFDL (SEQ ID NO: 12); or
(c)(i) a CDR-L1 comprising the amino acid sequence of QASESISTALA (SEQ ID NO: 13); a CDR-L2 comprising the amino acid sequence of KASTLPS (SEQ ID NO: 14); and a CDR-L3 comprising the amino acid sequence of QQGFSSGNVHNA (SEQ ID NO: 15); and
(ii) a CDR-H1 comprising the amino acid sequence of GPSLSHFDIT (SEQ ID NO: 16); a CDR-H2 comprising the amino acid sequence of TISPGVSTYYASWAKS (SEQ ID NO: 17); and a CDR-H3 comprising the amino acid sequence of ARGGVGSSWKAFDL (SEQ ID NO: 18).

2. The antibody or antigen-binding fragment thereof of claim 1, comprising
a) a light chain variable region comprising an amino acid sequence having at least 95% sequence identity to the amino acid sequence of SEQ ID NO: 19, and the CDRs of claim 1(a)(i), (b)(i), or (c)(i); or b) a light chain variable region comprising an amino acid sequence having at least 95% sequence identity to the amino acid sequence of SEQ ID NO: 21, and the CDRs of claim 1(a)(i), (b)(i), or (c)(i); or
c) a light chain variable region comprising an amino acid sequence having at least 95% sequence identity to the amino acid sequence of SEQ ID NO: 22, and the CDRs of claim 1(a)(i), (b)(i), or (c)(i); or
d) a light chain variable region comprising an amino acid sequence having at least 95% sequence identity to the amino acid sequence of SEQ ID NO: 23, and the CDRs of claim 1(a)(i), (b)(i), or (c)(i); or
e) a light chain variable region comprising an amino acid sequence having at least 95% sequence identity to the amino acid sequence of SEQ ID NO: 24, and the CDRs of claim 1(a)(i), (b)(i), or (c)(i); or
f) a light chain variable region comprising an amino acid sequence having at least 95% sequence identity to the amino acid sequence of SEQ ID NO: 25, and the CDRs of claim 1(a)(i), (b)(i), or (c)(i); or
g) a light chain variable region comprising an amino acid sequence having at least 95% sequence identity to the amino acid sequence of SEQ ID NO: 31, and the CDRs of claim 1(a)(i), (b)(i), or (c)(i).

3. The antibody or antigen-binding fragment thereof of claim 1, comprising
a) a heavy chain variable region comprising an amino acid sequence having at least 95% sequence identity to the amino acid sequence of SEQ ID NO: 20 and the CDRs of claim 1(a)(ii), (b)(ii), or (c)(ii); or
b) a heavy chain variable region comprising an amino acid sequence having at least 95% sequence identity to the amino acid sequence of SEQ ID NO: 26 and the CDRs of claim 1(a)(ii), (b)(ii), or (c)(ii); or
c) a heavy chain variable region comprising an amino acid sequence-having at least 95% sequence identity to the amino acid sequence of SEQ ID NO: 27 and the CDRs of claim 1(a)(ii), (b)(ii), or (c)(ii); or
d) a heavy chain variable region comprising an amino acid sequence having at least 95% sequence identity to the amino acid sequence of SEQ ID NO: 28 and the CDRs of claim 1(a)(ii), (b)(ii), or (c)(ii); or
e) a heavy chain variable region comprising an amino acid sequence having at least 95% sequence identity to the amino acid sequence of SEQ ID NO: 29 and the CDRs of claim 1(a)(ii), (b)(ii), or (c)(ii); or
f) a heavy chain variable region comprising an amino acid sequence having at least 95% sequence identity to the amino acid sequence of SEQ ID NO: 30 and the CDRs of claim 1(a)(ii), (b)(ii), or (c)(ii); or
g) a heavy chain variable region comprising an amino acid sequence having at least 95% sequence identity to the amino acid sequence of SEQ ID NO: 32 and the CDRs of claim 1(a)(ii), (b)(ii), or (c)(ii); or
h) a heavy chain variable region comprising an amino acid sequence having at least 95% sequence identity to the amino acid sequence of SEQ ID NO: 33 and the CDRs of claim 1(a)(ii), (b)(ii), or (c)(ii); or
i) a heavy chain variable region comprising an amino acid sequence having at least 95% sequence identity to the amino acid sequence of SEQ ID NO: 34 and the CDRs of claim 1(a)(ii), (b)(ii), or (c)(ii).

4. The antibody or antigen-binding fragment thereof of claim 1, wherein the antibody comprises a light chain variable region and a heavy chain variable region, wherein:
a) the light chain variable region comprises or consists of the amino acid sequence of SEQ ID NO: 19 and the heavy chain variable region comprises or consists of the amino acid sequence of SEQ ID NO: 20; or
b) the light chain variable region comprises or consists of the amino acid sequence of SEQ ID NO: 21 and the heavy chain variable region comprises or consists of the amino acid sequence of SEQ ID NO: 26; or
c) the light chain variable region comprises or consists of the amino acid sequence of SEQ ID NO: 21 and the heavy chain variable region comprises or consists of the amino acid sequence of SEQ ID NO: 27; or
d) the light chain variable region comprises or consists of the amino acid sequence of SEQ ID NO: 21 and the heavy chain variable region comprises or consists of the amino acid sequence of SEQ ID NO: 28; or
e) the light chain variable region comprises or consists of the amino acid sequence of SEQ ID NO: 21 and the heavy chain variable region comprises or consists of the amino acid sequence of SEQ ID NO: 29; or
f) the light chain variable region comprises or consists of the amino acid sequence of SEQ ID NO: 21 and the heavy chain variable region comprises or consists of the amino acid sequence of SEQ ID NO: 30; or
g) the light chain variable region comprises or consists of the amino acid sequence of SEQ ID NO: 22 and the heavy chain variable region comprises or consists of the amino acid sequence of SEQ ID NO: 26; or
h) the light chain variable region comprises or consists of the amino acid sequence of SEQ ID NO: 22 and the heavy chain variable region comprises or consists of the amino acid sequence of SEQ ID NO: 27; or
i) the light chain variable region comprises or consists of the amino acid sequence of SEQ ID NO: 22 and the heavy chain variable region comprises or consists of the amino acid sequence of SEQ ID NO: 28; or
j) the light chain variable region comprises or consists of the amino acid sequence of SEQ ID NO: 22 and the heavy chain variable region comprises or consists of the amino acid sequence of SEQ ID NO: 29; or
k) the light chain variable region comprises or consists of the amino acid sequence of SEQ ID NO: 22 and the heavy chain variable region comprises or consists of the amino acid sequence of SEQ ID NO: 30; or
l) the light chain variable region comprises or consists of the amino acid sequence of SEQ ID NO: 23 and the heavy chain variable region comprises or consists of the amino acid sequence of SEQ ID NO: 26; or
m) the light chain variable region comprises or consists of the amino acid sequence of SEQ ID NO: 23 and the heavy chain variable region comprises or consists of the amino acid sequence of SEQ ID NO: 27; or
n) the light chain variable region comprises or consists of the amino acid sequence of SEQ ID NO: 23 and the heavy chain variable region comprises or consists of the amino acid sequence of SEQ ID NO: 28; or
o) the light chain variable region comprises or consists of the amino acid sequence of SEQ ID NO: 23 and the heavy chain variable region comprises or consists of the amino acid sequence of SEQ ID NO: 29; or
p) the light chain variable region comprises or consists of the amino acid sequence of SEQ ID NO: 23 and the heavy chain variable region comprises or consists of the amino acid sequence of SEQ ID NO: 30; or
q) the light chain variable region comprises or consists of the amino acid sequence of SEQ ID NO: 24 and the heavy chain variable region comprises or consists of the amino acid sequence of SEQ ID NO: 26; or r) the light chain variable region comprises or consists of the amino acid sequence of SEQ ID NO: 24 and the heavy chain variable region comprises or consists of the amino acid sequence of SEQ ID NO: 27; or s) the light chain variable region comprises or consists of the amino acid sequence of SEQ ID NO: 24 and the heavy chain variable region comprises or consists of the amino acid sequence of SEQ ID NO: 28; or t) the light chain variable region comprises or consists of the amino acid sequence of SEQ ID NO: 24 and the heavy chain variable region comprises or consists of the amino acid sequence of SEQ ID NO: 29; or u) the light chain variable region comprises or consists of the amino acid sequence of SEQ ID NO: 24 and the heavy chain variable region comprises or consists of the amino acid sequence of SEQ ID NO: 30; or v) the light chain variable region comprises or consists of the amino acid sequence of SEQ ID NO: 25 and the heavy chain variable region comprises or consists of the amino acid sequence of SEQ ID NO: 26; or w) the light chain variable region comprises or consists of the amino acid sequence of SEQ ID NO: 25 and the heavy chain variable region comprises or consists of the amino acid sequence of SEQ ID NO: 27; or x) the light chain variable region comprises or consists of the amino acid sequence of SEQ ID NO: 25 and the heavy chain variable region comprises or consists of the amino acid sequence of SEQ ID NO: 28; or y) the light chain variable region comprises or consists of the amino acid sequence of SEQ ID NO: 25 and the heavy chain variable region comprises or consists of the amino acid sequence of SEQ ID NO: 29; or z) the light chain variable region comprises or consists of the amino acid sequence of SEQ ID NO: 25 and the heavy chain variable region comprises or consists of the amino acid sequence of SEQ ID NO: 30, or aa) the light chain variable region comprises or consists of the amino acid sequence of SEQ ID NO: 24 and the heavy chain variable region comprises or consists of the amino acid sequence of SEQ ID NO: 32; or bb) the light chain variable region comprises or consists of the amino acid sequence of SEQ ID NO: 24 and the heavy chain variable region comprises or consists of the amino acid sequence of SEQ ID NO: 33; or cc) the light chain variable region comprises or consists of the amino acid sequence of SEQ ID NO: 24 and the heavy chain variable region comprises or consists of the amino acid sequence of SEQ ID NO: 34; or dd) the light chain variable region comprises or consists of the amino acid sequence of SEQ ID NO: 25 and the heavy chain variable region comprises or consists of the amino acid sequence of SEQ ID NO: 32; or ee) the light chain variable region comprises or consists of the amino acid sequence of SEQ ID NO: 25 and the heavy chain variable region comprises or consists of the amino acid sequence of SEQ ID NO: 33; or ff) the light chain variable region comprises or consists of the amino acid sequence of SEQ ID NO: 25 and the heavy chain variable region comprises or consists of the amino acid sequence of SEQ ID NO: 34; or gg) the light chain variable region comprises or consists of the amino acid sequence of SEQ ID NO: 31 and the heavy chain variable region comprises or consists of the amino acid sequence of SEQ ID NO: 30; or hh) the light chain variable region comprises or consists of the amino acid sequence of SEQ ID NO: 31 and the heavy chain variable region comprises or consists of the amino acid sequence of SEQ ID NO: 32; or ii) the light chain variable region comprises or consists of the amino acid sequence of SEQ ID NO: 31 and the heavy chain variable region comprises or consists of the amino acid sequence of SEQ ID NO: 33; or jj) the light chain variable region comprises or consists of the amino acid sequence of SEQ ID NO: 31 and the heavy chain variable region comprises or consists of the amino acid sequence of SEQ ID NO: 34.

5. The antibody or antigen-binding fragment thereof according to claim 1, wherein the antibody or antigen-binding fragment thereof comprises a light chain variable region which comprises or consists of SEQ ID NO: 24 and a heavy chain variable region which comprises or consists of SEQ ID NO: 34.

6. The antibody or antigen-binding fragment thereof according to claim 1, wherein the antibody or antigen-binding fragment thereof comprises a light chain variable region which comprises or consists of SEQ ID NO: 31 and a heavy chain variable region which comprises or consists of SEQ ID NO: 34.

7. The antibody or antigen-binding fragment thereof according to claim 1, wherein the antibody or antigen-binding fragment thereof comprises a light chain constant region comprising an amino acid sequence having at least 95% sequence identity to SEQ ID NO: 35, and a heavy chain constant region comprising an amino acid sequence having at least 95% sequence identity to SEQ ID NO: 36 or SEQ ID NO: 2.

8. An antibody or antigen-binding fragment thereof with binding specificity for interleukin-1 receptor accessory protein (IL1RAP), wherein the antibody or antigen-binding fragment comprises a light chain variable region and a heavy chain variable region comprising (a)(i) a CDR-L1 comprising the amino acid sequence of ESISTA (SEQ ID NO: 1); a CDR-L2 comprising the amino acid sequence of KAS; and a CDR-L3 comprising the amino acid sequence of QQGFSSGNVHNA (SEQ ID NO: 3); and (ii) a CDR-H1 comprising the amino acid sequence of GPSLSHFD (SEQ ID NO: 4); a CDR-H2 comprising the amino acid sequence of ISPGVST (SEQ ID NO: 5); and a CDR-H3 comprising the amino acid sequence of ARGGVGSSWKAFDL (SEQ ID NO: 6); or (b)(i) a CDR-L1 comprising the amino acid sequence of QASESISTALA (SEQ ID NO: 7); a CDR-L2 comprising the amino acid sequence of KASTLPS (SEQ ID NO: 8); and a CDR-L3 comprising the amino acid sequence of QQGFSSGNVHNA (SEQ ID NO: 9); and (ii) a CDR-H1 comprising the amino acid sequence of HFDIT (SEQ ID NO: 10); a CDR-H2 comprising the amino acid sequence of TISPGVSTYYASWAKS (SEQ ID NO: 11); and a CDR-H3 comprising the amino acid sequence of GGVGSSWKAFDL (SEQ ID NO: 12); or (c) (i) a CDR-L1 comprising the amino acid sequence of QASESISTALA (SEQ ID NO: 13); a CDR-L2 comprising the amino acid sequence of KASTLPS (SEQ ID NO: 14); and a CDR-L3 comprising the amino acid sequence of QQGFSSGNVHNA (SEQ ID NO: 15); and (ii) a CDR-H1 comprising the amino acid sequence of GPSLSHFDIT (SEQ ID NO: 16); a CDR-H2 comprising the amino acid sequence of TISPGVSTYYAS-WAKS (SEQ ID NO: 17); and a CDR-H3 comprising the amino acid sequence of ARGGVGSSWKAFDL (SEQ ID NO: 18); and wherein the light chain variable region comprises SEQ ID NO: 24 and the heavy chain variable region comprises SEQ ID NO: 34.

9. An antibody or antigen-binding fragment thereof with binding specificity for interleukin-1 receptor accessory protein (IL1RAP), wherein the antibody or antigen-binding fragment comprises a light chain variable region and a heavy chain variable region comprising
  (a)(i) a CDR-L1 comprising the amino acid sequence of ESISTA (SEQ ID NO: 1); a CDR-L2 comprising the amino acid sequence of KAS; and a CDR-L3 comprising the amino acid sequence of QQGFSSGNVHNA (SEQ ID NO: 3); and
  (ii) a CDR-H1 comprising the amino acid sequence of GPSLSHFD (SEQ ID NO: 4); a CDR-H2 comprising the amino acid sequence of ISPGVST (SEQ ID NO: 5); and a CDR-H3 comprising the amino acid sequence of ARGGVGSSWKAFDL (SEQ ID NO: 6); or
  (b)(i) a CDR-L1 comprising the amino acid sequence of QASESISTALA (SEQ ID NO: 7); a CDR-L2 comprising the amino acid sequence of KASTLPS (SEQ ID NO: 8); and a CDR-L3 comprising the amino acid sequence of QQGFSSGNVHNA (SEQ ID NO: 9); and
  (ii) a CDR-H1 comprising the amino acid sequence of HFDIT (SEQ ID NO: 10); a CDR-H2 comprising the amino acid sequence of TISPGVSTYYASWAKS (SEQ ID NO: 11); and a CDR-H3 comprising the amino acid sequence of GGVGSSWKAFDL (SEQ ID NO: 12); or
  (c) (i) a CDR-L1 comprising the amino acid sequence of QASESISTALA (SEQ ID NO: 13); a CDR-L2 comprising the amino acid sequence of KASTLPS (SEQ ID NO: 14); and a CDR-L3 comprising the amino acid sequence of QQGFSSGNVHNA (SEQ ID NO: 15); and
  (ii) a CDR-H1 comprising the amino acid sequence of GPSLSHFDIT (SEQ ID NO: 16); a CDR-H2 comprising the amino acid sequence of TISPGVSTYYAS-WAKS (SEQ ID NO: 17); and a CDR-H3 comprising the amino acid sequence of ARGGVGSSWKAFDL (SEQ ID NO: 18); and
wherein the light chain variable region comprises SEQ ID NO: 24 and the heavy chain variable region comprises SEQ ID NO: 34, and wherein the light chain constant region comprises SEQ ID NO: 35 and the heavy chain constant region comprises SEQ ID NO: 2.

10. The antibody or antigen-binding fragment thereof according to claim 1, wherein the antibody or antigen-binding fragment is not capable of inducing ADCC of cells expressing IL1RAP.

11. The antibody or antigen-binding fragment thereof according to claim 1, wherein the antibody or antigen-binding fragment comprises a cytotoxic moiety or a detectable moiety.

12. A pharmaceutical composition comprising the antibody or antigen-binding fragment of claim 1 and a pharmaceutically-acceptable diluent, carrier or excipient.

13. A method for treating an inflammatory, fibrotic and/or neoplastic disease or disorder expressing IL1RAP comprising the step of administering to the subject an effective amount of the antibody or antigen-binding fragment thereof according to claim 1.

14. The method of claim 13, wherein the disease or disorder is an inflammatory and/or fibrotic disease or disorder selected from myocarditis, systemic sclerosis, psoriasis, psoriatic arthritis, atherosclerosis, rheumatoid arthritis, all types of arthritis, all types of juvenile arthritis, systemic onset juvenile idiopathic arthritis (SOJIA), osteoarthritis, familial cold auto-inflammatory syndrome (FCAS), Muckle-Wells disease, neonatal onset multi-system inflammatory disease (NOMID), familial Mediterranean fever (FMF), pyogenic arthritis pyoderma gangrenosum and acne (PAPA) syndrome, adult onset Still's disease, hyper IgD syndrome, type 2 diabetes mellitus, macrophage activation syndrome, TNF receptor-associated periodic syndrome, Blau disease, ankylosing spondylitis, Sweets disease, lupus arthritis, Alzheimer's disease, asthma, allergy, sarcoidosis, atopic dermatitis, systemic lupus erythematosus, bullous pemphigoid, type I diabetes mellitus, chronic obstructive pulmonary disease, *Helicobacter pylori* gastritis, inflammatory bowel disease, hepatitis, hepatitis C, ischaemia-reperfusion injury, multiple sclerosis, Neisserial or pneumococcal meningitis, tuberculosis, Bechet's syndrome, septic shock, graft versus host disease, adult T cell leukaemia, multiple myeloma, periodontitis, obesity and obesity-related diseases, intervertebral disc disease, irritable bowel syndrome, Schnitzler syndrome, allergy/atopic dermatitis, acne inversa, Behcet's disease, cardiac fibrosis, cardiovascular diseases, cryopyin-associated periodic syndromes, cystic fibrosis, Goodpasture's syndrome, Guillain-Barre syndrome, kidney fibrosis, liver fibrosis, lung fibrosis, skin fibrosis, autoimmune myocarditis, organ dysfunction associated with organ transplantation, pancreatitis, peritonitis, uveitis, vasculitis, pneumonia, pulmonary hypertension, sclerodermatous chronic graft-versus-host disease, sepsis, Sjögren's syndrome, Takayasu's arteritis and gout.

15. The method of claim 13, wherein the disease or disorder is a neoplastic disease or disorder.

16. The method of claim 15, wherein the neoplastic disease or disorder is a hematologic disease or disorder, or a solid tumour.

17. The method of claim 16, wherein the neoplastic hematologic disease or disorder is selected from chronic myeloid leukemia (CML), myeloproliferative disorders (MPD), myelodysplastic syndrome (MDS), acute lymphoblastic leukemia (ALL) and acute myeloid leukemia (AML).

18. The method of claim 16, wherein the solid tumour is selected from prostate cancer, breast cancer, lung cancer, colon cancer, colorectal cancer, melanomas, bladder cancer, brain/CNS cancer, cancer of urinary organs, biliary tract cancer, cervical cancer, oesophageal cancer, gastric cancer, head/neck cancer, kidney cancer, liver cancer, lymphomas, ovarian cancer, pancreatic cancer, sarcomas, skin cancer and uterus cancer.

19. The method of claim 13, wherein the inflammatory, fibrotic and/or neoplastic disease or disorder is a disease or disorder susceptible to treatment with an inhibitor of IL-1α, IL-1β, IL-33, IL-36α, IL-36p and/or IL-36γ signaling and/or a disease or disorder associated with cells expressing IL1RAP.

20. A method for inducing cell death and/or inhibiting growth and/or proliferation of pathological cells associated with a neoplastic disorder in a subject, or stem cells or progenitor cells thereof, wherein the cells express IL1RAP, comprising administering to the subject an effective amount of the antibody or antigen-binding fragment thereof according to claim 1.

21. An in vitro method for the detection of cells expressing IL1RAP in a subject, the method comprising:
  (a) providing a sample of cells from a subject to be tested;
  (b) extracting and/or purifying the cells present in the sample;
  (c) contacting an antibody or antigen-binding fragment thereof according to claim 1 with cells from the sample; and (d) detecting binding of the antibody or antigen-binding fragment to the cells, wherein the binding of the antibody or antigen-binding fragment thereof to the cells is indicative of the presence of a disease or disorder associated with cells expressing IL1RAP in the sample.

22. A polynucleotide encoding an antibody or antigen-binding fragment thereof according to claim 1.

23. A vector comprising the polynucleotide according to claim 22.

24. A host cell comprising the polynucleotide according to claim 22.

25. A method for producing an antibody or antigen-binding fragment comprising culturing the host cell of claim 24 under conditions which permit expression of the encoded antibody or antigen-binding fragment thereof.

26. The method of claim 25, further comprising purifying the antibody.

27. The method of claim 14, wherein the inflammatory bowel disease is ulcerative colitis or Crohn's disease.

28. The method of claim 14, wherein the obesity-related disease is metabolic syndrome, cardiomegaly, congestive heart failure, myocardial infarction, varicose veins, polcystic ovarian syndrome, gastroesophogeal reflux disease (GERD), fatty liver disease, colorectal cancer, breast cancer, uterine cancer, chronic renal failure, stroke, or hyperuricemia.

* * * * *

UNITED STATES PATENT AND TRADEMARK OFFICE
CERTIFICATE OF CORRECTION

PATENT NO. : 11,479,610 B2
APPLICATION NO. : 17/559227
DATED : October 25, 2022
INVENTOR(S) : David Liberg et al.

Page 1 of 1

It is certified that error appears in the above-identified patent and that said Letters Patent is hereby corrected as shown below:

In the Specification
Column 19, Line 13, "QASESISTALA" should read --QASESISTALA--
Column 19, Line 18, "KASTLPS" should read --KASTLPS--
Column 19, Line 22, "QQGFSSGNVHNA" should read --QQGFSSGNVHNA--
Column 19, Line 27, "GPSLSHFDIT" should read --GPSLSHFDIT--
Column 19, Line 32, "TISPGVSTYYASWAKS" should read --TISPGVSTYYASWAKS--
Column 19, Line 37, "ARGGVGSSWKAFDL" should read --ARGGVGSSWKAFDL--
Column 71, Line 24, "IL-36P" should read --IL-36$\beta$--
Column 81, Line 47, "IL-1$\alpha$/p" should read --IL-1$\alpha$/$\beta$--
Column 82, Line 28, "IL-1$\alpha$/p" should read --IL-1$\alpha$/$\beta$--
Column 82, Line 31, "IL-1$\alpha$/p" should read --IL-1$\alpha$/$\beta$--

In the Claims
Column 150, Line 50 in Claim 19, "IL-36p" should read --IL-36$\beta$--

Signed and Sealed this
Fourteenth Day of February, 2023

Katherine Kelly Vidal
*Director of the United States Patent and Trademark Office*